US012805729B2

(12) United States Patent
Gupta et al.

(10) Patent No.: US 12,805,729 B2
(45) Date of Patent: Nov. 24, 2026

(54) CATHETER INSERT WITH OPTICAL FIBER FOR RAMAN SIGNAL MEASUREMENT

(71) Applicant: Haemanthus, Inc., Austin, TX (US)

(72) Inventors: Nachiketa Gupta, Austin, TX (US); David C. Stat, Austin, TX (US); Joseph G. LaChapelle, Philomath, OR (US); Roger S. Cannon, Oviedo, FL (US)

(73) Assignee: Haemanthus, Inc., Austin, TX (US)

(*) Notice: Subject to any disclaimer, the term of this patent is extended or adjusted under 35 U.S.C. 154(b) by 0 days.

(21) Appl. No.: 19/069,535

(22) Filed: Mar. 4, 2025

(65) Prior Publication Data

US 2026/0165616 A1 Jun. 18, 2026

Related U.S. Application Data

(60) Provisional application No. 63/735,459, filed on Dec. 18, 2024.

(51) Int. Cl.
*A61B 5/00* (2006.01)
*A61B 5/145* (2006.01)
(Continued)

(52) U.S. Cl.
CPC .......... *A61B 5/0084* (2013.01); *A61B 5/0075* (2013.01); *A61B 5/14503* (2013.01);
(Continued)

(58) Field of Classification Search
CPC ................ A61B 5/0075; A61B 5/0084; A61B 5/0086; A61B 5/6848; A61B 5/6852
See application file for complete search history.

(56) References Cited

U.S. PATENT DOCUMENTS 4,193,690 A 3/1980 Levenson et al.
4,598,715 A 7/1986 Machler
(Continued)

FOREIGN PATENT DOCUMENTS

CN 112097953 12/2020
CN 218739076 3/2023
(Continued)

OTHER PUBLICATIONS

Notice of Allowance issued for U.S. Appl. No. 18/821,845, mailed Feb. 18, 2026, 12 pages.
(Continued)

*Primary Examiner* — Colin T. Sakamoto
(74) *Attorney, Agent, or Firm* — Sprinkle IP Law Group

(57) ABSTRACT

In one embodiment, an apparatus includes a catheter insert that includes a catheter connector and a sheath having a substantially cylindrical shape. The catheter insert is configured to be coupled to a catheter that includes a mating connector and a catheter tube, where at least a portion of the sheath is configured to be inserted into the catheter tube, and the catheter connector is configured to be connected to the mating connector. The apparatus also includes an optical fiber that includes an end face, where at least a portion of the optical fiber is contained within the sheath. The optical fiber is configured to transmit a pump-Stokes beam of light along the optical fiber to the end face, where the pump-Stokes beam is emitted from the end face and directed to a sample.

16 Claims, 78 Drawing Sheets

(51) Int. Cl.

| | |
|---|---|
| ***A61B 5/1455*** | (2006.01) |
| ***A61B 5/1459*** | (2006.01) |
| ***A61M 16/00*** | (2006.01) |
| *G01J 3/02* | (2006.01) |
| *G01J 3/28* | (2006.01) |
| *G01J 3/433* | (2006.01) |
| *G01J 3/44* | (2006.01) |
| *G01N 21/65* | (2006.01) |

(52) U.S. Cl.
CPC ...... *A61B 5/14532* (2013.01); *A61B 5/14552* (2013.01); *A61B 5/1459* (2013.01); *A61B 5/6848* (2013.01); *A61B 5/6852* (2013.01); *A61B 5/6876* (2013.01); *A61M 16/024* (2017.08); *A61B 2562/0233* (2013.01); *A61B 2562/228* (2013.01); *A61M 2230/20* (2013.01); *G01J 3/0202* (2013.01); *G01J 3/0208* (2013.01); *G01J 3/021* (2013.01); *G01J 3/0218* (2013.01); *G01J 3/0256* (2013.01); *G01J 3/0275* (2013.01); *G01J 3/0291* (2013.01); *G01J 2003/2843* (2013.01); *G01J 3/433* (2013.01); *G01J 3/4412* (2013.01); *G01N 21/65* (2013.01); *G01N 2021/656* (2013.01)

(56) References Cited

U.S. PATENT DOCUMENTS

| | | | | |
|---|---|---|---|---|
| 4,858,238 | A | 8/1989 | Cardimona | |
| 5,280,788 | A | 1/1994 | Janes | |
| 5,418,797 | A | 5/1995 | Bashkansky | |
| 5,510,895 | A | 4/1996 | Sahagen | |
| 5,526,112 | A | 6/1996 | Sahagen | |
| 5,565,982 | A | 10/1996 | Lee | |
| 5,769,791 | A | 6/1998 | Benaron | |
| 5,849,595 | A | 12/1998 | Alfano | |
| 5,983,125 | A | 11/1999 | Alfano | |
| 6,208,887 | B1 | 3/2001 | Clarke | |
| 6,485,413 | B1 | 11/2002 | Boppart | |
| 6,564,087 | B1 | 5/2003 | Pitris | |
| 7,388,668 | B2 | 6/2008 | Potma et al. | |
| 8,873,041 | B1 | 10/2014 | Chai | |
| 9,086,533 | B1 | 7/2015 | Wach | |
| 9,594,023 | B2 | 3/2017 | Tamada | |
| 9,638,638 | B2 | 5/2017 | Huber et al. | |
| 9,733,125 | B2 | 8/2017 | Liu et al. | |
| 12,203,862 | B1 | 1/2025 | LaChapelle et al. | |
| 12,618,714 | B2 | 5/2026 | LaChapelle et al. | |
| 2002/0122246 | A1 | 9/2002 | Teamey | |
| 2003/0045798 | A1 | 3/2003 | Hular | |
| 2004/0073120 | A1 | 4/2004 | Motz | |
| 2004/0127776 | A1 | 7/2004 | Walker | |
| 2004/0247268 | A1 | 12/2004 | Ishihara | |
| 2005/0203419 | A1 | 9/2005 | Ramanujam | |
| 2007/0078500 | A1 | 4/2007 | Ryan | |
| 2007/0239033 | A1 | 10/2007 | Teamey | |
| 2008/0037024 | A1 | 2/2008 | Backman | |
| 2008/0214940 | A1 | 9/2008 | Benaron | |
| 2008/0221456 | A1 | 9/2008 | Babchenko | |
| 2008/0267562 | A1 | 10/2008 | Wang | |
| 2008/0304074 | A1 | 12/2008 | Brennan, III | |
| 2009/0088615 | A1 | 4/2009 | Robinson | |
| 2009/0177094 | A1 | 7/2009 | Brown | |
| 2009/0185191 | A1 | 7/2009 | Boppart | |
| 2009/0213370 | A1 | 8/2009 | Kim et al. | |
| 2010/0020318 | A1 | 1/2010 | Lee | |
| 2010/0317964 | A1 | 12/2010 | Hendriks | |
| 2011/0218445 | A1 | 9/2011 | Braun | |
| 2011/0251494 | A1 | 10/2011 | Hendriks | |
| 2011/0270093 | A1 | 11/2011 | Desjardins | |
| 2011/0282166 | A1 | 11/2011 | Chen | |
| 2012/0029360 | A1 | 2/2012 | Hendriks | |
| 2012/0092662 | A1 | 4/2012 | Langbein | |
| 2012/0116234 | A1 | 5/2012 | Farcy | |
| 2012/0287428 | A1 | 11/2012 | Tamada | |
| 2013/0050683 | A1 | 2/2013 | Hendriks | |
| 2013/0217989 | A1 | 8/2013 | Hendriks | |
| 2013/0310680 | A1 | 11/2013 | Werahera | |
| 2014/0046197 | A1 | 2/2014 | Lucassen | |
| 2014/0121538 | A1 | 5/2014 | Hendriks | |
| 2014/0213911 | A1 | 7/2014 | Bierhoff | |
| 2014/0226157 | A1 | 8/2014 | Dogariu | |
| 2014/0236023 | A1 | 8/2014 | Day | |
| 2014/0236024 | A1 | 8/2014 | Bierhoff | |
| 2014/0268131 | A1 | 9/2014 | Tamada | |
| 2014/0354987 | A1 | 12/2014 | Satoh | |
| 2015/0080712 | A1 | 3/2015 | Van Keersop | |
| 2015/0148629 | A1 | 5/2015 | Wilson | |
| 2015/0182206 | A1 | 7/2015 | Hendriks | |
| 2015/0204790 | A1 | 7/2015 | Yonetani | |
| 2015/0265256 | A1 | 9/2015 | Bierhoff | |
| 2015/0313471 | A1 | 11/2015 | Dholakia | |
| 2015/0359525 | A1 | 12/2015 | Hendriks | |
| 2016/0178439 | A1 | 6/2016 | Freudiger et al. | |
| 2016/0278694 | A1 | 9/2016 | Aharoni | |
| 2016/0344158 | A1 | 11/2016 | Onose | |
| 2017/0023482 | A1 | 1/2017 | Cicerone et al. | |
| 2017/0052015 | A1 | 2/2017 | Swanson | |
| 2018/0238738 | A1 | 8/2018 | Alfano | |
| 2018/0323572 | A1 | 11/2018 | Mildren et al. | |
| 2020/0015684 | A1 | 1/2020 | Stone | |
| 2020/0085308 | A1 | 3/2020 | Day | |
| 2020/0124530 | A1 | 4/2020 | Stolow et al. | |
| 2021/0068665 | A1 | 3/2021 | Pahlevaninezhad | |
| 2021/0381985 | A1 | 12/2021 | Rigneault | |
| 2021/0404958 | A1 | 12/2021 | Min | |
| 2022/0015635 | A1 | 1/2022 | Sipple | |
| 2022/0042916 | A1 | 2/2022 | Notingher | |
| 2022/0155233 | A1 | 5/2022 | Zeng | |
| 2022/0202292 | A1 | 6/2022 | Anderson | |
| 2022/0317044 | A1 | 10/2022 | Anderson | |
| 2022/0409100 | A1 | 12/2022 | Sipple | |
| 2023/0172443 | A1 | 6/2023 | Bec | |
| 2024/0041328 | A1 | 2/2024 | Mannion | |
| 2024/0130171 | A1 | 4/2024 | Wang | |
| 2024/0131267 | A1* | 4/2024 | Wanner | A61B 5/0075 |
| 2025/0017471 | A1 | 1/2025 | Goth | |
| 2025/0134386 | A1 | 5/2025 | Puppels | |
| 2025/0277699 | A1 | 9/2025 | LaChapelle et al. | |
| 2025/0277701 | A1 | 9/2025 | LaChapelle et al. | |
| 2025/0277702 | A1 | 9/2025 | LaChapelle et al. | |
| 2025/0277742 | A1 | 9/2025 | LaChapelle et al. | |
| 2025/0277743 | A1 | 9/2025 | LaChapelle et al. | |
| 2025/0277744 | A1 | 9/2025 | LaChapelle et al. | |
| 2025/0277745 | A1 | 9/2025 | LaChapelle et al. | |
| 2025/0277746 | A1 | 9/2025 | LaChapelle et al. | |
| 2026/0000341 | A1 | 1/2026 | Alix | |
| 2026/0165585 | A1 | 6/2026 | Stat et al. | |
| 2026/0165587 | A1 | 6/2026 | Cannon et al. | |
| 2026/0168849 | A1 | 6/2026 | LaChapelle et al. | |
| 2026/0168850 | A1 | 6/2026 | Gupta et al. | |
| 2026/0168855 | A1 | 6/2026 | Stat et al. | |

FOREIGN PATENT DOCUMENTS

| | | |
|---|---|---|
| CN | 116327138 | 6/2023 |
| DE | 10311452 | 4/2006 |
| EP | 1760424 | 3/2007 |
| JP | 2011180504 | 9/2011 |
| JP | 2015222276 | 12/2015 |
| JP | 2016029340 | 3/2016 |
| WO | WO2008144831 | 12/2008 |
| WO | WO2009081358 | 7/2009 |
| WO | WO2013084621 | 6/2013 |
| WO | WO2015121115 | 8/2015 |
| WO | WO2020075548 | 9/2021 |
| WO | WO2022204441 | 9/2022 |

(56) References Cited

FOREIGN PATENT DOCUMENTS

| | | |
|---|---|---|
| WO | WO2023/058710 | 4/2023 |
| WO | WO 2023196388 | 10/2023 |

OTHER PUBLICATIONS

Notice of Allowance issued for U.S. Appl. No. 19/349,623, mailed Apr. 1, 2026, 15 pages.

Office Action issued for U.S. Appl. No. 18/930,095, mailed Mar. 30, 2026, 10 pages.

Office Action issued for U.S. Appl. No. 18/892,075, mailed Apr. 2, 2026, 35 pages.

Notice of Allowance issued for U.S. Appl. No. 19/020,938, mailed Jun. 3, 2026, 10 pages.

International Search Report and Written Opinion issued for International Application No. PCT/US2025/016826, mailed May 15, 2025, 10 pages.

Lin, Y., et al. "Multi-cancer early detection based on serum surface-enhanced Raman spectroscopy with deep learning: a large-scale case-control study." BMC Medicine, vol. 23, Article No. 97, 2025, https://doi.org/10.1186/s12916-025-03887-5.

Chen, X., et al. "Applications of Data Characteristic AI-Assisted Raman Spectroscopy in Pathological Classification." Analytical Chemistry, vol. 96, No. 16, Apr. 23, 2024, pp. 6158-6169, https://doi.org/10.1021/acs.analchem.3c04930.

Zhang, Y., et al. "From Genotype to Phenotype: Raman Spectroscopy and Machine Learning for Label-Free Single-Cell Analysis." ACS Nano, vol. 18, No. 28, Jul. 16, 2024, pp. 18101-18117, https://doi.org/10.1021/acsnano.4c04282.

Belmerabet, R., et al. "Multilayered assembly of graphene oxide and silver nanoprisms on pyramidal arrays as highly efficient SERS-assisted biosensing platform." Chinese Journal of Physics, vol. 97, Oct. 2025, pp. 839-849, https://doi.org/10.1016/j.cjph.2025.07.031.

Nesbitt, D., et al. "Vibrational Energy Flow in Highly Excited Molecules: Role of Intramolecular Vibrational Redistribution." The Journal of Physical Chemistry, vol. 100, 1996, pp. 12735-12756.

Toppings, N., et al. "A rapid near-patient detection system for SARS-CoV-2 using saliva." Scientific Reports, vol. 11, Article No. 13378, 2021, https://doi.org/10.1038/s41598-021-92677-z.

Carlomagno, C., et al. "Identification of the Raman Salivary Fingerprint of Parkinson's Disease Through the Spectroscopic-Computational Combinatory Approach." Frontiers in Neuroscience, vol. 15, Oct. 26, 2021, Article 704963, https://doi.org/10.3389/fnins.2021.704963.

Ryzhikova, E., et al. "Raman spectroscopy of blood serum for Alzheimer's disease diagnostics: specificity relative to other types of dementia." Journal of Biophotonics, vol. 8, No. 7, Jul. 2015, pp. 584-596, doi:10.1002/jbio.201400060.

Chen, C., et al. "Applications of Raman spectroscopy in the diagnosis and monitoring of neurodegenerative diseases." Frontiers in Neuroscience, vol. 18, Jan. 17, 2024, Article 1301107, https://doi.org/10.3389/fnins.2024.1301107.

Polykretis, P., et al. "Raman Spectroscopy Techniques for the Investigation and Diagnosis of Alzheimer's Disease." Frontiers in Bioscience (Scholar Edition), vol. 14, No. 3, Aug. 1, 2022, Article 22, https://doi.org/10.31083/j.fbs1403022.

Coles et al. "Molecular Insights into a-Synuclein Fibrillation: A Raman Spectroscopy and Machine Learning Approach." ACS Chemical Neuroscience, vol. 16, No. 4, Feb. 19, 2025, pp. 687-698, https://doi.org/10.1021/acschemneuro.4c00726.

Pruccoli, A., et al. "High Sensitivity Stimulated Raman Scattering Microscopy with Electronic Resonance Enhancement." ChemPhysChem, vol. 25, No. 19, Oct. 2024, https://doi.org/10.1002/cphc.202400309.

Jain et al. "Scientific Advances in Cancer Detection Using Raman Spectroscopy." Asian Pacific Journal of Cancer Prevention, vol. 25, No. 11, Nov. 1, 2024, pp. 3977-3986, https://doi.org/10.31557/APJCP.2024.25.11.3977.

Dzelve et al. "Utility of Raman Spectroscopy in Pulmonary Medicine." Advances in Respiratory Medicine, vol. 92, No. 5, 2024, pp. 421-428, https://doi.org/10.3390/arm92050038.

Khristoforova et al. "Raman spectroscopy in chronic heart failure diagnosis based on human skin analysis." Journal of Biophotonics, vol. 16, No. 7, Jul. 2023, https://doi.org/10.1002/jbio.202300016.

Thomas et al. "Raman spectroscopy assisted tear analysis: A label free, optical approach for noninvasive disease diagnostics." Experimental Eye Research, vol. 243, 2024, 109913, https://doi.org/10.1016/j.exer.2024.109913.

Hu et al. "Stimulated Raman scattering imaging by continuous-wave laser excitation." Optics Letters, vol. 38, No. 9, 2013, pp. 1479-1481, https://doi.org/10.1364/OL.38.001479.

Office Action issued for U.S. Appl. No. 18/762,415, mailed Jan. 16, 2026, 22 pages.

Nakae, et al., "Terahertz Coherent Raman Spectroscopy of Dimethyl Sulfoxide and Water Mixtures Using Frequency Chirped Pulses," IEEE, Dec. 1, 2016, 2 pages.

Office Action issued for U.S. Appl. No. 18/762,420, mailed Jan. 16, 2026, 23 pages.

Office Action issued for U.S. Appl. No. 18/774,723, mailed Jan. 9, 2026, 9 pages.

Freudiger, Christian W., et al. "Optical heterodyne-detected Raman-induced Kerr effect (OHD-RIKE) microscopy." *The Journal of Physical Chemistry B*, vol. 115, No. 18, Apr. 19, 2011, pp. 5574-5581, https://doi.org/10.1021/jp1113834.

Ideguchi, T., et al. "Raman-Induced Kerr-Effect Dual-Comb Spectroscopy." Optics Letters, vol. 37, No. 21, Oct. 26, 2012, p. 4498, doi:10.1364/ol.37.004498.

Evans, Conor L., et al. "Coherent Anti-Stokes Raman Scattering Spectral Interferometry: Determination of the Real and Imaginary Components of Nonlinear Susceptibility X/\(3) for Vibrational Microscopy." Optics Letters, vol. 29, No. 24, Dec. 15, 2004, p. 2923, doi: 10.1364/ol.29.002923.

Potma, Eric O., et al. "Heterodyne Coherent Anti-Stokes Raman Scattering (CARS) Imaging." Optics Letters, vol. 31, No. 2, Jan. 15, 2006, p. 241, doi: 10.1364/ol.31.000241.

Yu, Mengjie, et al. "Silicon-Chip-Based Mid-Infrared Dual-Comb Spectroscopy." *Nature Communications*, vol. 9, No. 1, May 14, 2018, doi: 10.1038/s41467-018-04350-1.

Ettabib, Mohamed A., et al. "Waveguide-Enhanced Raman Spectroscopy." *Nature Reviews Methods Primers*, vol. 4, No. 1, Jan. 11, 2024, doi:10.1038/s43586-023-00281-4.

"Waveguide-Enhanced Raman Spectroscopy." *Nature Reviews Methods Primers*, vol. 4, No. 1, Jan. 11, 2024, doi: 10.1038/s43586-024-00290-x.

Moawad, Amira A., et al. "A Machine Learning-Based Raman Spectroscopic Assay for the Identification of Burkholderia Mallei and Related Species." *Molecules*, vol. 24, No. 24, Dec. 10, 2019, p. 4516, doi:10.3390/molecules24244516.

Kita, Derek M., et al. "A Packaged, Fiber-Coupled Waveguide-Enhanced Raman Spectroscopic Sensor." *Optics Express*, vol. 28, No. 10, May 1, 2020, p. 14963, doi:10.1364/OE.392486.

Ye, Jiarong, et al. "Accurate Virus Identification with Interpretable Raman Signatures by Machine Learning." *Proceedings of the National Academy of Sciences*, vol. 119, No. 23, Jun. 2, 2022, doi:10.1073/pnas.2118836119.

Shi-An, Zhang, et al. "Achievement of Narrow-Band CARS Signal by Manipulating Broad-Band Laser Spectrum." Chinese Physics Letters, vol. 25, No. 9, Sep. 2008, pp. 3260-3263, doi:10.1088/0256-307x/25/9/045.

Pegoraro, Adrian F., et al. "All-Fiber CARS Microscopy of Live Cells." Optics Express, vol. 17, No. 23, Oct. 27, 2009, p. 20700, doi:10.1364/OE.17.020700.

Yu, Shixiang, et al. "Analysis of Raman Spectra by Using Deep Learning Methods in the Identification of Marine Pathogens." Analytical Chemistry, vol. 93, No. 32, Aug. 2, 2021, pp. 11089-11098, doi:10.1021/acs.analchem.1c00431.

Jurna, M., et al. "Background Free CARS Imaging by Phase Sensitive Heterodyne CARS." Optics Express, vol. 16, No. 20, 22 Sep. 2008, p. 15863, doi:10.1364/oe.16.015863.

(56) References Cited

OTHER PUBLICATIONS

Kuhar, Nikki, et al. "Challenges in Application of Raman Spectroscopy to Biology and Materials." RSC Advances, vol. 8, No. 46, 2018, pp. 25888-25908, doi:10.1039/c8ra04491k.

Marron, Joseph C., et al. "Coherent Detection with an Asynchronous Geiger Mode Array." Imaging and Applied Optics 2015, 2015, doi:10.1364/lsc.2015.Iw3d.1.

Brzozowski, K., et al. "Coherent Raman Spectroscopy: Quo Vadis?" Vibrational Spectroscopy, vol. 132, May 2024, p. 103684, doi:10.1016/j.vibspec.2024.103684.

Nakar, Amir, et al. "Detection of Multi-Resistant Clinical Strains of *E. coli* with Raman Spectroscopy." Analytical and Bioanalytical Chemistry, vol. 414, No. 4, Jan. 4, 2022, pp. 1481-1492, doi:10.1007/s00216-021-03800-y.

Zahn, Jessica, et al. "Discriminating Cell Line Specific Features of Antibiotic-resistant Strains of *Escherichia coli* from Raman Spectra via Machine Learning Analysis." Journal of Biophotonics, vol. 15, No. 7, Apr. 6, 2022, doi:10.1002/jbio.202100274.

Wang, Xi, et al. "Heterodyne Coherent Anti-Stokes Raman Scattering by the Phase Control of Its Intrinsic Background." Physical Review A, vol. 84, No. 2, Aug. 5, 2011, doi:10.1103/physreva.84.021801.

Wang, Xi, et al. "Heterodyne Coherent Anti-Stokes Raman Scattering for Spectral Phase Retrieval and Signal Amplification." Optics Letters, vol. 35, No. 5, Feb. 25, 2010, p. 721, doi:10.1364/ol.35.000721.

Müller, Christina, et al. "Heterodyne Single-beam CARS Microscopy." Journal of Raman Spectroscopy, vol. 40, No. 7, Apr. 8, 2009, pp. 809-816, doi:10.1002/jrs.2260.

Kieu, Khanh, et al. "High-Power Picosecond Fiber Source for Coherent Raman Microscopy." Optics Letters, vol. 34, No. 13, Jun. 29, 2009, p. 2051, doi:10.1364/ol.34.002051.

Xu, Jiabao, et al. "High-Speed Diagnosis of Bacterial Pathogens at the Single Cell Level by Raman Microspectroscopy with Machine Learning Filters and Denoising Autoencoders." ACS Chemical Biology, vol. 17, No. 2, Jan. 13, 2022, pp. 376-385, doi:10.1021/acschembio.1c00834.

Lim, Ryan S., et al. "Identification of Cholesterol Crystals in Plaques of Atherosclerotic Mice Using Hyperspectral CARS Imaging." Journal of Lipid Research, vol. 52, No. 12, Dec. 2011, pp. 2177-2186, doi:10.1194/jlr.m018077.

Lu, Wei, et al. "Improving the Signal-to-Noise Ratio of GM-APD Coherent Lidar System Based on Phase Synchronization Method." Optics & Laser Technology, vol. 150, Jun. 2022, p. 107994, doi:10.1016/j.optlastec.2022.107994.

Ji, Minbiao, et al. "Label-Free Imaging of Amyloid Plaques in Alzheimer's Disease with Stimulated Raman Scattering Microscopy." Science Advances, vol. 4, No. 11, Nov. 2, 2018, doi:10.1126/sciadv.aat7715.

Gottschall, Thomas, et al. "Fiber-based Light Sources for Biomedical Applications of Coherent Anti-stokes Raman Scattering Microscopy." Laser & Photonics Reviews, vol. 9, No. 5, Aug. 6, 2015, pp. 435-451, doi:10.1002/lpor.201500023.

Allen, Ashley, et al. "Miniature Spatial Heterodyne Spectrometer for Remote Laser Induced Breakdown and Raman Spectroscopy Using Fresnel Collection Optics." Spectrochimica Acta Part B: Atomic Spectroscopy, vol. 149, Nov. 2018, pp. 91-98, doi:10.1016/j.sab.2018.07.013.

Lin, Chia-Yu, et al. "Picosecond Spectral Coherent Anti-Stokes Raman Scattering Imaging with Principal Component Analysis of Meibomian Glands." Journal of Biomedical Optics, vol. 16, No. 2, 2011, p. 021104, doi:10.1117/1.3533716.

Germond, Arno, et al. "Raman Spectral Signature Reflects Transcriptomic Features of Antibiotic Resistance in *Escherichia coli*." Communications Biology, vol. 1, No. 1, Jul. 2, 2018, doi:10.1038/s42003-018-0093-8.

Walter, Angela, et al. "Raman Spectroscopic Detection of Physiology Changes in Plasmid-Bearing *Escherichia coli* with and without Antibiotic Treatment." Analytical and Bioanalytical Chemistry, vol. 400, No. 9, Mar. 20, 2011, pp. 2763-2773, doi:10.1007/s00216-011-4819-4.

Yan, Shuaishuai, et al. "Raman Spectroscopy Combined with Machine Learning for Rapid Detection of Food-Borne Pathogens at the Single-Cell Level." Talanta, vol. 226, May 2021, p. 122195, doi:10.1016/j.talanta.2021.122195.

Kukula, Kaitlyn, et al. "Rapid Detection of Bacteria Using Raman Spectroscopy and Deep Learning." 2021 IEEE 11th Annual Computing and Communication Workshop and Conference (CCWC), Jan. 27, 2021, doi:10.1109/ccwc51732.2021.9375955.

Ho, Chi-Sing, et al. "Rapid Identification of Pathogenic Bacteria Using Raman Spectroscopy and Deep Learning." Nature Communications, vol. 10, No. 1, Oct. 30, 2019, doi:10.1038/s41467-019-12898-9.

Lim, Sang-Hyun, et al. "Single-Pulse Phase-Control Interferometric Coherent Anti-Stokes Raman Scattering Spectroscopy." Physical Review A, vol. 72, No. 4, Oct. 17, 2005, doi:10.1103/physreva.72.041803.

Owyoung, Adelbert, et al. "Stimulated Raman Spectroscopy Using Low-Power CW Lasers." Optics Letters, vol. 1, No. 5, Nov. 1, 1977, p. 152, doi:10.1364/ol.1.000152.

Zong, Cheng, et al. "Surface-Enhanced Raman Spectroscopy for Bioanalysis: Reliability and Challenges." Chemical Reviews, vol. 118, No. 10, Apr. 11, 2018, pp. 4946-4980, doi:10.1021/acs.chemrev.7b00668.

Selm, Romedi, et al. "Ultrabroadband Background-Free Coherent Anti-Stokes Raman Scattering Microscopy Based on a Compact ER:Fiber Laser System." Optics Letters, vol. 35, No. 19, 28 Sep. 2010, p. 3282, doi:10.1364/ol.35.003282.

Ashok, Praveen C., et al. "Waveguide Confined Raman Spectroscopy for Microfluidic Interrogation." Lab on a Chip, vol. 11, No. 7, 2011, p. 1262, doi:10.1039/c0lc00462f.

Ettabib, Mohamed A., et al. "Waveguide Enhanced Raman Spectroscopy for Biosensing: A Review." ACS Sensors, vol. 6, No. 6, Jun. 11, 2021, pp. 2025-2045, doi:10.1021/acssensors.1c00366.

Tyndall, Nathan F., et al. "Waveguide-Enhanced Raman Spectroscopy of Trace Chemical Warfare Agent Simulants." Optics Letters, vol. 43, No. 19, 28 Sep. 2018, p. 4803, doi:10.1364/ol.43.004803.

Tyndall, Nathan F., et al. "Foundry-Based Waveguide-Enhanced Raman Spectroscopy in the Visible." Optics Express, vol. 32, No. 4, Jan. 29, 2024, p. 4745, doi:10.1364/oe.504195.

Ettabib, Mohamed A., et al. "Grating-Incoupled Waveguide-Enhanced Raman Sensor." PLOS One, vol. 18, No. 8, Aug. 10, 2023, doi:10.1371/journal.pone.0284058.

Ettabib, Mohamed A., et al. "Optimized Design for Grating-Coupled Waveguide-Enhanced Raman Spectroscopy." Optics Express, vol. 28, No. 25, Nov. 23, 2020, p. 37226, doi:10.1364/oe.410602.

Turk, Nina, et al. "Waveguide-Based Surface-Enhanced Raman Spectroscopy Detection of Protease Activity Using Non-Natural Aromatic Amino Acids." Biomedical Optics Express, vol. 11, No. 8, Jul. 31, 2020, p. 4800, doi:10.1364/boe.398038.

Robertson, John L., et al. "Alterations in the Molecular Composition of COVID-19 Patient Urine, Detected Using Raman Spectroscopic/Computational Analysis." PLOS One, vol. 17, No. 7, Jul. 18, 2022, doi:10.1371/journal.pone.0270914.

Robertson, John L., et al. "Cancer Detection in Dogs Using Rapid Raman Molecular Urinalysis." Frontiers in Veterinary Science, vol. 11, Feb. 7, 2024, doi:10.3389/fvets.2024.1328058.

Schröder, Ulrich-Christian, et al. "Combined Dielectrophoresis-Raman Setup for the Classification of Pathogens Recovered from the Urinary Tract." Analytical Chemistry, vol. 85, No. 22, Nov. 6, 2013, pp. 10717-10724, doi:10.1021/ac4021616.

Bispo, Jeyse Aliana, et al. "Correlating the Amount of Urea, Creatinine, and Glucose in Urine from Patients with Diabetes Mellitus and Hypertension with the Risk of Developing Renal Lesions by Means of Raman Spectroscopy and Principal Component Analysis." Journal of Biomedical Optics, vol. 18, No. 8, Aug. 8, 2013, p. 087004, doi:10.1117/1.jbo.18.8.087004.

Kloß, Sandra, et al. "Culture Independent Raman Spectroscopic Identification of Urinary Tract Infection Pathogens: A Proof of Principle Study." Analytical Chemistry, vol. 85, No. 20, Sep. 24, 2013, pp. 9610-9616, doi:10.1021/ac401806f.

(56) References Cited

OTHER PUBLICATIONS

Hu, Dayu, et al. "Detecting Urine Metabolites of Bladder Cancer by Surface-Enhanced Raman Spectroscopy." Spectrochimica Acta Part A: Molecular and Biomolecular Spectroscopy, vol. 247, Feb. 2021, p. 119108, doi:10.1016/j.saa.2020.119108.
Senger, Ryan S., et al. "Disease-Associated Multimolecular Signature in the Urine of Patients with Lyme Disease Detected Using Raman Spectroscopy and Chemometrics." Applied Spectroscopy, vol. 76, No. 3, Feb. 1, 2022, pp. 284-299, doi:10.1177/00037028211061769.
Brindha, Elumalai, et al. "High Wavenumber Raman Spectroscopy in the Characterization of Urinary Metabolites of Normal Subjects, Oral Premalignant and Malignant Patients." Spectrochimica Acta Part A: Molecular and Biomolecular Spectroscopy, vol. 171, Jan. 2017, pp. 52-59, doi:10.1016/j.saa.2016.06.048.
Bhattacharjee, T., et al. "A Preliminary Raman Spectroscopic Study of Urine: Diagnosis of Breast Cancer in Animal Models." The Analyst, vol. 140, No. 2, 2015, pp. 456-466, doi:10.1039/c4an01703j.
Huttanus, Herbert M., et al. "Raman Chemometric Urinalysis (Rametrix) as a Screen for Bladder Cancer." PLOS One, vol. 15, No. 8, Aug. 21, 2020, doi:10.1371/journal.pone.0237070.
Moreira, Letícia Parada, et al. "Raman Spectroscopy Applied to Identify Metabolites in Urine of Physically Active Subjects." Journal of Photochemistry and Photobiology B: Biology, vol. 176, Nov. 2017, pp. 92-99, doi:10.1016/j.jphotobiol.2017.09.019.
McMurdy, John W., et al. "Raman Spectroscopy-Based Creatinine Measurement in Urine Samples from a Multipatient Population." Applied Spectroscopy, vol. 57, No. 5, May 2003, pp. 522-525, doi:10.1366/000370203321666533.
Jeng, Ming-Jer, et al. "Raman Spectral Characterization of Urine for Rapid Diagnosis of Acute Kidney Injury." Journal of Clinical Medicine, vol. 11, No. 16, Aug. 18, 2022, p. 4829, doi:10.3390/jcm11164829.
Zhang, Xueqin, et al. "Rapid Diagnosis of Membranous Nephropathy Based on Serum and Urine Raman Spectroscopy Combined with Deep Learning Methods." Scientific Reports, vol. 13, No. 1, Feb. 28, 2023, doi:10.1038/s41598-022-22204-1.
Senger, Ryan S., et al. "Spectral Characteristics of Urine Specimens from Healthy Human Volunteers Analyzed Using Raman Chemometric Urinalysis (Rametrix)." PLOS One, vol. 14, No. 9, 27 Sep. 2019, doi:10.1371/journal.pone.0222115.
Dawuti, Wubulitalifu, et al. "Urine Surface-Enhanced Raman Spectroscopy Combined with SVM Algorithm for Rapid Diagnosis of Liver Cirrhosis and Hepatocellular Carcinoma." Photodiagnosis and Photodynamic Therapy, vol. 38, Jun. 2022, p. 102811, doi:10.1016/j.pdpdt.2022.102811.
Vigo, Francesco, et al. "Vibrational Spectroscopy in Urine Samples as a Medical Tool: Review and Overview on the Current State-of-the-Art." Diagnostics, vol. 13, No. 1, Dec. 22, 2022, p. 27, doi:10.3390/diagnostics13010027.
Sahu, Avinash, et al. A Novel Lab-on-Chip Cartridge Overcoming Centrifugation and Slide Preparation for Automated Urinalysis, Jan. 19, 2024, doi:10.21203/rs.3.rs-3872166/v1.
Álvarez, Rosa, et al. "Raman Spectroscopic Study of the Conformational Changes of Thyroxine Induced by Interactions with Phospholipid." European Biophysics Journal, vol. 31, No. 6, Oct. 1, 2002, pp. 448-453, doi:10.1007/s00249-002-0238-y.
Li, Yizhe, et al. "Serum Raman Spectroscopy Combined with Deep Neural Network for Analysis and Rapid Screening of Hyperthyroidism and Hypothyroidism." Photodiagnosis and Photodynamic Therapy, vol. 35, Sep. 2021, p. 102382, doi:10.1016/j.pdpdt.2021.102382.
Medina-Gutiérrez, C., et al. "The Application of NIR Raman Spectroscopy in the Assessment of Serum Thyroid-Stimulating Hormone in Rats." Spectrochimica Acta Part A: Molecular and Biomolecular Spectroscopy, vol. 61, No. 1-2, Jan. 2005, pp. 87-91, doi:10.1016/j.saa.2004.03.016.
V. K. Rizzon, et al. "Thyroxine: A Theoretical Study of the Vibrational and Electronic Properties." Quarks: Brazilian Electronic Journal of Physics, Chemistry and Materials Science, vol. 3, No. 1, Nov. 28, 2020, pp. 31-40, doi:10.34019/2674-9688.2020.v3.30941.
Borah, Mukunda Madhab, et al. "Vibrational Studies of Thyroxine Hormone: Comparative Study with Quantum Chemical Calculations." Journal of Molecular Structure, vol. 1148, Nov. 2017, pp. 293-313, doi:10.1016/j.molstruc.2017.07.063.
Burns, Kristen H., et al. "Absolute Cross Sections of Liquids from Broadband Stimulated Raman Scattering with Femtosecond and Picosecond Pulses." Analytical Chemistry, vol. 92, No. 15, Jun. 29, 2020, p. 10686-10692, doi:10.1021/acs.analchem.0c01785.
Li, Nan, et al. "A Noninvasive Accurate Measurement of Blood Glucose Levels with Raman Spectroscopy of Blood in Microvessels." Molecules, vol. 24, No. 8, Apr. 17, 2019, p. 1500, doi:10.3390/molecules24081500.
Lundsgaard-Nielsen, Signe M., et al. "Critical-Depth Raman Spectroscopy Enables Home-Use Non-Invasive Glucose Monitoring." PLOS One, vol. 13, No. 5, May 11, 2018, doi:10.1371/journal.pone.0197134.
Anand, Jaskaran Singh. "Development of an Electrochemical Surface Enhanced Raman Spectroscopy (EC-SERS) Fabric Sensor to Detect Cortisol for Early Diagnosis of Post-Traumatic Stress Disorder." Saint Mary's University, 2022.
Golparvar, Ata, et al. "Soft Epidermal Paperfluidics for Sweat Analysis by Ratiometric Raman Spectroscopy." Biosensors, vol. 14, No. 1, Dec. 25, 2023, p. 12, doi:10.3390/bios14010012.
Ju, Jian, et al. "Surface Enhanced Raman Spectroscopy Based Biosensor with a Microneedle Array for Minimally Invasive in Vivo Glucose Measurements." ACS Sensors, vol. 5, No. 6, May 19, 2020, pp. 1777-1785, doi:10.1021/acssensors.0c00444.
Liu, Guoran, et al. "Surface-Enhanced Raman Scattering as a Potential Strategy for Wearable Flexible Sensing and Point-of-Care Testing Non-Invasive Medical Diagnosis." Frontiers in Chemistry, vol. 10, Nov. 3, 2022, doi:10.3389/fchem.2022.1060322.
Carlomagno, C., et al. "Human Salivary Raman Fingerprint as Biomarker for the Diagnosis of Amyotrophic Lateral Sclerosis." Scientific Reports, vol. 10, No. 1, Jun. 23, 2020, doi:10.1038/s41598-020-67138-8.
Hardy, Mike, et al. "Methods in Raman Spectroscopy for Saliva Studies—A Review." Applied Spectroscopy Reviews, vol. 57, No. 3, Aug. 30, 2021, pp. 177-233, doi:10.1080/05704928.2021.1969944.
Calado, Genecy, et al. "Raman Spectroscopic Characterisation of Non Stimulated and Stimulated Human Whole Saliva." Clinical Spectroscopy, vol. 3, Dec. 2021, p. 100010, doi:10.1016/j.clispe.2021.100010.
Buchan, Emma, et al. "Raman Spectroscopic Molecular Fingerprinting of Biomarkers for Inflammatory Bowel Disease." Clinical and Translational Medicine, vol. 13, No. 11, Nov. 2023, doi:10.1002/ctm2.1345.
Pahlow, Susanne, et al. "Application of Vibrational Spectroscopy and Imaging to Point-of-Care Medicine: A Review." Applied Spectroscopy, vol. 72, No. 1_suppl, Sep. 2018, pp. 52-84, doi:10.1177/0003702818791939.
Baker, Matthew J., et al. "Clinical Applications of Infrared and Raman Spectroscopy: State of Play and Future Challenges." The Analyst, vol. 143, No. 8, 2018, pp. 1735-1757, doi:10.1039/c7an01871a.
Atkins, Chad G., et al. "Raman Spectroscopy of Blood and Blood Components." Applied Spectroscopy, vol. 71, No. 5, Apr. 11, 2017, pp. 767-793, doi:10.1177/0003702816686593.
Freudiger, Christian W., et al. "Label-Free Biomedical Imaging with High Sensitivity by Stimulated Raman Scattering Microscopy." Science, vol. 322, No. 5909, Dec. 19, 2008, pp. 1857-1861, doi:10.1126/science.1165758.
Casacio, Catxere A., et al. "Quantum-Enhanced Nonlinear Microscopy." Nature, vol. 594, No. 7862, Jun. 9, 2021, pp. 201-206, doi:10.1038/s41586-021-03528-w.
Saar, Brian G., et al. "Video-Rate Molecular Imaging in Vivo with Stimulated Raman Scattering." Science, vol. 330, No. 6009, Dec. 3, 2010, pp. 1368-1370, doi:10.1126/science.1197236.
Borges, Rita De, et al. "Detecting Alterations of Glucose and Lipid Components in Human Serum by Near-Infrared Raman Spectros-

(56) References Cited

OTHER PUBLICATIONS copy." Research on Biomedical Engineering, vol. 31, No. 2, Jun. 2015, pp. 160-168, doi:10.1590/2446-4740.0593.
Gracie, Kirsten, et al. "Detection of Cortisol in Serum Using Quantitative Resonance Raman Spectroscopy." Analytical Methods, vol. 9, No. 10, 2017, pp. 1589-1594, doi:10.1039/c6ay03296f.
"Detection of Glucose Levels Using Excitation and Difference Raman Spectroscopy at the IUSL." (2004).
El-Mashtoly, Samir F., et al. "Diagnostics and Therapy Assessment Using Label-Free Raman Imaging." Analytical Chemistry, vol. 94, No. 1, Dec. 1, 2021, pp. 120-142, doi:10.1021/acs.analchem.1c04483.
Shao, Jingwei, et al. "In Vivo Blood Glucose Quantification Using Raman Spectroscopy." PLOS One, vol. 7, No. 10, Oct. 25, 2012, doi:10.1371/journal.pone.0048127.
Tubbesing, Kate, et al. "Iron-Binding Cellular Profile of Transferrin Using Label-Free Raman Hyperspectral Imaging and Singular Value Decomposition (SVD)." Free Radical Biology and Medicine, vol. 169, Jun. 2021, pp. 416-424, doi:10.1016/j.freeradbiomed.2021.04.030.
Berger, Andrew J., et al. "Multicomponent Blood Analysis by Near-Infrared Raman Spectroscopy." Applied Optics, vol. 38, No. 13, May 1, 1999, p. 2916, doi:10.1364/ao.38.002916.
Kawagoe, Hiroyuki, et al. "Multiwell Raman Plate Reader for High-Throughput Biochemical Screening." Scientific Reports, vol. 11, No. 1, Aug. 3, 2021, doi:10.1038/s41598-021-95139-8.
Bergholt, M. S., et al. "Quantification of C-Reactive Protein in Human Blood Plasma Using near-Infrared Raman Spectroscopy." The Analyst, vol. 134, No. 10, 2009, p. 2123, doi:10.1039/b903089a.
Byrne, Hugh J., et al. "Quantitative Analysis of Human Blood Serum Using Vibrational Spectroscopy." Clinical Spectroscopy, vol. 2, Dec. 2020, p. 100004, doi:10.1016/j.clispe.2020.100004.
Pelletier, M. J. "Quantitative Analysis Using Raman Spectrometry." Applied Spectroscopy, vol. 57, No. 1, Jan. 2003, doi:10.1366/000370203321165133.
Shih, Wei-Chuan, et al. "Quantitative Biological Raman Spectroscopy." Handbook of Optical Sensing of Glucose in Biological Fluids and Tissues, Editor: Valery V. Tuchin (Taylor & Francis 2008), pp. 365-397.
Parachalil, Drishya Rajan, et al. "Raman Spectroscopic Screening of High and Low Molecular Weight Fractions of Human Serum." The Analyst, vol. 144, No. 14, 2019, pp. 4295-4311, doi:10.1039/c9an00599d.
Ricciardi, Alessandra, et al. "Raman Spectroscopy Characterization of the Major Classes of Plasma Lipoproteins." Vibrational Spectroscopy, vol. 109, Jul. 2020, p. 103073, doi:10.1016/j.vibspec.2020.103073.
Dodo, Kosuke, et al. "Raman Spectroscopy for Chemical Biology Research." Journal of the American Chemical Society, vol. 144, No. 43, Oct. 10, 2022, pp. 19651-19667, doi:10.1021/jacs.2c05359.
Sheehy, Guillaume, et al. "Open-Sourced Raman Spectroscopy Data Processing Package Implementing a Baseline Removal Algorithm Validated from Multiple Datasets Acquired in Human Tissue and Biofluids." Journal of Biomedical Optics, vol. 28, No. 02, Feb. 21, 2023, doi:10.1117/1.jbo.28.2.025002.
Schmidt, Robert W, et al. "RamanLIGHT—a Graphical User-Friendly Tool for Pre-Processing and UNMIXING Hyperspectral Raman Spectroscopy Images." Journal of Optics, vol. 24, No. 6, May 6, 2022, p. 064011, doi:10.1088/2040-8986/ac6883.
Senger, Ryan S., et al. "The RametrixTM pro Toolbox v1.0 for Matlab®." PeerJ, vol. 8, Jan. 6, 2020, doi:10.7717/peerj.8179.
Chen, Kuan-Hung, et al. "A 3D-ACEK/SERS System for Highly Efficient and Selectable Electrokinetic Bacteria Concentration/Detection/ Antibiotic-Susceptibility-Test on Whole Blood." Biosensors and Bioelectronics, vol. 197, Feb. 2022, p. 113740, doi:10.1016/j.bios.2021.113740.
Carlomagno, C., et al. "Covid-19 Salivary Raman Fingerprint: Innovative Approach for the Detection of Current and Past SARS-COV-2 Infections." Scientific Reports, vol. 11, No. 1, Mar. 2, 2021, doi:10.1038/s41598-021-84565-3.
Novelli-Rousseau, A., et al. "Culture-Free Antibiotic-Susceptibility Determination from Single-Bacterium Raman Spectra." Scientific Reports, vol. 8, No. 1, Mar. 2, 2018, doi:10.1038/s41598-018-22392-9.
Deckert, Volker, et al. "Laser Spectroscopic Technique for Direct Identification of a Single Virus I: Faster Cars." Proceedings of the National Academy of Sciences, vol. 117, No. 45, Oct. 22, 2020, pp. 27820-27824, doi:10.1073/pnas.2013169117.
Ali, Ahmed, et al. "Miniaturized Raman Instruments for SERS-Based Point-of-Care Testing on Respiratory Viruses." Biosensors, vol. 12, No. 8, Aug. 2, 2022, p. 590, doi:10.3390/bios12080590.
Duarte, Janaína, et al. "Near-Infrared Raman Spectroscopy to Detect Anti-Toxoplasma Gondii Antibody in Blood Sera of Domestic Cats: Quantitative Analysis Based on Partial Least-Squares Multivariate Statistics." Journal of Biomedical Optics, vol. 15, No. 4, 2010, p. 047002, doi:10.1117/1.3463006.
Brewster, Victoria L., et al. "Monitoring the Glycosylation Status of Proteins Using Raman Spectroscopy." Analytical Chemistry, vol. 83, No. 15, Jul. 7, 2011, pp. 6074-6081, doi:10.1021/ac2012009.
Acri, Giuseppe, et al. "Raman Spectroscopy as Noninvasive Method of Diagnosis of Pediatric Onset Inflammatory Bowel Disease." Applied Sciences, vol. 10, No. 19, Oct. 5, 2020, p. 6974, doi:10.3390/app10196974.
Westley, Chloe, et al. "Real-time Monitoring of Enzyme-catalysed Reactions Using Deep UV Resonance Raman Spectroscopy." Chemistry—A European Journal, vol. 23, No. 29, May 2, 2017, pp. 6983-6987, doi:10.1002/chem.201701388.
Larmour, Iain A., et al. "The Past, Present and Future of Enzyme Measurements Using Surface Enhanced Raman Spectroscopy." Chemical Science, vol. 1, No. 2, 2010, p. 151, doi:10.1039/c0sc00226g.
Fan, Xiaqiong, et al. "A Universal and Accurate Method for Easily Identifying Components in Raman Spectroscopy Based on Deep Learning." Analytical Chemistry, vol. 95, No. 11, Mar. 13, 2023, pp. 4863-4870, doi:10.1021/acs.analchem.2c03853.
Fan, Xiaqiong, et al. "A Universal and Accurate Method for Easily Identifying Components in Raman Spectroscopy Based on Deep Learning—Supporting Information." Analytical Chemistry, vol. 95, No. 11, Mar. 13, 2023, doi:10.1021/acs.analchem.2c03853.s001.
Luo, Ruihao, et al. "Deep Learning for Raman Spectroscopy: A Review." Analytica, vol. 3, No. 3, Jul. 19, 2022, pp. 287-301, doi:10.3390/analytica3030020.
Fan, Xiaqiong, et al. "Deep Learning-Based Component Identification for the Raman Spectra of Mixtures." The Analyst, vol. 144, No. 5, 2019, pp. 1789-1798, doi:10.1039/c8an02212g.
Jensen, Emil Alstrup, et al. "Label-Free Blood Typing by Raman Spectroscopy and Artificial Intelligence." Advanced Materials Technologies, vol. 9, No. 2, Dec. 6, 2023, doi:10.1002/admt.202301462.
Qi, Yaping, et al. "Recent Progresses in Machine Learning Assisted Raman Spectroscopy." Advanced Optical Materials, vol. 11, No. 14, Apr. 26, 2023, doi:10.1002/adom.202203104.
Lopes, Daniela Franco, et al. "Characterization of Biomarkers in Blood Serum for Cancer Diagnosis in Dogs Using Raman Spectroscopy." Journal of Biophotonics, vol. 17, No. 3, Dec. 15, 2023, doi:10.1002/jbio.202300338.
Papadakis, Vassilis M., et al. "Label-Free Human Disease Characterization through Circulating Cell-Free DNA Analysis Using Raman Spectroscopy." International Journal of Molecular Sciences, vol. 24, No. 15, Aug. 3, 2023, p. 12384, doi:10.3390/ijms241512384.
Shin, Hyunku, et al. "Single Test-Based Diagnosis of Multiple Cancer Types Using Exosome-SERS-AI for Early Stage Cancers." Nature Communications, vol. 14, No. 1, Mar. 24, 2023, doi:10.1038/s41467-023-37403-1.
Maiti, Kiran Sankar, et al. "Detection of Disease-Specific Volatile Organic Compounds Using Infrared Spectroscopy." The 16th International Workshop on Advanced Infrared Technology & Applications, Nov. 22, 2021, doi:10.3390/engproc2021008015.
Hanf, Stefan, et al. "Fast and Highly Sensitive Fiber-Enhanced Raman Spectroscopic Monitoring of Molecular H2 and CH4 for Point-of-Care Diagnosis of Malabsorption Disorders in Exhaled

(56) References Cited

OTHER PUBLICATIONS

Human Breath." Analytical Chemistry, vol. 87, No. 2, Dec. 29, 2014, pp. 982-988, doi:10.1021/ac503450y.
Bögözi, Timea, et al. "Fiber-Enhanced Raman Multi-Gas Spectroscopy: What Is the Potential of Its Application to Breath Analysis?" Bioanalysis, vol. 7, No. 3, Feb. 2015, pp. 281-284, doi:10.4155/bio.14.299.
Huang, Liping, et al. "Noninvasive Diagnosis of Gastric Cancer Based on Breath Analysis with a Tubular Surface-Enhanced Raman Scattering Sensor." ACS Sensors, vol. 7, No. 5, May 13, 2022, pp. 1439-1450, doi:10.1021/acssensors.2c00146.
Popov, Evgeniy, et al. "Raman Spectroscopy for Urea Breath Test." Biosensors, vol. 13, No. 6, Jun. 2, 2023, p. 609, doi:10.3390/bios13060609.
Shen, Yujie, et al. "A Versatile Setup Using Femtosecond Adaptive Spectroscopic Techniques for Coherent Anti-Stokes Raman Scattering." Review of Scientific Instruments, vol. 86, No. 8, Aug. 1, 2015, doi:10.1063/1.4929380.
Shutova, Mariia, et al. "Adaptive Optics Approach to Surface-Enhanced Raman Scattering." Optics Letters, vol. 45, No. 13, Jun. 30, 2020, p. 3709, doi:10.1364/ol.394548.
Christopher B. Marble, et al. "Biomedical Optics Applications of Advanced Lasers and Nonlinear Optics." Journal of Biomedical Optics, vol. 25, No. 04, Apr. 23, 2020, p. 1, doi: 10.1117/1.jbo.25.4.040902.
Shutov, Anton D., et al. "Coherent Anti-Stokes Raman Scattering Microspectroscopy: An Emerging Technique for Non-Invasive Optical Assessment of a Local Bio-Nano-Environment." IEEE Journal of Selected Topics in Quantum Electronics, vol. 27, No. 5, Sep. 2021, pp. 1-6, doi: 10.1109/jstqe.2021.3083687.
Shutova, Mariia, et al. "Coherent Raman Generation Controlled by Wavefront Shaping." Scientific Reports, vol. 9, No. 1, Feb. 7, 2019, doi: 10. 1038/s41598-018-38302-y.
Arora, Rajan, et al. "Detecting Anthrax in the Mail by Coherent Raman Microspectroscopy." Proceedings of the National Academy of Sciences, vol. 109, No. 4, Jan. 3, 2012, pp. 1151-1153, doi: 10.1073/pnas. 1115242108.
Petrov, Georgi I., et al. "Detection of Bacillus Subtilis Spores in Water by Means of Broadband Coherent Anti-Stokes Raman Spectroscopy." Optics Express, vol. 13, No. 23, 2005, p. 9537, doi: 10.1364/opex. 13.009537.
Traverso, Andrew J., et al. "Dual Raman-Brillouin Microscope for Chemical and Mechanical Characterization and Imaging." Analytical Chemistry, vol. 87, No. 15, Jul. 24, 2015, pp. 7519-7523, doi: 10.1021/acs.analchem.5b02104.
Petrov, Georgi I., et al. "Electronically Tunable Coherent Raman Spectroscopy Using Acousto-Optics Tunable Filter." Optics Express, vol. 23, No. 19, 10 Sep. 2015, p. 24669, doi: 10.1364/OE.23.024669.
Hokr, Brett H., et al. "Enabling Time Resolved Microscopy with Random Raman Lasing." Scientific Reports, vol. 7, No. 1, Mar. 15, 2017, doi: 10. 1038/srep44572.
Zhu, Hanlin, et al. "Enhanced Chemical Sensing with Multiorder Coherent Raman Scattering Spectroscopic Dephasing." Analytical Chemistry, vol. 94, No. 23, May 27, 2022, pp. 8409-8415, doi: 10.1021/acs.analchem.2c01060.
Zhang, Zhedong, et al. "Entangled Photons Enabled Time-Frequency- Resolved Coherent Raman Spectroscopy and Applications to Electronic Coherences at Femtosecond Scale." Light: Science & Applications, vol. 11, No. 1, 14 Sep. 2022, doi: 10.1038/s41377-022-00953-y.
Hokr, Brett H., et al. "Higher Order Processes in Random Raman Lasing." Applied Physics A, vol. 117, No. 2, Aug. 27, 2014, pp. 681-685, doi:10.1007/s00339-014-8722-7.
Shutov, Anton D., et al. "Highly Efficient Tunable Picosecond Deep Ultraviolet Laser System for Raman Spectroscopy." Optics Letters, vol. 44, No. 23, Nov. 27, 2019, p. 5760, doi:10.1364/ol.44.005760.
Zhang, Yingchao, et al. "Improving Resolution in Quantum Subnanometre-Gap Tip-Enhanced Raman Nanoimaging." Scientific Reports, vol. 6, No. 1, May 25, 2016, doi:10.1038/srep25788.
Altangerel, Narangerel, et al. "In Vivo Diagnostics of Early Abiotic Plant Stress Response via Raman Spectroscopy." Proceedings of the National Academy of Sciences, vol. 114, No. 13, Mar. 13, 2017, pp. 3393-3396, doi:10.1073/pnas.1701328114.
Altangerel, Narangerel, et al. "Label-Free Drug Interaction Screening via Raman Microscopy." Proceedings of the National Academy of Sciences, vol. 120, No. 30, Jul. 18, 2023, doi:10.1073/pnas.2218826120.
Meng, Zhaokai, et al. "Lightweight Raman Spectroscope Using Time-Correlated Photon-Counting Detection." Proceedings of the National Academy of Sciences, vol. 112, No. 40, Sep. 21, 2015, pp. 12315-12320, doi:10.1073/pnas.1516249112.
Shen, Yujie, et al. "Picosecond Supercontinuum Generation in Large Mode Area Photonic Crystal Fibers for Coherent Anti-Stokes Raman Scattering Microspectroscopy." Scientific Reports, vol. 8, No. 1, Jun. 22, 2018, doi:10.1038/s41598-018-27811-5.
Meng, Zhaokai, et al. "Pure Electrical, Highly-Efficient and Sidelobe Free Coherent Raman Spectroscopy Using Acousto-Optics Tunable Filter (AOTF)." Scientific Reports, vol. 6, No. 1, Feb. 1, 2016, doi:10.1038/srep20017.
Altangerel, Narangerel, et al. "Raman Spectroscopy as a Robust New Tool for Rapid and Accurate Evaluation of Drought Tolerance Levels in Both Genetically Diverse and Near-Isogenic Maize Lines." Frontiers in Plant Science, vol. 12, Jul. 12, 2021, doi:10.3389/fpls.2021.621711.
Thompson, Jonathan V., et al. "Single-Shot Chemical Detection and Identification with Compressed Hyperspectral Raman Imaging." Optics Letters, vol. 42, No. 11, May 30, 2017, p. 2169, doi:10.1364/ol.42.002169.
Yakovlev, Vladislav V., et al. "Stimulated Raman Photoacoustic Imaging." Proceedings of the National Academy of Sciences, vol. 107, No. 47, Nov. 8, 2010, pp. 20335-20339, doi:10.1073/pnas.1012432107.
Zhu, Hanlin, et al. "Time-Resolved Vibrational Dynamics: Novel Opportunities for Sensing and Imaging." Talanta, vol. 266, Jan. 2024, p. 125046, doi:10.1016/j.talanta.2023.125046.
Traverso, Andrew J., et al. "Two-Photon Infrared Resonance Can Enhance Coherent Raman Scattering." Physical Review Letters, vol. 120, No. 6, Feb. 6, 2018, doi:10.1103/physrevlett.120.063602.
Karpf, Sebastian, et al. "A Time-Encoded Technique for Fibre-Based Hyperspectral Broadband Stimulated Raman Microscopy." Nature Communications, vol. 6, No. 1, Apr. 17, 2015, doi:10.1038/ncomms7784.
Safir, Fareeha, et al. "Combining Acoustic Bioprinting with AI-Assisted Raman Spectroscopy for High-Throughput Identification of Bacteria in Blood." Nano Letters, vol. 23, No. 6, Mar. 1, 2023, pp. 2065-2073, doi:10.1021/acs.nanolett.2c03015.
Song, Jeonggeun, et al. "Swept-Source Raman Spectroscopy of Chemical and Biological Materials." Journal of Biomedical Optics, vol. 29, No. S2, Apr. 3, 2024, doi:10.1117/1.jbo.29.s2.s22703.
Koster, Hanna J., et al. "Fused Raman Spectroscopic Analysis of Blood and Saliva Delivers High Accuracy for Head and Neck Cancer Diagnostics." Scientific Reports, vol. 12, No. 1, Nov. 2, 2022, doi:10.1038/s41598-022-22197-x.
Hobbs, Philip C.D., "Ultrasensitive Laser Measurements without Tears." Optical Society of America, vol. 36, No. 4, Feb. 1, 1997, pp. 903-920.
Notice of Allowance issued for U.S. Appl. No. 18/762,412, mailed Sep. 9, 2024, 10 pages.
International Search Report and Written Opinion issued for International Application No. PCT/US2024/053635, mailed Nov. 21, 2024, 6 pages.
Wolfe, T. J., et al. "A study of major cannabinoids via Raman spectroscopy and density functional theory." Spectrochimica Acta Part A: Molecular and Biomolecular Spectroscopy, vol. 303, Jul. 11, 2023, p. 123133, https://doi.org/10.1016/j.saa.2023.123133.
Hédoux, A., et al. "Raman spectroscopy of racemic ibuprofen: Evidence of molecular disorder in phase II." International Journal of Pharmaceutics, vol. 421, No. 1, 2011, pp. 45-52, https://doi.org/10.1016/j.ijpharm.2011.09.015.

(56) References Cited

OTHER PUBLICATIONS

Zhang, S., et al. "Raman spectroscopy study on xylitol at low- and high-temperature conditions." Journal of Molecular Structure, vol. 1321, No. 3, 2025, p. 140032, https://doi.org/10.1016/j.molstruc.2024.140032.
Balcers, O., et al. "Study of ergocalciferol and cholecalciferol (Vitamin D): Modeled optical properties and optical detection using absorption and Raman spectroscopy." Spectrochimica Acta Part A: Molecular and Biomolecular Spectroscopy, vol. 269, 2022, p. 120725, https://doi.org/10.1016/j.saa.2021.120725.
Jenkins, C. A., et al. "A high-throughput serum Raman spectroscopy platform and methodology for colorectal cancer diagnostics." Analyst, vol. 143, No. 24, 2018, pp. 6014-6024, https://doi.org/10.1039/C8AN01323C.
Xia, Z., et al. "Giant Enhancement of Raman Scattering by a Hollow-Core Microstructured Optical Fiber Allows Single Exosome Probing." ACS Sensors, vol. 8, No. 4, 2023, pp. 1799-1809, https://doi.org/10.1021/acssensors.3c00131.
Bilal, M., et al. "Optical Screening of Female Breast Cancer from Whole Blood Using Raman Spectroscopy." Applied Spectroscopy, vol. 71, No. 5, 2017, pp. 1004-1013, https://doi.org/10.1177/0003702816667516.
Gaba, F., et al. "Raman Spectroscopy in Prostate Cancer: Techniques, Applications and Advancements." Cancers, vol. 14, No. 6, 2022, p. 1535, https://doi.org/10.3390/cancers 14061535.
Xiong, C. C., et al. "Rapid and precise detection of cancers via label-free SERS and deep learning." Analytical and Bioanalytical Chemistry, vol. 415, 2023, pp. 3449-3462, https://doi.org/10.1007/s00216-023-04730-7.
Enejder, A. M. K., et al. "Blood analysis by Raman spectroscopy." Optics Letters, vol. 27, 2002, pp. 2004-2006, https://doi.org/10.1364/OL.27.002004.
Casella, M., et al. "Raman and SERS recognition of β-carotene and haemoglobin fingerprints in human whole blood." Spectrochimica Acta Part A: Molecular and Biomolecular Spectroscopy, vol. 79, No. 5, 2011, pp. 915-919, https://doi.org/10.1016/j.saa.2011.03.048.
Da Silva, A. M., et al. "Spectral model for diagnosis of acute leukemias in whole blood and plasma through Raman spectroscopy." Journal of Biomedical Optics, vol. 23, No. 10, 2018, pp. 1-11, https://doi.org/10.1117/1.JBO.23.10.107002.
Wang, Q., et al. "Simultaneous detection of glucose, triglycerides, and total cholesterol in whole blood by Fourier-Transform Raman spectroscopy." Spectrochimica Acta Part A: Molecular and Biomolecular Spectroscopy, vol. 260, 2021, p. 119906, https://doi.org/10.1016/j.saa.2021.119906.
Premasiri, W. R., et al. "Surface-Enhanced Raman Scattering of Whole Human Blood, Blood Plasma, and Red Blood Cells: Cellular Processes and Bioanalytical Sensing." The Journal of Physical Chemistry B, vol. 116, No. 31, 2012, pp. 9376-9386, https://doi.org/10.1021/jp304932g.
Gottschall, T., et al. "Advances in laser concepts for multiplex, coherent Raman scattering micro-spectroscopy and imaging." TrAC Trends in Analytical Chemistry, vol. 102, 2018, pp. 103-109, https://doi.org/10.1016/j.trac.2018.01.010.
Biswas, S., et al. "Coherent Two-Dimensional and Broadband Electronic Spectroscopies." Chemical Reviews, vol. 122, No. 3, 2022, pp. 4257-4321, https://doi.org/10.1021/acs.chemrev.1c00623.
Cho, M., et al. "Coherent Two-Dimensional Optical Spectroscopy." Chemical Reviews, vol. 108, No. 4, 2008, pp. 1331-1418, https://doi.org/10.1021/cr078377b.
Lee, J. H., et al. "Detection of hazardous chemical using dual-wavelength Raman spectroscopy in the ultraviolet region." Spectrochimica Acta Part A: Molecular and Biomolecular Spectroscopy, vol. 287, No. 1, 2023, p. 122061, https://doi.org/10.1016/j.saa.2022.122061.
McDonnell, R. P., et al. "Direct Probe of Vibrational Fingerprint and Combination Band Coupling." The Journal of Physical Chemistry Letters, vol. 15, No. 14, 2024, pp. 3975-3981, https://doi.org/10.1021/acs.jpclett.4c00297.
Chen, P. C., et al. "High Resolution Coherent 2D Spectroscopy." The Journal of Physical Chemistry A, vol. 114, No. 43, 2010, pp. 11365-11375, https://doi.org/10.1021/jp102401s.
Yellampalle, B., et al. "High-sensitivity explosives detection using dual-excitation-wavelength resonance-Raman detector." Proceedings of SPIE, vol. 9073, 2014, p. 90730H, https://doi.org/10.1117/12.2050441.
Chen, P. C., et al. "Multidimensional Pattern Recognition in High-Resolution 2D and 3D Spectra of Gas-Phase Molecules." Accounts of Chemical Research, vol. 56, No. 11, 2023, pp. 1295-1303, https://doi.org/10.1021/acs.accounts.2c00637.
Yellampalle, B., et al. "Performance comparison of single and dual-excitation-wavelength resonance-Raman explosives detectors." Proceedings of SPIE, vol. 10183, 2017, p. 101830E, https://doi.org/10.1117/12.2262636.
Fu, D., et al. "Quantitative Chemical Imaging with Multiplex Stimulated Raman Scattering Microscopy." Journal of the American Chemical Society, vol. 134, No. 8, 2012, pp. 3623-3626, https://doi.org/10.1021/ja210081h.
Zhang, D., et al. "Quantitative Vibrational Imaging by Hyperspectral Stimulated Raman Scattering Microscopy and Multivariate Curve Resolution Analysis." Analytical Chemistry, vol. 85, No. 1, 2013, pp. 98-106, https://doi.org/10.1021/ac3019119.
Spencer, A. P., et al. "Quantum coherence selective 2D Raman-2D electronic spectroscopy." Nature Communications, vol. 8, No. 1, 2017, p. 14732, https://doi.org/10.1038/ncomms14732.
Schulze, H. G., et al. "Rapid Vector-Based Peak Fitting and Resolution Enhancement for Correlation Analyses of Raman Hyperspectra." Applied Spectroscopy, vol. 77, No. 8, 2023, pp. 957-969, https://doi.org/10.1177/00037028231176805.
Chen, P.C., et al. "Two-Dimensional Coherent Double Resonance Electronic Spectroscopy." The Journal of Physical Chemistry A, vol. 112, No. 14, 2008, pp. 2999-3001, https://doi.org/10.1021/jp710247h.
Chen, P.C., et al. "Two-Dimensional Spectroscopy Isolates Infrared Rovibrational Patterns." The Journal of Physical Chemistry Letters, vol. 15, No. 5, 2024, pp. 1234-1240, https://doi.org/10.1021/acs.jpclett.3c03254.
Gogal'ová, Z., et al. "An improved design of the fused silica capillary flow cell for absorbance detection in microcolumn liquid chromatography." Analytica Chimica Acta, vol. 1238, 2023, p. 340637, https://doi.org/10.1016/j.aca.2022.340637.
Compaan, A., et al. "Coherent anti-Stokes Raman scattering with counterpropagating laser beams." Optics Letters, vol. 4, 1979, pp. 170-172, https://doi.org/10.1364/OL.4.000170.
Smetanin, S. N., et al. "Determination of the stimulated raman scattering threshold for a pump pulse of arbitrary width." Optics and Spectroscopy, vol. 121, No. 3, 2016, pp. 395-404, https://doi.org/10.1134/S0030400X1608021X.
Ginovart, F., et al. "Polarization effects in stimulated Raman scattering." Physics Letters A, vol. 194, No. 5-6, 1994, pp. 397-404, https://doi.org/10.1016/0375-9601(94)90330-1.
Baranov, A. V., et al. "Spectroscopy of resonance hyper-Raman scattering of light." Soviet Physics Uspekhi, vol. 33, No. 10, 1990, p. 812, https://doi.org/10.1070/PU1990v033n10ABEH002635.
Xiong, H., et al. "Stimulated Raman excited fluorescence spectroscopy and imaging." Nature Photonics, vol. 13, No. 6, 2019, pp. 412-417, https://doi.org/10.1038/s41566-019-0396-4.
Nestor, J., et al. "Stimulated Raman Gain Spectroscopy Utilizing Counter-propagating Pulsed Dye Lasers." Applied Spectroscopy, vol. 35, 1981, pp. 81-85.
Perry, B., et al. "Stimulated Raman scattering with a tightly focused pump beam." Optics Letters, vol. 10, 1985, pp. 146-148, https://doi.org/10.1364/OL.10.000146.
Min, W., et al. "The Duality of Raman Scattering." Accounts of Chemical Research, vol. 57, No. 14, 2024, pp. 1896-1905, https://doi.org/10.1021/acs.accounts.4c00159.
Verma, S.P., et al. "Erythrocyte membranes undergo cooperative, pH-sensitive state transitions in the physiological temperature range: evidence from Raman spectroscopy." Proc. Natl. Acad. Sci. USA, vol. 73, 1976, pp. 3558-3561, https://doi.org/10.1073/pnas.73.10.3558.

(56) References Cited

OTHER PUBLICATIONS

Aslanian, D., et al. “Thermotropic State Transition in Isolated Platelet Membranes Studied by Raman Spectroscopy.” European Journal of Biochemistry, vol. 131, 1983, pp. 555-558, https://doi.org/10.1111/j.1432-1033.1983.tb07298.x.
Tuschel, D. “Raman Thermometry.” Spectroscopy, vol. 31, 2016, pp. 8-13.
Ghita, A., et al. “Sensitivity of Transmission Raman Spectroscopy Signals to Temperature of Biological Tissues.” Scientific Reports, vol. 8, 2018, pp. 8379, https://doi.org/10.1038/s41598-018-25465-x.
Arachchige, C.M., et al. “Raman scattering applied to human breath analysis.” TrAC Trends in Analytical Chemistry, vol. 177, 2024, p. 117791, https://doi.org/10.1016/j.trac.2024.117791.
Han, Y., et al. “Sweat Sensor Based on Wearable Janus Textiles for Sweat Collection and Microstructured Optical Fiber for Surface-Enhanced Raman Scattering Analysis.” ACS Sensors, vol. 8, 2023, pp. 4774-4781, https://doi.org/10.1021/acssensors.3c01863.
Li, Y., et al. “Flexible Wearable Plasmonic Paper-Based Microfluidics with Expandable Channel and Adjustable Flow Rate for Portable Surface-Enhanced Raman Scattering Sweat Sensing.” ACS Photonics, vol. 11, 2024, pp. 613-625, https://doi.org/10.1021/acsphotonics.3c01490.
Dybas, J., et al. “Trends in biomedical analysis of red blood cells—Raman spectroscopy against other spectroscopic, microscopic and classical techniques.” TrAC Trends in Analytical Chemistry, vol. 146, 2022, pp. 116481, https://doi.org/10.1016/j.trac.2021.116481.
Goulart, A.C.C., et al. “Diagnosing COVID-19 in human serum using Raman spectroscopy.” Lasers in Medical Science, vol. 37, 2022, pp. 2217-2226, https://doi.org/10.1007/s10103-021-03488-7.
Lister, A.P., et al. “Multi-Excitation Raman Spectroscopy for Label-Free, Strain-Level Characterization of Bacterial Pathogens in Artificial Sputum Media.” Analytical Chemistry, vol. 94, 2022, pp. 669-677, https://doi.org/10.1021/acs.analchem.1c02501.
Cheng, I-F., et al. “Rapid (<5 min) Identification of Pathogen in Human Blood by Electrokinetic Concentration and Surface-Enhanced Raman Spectroscopy.” Scientific Reports, vol. 3, 2013, pp. 2365, https://doi.org/10.1038/srep02365.
Xiong, C., et al. “Multi-branch attention Raman network and surface-enhanced Raman spectroscopy for the classification of neurological disorders.” Biomedical Optics Express, vol. 15, 2024, pp. 3523-3540, https://doi.org/10.1364/BOE.514196.
Macleod, N., et al. “Broadband standoff detection of large molecules by mid-infrared active coherent laser spectrometry.” Optics Express, vol. 23, 2015, pp. 912-928, https://doi.org/10.1364/OE.23.000912.
Sharma, S.K., et al. “Detection of Chemicals with Standoff Raman Spectroscopy.” Spectroscopy Supplements, 2011.
MacLeod, N.A., et al. “High sensitivity stand-off detection and quantification of chemical mixtures using an active coherent laser spectrometer (ACLaS).” Proceedings of SPIE, vol. 9824, 2016, pp. 98240B, https://doi.org/10.1117/12.2223045.
Narlagiri, L.M., et al. “Recent trends in laser-based standoff detection of hazardous molecules.” TrAC Trends in Analytical Chemistry, vol. 153, 2022, pp. 116645, https://doi.org/10.1016/j.trac.2022.116645.
Glenn, R., et al. “Single Broadband Phase-Shaped Pulse Stimulated Raman Spectroscopy for Standoff Trace Explosive Detection.” The Journal of Physical Chemistry Letters, vol. 7, 2016, pp. 117-125, https://doi.org/10.1021/acs.jpclett.5b01894.
Coluccelli, N., et al. “Standoff detection of bacterial spores by field deployable coherent Raman spectroscopy.” Scientific Reports, vol. 13, 2023, pp. 2634, https://doi.org/10.1038/s41598-023-29589-7.
Zachhuber, B., et al. “Stand-off Raman spectroscopy of explosives.” Proceedings of SPIE, vol. 7838, 2010, pp. 78380F, https://doi.org/10.1117/12.864564.
Zachhuber, B., et al. “Stand-Off Spatial Offset Raman Spectroscopy for the Detection of Concealed Content in Distant Objects.” Analytical Chemistry, vol. 83, 2011, pp. 9438-9442, https://doi.org/10.1021/ac2021008.
Emmons, E., et al. “Waveguide-Enhanced Raman Spectroscopy for Field Detection of Threat Materials.” Devcom CBC @ DTRA CBD S&T Conference, 2022.
Khristoforova, Y., et al. “Raman-Based Techniques in Medical Applications for Diagnostic Tasks: A Review.” International Journal of Molecular Sciences, vol. 24, 2023, pp. 15605, https://doi.org/10.3390/ijms242115605.
Cherukulappurath, S. “Surface-Enhanced Raman Spectroscopy for Biomedical Applications: A Review.” Sensors & Transducers, vol. 197, 2016, pp. 1-13.
Buhas, B.A., et al. “Label-Free SERS of Urine Components: A Powerful Tool for Discriminating Renal Cell Carcinoma through Multivariate Analysis and Machine Learning Techniques.” International Journal of Molecular Sciences, vol. 25, 2024, pp. 3891, https://doi.org/10.3390/ijms25073891.
Almasoud, N., et al. “Rapid detection and quantification of paracetamol and its major metabolites using surface enhanced Raman scattering.” Analyst, vol. 148, 2023, pp. 1805-1814, https://doi.org/10.1039/D3AN00249G.
Fu, Q., et al. “Rapid identification of the resistance of urinary tract pathogenic bacteria using deep learning-based spectroscopic analysis.” Analytical and Bioanalytical Chemistry, vol. 413, 2021, pp. 7401-7410, https://doi.org/10.1007/s00216-021-03691-z.
Aitekenov, S., et al. “Surface-enhanced Raman spectroscopy (SERS) for protein determination in human urine.” Sensing and Bio-Sensing Research, vol. 38, 2022, pp. 100535, https://doi.org/10.1016/j.sbsr.2022.100535.
Gala De Pablo, J., et al. “High-Throughput Raman Flow Cytometry and Beyond.” Accounts of Chemical Research, vol. 54, 2021, pp. 2132-2143, https://doi.org/10.1021/acs.accounts.1c00001.
Vyas, B., et al. “Raman hyperspectroscopy of saliva and machine learning for Sjögren’s disease diagnostics.” Scientific Reports, vol. 14, 2024, pp. 11135, https://doi.org/10.1038/s41598-024-59850-6.
Begin, S., et al. “Coherent anti-Stokes Raman scattering hyperspectral tissue imaging with a wavelength-swept system.” Biomedical Optics Express, vol. 2, 2011, pp. 1296-1306, https://doi.org/10.1364/BOE.2.001296.
Eravuchira, p. J., et al. “Hollow core photonic crystal fiber-assisted Raman spectroscopy as a tool for the detection of Alzheimer’s disease biomarkers.” Journal of Biomedical Optics, vol. 25, 2020, pp. 077001, https://doi.org/10.1117/1.JBO.25.7.077001.
Qi, D., et al. “Chemical concentration measurement in blood serum and urine samples using liquid-core optical fiber Raman spectroscopy.” Applied Optics, vol. 46, 2007, pp. 1726-1734, https://doi.org/10.1364/AO.46.001726.
Aitekenov, S., et al. “Raman, Infrared and Brillouin Spectroscopies of Biofluids for Medical Diagnostics and for Detection of Biomarkers.” Critical Reviews in Analytical Chemistry, vol. 53, 2022, pp. 1561-1590, https://doi.org/10.1080/10408347.2022.2036941.
Staritzbichler, R., et al. “Raman spectroscopy on blood serum samples of patients with end-stage liver disease.” PLOS One, vol. 16, 2021, pp. e0256045, https://doi.org/10.1371/journal.pone.0256045.
Chu, Q., et al. “Volumetric enhancement of Raman scattering for fast detection based on a silver-lined hollow-core fiber.” Optics Express, vol. 27, 2019, pp. 10370-10382, https://doi.org/10.1364/OE.27.010370.
Nagli, L., et al. “Absolute Raman cross-sections of some explosives: Trend to UV.” Optical Materials, vol. 30, 2008, pp. 1747-1754, https://doi.org/10.1016/j.optmat.2007.11.019.
Gao, X., et al. “Absolute Stimulated Raman Cross Sections of Molecules.” The Journal of Physical Chemistry Letters, vol. 14, 2023, pp. 5701-5708, https://doi.org/10.1021/acs.jpclett.3c01064.
McAnally, M.O., et al. “Quantitative Determination of the Differential Raman Scattering Cross Sections of Glucose by Femtosecond Stimulated Raman Scattering.” Analytical Chemistry, vol. 89, 2017, pp. 6931-6935, https://doi.org/10.1021/acs.analchem.7b01335.

(56) References Cited

OTHER PUBLICATIONS

Wilcox, P.G., et al. "Raman Spectra and Cross Sections of Chemical Warfare Agents, Agent Simulants, and Explosives Using 213 NM Deep-Ultraviolet Laser Excitation." Defense Technical Information Center, 2018.
Colles, M.J., et al. "Relative and Absolute Raman Scattering Cross Sections in Liquids." The Journal of Chemical Physics, vol. 56, 1972, pp. 3384-3391, https://doi.org/10.1063/1.1677709.
De Gelder, J., et al. "Reference database of Raman spectra of biological molecules." Journal of Raman Spectroscopy, vol. 38, 2007, pp. 1133-1147, https://doi.org/10.1002/jrs.1734.
Lee, W., et al. "Spread spectrum SERS allows label-free detection of attomolar neurotransmitters." Nature Communications, vol. 12, 2021, pp. 159, https://doi.org/10.1038/s41467-020-20413-8.
Suchita, et al. "Stimulated Raman Scattering in Toluene for Efficient New Wavelength Generation." 12th International Conference on Fiber Optics and Photonics, 2014, pp. S5A.34, https://doi.org/10.1364/PHOTONICS.2014.S5A.34.
Miao, R., et al. "Hollow-core anti-resonant optical fibers for chemical and biomedical sensing." Sensing and Bio-Sensing Research, vol. 46, 2024, pp. 100701, https://doi.org/10.1016/j.sbsr.2024.100701.
Cundiff, S.T., et al. "Optical multidimensional coherent spectroscopy." Physics Today, vol. 66, 2013, pp. 44-49, https://doi.org/10.1063/PT.3.2047.
Coherent, Inc. "Simplified One-Beam 2D Electronic Spectroscopy using a Millijoule Amplifier and HCF." Coherent White Paper, 2019.
Notice of Allowance issued for U.S. Appl. No. 18/762,415, mailed May 7, 2026, 8 pages.
Office Action issued for U.S. Appl. No. 18/762,420, mailed May 5, 2026, 23 pages.
Notice of Allowance issued for U.S. Appl. No. 18/774,723, mailed May 11, 2026, 9 pages.
Notice of Allowance issued for U.S. Appl. No. 19/069,522, mailed Jun. 17, 2026, 17 pages.
Office Action issued for U.S. Appl. No. 19/069,507, mailed Jun. 17, 2026, 27 pages.
Office Action issued for U.S. Appl. No. 19/069,513, mailed Jun. 17, 2026, 21 pages.

* cited by examiner

Needle with optical waveguide
400-W

900

CATHETER INSERT WITH OPTICAL FIBER FOR RAMAN SIGNAL MEASUREMENT

CROSS-REFERENCE TO RELATED APPLICATIONS

This application claims the benefit, under 35 U.S.C. § 119(e), of U.S. Provisional Patent Application No. 63/735,459, filed 18 Dec. 2024, which is incorporated by reference herein.

TECHNICAL FIELD

This disclosure generally relates to Raman spectroscopy systems and methods that use Raman scattering.

BACKGROUND

Raman spectroscopy is an optical measurement technique that can be applied to the study of molecular dynamics (e.g., to investigate vibrational and rotational states of molecules). Molecules typically exhibit molecular vibrations with frequencies ranging from less than 10 terahertz (THz) to approximately 100 THz, which corresponds to wavenumbers of approximately 300 $cm^{-1}$ to 3000 $cm^{-1}$ and wavelengths of approximately 30 to 3 micrometers (μm). Raman spectroscopy is based on the inelastic scattering of photons (referred to as Raman scattering) that occurs when light interacts with molecular vibrations or phonons in a sample. Raman scattering causes the energy (or equivalently, the frequency) of scattered light to be shifted, and this shift in energy can provide information about the vibrational modes of molecules in the sample.

Raman spectroscopy can be used in various chemical sensing applications to identify molecular components in a sample. Since many molecules exhibit a unique Raman scattering spectrum, the spectrum of Raman-scattered light produced when light interacts with a sample can serve as a fingerprint to sense or identify various molecular species within the sample. A sample illuminated with light may produce Raman scattered light at different wavelengths from the illumination light, and measurement of the spectrum of the Raman scattered light is typically performed in the optical domain. For example, the spectrum of Raman scattered light can be measured using an optical spectrometer which separates the Raman scattered light into its optical frequency components using a diffractive element, such as a diffraction grating.

DETAILED DESCRIPTION

Figure 1:
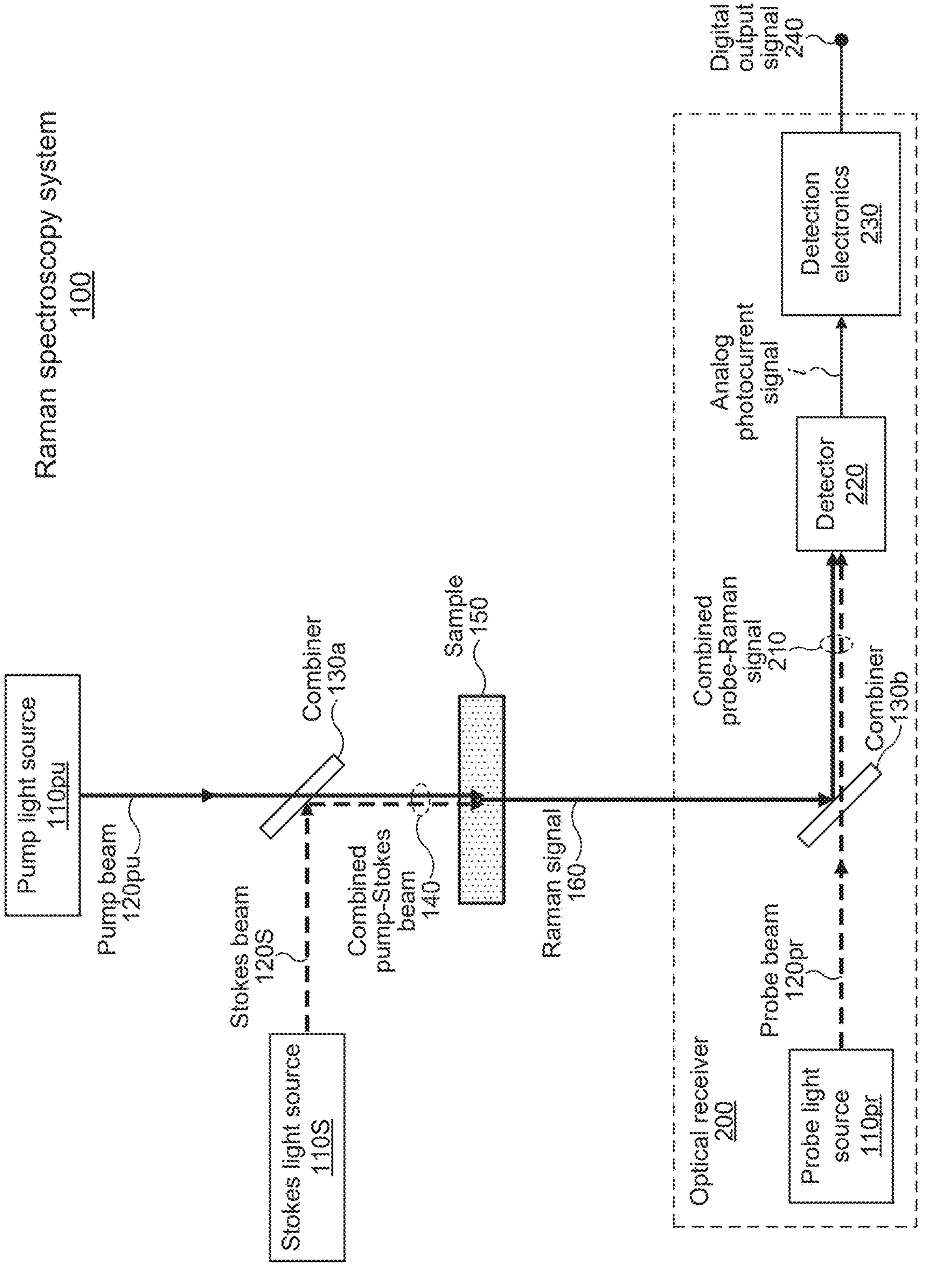
FIGS. 1-2 each illustrate an example Raman spectroscopy system.
Figure 2:
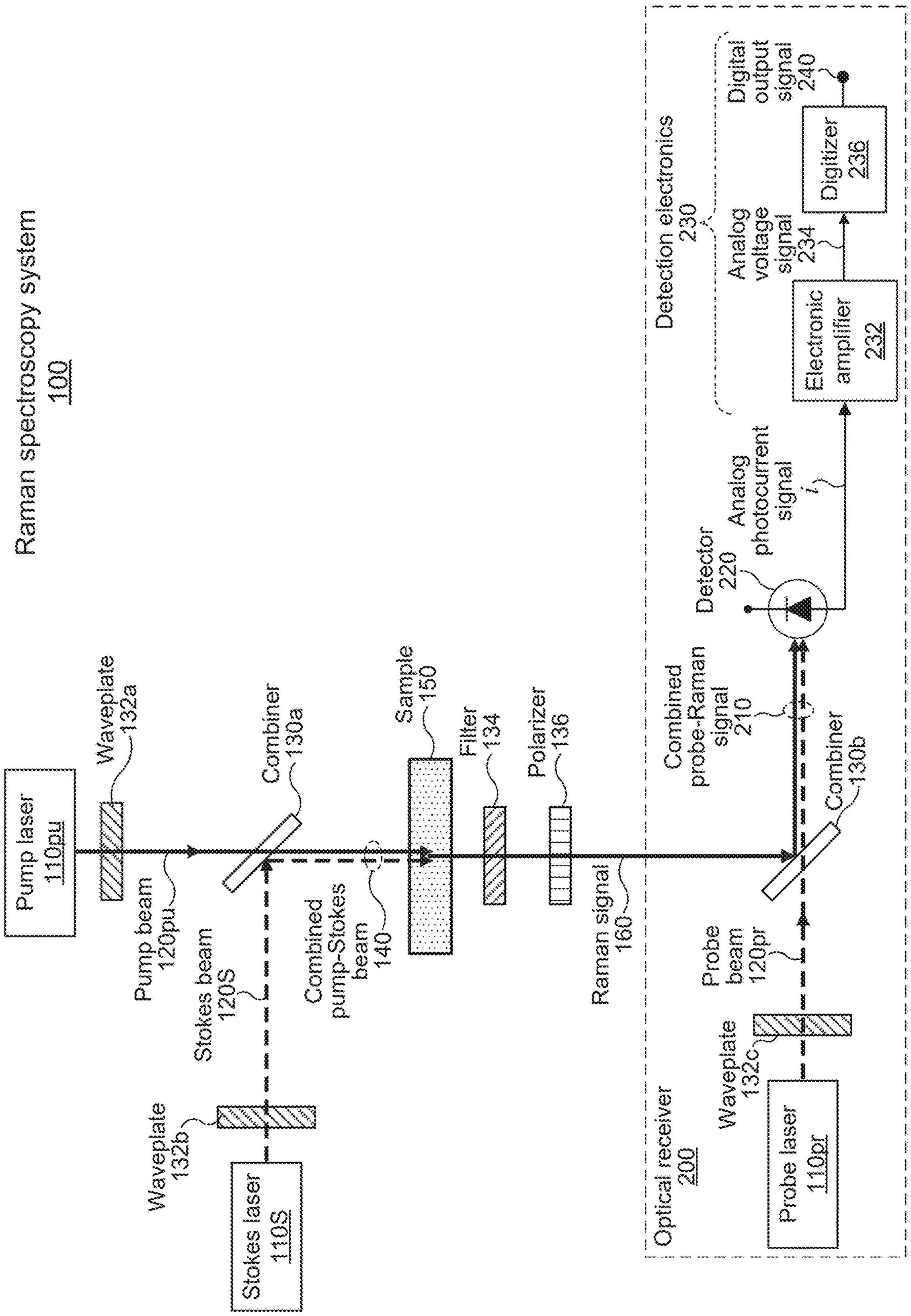

FIGS. 1-2 each illustrate an example Raman spectroscopy system 100. The Raman spectroscopy system 100 in each of FIGS. 1-2 may detect a Raman signal 160 by coherently mixing the Raman signal 160 with a probe beam of light 120*pr* produced by a probe light source 110*pr*. The Raman spectroscopy system 100 in each of FIGS. 1-2 may be referred to as a coherent Raman spectroscopy system, a coherent Raman spectroscopy system with heterodyne detection, or a high-resolution coherent Raman spectroscopy system. One or more of the systems or methods described herein may be applied to any suitable form of coherent Raman spectroscopy or coherent Raman scattering (CRS), such as for example, coherent anti-Stokes Raman scattering (CARS), stimulated Raman scattering (SRS), or Raman-induced Kerr effect (RIKE).

The Raman spectroscopy system 100 in FIG. 1 includes a pump light source 110*pu* that produces a pump beam of light 120*pu* and a Stokes light source 110S that produces a Stokes beam of light 120S. The pump light source 110*pu* produces the pump beam of light 120*pu* at a pump frequency, which may be referred to as a first frequency and may be represented by $v_1$, $v_{pu}$, $\omega_1$, or $\omega_{pu}$. The pump light source 110*pu* may be referred to as a first light source, and the pump beam of light 120*pu* may be referred to as a first beam of light. The Stokes light source 110S produces the Stokes beam of light 120S at a Stokes frequency, which may be referred to as a second frequency and may be represented by $v_2$, $v_S$, $\omega_2$, or $\omega_S$. The Stokes light source 110S may be referred to as a second light source, and the Stokes beam of light 120S may be referred to as a second beam of light. The pump and Stokes frequencies may be offset by a frequency offset $\Omega$, where $\Omega$ equals $v_{pu}-v_S$ (or equivalently, $\Omega=v_1-v_2$). Generally, the pump frequency $v_{pu}$ is greater than the Stokes frequency $v_S$, and the frequency offset $\Omega$ is a positive value. The pump and Stokes light sources in FIG. 1 may each include a laser. For example, the Raman spectroscopy system 100 in FIG. 2 includes a pump laser 110*pu* that produces a pump beam of light 120*pu* and a Stokes laser 110S that produces a Stokes beam of light 120S.

In FIGS. 1-2, the pump beam 120*pu* and the Stokes beam 120S are directed to a sample 150, and the sample 150 produces a Raman signal 160 in response to the pump and Stokes beams. For example, the Raman signal 160 may be produced by coherent Raman scattering of the pump and Stokes beams within the sample 150. A Raman spectroscopy system may include one or more optical elements that direct the pump beam 120*pu* and the Stokes beam 120S to a sample 150. Additionally, the optical elements may collect the Raman signal 160 produced by the sample 150 in response to the pump beam 120*pu* and Stokes beam 120S and may direct the Raman signal 160 to an optical receiver 200. The optical elements may include free-space optics (which may be referred to as bulk optics), fiber-optic components, waveguide-based optics, metamaterials, or any suitable combination thereof. For example, the optical elements may include a mirror, lens, optical combiner (e.g., beamsplitter), optical fiber, photonic integrated circuit (PIC), optical waveguide, or metamaterial-based optic. As another example, the optical combiner 130*a* in each of FIGS. 1-2 may be a free-space dichroic beamsplitter that transmits light at the pump-beam wavelength and reflects light at the Stokes-beam wavelength. The combiner 130*a* may combine the pump beam 120*pu* and the Stokes beam 120S to produce a combined pump-Stokes beam 140 that is directed to the sample 150. The pump and Stokes beams may be combined so that they are substantially overlapped with one another and propagate in the same direction along approximately the same optical axis. Alternatively, a Raman spectroscopy system 100 may not include a pump-Stokes optical combiner 130*a*, and the pump beam 120*pu* and the Stokes beam 120S may be directed to a sample 150 as separate beams (e.g., the pump and Stokes beams may be overlapped or combined at the sample rather than being combined earlier). In this embodiment, the pump and Stokes beams may enter the sample 150 from opposite sides (e.g., the pump and Stokes beams may propagate to the sample in opposite directions along approximately the same optical axis). As another example, the optical elements may include a lens (not illustrated in FIGS. 1-2) that focuses the pump-Stokes beam 140 onto the sample 150. Additionally, the optical elements may include a lens (not illustrated in FIGS. 1-2) that collects the Raman signal 160 to produce a Raman-signal beam that is directed to the optical receiver 200.

In FIGS. 1-2 the combined pump-Stokes beam 140 is directed to one side of the sample 150, and the Raman signal 160 is emitted from the opposite side of the sample. A Raman signal 160 that is collected and directed to an optical receiver 200 may be emitted from a sample 150 in any suitable direction. For example, a Raman signal 160 that is sent to an optical receiver 200 may be emitted from a sample 150 in a forward-scattered direction (e.g., as illustrated in FIGS. 1-2), in a backward-scattered direction (e.g., back toward the pump or Stokes beam), or in a sideways-scattered direction (e.g., in a direction approximately orthogonal to the combined pump-Stokes beam 140 in FIGS. 1-2).

The Raman spectroscopy system 100 in each of FIGS. 1-2 includes an optical receiver 200 that detects the Raman signal 160 produced by the sample 150. The optical receiver 200 (which may be referred to as a heterodyne optical receiver or a high-resolution optical receiver) may detect the Raman signal 160 using an optical heterodyne technique in which the Raman signal 160 is coherently mixed with a probe beam of light 120*pr*. The optical receiver 200 in FIG. 1 includes a probe light source 110*pr* that produces a probe beam of light 120*pr* at a probe frequency. The probe light source 110*pr* may be referred to as a third light source, and the probe beam of light 120*pr* may be referred to as a third beam of light. The probe frequency may be referred to as a third frequency and may be represented by $v_3$, $v_{pr}$, $\omega_3$, or $\omega_{pr}$. The probe light source 110*pr* in FIG. 1 may include a laser. For example, the optical receiver 200 in FIG. 2 includes a probe laser 110*pr* that produces a probe beam of light 120*pr*.

The optical combiner 130*b* in each of FIGS. 1-2 may be a dichroic or a non-dichroic beamsplitter that combines the Raman signal 160 and the probe beam 120*pr* to produce a combined probe-Raman signal 210 that is directed to a detector 220. An optical receiver 200 may include one or more optical detectors 220, where each detector is configured to coherently mix a portion of a Raman signal 160 with at least a portion of a probe beam 120*pr* to produce an electronic signal. Each of the optical receivers 200 in FIGS. 1-2 includes one detector 220 that receives the combined probe-Raman signal 210. The Raman signal 160 and the probe beam 120*pr* are coherently mixed at the detector 220, and this heterodyne mixing process produces an electronic signal, which in FIGS. 1-2 is indicated as analog photocurrent signal i. In FIGS. 1-2, the detection electronics 230 receives the photocurrent signal i and produces a digital output signal 240 that corresponds to the photocurrent signal. Detection electronics 230 may include or may be referred to as an electronic circuit. The digital output signal 240 may be sent to a processor, and the processor may determine a characteristic of the analog photocurrent signal i based on the digital output signal 240. For example, the characteristic of the analog photocurrent signal (or the characteristic of an analog voltage signal that corresponds to the photocurrent signal) determined by the processor may include one or more of: a peak amplitude (e.g., a peak amplitude of the photocurrent signal or a peak amplitude of the corresponding voltage signal), an average amplitude, an amplitude at a particular frequency, an amplitude at a particular time, an amplitude at a frequency center, an amplitude at a temporal center, a DC offset, an area, a frequency, a phase, and a polarization (e.g., a polarization of a Raman signal). An analog photocurrent signal may be referred to as a photocurrent, a photocurrent signal, or a current signal, and an analog voltage signal may be referred to as a voltage signal. A processor of a Raman spectroscopy system 100 may include or may be referred to as a computer system, a controller, a computing device, a computing system, a computer, or a data-processing apparatus. A processor may be similar to the computer system 1000 illustrated in FIG. 122 and described herein. In some embodiments, a processor or a portion of a processor may be located in the detection electronics 230. For example, a processor located in the detection electronics 230 may receive a digital output signal 240 and perform some preprocessing of the digital signal or determine a characteristic of a photocurrent signal based on the digital signal.

In FIGS. 1-2, the probe beam 120*pr* does not travel through the sample 150, and the probe beam is combined with the Raman signal 160 after the Raman signal has exited the sample 150. In other embodiments, a Raman spectroscopy system 100 may include a probe laser 110*pr* that produces a probe beam 120*pr* that is directed through the sample 150. For example, the probe beam 120*pr* may be combined with the pump beam 120*pu* and the Stokes beam 120S, and all three beams may be directed to the sample 150. The probe beam 120*pr* may travel through the sample 150 and may exit the sample along with the Raman signal 160. The optical receiver 200 may not include a combiner 130*b*, since the probe beam 120*pr* and the Raman signal 160 may already be combined after they exit the sample 150. The probe beam 120*pr* and the Raman signal 160 may be directed to a detector 220 without being transmitted or reflected by an optical combiner 130*b*.

The detection electronics 230 in FIG. 2 includes an electronic amplifier 232 and a digitizer 236. The electronic amplifier 232 may include a transimpedance amplifier that amplifies the photocurrent signal i to produce an analog voltage signal 234 that corresponds to the photocurrent signal i (e.g., the photocurrent signal i and the analog voltage signal 234 may have similar temporal shapes or may include similar electronic frequency components). The electronic amplifier 232 may include an additional gain stage that further amplifies an intermediate voltage signal produced by the transimpedance amplifier to produce the voltage signal 234. Additionally, the electronic amplifier 232 may include an electronic filter (e.g., a low-pass, high-pass, or band-pass filter) that filters the photocurrent signal or voltage signal. For example, the electronic amplifier 232 may include (i) a high-pass filter that removes a DC offset and low-frequency components (e.g., frequency components below 10 MHz) from the photocurrent signal or (ii) a band-pass filter that removes the DC and low-frequency components as well as high-frequency components (e.g., frequency components above 5 GHz). Herein, an electronic signal produced in response to coherent mixing may refer to a current signal (e.g., a photocurrent i produced by a detector 220) or may refer to a corresponding voltage signal (e.g., a voltage signal 234 produced by an electronic amplifier that amplifies a photocurrent produced by a detector to produce the voltage signal). In FIG. 2, the digitizer 236 receives the voltage signal 234 and produces a digital output signal 240 that includes a digital representation of the voltage signal 234. The digital output signal 240 may be a time-domain digital representation of the voltage signal 234. The digital output signal 240 may be referred to as corresponding to or representing the voltage signal 234 or the photocurrent signal i. The digitizer 236 may include an analog-to-digital converter (ADC) that produces a digital version of the voltage signal 234. Additionally or alternatively, the digitizer 236 may include a peak detector that determines a peak value of the voltage signal 234.

A Raman spectroscopy system 100 may include one or more optical detectors 220. An optical detector 220 (which may be referred to as a detector, photodetector, or photodiode) may include a PN photodiode, PIN photodiode, avalanche photodiode (APD), single-photon avalanche diode (SPAD), silicon photomultiplier (SiPM), or photomultiplier tube (PMT). A PN photodiode refers to a photodiode structure formed by a p-doped semiconductor and an n-doped semiconductor, where the PN acronym refers to the structure having p-doped and n-doped regions. A PIN photodiode refers to a photodiode structure formed by an undoped intrinsic semiconductor region located between p-doped and n-doped regions, where the PIN acronym refers to the structure having p-doped, intrinsic, and n-doped regions.

A PN photodiode, PIN photodiode, APD, or SPAD may include any suitable semiconductor material, such as for example: silicon, germanium, gallium arsenide (GaAs), indium phosphide (InP), indium arsenide (InAs), aluminum arsenide (AlAs), indium antimonide (InSb), aluminum antimonide (AlSb), gallium antimonide (GaSb), aluminum gallium arsenide (AlGaAs), indium gallium arsenide (InGaAs), indium aluminum arsenide (InAlAs), indium arsenide antimonide (InAsSb), aluminum arsenide antimonide (AlAsSb), aluminum gallium antimonide (AlGaSb), gallium arsenide antimonide (GaAsSb), aluminum indium arsenide antimonide (AlInAsSb), indium gallium arsenide antimonide (InGaAsSb), indium gallium aluminum arsenide (InGaAlAs), aluminum gallium arsenide antimonide (AlGaAsSb), or silicon germanium (SiGe). For example, the Raman signal 160 and the probe beam **120*pr* in FIGS. 1-2 may each have a wavelength in the 400-1100 nanometer (nm) range, and the detector 220 may include a silicon PIN photodiode. As another example, the Raman and probe beams in FIGS. 1-2 may each have a wavelength in the 1000-1700 nm range, and the detector 220 may include an InGaAs PIN photodiode. As another example, a detector 220** may include an APD that includes a semiconductor material with antimonide (e.g., InSb, AlSb, GaSb, InAsSb, AlAsSb, AlGaSb, GaAsSb, AlInAsSb, InGaAsSb, or AlGaAsSb).

In order for a detector 220 to detect an optical signal, the wavelength of the optical signal must be within the detector's wavelength range of responsivity (e.g., approximately 400-1100 nm for a silicon detector, and approximately 1000-1700 nm for an InGaAs detector) and a frequency of an amplitude modulation of the optical signal must be within the electronic bandwidth of the detector. The electronic bandwidth (Δf) of a detector 220 refers to the range of electronic modulation frequencies over which a detector may detect an optical signal, where detection of the optical signal refers to (i) the detector producing a photocurrent signal i that corresponds to the optical signal and (ii) an electronic amplifier 232 producing a voltage signal 234 that corresponds to the photocurrent signal. If a silicon detector 220 has an electronic bandwidth that extends from 100 MHz to 5 GHz, then the detector may detect optical signals with (i) wavelengths between approximately 400 nm and 1100 nm and (ii) amplitude modulation between 100 MHz and 5 GHz. For example, a 900-nm optical signal with an amplitude modulation at a frequency between 100 MHz and 5 GHz may be detected by the silicon detector 220. The silicon detector 220 may not detect a continuous-wave or substantially constant portion of a 900-nm optical signal (e.g., the substantially constant portion of the optical signal may produce a DC current in the detector that may be electronically filtered out), and the silicon detector 220 may not detect a portion of the optical signal with an amplitude modulation greater than approximately 5 GHz. Herein, reference to the electronic bandwidth (Δf) of a detector 220 may refer to (i) the electronic bandwidth of just the detector or (ii) the overall bandwidth of the detector in combination with an electronic amplifier 232.

A detector 220 may have an electronic bandwidth Δf between approximately 100 MHz and approximately 50 GHz. For example, the detector 220 in each of FIGS. 1-2 may have an electronic bandwidth between 100 MHz and 10 GHz. As another example, the detector 220 in each of FIGS. 1-2 may have an electronic bandwidth that extends from a low-frequency cutoff to a high-frequency cutoff. The low-frequency cutoff may be approximately DC (i.e., zero hertz), 1 MHz, 10 MHz, 50 MHz, or 100 MHz, and the high-frequency cutoff may be approximately 500 MHz, 1 GHz, 2 GHz, 5 GHz, 10 GHz, 20 GHz, or 50 GHz. The electronic bandwidth of a detector 220 may refer to the bandwidth of only the detector 220. For example, a detector 220 may have an electronic bandwidth that extends from DC to 10 GHz, and the detector may be referred to as having a 10-GHz bandwidth that extends from DC to 10 GHz. Alternatively, the electronic bandwidth of a detector 220 may refer to the overall bandwidth of the detector in combination with an electronic amplifier 232 that amplifies the photocurrent signal i produced by the detector. An electronic amplifier 232 may have a low-frequency cutoff (e.g., DC, 1 MHz, 10 MHz, 50 MHz, or 100 MHz) and a high-frequency cutoff (e.g., 500 MHz, 1 GHz, 2 GHz, 5 GHz, 10 GHz, 20 GHz, or 50 GHz), and a detector-amplifier combination may be referred to as having an electronic bandwidth that extends from the low-frequency cutoff to the high-frequency cutoff. For example, if the detector bandwidth extends from DC to 10 GHz, and the electronic amplifier bandwidth extends from DC to 5 GHz, then the detector (or, the detector-amplifier combination) may be referred to as having an electronic bandwidth of 5 GHz that extends from DC to 5 GHz. As another example, if the detector bandwidth extends from DC to 10 GHz, and the electronic amplifier bandwidth extends from 100 MHz to 5 GHz, then the detector may be referred to as having an electronic bandwidth of 4.9 GHz that extends from 100 MHz to 5 GHz.

A Raman spectroscopy system 100 may include one or more optical waveplates that change or rotate the polarization of a beam of light. For example, a half-wave plate may be used to rotate a linearly polarized beam of light to a different polarization orientation (e.g., from vertically polarized to horizontally polarized), and a quarter-wave plate may be used to convert a linearly polarized beam of light to a circular or elliptical polarization. The pump laser 110*pu* in FIG. 2 may produce linearly polarized light, and the waveplate 132*a* may be a half-wave plate that rotates the polarization of the pump beam 120*pu* prior to the pump beam being directed to the sample 150. Alternatively, the waveplate 132*a* may be a quarter-wave plate that converts the linearly polarized pump beam 120*pu* to a circular or elliptical polarization prior to the pump beam being directed to the sample 150. Similarly, the Stokes laser 110S in FIG. 2 may produce linearly polarized light, and the waveplate 132*b* may be (i) a half-wave plate that rotates the polarization of the Stokes beam 120S or (ii) a quarter-wave plate that converts the Stokes beam 120S to a circular or elliptical polarization.

The probe laser 110*pr* in FIG. 2 may produce linearly polarized light, and the waveplate 132*c* may be (i) a half-wave plate that rotates the polarization of the probe beam 120*pr* or (ii) a quarter-wave plate that converts the probe beam 120*pr* to a circular or elliptical polarization prior to the probe beam being combined with the Raman signal 160. Changing the polarization of the probe beam 120*pr* may allow the Raman signal 160 and the probe beam to be coherently mixed. The polarization of the probe beam 120*pr* can be changed so that it has both horizontal and vertical polarization components, which ensures that at least a portion of the probe beam 120*pr* and the Raman signal 160 have polarizations that are oriented in the same direction so that their electric fields may be added together.

Each of the optical waveplates 132 in FIG. 2 may be a free-space optical element, a fiber-optic component, a waveguide-based optical element, or a metamaterial-based optic. Additionally, each of the optical waveplates 132 in FIG. 2 may be a fixed waveplate or an adjustable waveplate. A fixed waveplate may have a fixed optical phase difference between the two axes of the waveplate (e.g., a quarter-wave plate may have a one-quarter wavelength phase difference, and a half-wave plate may have a one-half wavelength phase difference). An adjustable waveplate may allow for the phase difference between the two axes of the waveplate to be dynamically changed. For example, an electronically adjustable waveplate may include a Pockels cell, a liquid crystal device, or a photoelastic modulator that allows the phase difference to be adjusted electronically so that the waveplate can be dynamically configured to act as a waveplate having any suitable phase difference (e.g., a phase difference between zero wavelengths and one-half wavelength). An adjustable waveplate may switch between (i) applying no phase difference to incident light so that the transmitted light has the same polarization as the incident light and (ii) applying a one-quarter wavelength or one-half wavelength phase difference so that linearly polarized incident light is converted to circularly polarized light or is rotated to a different polarization. For example, the pump laser 110*pu* in FIG. 2 may produce vertically polarized light, and the waveplate 132*a* may be an adjustable waveplate that switches between (i) applying no polarization rotation to the pump beam 120*pu* so that the pump beam remains vertically polarized and (ii) applying a 90-degree rotation to the pump-beam polarization so that the pump beam 120*pu* after the waveplate 132*a* is horizontally polarized. Dynamically changing the polarization of the pump beam 120*pu* may allow the Raman spectroscopy system 100 in FIG. 2 to perform measurements at two different pump-beam polarizations, which may produce additional data for characterization of the sample 150.

In some embodiments, an optical waveplate 132 may be a metamaterial-based waveplate. A metamaterial refers to an engineered material having features or repeating patterns at scales smaller than the wavelength of light interacting with the metamaterial. A metamaterial may be configured to act as a mirror, lens, waveplate, diffractive optical element, optical combiner, or optical waveguide. A metamaterial-based waveplate may affect the polarization of a beam of light based on wavelength. For example, the Raman spectroscopy system 100 in FIG. 2 may include a metamaterial-based waveplate (not illustrated in FIG. 2) located after the combiner 130*a* and before the sample 150. The metamaterial waveplate may change the polarization of the pump beam 120*pu* from linear to circular while preserving the polarization of the Stokes beam 120S (e.g., the Stokes beam may remain linearly polarized and may not be significantly changed by the waveplate).

A Raman spectroscopy system 100 may include an optical filter that transmits light at one or more wavelengths and blocks light at one or more other wavelengths. The optical filter 134 in FIG. 2 is located between the sample 150 and the optical receiver 200 and may be configured to substantially transmit one or more optical wavelengths associated with the Raman signal 160 and substantially block one or more wavelengths associated with the pump beam 120*pu* or the Stokes beam 120S. For example, the optical filter 134 may transmit greater than 90% of the Raman signal 160 and may block greater than 90% of both the pump and Stokes beams. As another example, the optical filter 134 may transmit greater than 90% of the Raman signal 160 and the Stokes beam 120S, and the optical filter 134 may block greater than 98% of the pump beam 120*pu*.

A Raman spectroscopy system 100 may include an optical polarizer that transmits light having a particular polarization (e.g., horizontal) and blocks light having an orthogonal polarization (e.g., vertical). The optical polarizer 136 in FIG. 2 is located between the sample 150 and the optical receiver 200 and may be oriented to transmit light with a polarization associated with the Raman signal. Additionally, the polarizer 136 may block a polarization associated with the pump or Stokes beams. For example, the Stokes beam 120S incident on the sample 150 may be vertically polarized, and the Raman signal 160 may be at least partially horizontally polarized. The polarizer 136 may be oriented to block vertically polarized light and transmit horizontally polarized light so that the Stokes beam 120S is blocked and the Raman signal 160 is at least partially transmitted by the polarizer. A Raman spectroscopy system 100 may include both an optical filter 134 and an optical polarizer 136. For example, the optical filter 136 in FIG. 2 may be configured to transmit the Raman signal 160 and the Stokes beam 120S and block the pump beam 120*pu*. Additionally, the Raman signal 160 and the Stokes beam 120S may be orthogonally polarized, and the polarizer 136 may be oriented to transmit the Raman signal 160 and block the Stokes beam 120S. Using a filter or polarizer located after the sample 150 to block light from the pump beam 120*pu* or the Stokes beam 120S may reduce noise in the system by reducing the amount of unwanted background light that reaches the detector 220.

The sample 150 in FIGS. 1-2 may be a solid, liquid, or gas, or any combination thereof. The sample 150 may include a biological material, an organic material, an inorganic material, a crystalline material, an amorphous solid material, or any other suitable material or combination of suitable materials. For example, the sample 150 may include a drug, mineral, food, contaminant, or explosive material that produces a Raman signal 160 in response to excitation by the pump and Stokes beams. As another example, the sample 150 may be a biological material (e.g., blood, urine, saliva, sweat, or cerebrospinal fluid) and a component or molecule (e.g., glucose or cortisol) that is part of the biological material may produce a Raman signal 160. As another example, the sample 150 may be water or wastewater that may include a contaminant, virus, bacteria, or an indicator of an infectious disease. The Raman signal 160 may be produced by coherent Raman scattering of the pump and Stokes beams within the sample 150, and the frequency offset Ω between the pump and Stokes beams may be approximately equal to a vibrational frequency or an electronic-transition frequency of a particular material that is part of the sample. The vibrational frequency of the particular material may correspond to a molecular vibration of a molecule, or in the case of a crystalline material, may correspond to a lattice vibration of a crystal. For example, the sample 150 may include glucose, and the frequency offset Ω may be approximately equal to a frequency of a molecular vibration of glucose.

The Raman spectroscopy systems 100 in FIGS. 1-2 may perform one or more measurements of a sample 150, and each measurement may include determining a characteristic of an electronic signal that results from the coherent mixing of the Raman signal 160 and the probe beam 120*pr*. The electronic signal may include a photocurrent i or a corresponding voltage signal 234. The frequency offset Ω may be approximately equal to a vibrational frequency or electronic-transition frequency of a particular material, and based on the one or more measurements, a processor may determine whether the particular material is present in the sample 150. Additionally or alternatively, the processor may determine an amount or a concentration of the particular material in the sample based on the measurements. For example, the frequency offset Ω may be approximately equal to a vibrational frequency of glucose, and, based on one or more optical heterodyne measurements of a Raman signal 160 produced by a sample 150, the processor may determine (i) whether glucose is present in the sample or (ii) an amount or a concentration of glucose in the sample. The amount of glucose that is present in the sample 150 may be proportional to the amplitude of a photocurrent signal i produced by coherent mixing of the Raman signal 160 and the probe beam 120*pr*. Based on the amplitude of the photocurrent signal i, the processor may determine the amount or concentration of glucose in the sample 150.

A technical advantage of a coherent Raman spectroscopy system 100 as described herein is a higher spectral resolution or a better chemical sensitivity than a conventional Raman spectroscopy system. As such, a Raman spectroscopy system 100 as described herein may be referred to as a high-resolution Raman spectroscopy system or as a high-resolution coherent Raman spectroscopy system. In a conventional Raman spectroscopy system, a Raman signal produced by a sample may be measured in the optical domain using an optical spectrometer. A spectrometer typically uses a dispersive optical element (e.g., a diffraction grating) to separate the Raman signal into its various spectral components. However, this type of measurement performed in the optical domain typically has a spectral resolution on the order of 1 $cm^{-1}$ (or, about 30 GHz). In contrast, the spectral resolution of a coherent Raman spectroscopy system with heterodyne detection, as described herein, is determined primarily by the spectral linewidth $\Delta v_{pr}$ of the probe beam 120*pr* that is coherently mixed with the Raman signal 160. The probe laser 110*pr* may include a wavelength-tunable laser diode with a linewidth of 200 MHz or less, which corresponds to a spectral resolution of the Raman spectroscopy system 100 of less than 200 MHz (or, less than 0.007 $cm^{-1}$). This 200-MHz spectral resolution is more than 100 times better than the 30-GHz spectral resolution of a conventional Raman spectroscopy system. In some embodiments, the probe laser 110*pr* may have a linewidth of 1 MHz or less, which corresponds to a spectral resolution of the Raman spectroscopy system 100 of less than 1 MHz (or, less than $33\times10^{-6}$ $cm^{-1}$). A related advantage of a coherent Raman spectroscopy system 100 is that the signal capture and analysis are performed in the electronic domain (e.g., at electronic frequencies between DC and 50 GHz) rather than in the optical domain (e.g., at optical frequencies between 60 THz and 1,000 THz). The coherent mixing of two optical signals (Raman signal 160 and probe beam 120*pr*) produces an electronic signal which can be analyzed with relatively high resolution compared to an optical signal. This electronic signal analysis, along with the relatively narrow spectral linewidth of the probe laser 110*pr*, provides a coherent Raman spectroscopy system 100 with a high spectral resolution. Additionally, the wavelength tunability of the probe laser 110*pr* allows a Raman spectrum of a material to be determined at multiple frequencies with high spectral resolution.

The higher spectral resolution of a coherent Raman spectroscopy system 100 may provide a corresponding improvement in the ability of the coherent Raman spectroscopy system to sense various chemical species. For example, a high-resolution coherent Raman spectroscopy system 100 may be able to distinguish between different chemical species that have Raman peaks located relatively close together, whereas a conventional Raman spectroscopy system may not be able to resolve spectral features below about 1 $cm^{-1}$. Additionally, the higher spectral resolution of a coherent Raman spectroscopy system 100 may allow for lower concentrations of materials to be detected, as compared to a conventional Raman spectroscopy system. For example, a coherent Raman spectroscopy system 100 may be able to detect small deviations in the chemical signature of a biological sample, which may indicate the presence of damage or a mutation, which in turn may be correlated with a disease or pathogen.

Another technical advantage of a coherent Raman spectroscopy system 100 as described herein is its relatively compact size. A coherent Raman spectroscopy system may be packaged in a relatively compact enclosure as compared to a conventional Raman spectroscopy system. Since the spectral resolution of an optical spectrometer scales inversely with the optical path length of the spectrometer (e.g., a longer path length provides better spectral resolution), an optical spectrometer with a spectral resolution around 1 $cm^{-1}$ can be quite large or bulky. In contrast, since the spectral resolution of a coherent Raman spectroscopy system is determined primarily by the spectral linewidth of the probe laser 110*pr*, a coherent Raman spectroscopy system does not require a long optical path length to provide high spectral resolution. Thus, an enclosure for a coherent Raman spectroscopy system may be significantly smaller than that for a conventional Raman spectroscopy system. In some embodiments, a coherent Raman spectroscopy system may be packaged as a compact device that may be referred to as a lab-on-a-chip or a spectrometer on a chip. For example, a coherent Raman spectroscopy system may be packaged as a wearable device that provides ongoing, continual monitoring for a person or an animal.

Figure 3:
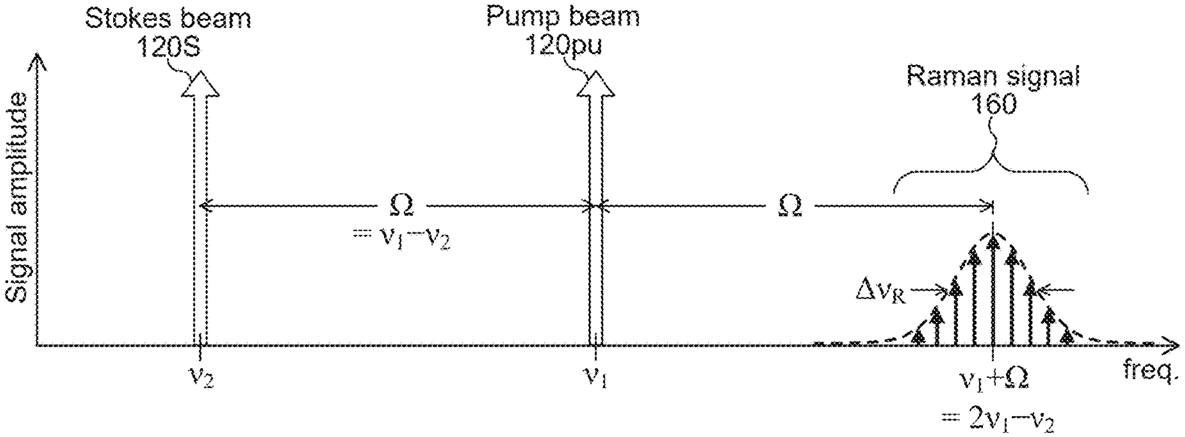
FIGS. 3-4 each illustrate an example Raman signal produced by coherent Raman scattering.
Figure 4:
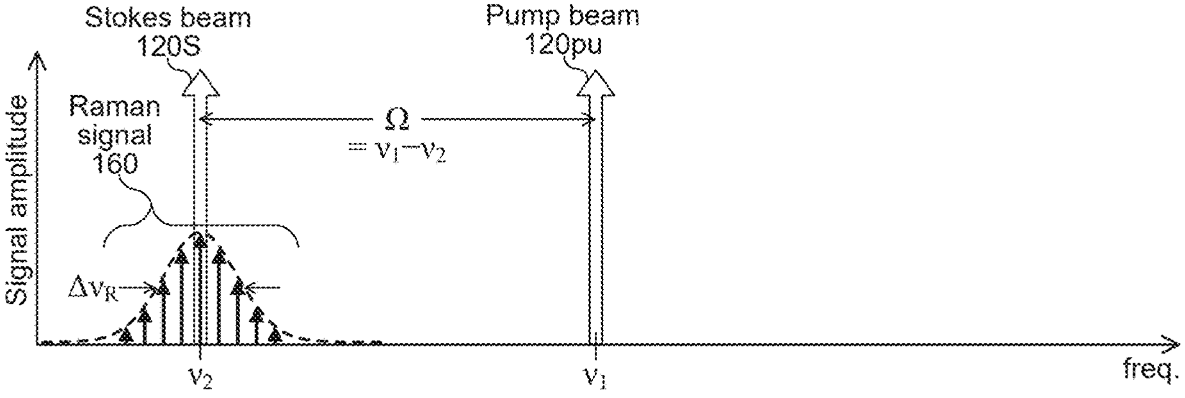

FIGS. 3-4 each illustrate an example Raman signal 160 produced by coherent Raman scattering. In a coherent Raman spectroscopy system 100, the pump beam 120*pu* and the Stokes beam 120S are directed to a sample 150, which produces a Raman signal 160 by coherent Raman scattering of the pump and Stokes beams within the sample. The frequency of the pump beam 120*pu* is $v_1$, and the frequency of the Stokes beam 120S is $v_2$. The frequency offset Ω between the pump and Stokes beams equals $v_1-v_2$. The frequencies of the pump and Stokes beams may be set so that the frequency offset Ω is approximately equal to a vibrational frequency or an electronic-transition frequency of a particular material. A coherent Raman spectroscopy system 100 may measure a Raman signal 160 produced by a sample 150 to determine (i) whether the particular material is present in the sample or (ii) an amount or a concentration of the particular material within the sample.

The frequency offset Ω between the pump and Stokes beams may be any suitable fixed or adjustable value between approximately 5 terahertz (THz) and approximately 100 THz. Expressed in wavenumbers, this corresponds to the frequency offset Ω being between approximately 167 $cm^{-1}$ and approximately 3336 $cm^{-1}$. For example, in a coherent Raman spectroscopy system 100, the pump beam 120*pu* may have a wavelength between approximately 1220 nanometers (nm) and approximately 1450 nm (which corresponds to a pump-beam frequency $v_1$ between approximately 246 THz and approximately 207 THz), and the Stokes beam 120S may have a wavelength between approximately 1490 nm and approximately 1570 nm (which corresponds to a Stokes-beam frequency $v_2$ between approximately 201 THz and approximately 191 THz). This system may produce pump and Stokes beams having a frequency offset Ω between approximately 5.6 THz and approximately 54.8 THz (or, in wavenumbers, between approximately 185 $cm^{-1}$ and 1827 $cm^{-1}$). For example, if the pump beam 120*pu* has a wavelength of 1330 nm (or equivalently, a frequency $v_1$ of 225.4 THz) and the Stokes beam 120S has a wavelength of 1550 nm (or equivalently, a frequency $v_2$ of 193.4 THz), then the frequency offset Ω between the pump and Stokes beams is approximately 32 THz (or, in wavenumbers, $10^{67}$ $cm^{-1}$). The pump and Stokes beams in a Raman spectroscopy system 100 may each have any suitable wavelength between approximately 300 nm and approximately 5,000 nm. For example, if the pump beam 120*pu* has a wavelength of approximately 785 nm (or equivalently, a frequency $v_1$ of 381.9 THz) and the Stokes beam 120S has a wavelength of approximately 840 nm (or equivalently, a frequency $v_2$ of 356.9 THz), then the frequency offset Ω between the pump and Stokes beams is approximately 25 THz (or, in wavenumbers, 834 $cm^{-1}$). As another example, the pump beam 120*pu* may have a wavelength between approximately 700 nm and approximately 850 nm, between approximately 890 nm and approximately 920 nm, or between approximately 1000 nm and approximately 1100 nm.

The Raman signal 160 in each of FIGS. 3-4 is an optical signal with a spectral linewidth of $\Delta v_R$. In FIG. 3, the Raman signal 160 has a center frequency approximately equal to $2v_1-v_2$ (which is equal to $v_1+\Omega$, since $\Omega=v_1-v_2$). The center frequency of a Raman signal 160 may refer to the frequency of a central peak or the frequency of an approximate center of the Raman signal. Additionally or alternatively, the center frequency of a Raman signal 160 may correspond to a Raman peak of an associated Raman spectrum. The Raman signal 160 in FIG. 3 may be produced by coherent anti-Stokes Raman scattering (CARS) in which the pump and Stokes beams interact with a sample 150 to produce a Raman signal 160 at or around the frequency $2v_1-v_2$. For example, if the pump and Stokes beams have respective wavelengths of 1064 nm and 1550 nm (which corresponds to frequencies of approximately 281.8 THz and 193.4 THz), then the frequency offset Ω is 88.3 THz (or, 2947 $cm^{-1}$), and the anti-Stokes Raman signal 160 has a center wavelength of approximately 810 nm (which corresponds to a frequency of approximately 370 THz). The Raman signal 160 in FIG. 4, which overlaps the frequency of the Stokes beam 120S, may be produced by stimulated Raman scattering. The Raman signal 160 in FIG. 4 may be centered at or near the frequency $v_2$ of the Stokes beam 120S. For example, the Raman signal 160 in FIG. 4 may have a center frequency that is within approximately 200 GHz (or, 6.7 $cm^{-1}$) of the Stokes-beam frequency $v_2$.

Figure 5:
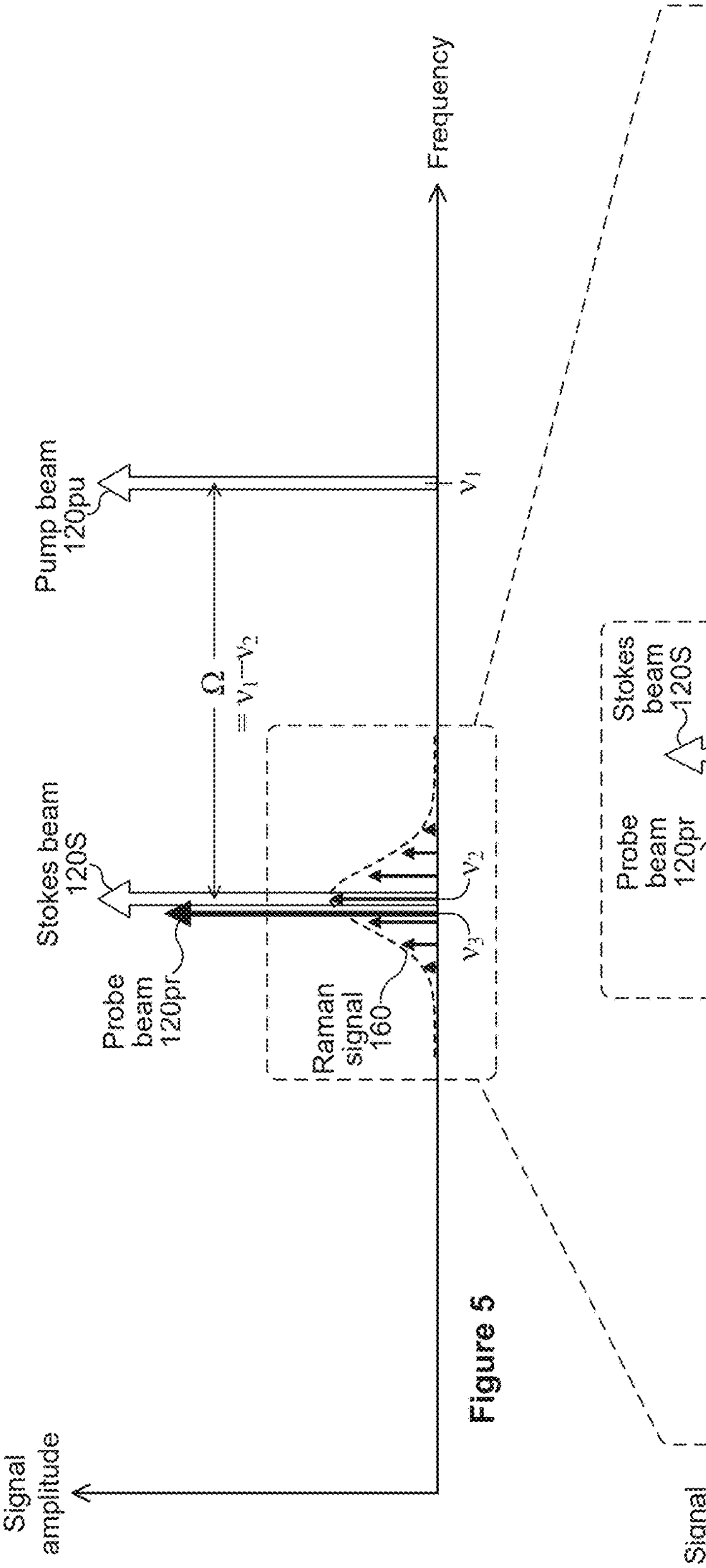
FIG. 5 illustrates the example Raman signal of FIG. 4 along with a probe beam.

FIG. 5 illustrates the example Raman signal 160 of FIG. 4 along with a probe beam 120*pr*. The Raman signal 160 may be produced by stimulated Raman scattering of the pump beam 120*pu* and Stokes beam 120S, and the probe beam 120*pr* may be used to measure the Raman signal. The Raman signal 160 is centered at or near the frequency $v_2$ of the Stokes beam 120S, and the frequency $v_3$ of the probe beam of light 120*pr* overlaps the Raman signal 160 and is relatively close to the frequency $v_2$ of the Stokes beam of light 120S (e.g., the probe-beam frequency $v_3$ may be within 200 GHz of the Stokes-beam frequency $v_2$). In a coherent Raman spectroscopy system 100, the pump frequency $v_1$, Stokes frequency $v_2$, and probe frequency $v_3$ may each be between approximately 60 THz and approximately 1,000 THz (which corresponds to a wavelength between approximately 5,000 nm and approximately 300 nm). For example, in FIG. 5 the pump frequency $v_1$ may be 291 THz (which corresponds to a wavelength of approximately 1030 nm), the Stokes frequency $v_2$ may be 240.03 THz (which corresponds to a wavelength of approximately 1249.00 nm), and the probe frequency $v_3$ may be 240.00 THz (which corresponds to a wavelength of approximately 1249.14 nm).

Each of the light sources 110 of a coherent Raman spectroscopy system 100 may include a wavelength-tunable light source. A wavelength-tunable light source refers to a light source 110 that can produce light at multiple different wavelengths within a range of wavelengths (or equivalently, at multiple different frequencies within a range of frequencies). For example, the probe light source 110*pr* in FIG. 1 may be a wavelength-tunable light source where the wavelength of the probe beam 120*pr* is adjustable over an 80-nm wavelength range from 1490 nm to 1570 nm (which corresponds to a 10.3 THz frequency range from approximately 201.2 THz to approximately 191.0 THz). At any given time, a wavelength-tunable light source 110 may operate at any one of the different wavelengths within its wavelength-tuning range. For example, during a first period of time, the probe light source 110*pr* with a 1490-1570 nm wavelength-tuning range may produce a probe beam 120*pr* at 1500 nm, and during a subsequent second period of time, the probe light source may be tuned to operate at 1560 nm. A wavelength-tunable light source may be adjustable over a frequency range that corresponds to a wavelength range having a width or span between approximately 10 nm and approximately 100 nm. For example, the width of the wavelength-tuning range of a wavelength-tunable light source may be approximately 10 nm, 20 nm, 30 nm, 40 nm, 50 nm, 60 nm, 80 nm, or 100 nm. A wavelength-tuning range from 1490 nm to 1570 nm may be referred to as having an 80-nm width or an 80-nm span. Around 1550 nm, a 10-nm wavelength-tuning range corresponds to a frequency-tuning range of approximately 1.25 THz (or equivalently, 41.6 $cm^{-1}$), and a 100-nm wavelength-tuning range corresponds to a frequency-tuning range of approximately 12.5 THz (or equivalently, 416 $cm^{-1}$). Around 1050 nm, a 10-nm wavelength-tuning range corresponds to a frequency-tuning range of approximately 2.72 THz (or equivalently, 90.7 $cm^{-1}$), and a 100-nm wavelength-tuning range corresponds to a frequency-tuning range of approximately 27.3 THz (or equivalently, 909 $cm^{-1}$). A wavelength-tunable light source may be referred to as a frequency-tunable light source or a tunable light source.

Each of the light sources 110 of a coherent Raman spectroscopy system 100 may include one or more laser diodes, and each of the laser diodes may be a fixed-wavelength laser diode or a wavelength-tunable laser diode. A fixed-wavelength laser diode may operate at a single wavelength or within a relatively narrow wavelength range (e.g., within 0.1 nm of a particular wavelength). A fixed-wavelength laser diode may include a distributed feedback (DFB) laser diode, a distributed Bragg reflector (DBR) laser diode, a fiber-Bragg-grating (FBG) stabilized laser diode, a temperature-stabilized laser diode, or any other suitable fixed-wavelength laser diode. A wavelength-tunable laser diode may produce light at multiple different wavelengths within a range of wavelengths. For example, a wavelength-tunable laser diode may be configured to produce light at any wavelength within a wavelength range having a width between approximately 10 nm and approximately 100 nm. At any given time, a wavelength-tunable laser diode may operate at any one wavelength of multiple different wavelengths within a range of wavelengths. A wavelength-tunable laser diode may include an external-cavity laser diode, a thermally tuned laser diode, or a sampled-grating distributed Bragg reflector (SG-DBR) laser. For example, a wavelength-tunable SG-DBR laser may have a 40-nm wavelength-tuning range that extends from 1530 nm to 1570 nm, and the SG-DBR laser may be adjustable to operate at any single wavelength within the 40-nm wavelength range. A wavelength-tunable laser diode may be referred to as a frequency-tunable laser diode or a tunable laser diode. For example, a tunable laser with a 40-nm wavelength-tuning range that extends from 1530 nm to 1570 nm may also be referred to as a frequency-tunable laser with a 5.0-THz frequency-tuning range that extends from approximately 191 THz to approximately 196 THz.

Each of the light sources 110 of a coherent Raman spectroscopy system 100 may include one or more of the following: light-emitting diode (LED), super-luminescent light source, short-pulse laser, broadband light source, fiber laser, solid-state laser, quantum-cascade laser. For example, a light source that produces light over a relatively broad range of wavelengths (e.g., a super-luminescent light source, short-pulse laser, or broadband light source) may be used to investigate a sample over the broad range of wavelengths without having to use a wavelength-tunable light source.

Figure 6:
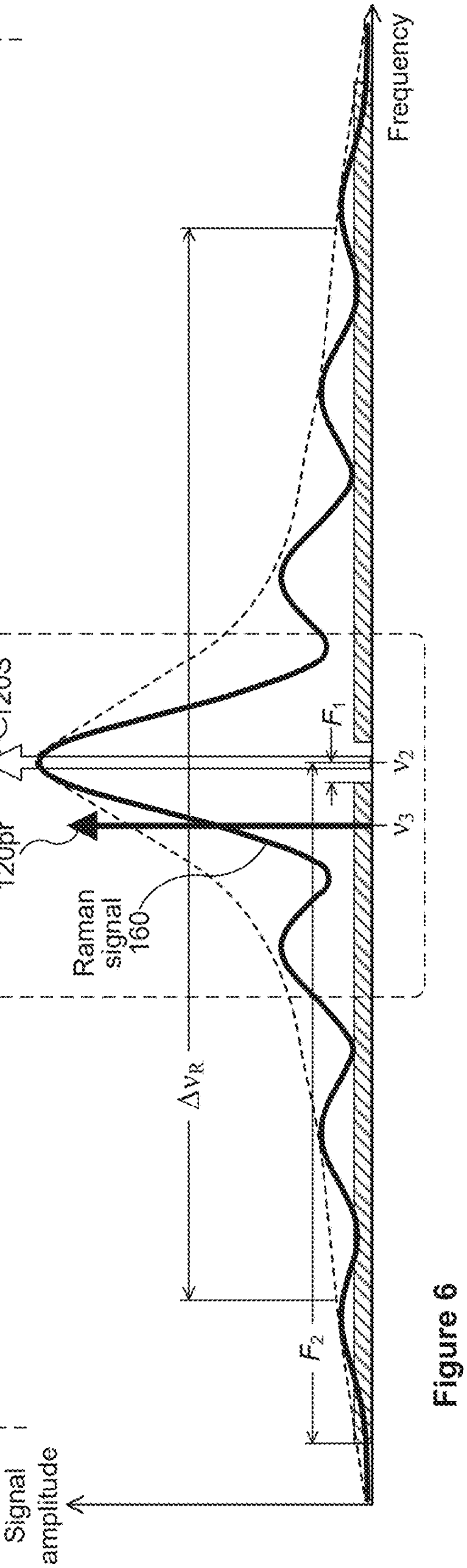
FIG. 6 illustrates an expanded view of a portion of the Raman signal of FIG. 5.

FIG. 6 illustrates an expanded view of a portion of the Raman signal 160 of FIG. 5. The portion of FIG. 5 enclosed by the dashed-line box is expanded in FIG. 6. The peak of the Raman signal 160 in FIG. 6 is approximately coincident with the frequency $v_2$ of the Stokes beam 120S, and the frequency $v_3$ of the probe beam 120*pr* overlaps the Raman signal.

The Raman signal 160 in FIG. 6 is an optical signal with a spectral linewidth of $\Delta v_R$. The spectral linewidth of a Raman signal 160 may have a value between approximately 30 GHz and 300 GHz (or, in wavenumbers, between approximately 1 $cm^{-1}$ and approximately 10 $cm^{-1}$). The spectral linewidth $\Delta v_R$ of a Raman signal 160 may represent the spectral width of a peak of the Raman signal (e.g., a full-width-at-half-maximum of the peak) or may represent an approximate extent or width of the full Raman signal. For example, the spectral linewidth $\Delta v_R$ of the Raman signal 160 in FIG. 13 corresponds to a full-width-at-half-maximum of a peak of the Raman signal. In FIG. 6, the spectral linewidth $\Delta v_R$ of the Raman signal 160 corresponds to an extent or width of the full Raman signal. For example, the spectral linewidth of a Raman signal 160 may equal a spectral width at which an envelope of the Raman signal has decreased to a particular level (e.g., to 50%, 20%, or 10% of a peak value). The envelope may be a curve that decreases monotonically away from a peak of the Raman signal and approximately follows an overall shape of the Raman signal. In FIG. 6, the dashed-line curve that traces the peaks of the Raman signal 160 represents an envelope of the Raman signal, and the spectral linewidth $\Delta v_R$ corresponds to a full-width-at-10% of the Raman-signal envelope (i.e., the points at which the envelope has decreased to 10% of its maximum value).

In a coherent Raman spectroscopy system 100, the difference between the frequency $v_2$ of the Stokes beam 120S and the frequency $v_3$ of the probe beam 120*pr* may be greater than a low-frequency limit $F_1$ and less than a high-frequency limit $F_2$ (i.e., $F_1<|v_2-v_3|<F_2$). For example, the low-frequency limit $F_1$ may be approximately 1 MHz, 10 MHz, 50 MHz, 100 MHz, 200 MHz, 500 MHz, or 1 GHz, and the high-frequency limit $F_2$ may be approximately 10 GHz, 20 GHz, 50 GHz, 100 GHz, 200 GHz, 500 GHz, or 1 THz. As another example, the low-frequency limit $F_1$ may be related to the spectral linewidth $\Delta v_{pr}$ of the probe beam 120*pr* and the spectral linewidth $\Delta v_S$ of the Stokes beam 120S (e.g., $F_1$ may be greater than $\Delta v_{pr}+\Delta v_S$). As another example, the high-frequency limit $F_2$ may be related to the spectral linewidth $\Delta v_R$ of a Raman signal 160 (e.g., $F_2$ may be approximately equal (0.5) $\Delta v_R$, $\Delta v_R$, or $2\Delta v_R$). As another example, $F_1$ may be 100 MHz and $F_2$ may be 200 GHz, which indicates that the frequency $v_2$ of the Stokes beam 120S and the frequency $v_3$ of the probe beam 120*pr* may differ by greater than 100 MHz and less than 200 GHz (i.e., 100 MHz$<|v_2-v_3|<$200 GHz). The frequencies $F_1$ and $F_2$ represent the frequency range with respect to the Stokes-beam frequency $v_2$ over which the probe-beam frequency $v_3$ may be scanned. The two hatched rectangles along the frequency axis in FIG. 6 represent the allowed frequency ranges for the probe beam 120*pr*. The frequency of the probe beam 120*pr* may be (i) between $v_2-F_2$ and $v_2-F_1$ or (ii) between $v_2+F_1$ and $v_2+F_2$. In an optical receiver 200, the probe beam 120*pr* and the Raman signal 160 may be coherently mixed together at an optical detector 220. The frequency $v_3$ of the probe beam 120*pr* may be kept away from the frequency $v_2$ of the Stokes beam 120S by at least the low-frequency limit $F_1$ (e.g., $|v_2-v_3|>F_1$) to avoid mixing between the probe and Stokes beams, which could cause the detector to produce an unwanted electronic signal not related to the mixing between the probe beam and Raman signal. Additionally, the frequency $v_3$ of the probe beam 120*pr* may be kept within the high-frequency limit $F_2$ of the frequency $v_2$ of the Stokes beam 120S (e.g., $|v_2-v_3|<F_2$), since measurements outside the high-frequency limit may not produce a significant electronic signal.

Figure 7:
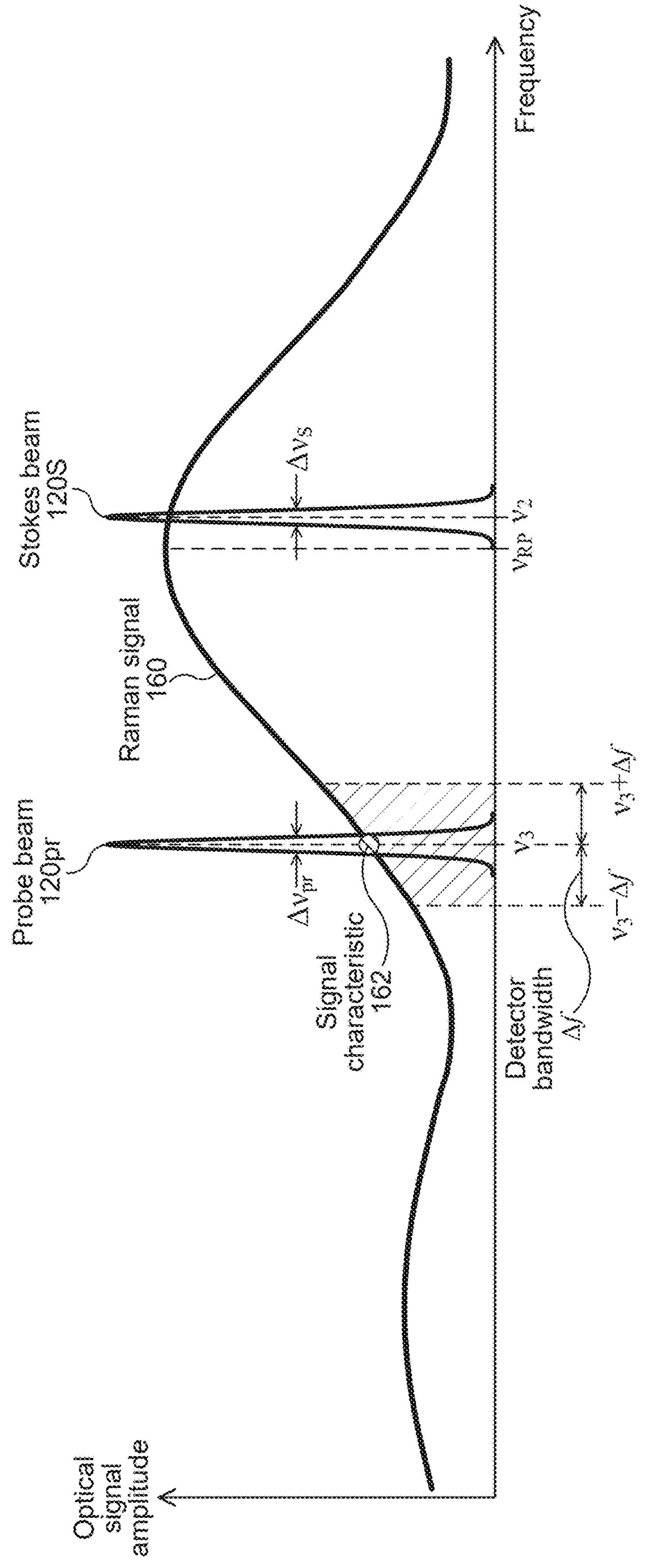
FIG. 7 illustrates an expanded view of a portion of the Raman signal of FIG. 6.

FIG. 7 illustrates an expanded view of a portion of the Raman signal 160 of FIG. 6. The portion of FIG. 6 enclosed by the dashed-line box is expanded in FIG. 7. The peak of the Raman signal 160 in FIG. 7 is located at frequency $v_{RP}$, and the Stokes beam 120S is located at the Stokes frequency $v_2$. The Raman-signal peak frequency $v_{RP}$ may correspond to a Raman peak of a material that is part of a sample 150 being measured by a Raman spectroscopy system 100. For example, the difference between the pump-beam frequency $v_1$ and the Raman-signal peak frequency $v_{RP}$ may equal a vibrational frequency Ω of the material (e.g., $v_1-v_{RP}=\Omega$). In some embodiments, a Stokes light source 110S may be operated so that the Stokes-beam frequency $v_2$ is approximately equal to the Raman-signal peak frequency $v_{RP}$, and in other embodiments (e.g., as illustrated in FIG. 7), the Stokes-beam frequency $v_2$ may be slightly off-resonance or detuned with respect to the Raman-signal peak frequency $v_{RP}$. For example, in FIG. 7, the Stokes-beam frequency $v_2$ may differ from the Raman-signal peak frequency $v_{RP}$ by less than or equal to 30 GHz, 10 GHz, 5 GHz, or 1 GHz.

The beams of light 120 produced by the pump, Stokes, and probe light sources 110 in a Raman spectroscopy system 100 may each have a spectral linewidth of less than 200 MHz. Additionally, one or more of the beams of light 120 may have a spectral linewidth of less than 1 MHz. For example, the spectral linewidth of a beam of light 120 may be less than 200 MHz, 100 MHz, 50 MHz, 10 MHz, 1 MHz, or 100 KHz. In FIG. 7, the spectral linewidth $\Delta v_{pr}$ of the probe beam 120*pr* and the spectral linewidth $\Delta v_S$ of the Stokes beam 120S may each be less than 200 MHz. In some embodiments, the probe light source 110*pr* may be configured to produce a probe beam 120*pr* having a relatively narrow spectral linewidth, which may allow a Raman spectroscopy system 100 to measure a Raman spectrum with a high degree of spectral resolution. For example, the spectral linewidth $\Delta v_{pr}$ of the probe beam 120*pr* in FIG. 7 may be less than 1 MHz.

An optical receiver 200 of a coherent Raman spectroscopy system 100 may include one or more detectors 220, where each detector is configured to coherently mix a portion of a Raman signal 160 with at least a portion of a probe beam of light 120*pr* to produce an electronic signal. For an optical receiver 200 with a single detector 220, all or most of the probe beam of light 120*pr* may be mixed with the Raman signal 160. For an optical receiver 200 with multiple detectors 220, the probe beam of light 120*pr* may be split so that a portion of the probe beam of light is sent to each of the detectors. For example, in an optical receiver 200 with four detectors 220, the probe beam 120*pr* may be split into four portions, and each detector may receive one of the four portions of the probe beam. Similarly, for an optical receiver 200 with a single detector 220, all or most of the Raman signal 160 may be sent to the single detector, and for an optical receiver with multiple detectors 220, the Raman signal 160 may be split so that a portion of the Raman signal is sent to each of the detectors.

Coherent mixing of a probe beam 120*pr* and a Raman signal 160, which may be referred to as heterodyne detection, may occur when the two optical signals are optically combined and then detected by a detector 220. Optically combining the probe beam 120*pr* and the Raman signal 160 may refer to combining the two optical signals so that their electric fields are summed together. For example, the probe beam and Raman signal may be combined (e.g., with an optical combiner 130) so that the two signals are substantially coaxial and travel together in the same direction and along approximately the same optical path. Additionally, the probe beam and Raman signal may be combined so that at least a portion of their polarizations have the same orientation to allow at least a portion of their electric fields to be summed together. Once the probe beam and Raman signal are optically combined to produce a combined probe-Raman signal 210, the probe beam and Raman signal may be coherently mixed at a detector 220. The detector 220 may produce a photocurrent signal i corresponding to the coherent mixing of the probe beam 120*pr* and a portion of the Raman signal 160.

The portion of a Raman signal 160 that is coherently mixed with a probe beam of light 120*pr* at a detector 220 to produce an electronic signal may refer to a spectral portion of the Raman signal. The spectral portion of a Raman signal 160 that is coherently mixed with a probe beam 120*pr* may include optical frequency components of the Raman signal that are within a particular frequency range of the frequency $v_3$ of the probe beam of light, where the particular frequency range is based on or depends on the electronic bandwidth Δf of the optical detector 220. In FIG. 7, the hatched region around the probe frequency $v_3$ represents the spectral portion of the Raman signal 160 that is coherently mixed with the probe beam 120*pr*. The particular frequency range illustrated by the hatched region extends from $v_3-\Delta f$ to $v_3+\Delta f$, where Δf is the electronic bandwidth of the detector. The particular frequency range includes the optical frequency components of the Raman signal 160 that are coherently mixed with the probe beam 120*pr* to produce an electronic signal.

The electronic signal produced by the detector 220 in response to the coherent mixing of the portion of the Raman signal 160 and probe beam 120*pr* may include one or more electronic frequency components, where each electronic frequency component has a frequency less than or equal to approximately Δf. For example, the electronic bandwidth Δf of the optical detector may be 10 GHz, and the electronic signal produced by the detector may include one or more electronic frequency components having frequencies less than or equal to approximately 10 GHz. Other optical frequency components of the Raman signal 160 that are outside the hatched region (e.g., optical frequencies less than $v_3-\Delta f$ and greater than $v_3+\Delta f$) may produce a coherent-mixing response in the detector 220. However, since these Raman-signal optical frequency components would produce an electronic response at frequencies greater than Δf (which is outside of the electronic bandwidth of the detector), these optical frequency components will not result in any significant contribution to the electronic signal. The electronic bandwidth of the detector 220 effectively limits or filters the optical frequency components of the Raman signal 160 that are measured by the optical receiver 200 to optical frequency components that are within a particular frequency range of the probe frequency. Accordingly, the electronic bandwidth of the detector 220, in combination with the relatively narrow spectral linewidth of the probe beam 120*pr*, may allow a Raman spectroscopy system 100 to measure a Raman signal 160 with a high degree of spectral resolution. Herein, an optical frequency or an optical frequency component refers to a signal in the optical domain between approximately 60 THz and approximately 1,000 THz, and an electronic frequency or an electronic frequency component refers to a signal in the electronic domain between 0 Hz and approximately 50 GHz.

The electronic signal that results from coherent mixing of a Raman signal 160 and a probe beam 120*pr* may include a coherent-mixing term that is proportional to a product of (i) $E_R$, the amplitude of the electric field of the Raman signal and (ii) $E_{pr}$, the amplitude of the electric field of the probe beam. The photocurrent signal i produced by a detector 220 in response to the coherent mixing of a Raman signal 160 and a probe beam 120*pr* may be proportional to the square of the summed electric fields of the probe beam 120*pr* and a spectral portion of the Raman signal 160. This type of detector 220 that produces a photocurrent signal i that is proportional to the square of a received electric field may be referred to as a square-law detector. The photocurrent signal i may be expressed as $i(t)=k|\varepsilon_R(t)+\varepsilon_{pr}(t)|^2$, where k is a constant (e.g., k may account for the responsivity of the detector 220 as well as other constant parameters or conversion factors). For clarity, the constant k or other constants (e.g., conversion constants or factors of 2 or 4) may be excluded from expressions herein related to the photocurrent i or the voltage signal 234. In the above expression for i(t), $\varepsilon_R(t)$ is the electric field of the Raman signal 160, and $\varepsilon_{pr}(t)$ is the electric field of the probe beam 120*pr*. The electric field of the Raman signal 160 may be expressed as $E_R \cos[2\pi v_R t+\phi_R]$, where $E_R$ is the amplitude of the electric field of the Raman signal. The electric field of the probe beam 120*pr* may be expressed as $E_{pr} \cos[2\pi v_3 t+\phi_{pr}]$, where $E_{pr}$ is the amplitude of the electric field of probe beam. The frequency $v_R$ is the optical frequency of the electric field of the spectral portion of the Raman signal 160 that is coherently mixed with the probe beam 120*pr*. The frequency $v_R$ may include the optical frequency components of the Raman signal 160 from $v_3-\Delta f$ to $v_3+\Delta f$, where $\Delta f$ is the electronic bandwidth of the detector. The frequency $v_3$ is the optical frequency of the electric field of the probe beam 120*pr*. The term $\phi_R$ is the phase of the electric field of the Raman signal 160, and the term $\phi_{pr}$ is the phase of the electric field of the probe beam 120*pr*.

The above expression for the photocurrent signal i may be expanded and written as $$i(t) = E_R^2 + E_{pr}^2 + 2E_R E_{pr} \cos[2\pi(v_R - v_3)t + \Delta\phi],$$

where, for clarity, the constant k is not included. In this expanded expression for the photocurrent signal i(t), the first term $$E_R^2$$

corresponds to the optical power ($P_R$) of the Raman signal 160, and the second term $$E_{pr}^2$$

corresponds to the optical power ($P_{pr}$) of the probe beam 120*pr*. The third term in the above expression is $2E_R E_{pr} \cos[2\pi(v_R-v_3)t+\Delta\phi]$ and may be referred to as a coherent-mixing term that represents coherent mixing between the electric fields of the Raman signal 160 and probe beam 120*pr*. The phase difference $\Delta\phi$ is the phase difference between the electric fields of the Raman signal and the probe beam (e.g., $\Delta\phi=\phi_R-\phi_{pr}$). The coherent-mixing term is proportional to $E_R \times E_{pr}$, which is the product of the electric-field amplitudes of the Raman signal 160 and the probe beam 120*pr*. Additionally, the coherent-mixing term includes a cosine function that varies in time based on the frequency difference ($v_R-v_3$) between the Raman signal 160 and the probe beam 120*pr*. Since the spectral portion of the Raman signal 160 that is coherently mixed with the probe beam 120*pr* includes the optical frequency components of the Raman signal from $v_3-\Delta f$ to $v_3+\Delta f$, the frequency-difference term ($v_R-v_3$) may include frequency components from zero to $\Delta f$. Accordingly, the coherent-mixing term may be referred to as including multiple electronic frequency components, where each electronic frequency component is proportional to $E_R E_{pr} \cos[2\pi ft+\Delta\phi]$. The frequency f, which may be referred to as an electronic frequency, is equal to the frequency difference ($v_R-v_3$) and has a value between zero and $\Delta f$. The coherent-mixing term may also be expressed as $2\sqrt{P_R}\sqrt{P_{pr}} \cos[2\pi ft+\Delta\phi]$, where $P_R$ is the optical power of the Raman signal 160 and $P_{pr}$ is the optical power of the probe beam 120*pr*.

Figure 8:
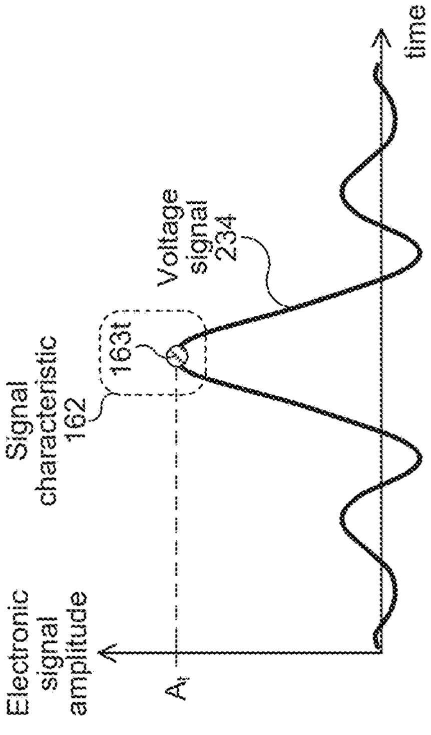
FIGS. 8-10 illustrate time-domain and frequency-domain plots of an example electronic signal resulting from coherent mixing of the Raman signal and probe beam of FIG. 7.
Figure 9:
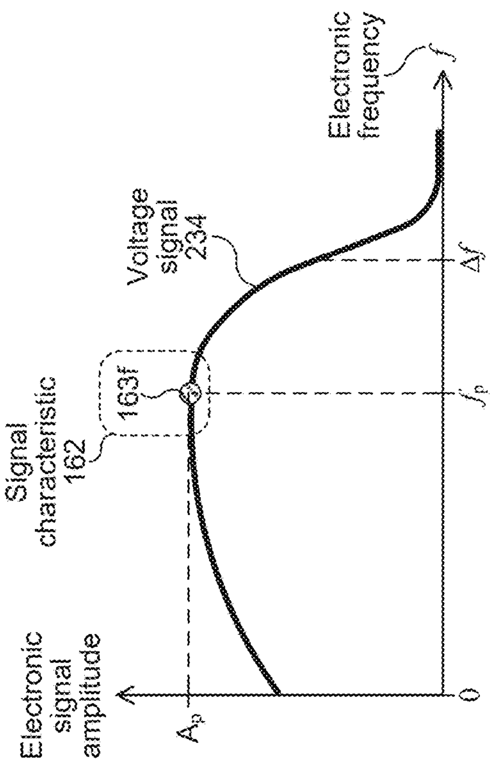
Figure 10:
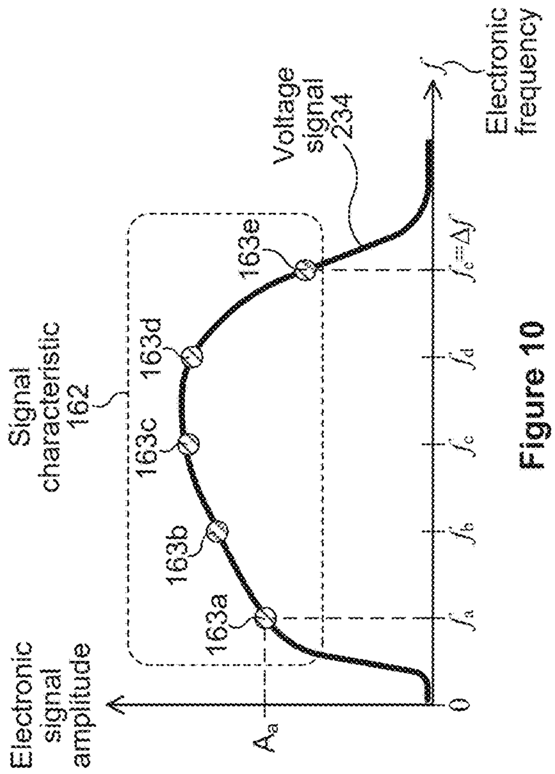

FIGS. 8-10 illustrate time-domain and frequency-domain plots of an example electronic signal resulting from coherent mixing of the Raman signal 160 and probe beam 120*pr* of FIG. 7. The electronic signal produced by a detector 220 may be a photocurrent signal i, and an electronic amplifier 232 may produce a voltage signal 234 that corresponds to the photocurrent signal i. The voltage signal 234 may be approximately proportional to the photocurrent signal i, and both the voltage and photocurrent signals may be proportional to $P_R+P_{pr}+2\sqrt{P_R}\sqrt{P_{pr}} \cos[2\pi ft+\Delta\phi]$, where the electronic frequency f is equal to the frequency difference ($v_R-v_3$). The electronic frequency f may take on multiple values (or a continuous range of values) between zero and $\Delta f$, and so, the voltage signal 234 in the time domain may be viewed as a summation over these multiple frequency components. In the frequency domain, the voltage signal 234 may have frequency components that extend from DC to $\Delta f$ (or, for an amplifier 232 with a low-frequency cutoff filter, from the low-frequency cutoff to $\Delta f$). The two terms $P_R$ and $P_{pr}$ represent the optical powers of the Raman signal and probe beam. Over the time duration of a measurement, the powers of the Raman signal and probe beam may be approximately constant, and so the contribution of $P_R+P_{pr}$ in the above expression may correspond to a DC offset with little or no time variation. An electronic amplifier 232 may include a high-pass or band-pass filter that removes or attenuates the DC or low-frequency components, resulting in an electronic signal with little or no DC offset (e.g., as illustrated by the time-domain voltage signal 234 in FIG. 8).

The signal characteristic 162 in each of FIGS. 7-10 represents a characteristic of an electronic signal (e.g., a characteristic of a photocurrent signal i or a characteristic of a corresponding voltage signal 234) associated with a Raman signal 160. A signal characteristic 162 may be determined from a digital signal 240, where the digital signal is a digital representation of a photocurrent signal i or a voltage signal 234. A characteristic 162 of an electronic signal may be determined by a processor of a Raman spectroscopy system 100 and may include one or more data points 163, where each data point represents: a peak amplitude, an average amplitude, an amplitude at a particular frequency, an amplitude at a particular time, an amplitude at a frequency center, an amplitude at a temporal center, a DC offset, an area, a frequency (e.g., an electronic frequency or an optical frequency), a phase, or a polarization. A Raman spectroscopy system 100 may measure one or more signal characteristics 162 associated with one or more Raman signals 160, and based on the measured characteristics, a processor may determine (i) whether a particular material is present in a sample or (ii) an amount or a concentration of the particular material in the sample.

FIG. 8 illustrates an example time-domain plot of a voltage signal 234 resulting from coherent mixing of the Raman signal 160 and probe beam 120*pr* of FIG. 7. A digitizer 236 (e.g., an ADC) may produce a digital signal 240 that represents the voltage signal 234 in the time domain, and a processor may determine a characteristic 162 of the electronic signal based on the digital signal. The signal characteristic 162 in FIG. 8 includes a single data point 163*t* which represents a peak amplitude $A_t$ of the time-domain voltage signal 234. The signal characteristic 162 may also include the optical frequency $v_3$ that the probe beam 120*pr* was set to when the electronic signal was obtained. Other time-domain-type data points 163 associated with the signal characteristic 162 in FIG. 8 may include (i) an amplitude of the time-domain voltage signal 234 at a particular time (e.g., at a temporal center) or (ii) an area associated with the voltage signal. For an area associated with the voltage signal 234, a processor may first convert the voltage signal into a non-negative signal (e.g., by taking the absolute value or by squaring the values of the voltage signal) and then integrate the non-negative signal to determine an area under the curve.

A processor of a Raman spectroscopy system 100 may determine a Fourier transform of a digital signal 240. A voltage signal 234 may be a time-domain signal, and the digital signal 240 may be a time-domain digital representation of the voltage signal 234. The Fourier transform of the digital signal 240 may produce a frequency-domain representation of the voltage signal 234. From the Fourier transform, the processor may determine one or more electronic frequency components of the voltage signal 234. Determining a frequency component of a voltage signal 234 may include determining an amplitude of the frequency-domain voltage signal at a particular frequency (e.g., at 4 GHz). FIGS. 9-10 each illustrate an example frequency-domain plot of a voltage signal 234 resulting from coherent mixing of the Raman signal 160 and probe beam 120*pr* of FIG. 7. The frequency-domain plots may be determined by taking a Fourier transform (e.g., a discrete Fourier transform or a fast Fourier transform) of a time-domain digital signal 240 that represents a time-domain voltage signal 234. The x-axis of each of the frequency-domain plots in FIGS. 9-10 is labeled as “electronic frequency” to clarify and distinguish it from the x-axis of the frequency-domain plots in FIGS. 3-7. The x-axis of each of the frequency-domain plots in FIGS. 3-7 may be referred to as an “optical frequency,” where the pump beam 120*pu*, Stokes beam 120S, Raman signal 160, and probe beam 120*pr* each have frequencies in the optical domain (e.g., in the range of 60-1,000 THz). In contrast, the x-axis of each of the frequency-domain plots in FIGS. 9-10 includes frequencies in the electronic domain (e.g., in the range of DC to 50 GHz). Coherent mixing of a Raman signal 160 and probe beam 120*pr* (which are signals in the optical domain) produces an electronic signal that can be detected and analyzed using electronic techniques. The y-axis of each of the plots in FIGS. 8-10 is labeled “electronic signal amplitude” and may have units of voltage, current, or electrical power (e.g., watts).

In FIG. 9, the frequency-domain voltage signal 234 has nonzero frequency components that extend from DC (i.e., zero hertz) to the detector-bandwidth frequency Δf. In FIG. 10, the frequency-domain voltage signal drops off before reaching zero hertz, indicating that the corresponding voltage signal 234 may have been AC-coupled or high-pass filtered to remove the DC or low-frequency components. The signal characteristic 162 in FIG. 9 includes a single data point 163*f* which represents a peak amplitude $A_p$ of the frequency-domain voltage signal 234. The data point 163*f* may include the peak amplitude $A_p$ or the frequency $f_p$ at which the peak amplitude is located. The signal characteristic 162 in FIG. 10 includes five data points: data point 163*a* at frequency $f_a$, data point 163*b* at frequency $f_b$, data point 163*c* at frequency $f_c$, data point 163*d* at frequency $f_d$, and data point 163*e* at frequency $f_e$. Each data point 163 in FIG. 10 may include an amplitude value (e.g., amplitude $A_a$ may be associated with data point 163*a*) or a frequency (e.g., frequency $f_a$ may be associated with data point 163*a*). The frequencies associated with the data points 163 in FIG. 10 may have particular values. For example, the detector bandwidth Δf may be 5 GHz, and the frequencies $f_a$, $f_b$, $f_c$, $f_d$, and $f_e$ may have respective values of approximately 1 GHz, 2 GHz, 3 GHz, 4 GHz, and 5 GHz. Other frequency-domain-type data points 163 associated with the signal characteristic 162 in FIG. 9 or 10 may include (i) an amplitude of the frequency-domain voltage signal 234 at a particular frequency or at a center frequency or (ii) an area or an average amplitude associated with the frequency-domain voltage signal 234. Additionally, the signal characteristic 162 in FIG. 9 or 10 may include the optical frequency $v_3$ that the probe beam 120*pr* was set to when the voltage signal 234 was obtained.

A processor of a coherent Raman spectroscopy system 100 may associate a determined signal characteristic 162 with a Raman frequency shift. For example, the signal characteristic 162 in FIG. 7 may be associated with a Raman frequency shift having a frequency $v_1-v_3$, which is the difference between the pump-beam frequency $v_1$ and the probe-beam frequency $v_3$. A sample 150 under investigation may include a material with a Raman spectrum having a peak at a frequency Ω, which is approximately equal to $v_1-v_{RP}$, the difference between the pump-beam frequency $v_1$ and the Raman-signal peak frequency $v_{RP}$. The peak frequency Ω may be approximately equal to a vibrational frequency of the material and may correspond to a Raman frequency shift of Ω (e.g., when excited with light at a frequency v, the material may produce Raman-shifted light at the frequencies $v+\Omega$ and $v-\Omega$). In FIG. 7, the probe beam 120*pr* is being used to measure the Raman signal 160 at the probe-frequency $v_3$, and the resulting signal characteristic 162 that is determined may be associated with a Raman spectrum of the material at the frequency $v_1-v_3$, which may be referred to as a Raman frequency shift of $v_1-v_3$.

Figure 11:
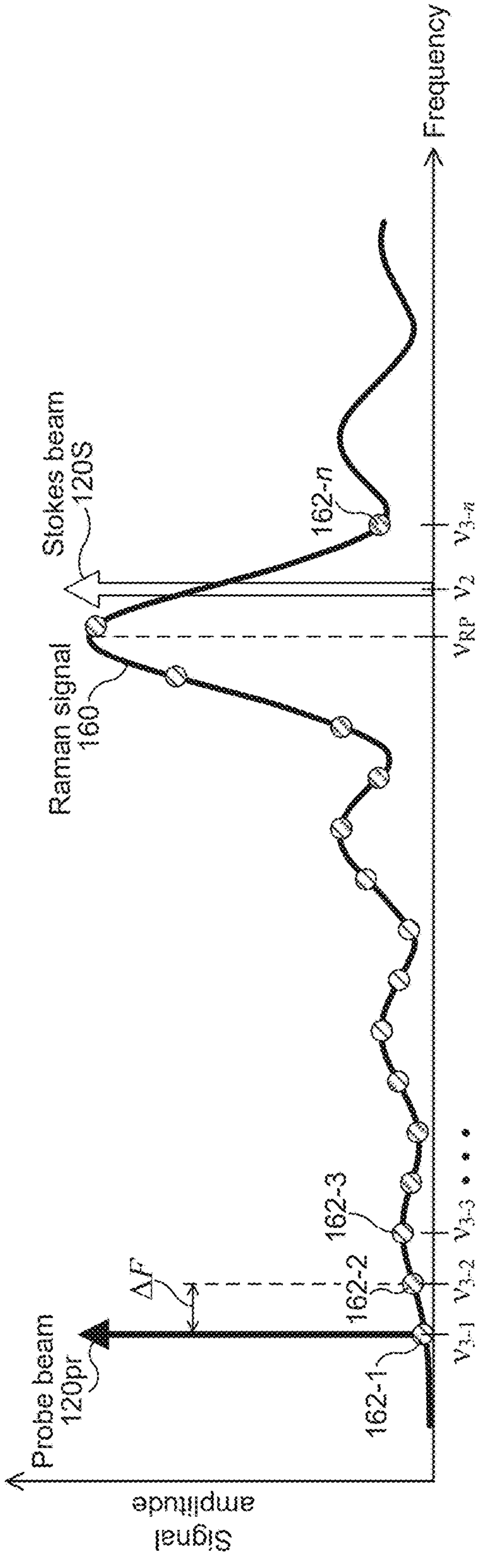
FIG. 11 illustrates an example Raman signal that is measured at multiple probe frequencies.

FIG. 11 illustrates an example Raman signal 160 that is measured at multiple probe frequencies $v_3$. The probe beam 120*pr* is tuned to multiple different probe frequencies ($v_{3-1}$, $v_{3-2}$, $v_{3-3}$, . . . $v_{3-n}$) to measure multiple respective signal characteristics (162-1, 162-2, 162-3, . . . 162-*n*) of the Raman signal 160. The Raman signal 160 is produced by coherent Raman scattering of pump and Stokes beams within a sample 150. Throughout the measurements of the multiple signal characteristics 162 in FIG. 11, the pump-beam frequency $v_1$ and the Stokes-beam frequency $v_2$ may remain substantially constant so that the resulting Raman signal 160 also remains substantially constant (e.g., the Raman signal may exhibit substantially the same shape and amplitude throughout the measurements). The number n of signal characteristics 162 that are measured may be 1, 5, 10, 50, 100, 500, 1,000, or any other suitable number of signal characteristics. At each of the n probe frequencies, the probe beam 120*pr* may be coherently mixed with a spectral portion of the Raman signal 160 that is within a particular frequency range of the probe frequency $v_3$ (e.g., within Δf of the probe frequency, as illustrated in FIG. 7) to measure one signal characteristic 162. Each signal characteristic 162 may provide information about the Raman signal 160 in the frequency region from $v_3-\Delta f$ to $v_3+\Delta f$. Based on one or more measured signal characteristics 162, a processor may determine (i) whether a particular material is present in a sample or (ii) an amount or a concentration of the particular material in the sample.

At each of the n probe frequencies, a single measurement may be performed, or multiple measurements may be performed. For example, with the probe beam 120*pr* in FIG. 11 set to the probe-beam frequency $v_{3-1}$, an optical receiver 200 may measure a single photocurrent signal i and produce a corresponding single digital output signal 240. From that one output signal 240, a processor may determine a signal characteristic 162-1. Alternatively, with the probe beam 120*pr* in FIG. 11 set to the probe-beam frequency $v_{3-1}$, an optical receiver 200 may measure a series of multiple photocurrent signals i (e.g., 2, 4, 10, 20, 50, 100, or any other suitable number of signals) and produce multiple corresponding digital output signals 240. A processor may determine one signal characteristic 162-1 from the multiple digital output signals. For example, the processor may average or otherwise combine the multiple digital output signals 240 to produce one signal characteristic 162-1. Measurement of a series of multiple photocurrent signals i may improve the measurement accuracy by averaging out noise or removing outliers from the measurements.

By tuning the probe-beam frequency $v_3$ to multiple frequencies across at least a portion of a Raman signal 160, a coherent Raman spectroscopy system 100 may measure the Raman signal at multiple points 162. For example, the probe-beam frequency $v_3$ in FIG. 6 may be tuned across at least a portion of the frequency range between $v_2-F_2$ and $v_2-F_1$ or between $v_2+F_1$ and $v_2+F_2$. Each of the different probe-beam frequencies to which the probe beam 120*pr* is changed may be offset from an adjacent probe-beam frequency by a frequency increment ΔF between approximately 10 MHz and approximately 10 GHz. For example, the probe-beam frequency in FIG. 11 may be changed in frequency increments ΔF of approximately 5 GHz as it is tuned across at least a portion of the Raman signal 160. Each signal characteristic 162 in FIG. 11 is plotted along the x-axis at the probe frequency $v_3$ at which the signal characteristic was obtained. The y-axis in FIG. 11 may represent an amplitude or area associated with the signal characteristics 162. For example, each signal characteristic 162 in FIG. 11 may be plotted along the y-axis at a value corresponding to an amplitude or an area of an electronic signal from which the signal characteristic was obtained.

A probe light source 110*pr* of a coherent Raman spectroscopy system 100 may include a wavelength-tunable laser, where the frequency $v_3$ of the probe beam 120*pr* is adjustable by changing the wavelength of light produced by the wavelength-tunable laser. For example, a wavelength-tunable laser may be adjustable over a wavelength range having a width between approximately 10 nm and approximately 100 nm. As another example, the wavelength-tuning range of a wavelength-tunable laser may be between approximately 1000 nm and approximately 1100 nm, between approximately 1490 nm and approximately 1570 nm, or between approximately 1600 nm and approximately 1690 nm. A wavelength-tunable laser may be continuously tunable over a wavelength-tuning range or may be tunable to multiple discrete wavelengths within a wavelength-tuning range. For example, a wavelength-tunable laser may be continuously tunable to any wavelength between 1530 nm and 1570 nm. Alternatively, a wavelength-tunable laser may be tunable to a set of approximately 10, 100, or 1,000 discrete wavelengths between 1530 nm and 1570 nm (e.g., the wavelengths may be separated from one another by approximately 4 nm, 0.4 nm, or 0.04 nm, respectively). A probe light source 110*pr* may include a wavelength-tunable laser that sequentially changes the probe-beam frequency $v_3$ to multiple different frequencies. For example, the probe-beam frequency in FIG. 6 may be tuned to approximately 100 different frequencies between the frequencies $v_2-F_2$ and $v_2-F_1$. At each of the different probe-beam frequencies, the probe beam 120*pr* and a spectral portion of the Raman signal 160 may be coherently mixed at a detector 220 to produce a corresponding electronic signal, and a processor may determine a signal characteristic 162 based on the electronic signal.

In FIG. 11, the probe beam 120*pr* may initially be set to the probe-beam frequency $v_{3-1}$ and coherently mixed at a detector 220 with a spectral portion of the Raman signal 160 around the probe frequency $v_{3-1}$. For example, the spectral portion of the Raman signal 160 may include optical frequency components of the Raman signal from $v_{3-1}-\Delta f$ to $v_{3-1}+\Delta f$, where Δf is the electronic bandwidth of the optical detector 220. A processor may determine a signal characteristic 162-1 based on the electronic signal resulting from the coherent mixing of the probe beam 120*pr* at frequency $v_{3-1}$ and the associated spectral portion of the Raman signal 160. After measuring the Raman signal 160 around the probe frequency $v_{3-1}$, the probe light source 110*pr* may change the probe-beam frequency by a frequency change ΔF to the frequency $v_{3-2}$. The probe frequency $v_{3-2}$ is equal to $v_{3-1}+\Delta F$, and the frequency change ΔF between adjacent frequencies may be between approximately 10 MHz and approximately 10 GHz. The frequency change ΔF may be a fixed value or may be dynamically adjusted during a measurement of a Raman signal 160. After the probe-beam frequency is changed to $v_{3-2}$, the probe beam 120*pr* may be coherently mixed with the spectral portion of the Raman signal 160 around the probe frequency $v_{3-2}$ (e.g., the spectral portion may include optical frequency components of the Raman signal from $v_{3-2}-\Delta f$ to $v_{3-2}+\Delta f$). A processor may determine a signal characteristic 162-2 based on the electronic signal resulting from the coherent mixing of the probe beam 120*pr* at frequency $v_{3-2}$ and the associated spectral portion of the Raman signal 160. After measuring the Raman signal 160 around the probe frequency $v_{3-2}$, the probe light source 110*pr* may change the probe-beam frequency by the frequency change ΔF to the frequency $v_{3-3}$, and a measurement of the Raman signal 160 around the frequency $v_{3-3}$ may be performed. The Raman spectroscopy system 100 may sequentially change the frequency $v_3$ of the probe light source and measure a spectral portion of the Raman signal 160 at each frequency until reaching the final probe frequency $v_{3-n}$. During the measurements, the probe-beam frequency $v_3$ may be tuned so that it avoids overlapping with the frequency $v_2$ of the Stokes beam to prevent mixing between the probe and Stokes beams.

Figure 12:
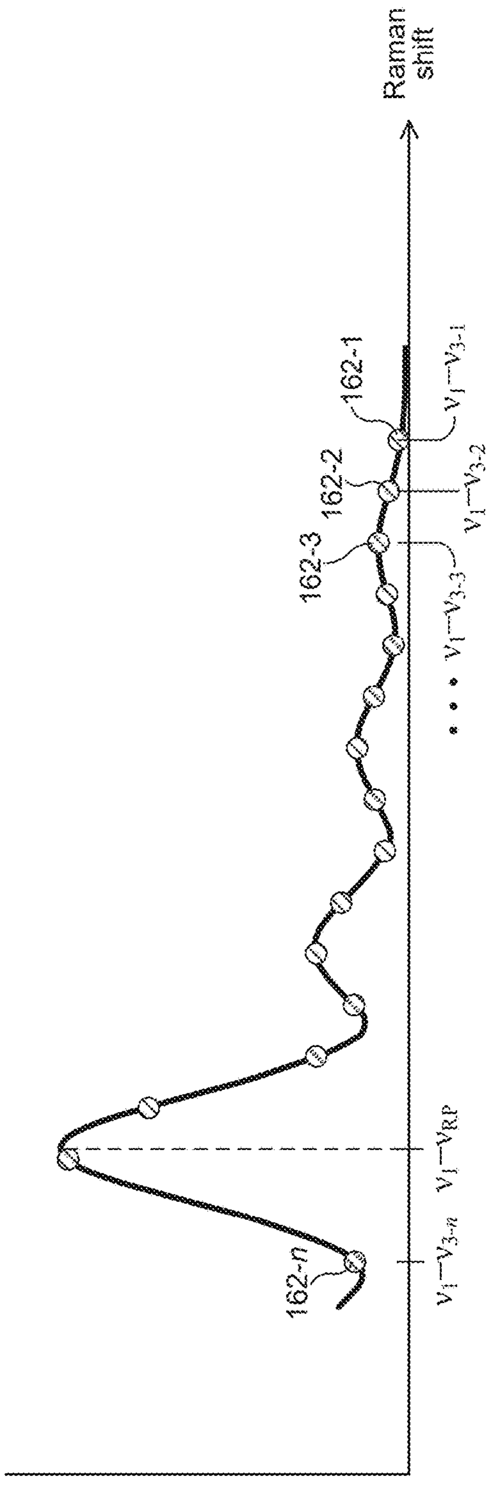
FIG. 12 illustrates an example Raman spectrum corresponding to the Raman signal of FIG. 11.

FIG. 12 illustrates an example Raman spectrum corresponding to the Raman signal of FIG. 11. A Raman spectroscopy system 100 may measure a sample 150 and determine the signal characteristics 162 of the Raman signal 160 in FIG. 11, and the corresponding Raman spectrum in FIG. 12 may represent the Raman spectrum of one or more materials that are part of the sample 150. For example, the sample 150 may include glucose and the peak frequency $v_1-v_{RP}$ of the Raman spectrum may be approximately equal to a frequency Ω of a molecular vibration of glucose. A processor of the Raman spectroscopy system 100 may determine the Raman spectrum in FIG. 12 based on the signal characteristics 162 (and the associated probe-beam frequencies $v_3$) of the Raman signal 160 in FIG. 11. Each signal characteristic 162 of a Raman signal 160 measured at a probe frequency $v_3$ may be associated with a Raman frequency shift having a frequency $v_1-v_3$, where $v_1$ is the pump-beam frequency. To determine the Raman spectrum, each signal characteristic 162 may be transformed from its Raman-signal frequency $v_3$ to a corresponding Raman-shift frequency $v_1-v_3$. For example, the processor may associate the signal characteristic 162-1 at frequency $v_{3-1}$ in FIG. 11 with a Raman shift having the frequency $v_1-v_{3-1}$ in FIG. 12. Similarly, the signal characteristic 162-2 at frequency $v_{3-2}$ in FIG. 11 may be associated with a Raman shift having the frequency $v_1-v_{3-2}$ in FIG. 12, and the signal characteristic 162-3 at frequency $v_{3-3}$ in FIG. 11 may be associated with a Raman shift having the frequency $v_1-v_{3-3}$ in FIG. 12. Additionally, the peak frequency $v_{RP}$ of the Raman signal 160 in FIG. 11 may correspond to the Raman-signal peak in FIG. 12 with a frequency of $v_1-v_{RP}$, which in turn may correspond to the vibrational frequency Ω of a particular material.

Based on the Raman spectrum in FIG. 12, a processor may determine (i) whether a particular material is present in a sample 150 or (ii) an amount or a concentration of the particular material in the sample 150. For example, the processor may compare one or more peaks, signal characteristics 162, or other features of the Raman spectrum in FIG. 12 to a previously determined Raman spectrum for glucose. If one or more peaks or characteristics 162 of the Raman spectrum in FIG. 12 match or line up with peaks or characteristics of the Raman spectrum for glucose, then the processor may determine that glucose is present in the sample 150. Alternatively, if the Raman spectrum in FIG. 12 is missing one or more peaks or characteristics of the Raman spectrum for glucose, then the processor may determine that little or no glucose is present in the sample 150. As another example, the processor may determine the amount or concentration of glucose in the sample 150 based on the Raman spectrum in FIG. 12. The concentration of glucose in the sample 150 may be related to the amplitude or height of one or more peaks of the Raman spectrum in FIG. 12 (e.g., the glucose concentration may be approximately proportional to the height of one or more Raman peaks). The concentration of glucose may then be determined based at least in part on the height of the Raman peak located at the Raman-shift frequency $v_1-v_{RP}$.

Figure 13:
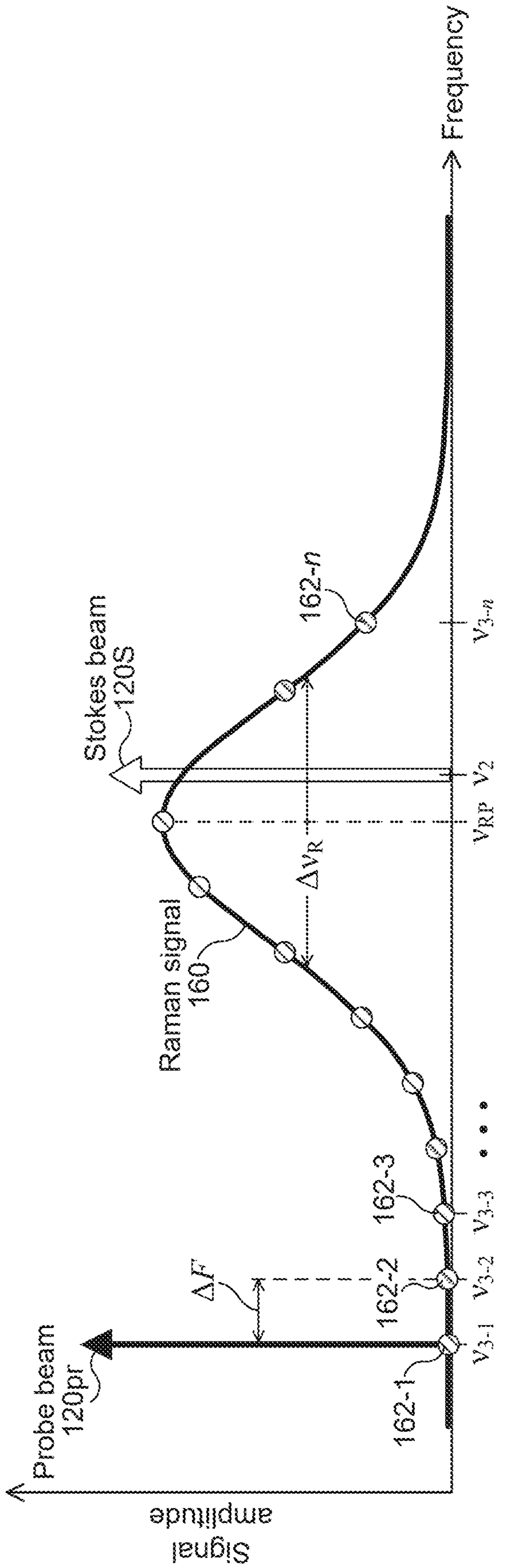
FIG. 13 illustrates another example Raman signal that is measured at multiple probe frequencies.

FIG. 13 illustrates another example Raman signal 160 that is measured at multiple probe frequencies. The probe beam 120*pr* is tuned to multiple different probe frequencies ($v_{3-1}$, $v_{3-2}$, $v_{3-3}$, . . . $v_{3-n}$) to measure multiple respective signal characteristics (162-1, 162-2, 162-3, . . . 162-*n*) of the Raman signal 160. The Raman signal 160 in FIG. 13 has a single peak centered at frequency $v_{RP}$ with a spectral linewidth of $\Delta v_R$. The Raman signal 160 in FIG. 11 has one main peak located at frequency $v_{RP}$ along with multiple smaller peaks located on either side of the main peak. A Raman signal 160 may include a single peak (e.g., as illustrated in FIG. 13) or may include multiple peaks (e.g., as illustrated in FIG. 11).

Figure 14:
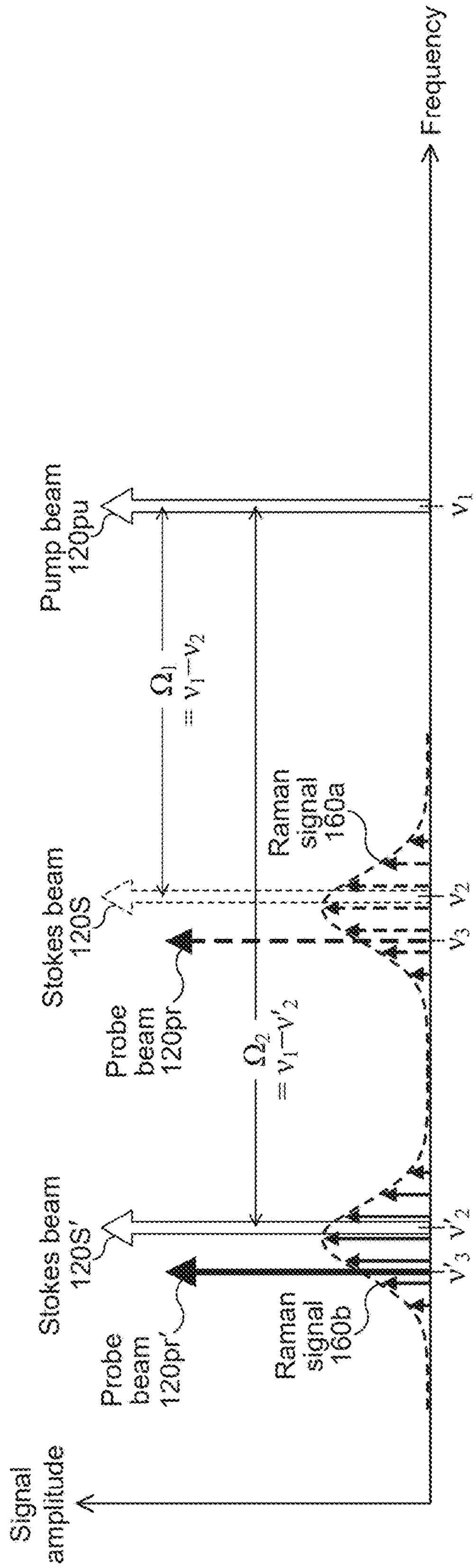
FIGS. 14-15 each illustrate a second example Raman signal obtained by changing the frequency offset between a pump beam and a Stokes beam.
Figure 15:
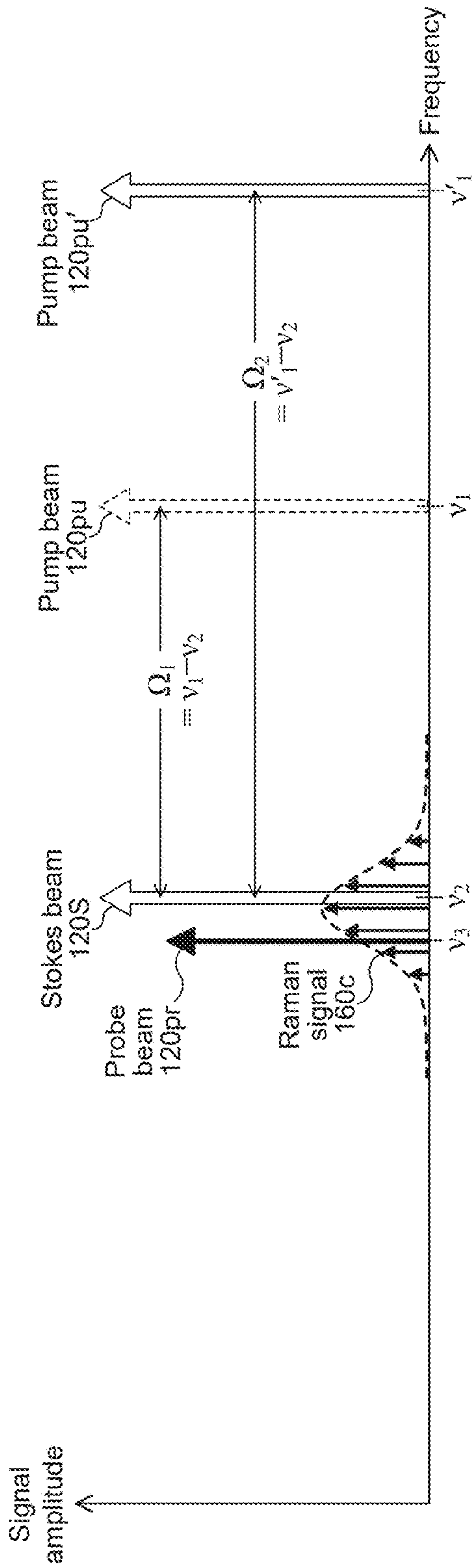

FIGS. 14-15 each illustrate a second example Raman signal obtained by changing the frequency offset Ω between a pump beam 120*pu* and a Stokes beam 120S. A coherent Raman spectroscopy system 100 may include a pump light source 110*pu* or a Stokes light source 110S with a wavelength-tunable laser, and the frequency offset Ω may be adjustable by changing the wavelength of the wavelength-tunable laser. A wavelength-tunable pump or Stokes laser may be continuously tunable over a wavelength-tuning range or may be tunable to multiple discrete wavelengths within a wavelength-tuning range. For example, Stokes beam 120 in FIG. 14 may be produced by a continuously tunable laser diode that can produce light at the frequencies $v_2$ and $$v_2'.$$

As another example, a Stokes laser 110S may include two fixed-wavelength laser diodes that operate at the respective frequencies $v_2$ and $$v_2'.$$

Similarly, pump beam 120*pu* in FIG. 15 may be produced by a continuously tunable laser diode that can produce light at the frequencies $v_1$ and $$v_1',$$

or a pump laser 110*pu* may include two fixed-wavelength laser diodes that operate at the respective frequencies $v_1$ and $$v_1'.$$

In FIG. 14, the pump frequency $v_1$ is fixed, and the Stokes frequency is changed from $v_2$ to $$v_2'$$

to change the frequency offset from $\Omega_1$ to $\Omega_2$. Frequency offset $\Omega_1$ equals $v_1-v_2$, and frequency offset $\Omega_2$ equals $$v_1 - v_2'.$$

In FIG. 15, the Stokes frequency $v_2$ is fixed, and the pump frequency is changed from $v_1$ to $v'_1$ to change the frequency offset from $\Omega_1$ to $\Omega_2$. Frequency offset $\Omega_1$ equals $v_1-v_2$, and frequency offset $\Omega_2$ equals $$v_1' - v_2.$$

In other embodiments, both the pump and Stokes frequencies may be changed to change the frequency offset Ω from one value to another.

FIG. 14 includes two Raman signals 160*a* and 160*b*. Initially, a Stokes light source 110S may produce a Stokes beam 120S at the frequency $v_2$ to produce the frequency offset $\Omega_1$ between the Stokes beam and the pump beam 120*pu*, where $\Omega_1=v_1-v_2$. For example, the Stokes beam 120S may have a frequency $v_2$ of 193 THz, and the pump beam 120*pu* may have a frequency $v_1$ of 207 THz, which corresponds to a frequency offset $\Omega_1$ of 14 THz (or, 467 $cm^{-1}$). The Raman signal 160*a* is produced by coherent Raman scattering of the Stokes beam 120S and pump beam 120*pu* within a sample 150. The Raman signal 160*a* is centered at or near the frequency $v_2$ of the Stokes beam 120S, and the frequency $v_3$ of the probe beam 120*pr* overlaps the Raman signal 160*a* and is relatively close to the frequency $v_2$ of the Stokes beam 120S (e.g., the probe-beam frequency $v_3$ may be within 200 GHz of the Stokes-beam frequency $v_2$). The probe beam 120*pr* and a spectral portion of the Raman signal 160*a* may be coherently mixed at a detector 220 to produce an electronic signal, from which a signal characteristic 162 may be determined. Additionally, the frequency $v_3$ of the probe beam 120*pr* may be tuned across at least a portion of the Raman signal 160*a* to measure multiple signal characteristics 162 associated with the Raman signal.

After measuring the first Raman signal 160*a*, the Stokes light source 110S may change the frequency of the Stokes beam to produce a Stokes beam 120S' at the frequency $$v_2',$$

resulting in a frequency offset of $\Omega_2$ between the Stokes beam 120S' and the pump beam 120*pu*, where $$\Omega_2 = v_1 - v_2'.$$

For example, the Stokes beam 120S may be changed to a frequency $$v_2'$$

of 182 THz, and the pump-beam frequency $v_1$ may remain at 207 THz, which corresponds to a frequency offset $\Omega_1$ of 25 THz (or, 834 $cm^{-1}$). The second Raman signal 160*b* is produced by coherent Raman scattering of the Stokes beam 120S' and pump beam 120*pu* within the sample 150. The Raman signal 160*b* is centered at or near the frequency $$v_2'$$

of the Stokes beam 120S'. Additionally, a probe light source 110*pr* may change the frequency of the probe beam to produce a probe beam 120*pr*' at a frequency $$v_3'$$

that overlaps the Raman signal 160*b* and is relatively close to the frequency $$v_2'$$

of the Stokes beam 120S' (e.g., the probe-beam frequency $$v_3'$$

may be within 200 GHz of the Stokes-beam frequency $$v_2').$$

The probe beam 120*pr*' and a spectral portion of the Raman signal 160*b* may be coherently mixed at a detector 220 to produce an electronic signal, from which a signal characteristic 162 may be determined. Additionally, the frequency $$v_3'$$

of the probe beam 120*pr*' may be tuned across at least a portion of the second Raman signal 160*b* to measure multiple signal characteristics 162 associated with the Raman signal.

The two Raman signals 160*a* and 160*b* in FIG. 14 may correspond to two respective peaks of a Raman spectrum of a material that is in the sample 150. One Raman peak, associated with Raman signal 160*a*, is located at a frequency of approximately $\Omega_1$, and the frequency $\Omega_1$ may correspond to a vibrational frequency of the material. The other Raman peak, associated with Raman signal 160*b*, is located at a frequency of approximately $\Omega_2$, and the frequency $\Omega_2$ may correspond to another vibrational frequency of the material. A Raman spectroscopy system 100 may perform measurements of signal characteristics 162 at 1, 2, 4, 10, 20, or 50 different values of the frequency offset Ω. The frequency offset Ω between the Stokes beam 120S and the pump beam 120*pu* may be set to each of the different frequency-offset values to produce an associated Raman signal 160. At each value of Ω, the frequency $v_3$ of the probe beam 120*pr* may be tuned across at least a portion of the Raman signal 160 to measure multiple signal characteristics 162 associated with the Raman signal. Then, the frequency of the Stokes beam or pump beam may be adjusted to the next value of Ω, where another measurement of an associated Raman signal 160 is performed. Based on the signal characteristics 162 associated with each of the values of the frequency offset Ω, a processor may determine (i) whether a particular material is present in a sample or (ii) an amount or a concentration of the particular material in the sample.

FIG. 15 includes the Raman signal 160*c*. A first Raman signal (similar to Raman signal 160*a* in FIG. 14) may be approximately overlapped with the second Raman signal 160*c* in FIG. 15, and for clarity, the first Raman signal is not included in FIG. 15. Initially, a Stokes light source 110S may produce a Stokes beam 120S at the frequency $v_2$, and a pump light source 110*pu* may produce a pump beam 120*pu* at the frequency $v_1$, which results in the frequency offset $\Omega_1$ between the Stokes and pump beams in FIG. 15. For example, the Stokes beam 120S may have a frequency $v_2$ of 193 THz, and the pump beam 120_pu_ may have a frequency $v_1$ of 207 THz, which corresponds to a frequency offset $\Omega_1$ of 14 THz (or, 467 $cm^{-1}$). A first Raman signal (similar to Raman signal 160_a_ in FIG. 14) is produced by coherent Raman scattering of the Stokes beam 120S and pump beam 120_pu_ within a sample 150. The first Raman signal may be centered at or near the frequency $v_2$ of the Stokes beam 120S, and the frequency $v_3$ of the probe beam 120_pr_ may overlap the first Raman signal and may be relatively close to the frequency $v_2$ of the Stokes beam of light 120S. The probe beam 120_pr_ and a spectral portion of the first Raman signal may be coherently mixed at a detector 220 to produce an electronic signal, from which a signal characteristic 162 may be determined. Additionally, the frequency $v_3$ of the probe beam 120_pr_ may be tuned across at least a portion of the first Raman signal to measure multiple signal characteristics 162 associated with the first Raman signal.

In FIG. 15, after measuring the first Raman signal, the pump light source 110_pu_ may change the frequency of the pump beam 120_pu_ from $v_1$ to $$v_1'.$$

This results in a frequency offset of $\Omega_2$ between the Stokes beam 120S and the pump beam 120_pu_', where $$\Omega_2 = v_1' - v_2.$$

For example, the pump beam may be changed to a frequency $$v_1'$$

of 218 THz, and the Stokes-beam frequency $v_2$ may remain at 193 THz, which corresponds to a frequency offset $\Omega_1$ of 25 THz (or, 834 $cm^{-1}$). The second Raman signal 160_c_ is produced by coherent Raman scattering of the Stokes beam 120S and pump beam 120_pu_' within the sample 150. As with the first Raman signal, the Raman signal 160_c_ is centered at or near the frequency $v_2$ of the Stokes beam 120S, and the frequency $v_3$ of the probe beam 120_pr_ overlaps the Raman signal 160_c_ and is relatively close to the frequency $v_2$ of the Stokes beam of light 120S (e.g., the probe-beam frequency $v_3$ may be within 200 GHz of the Stokes-beam frequency $v_2$). The probe beam 120_pr_ and a spectral portion of the Raman signal 160_c_ may be coherently mixed at a detector 220 to produce an electronic signal, from which a signal characteristic 162 may be determined. Additionally, the frequency $v_3$ of the probe beam 120_pr_ may be tuned across at least a portion of the Raman signal 160_c_ to measure multiple signal characteristics 162 associated with the Raman signal.

In FIG. 15, the first Raman signal (which may be similar to Raman signal 160_a_ in FIG. 14) and the second Raman signal 160_c_ may correspond to two different peaks of a Raman spectrum of a material that is in the sample 150. One Raman peak, associated with the first Raman signal, is located at a frequency of approximately $\Omega_1$, and the frequency $\Omega_1$ may correspond to a vibrational frequency of the material. The other Raman peak, associated with Raman signal 160_c_, is located at a frequency of approximately $\Omega_2$, and the frequency $\Omega_2$ may correspond to another vibrational frequency of the material. Based at least in part on the signal characteristics 162 associated with the two frequency offsets $\Omega_1$ and $\Omega_2$, a processor may determine (i) whether a particular material is present in a sample or (ii) an amount or a concentration of the particular material in the sample.

Figure 16:
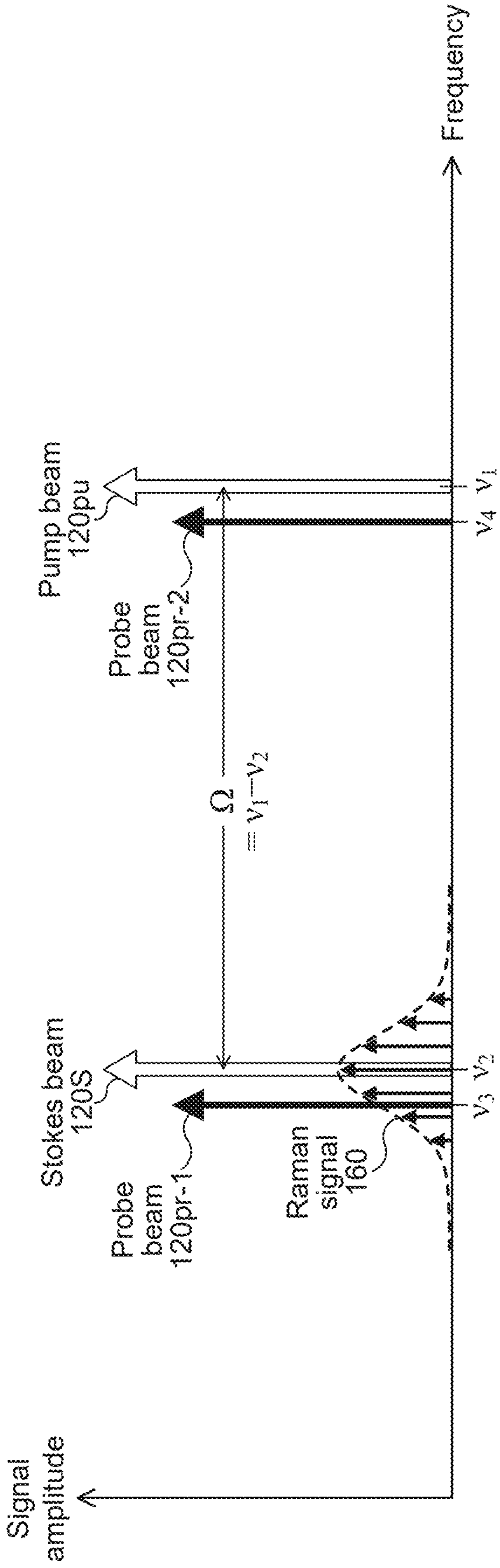
FIG. 16 illustrates an example Raman signal along with two probe beams of light.

FIG. 16 illustrates an example Raman signal 160 along with two probe beams of light 120_pr_-1 and 120_pr_-2. The Raman signal 160 may be produced by coherent Raman scattering of the pump beam 120_pu_ and Stokes beam 120S within a sample 150. The frequency of the pump beam 120_pu_ is $v_1$, and the frequency of the Stokes beam 120S is $v_2$, which corresponds to a frequency offset $\Omega$ equal to $v_1-v_2$. The Raman signal 160 is centered at or near the frequency $v_2$ of the Stokes beam 120S (e.g., the center frequency of the Raman signal 160 may be within 200 GHz of $v_2$). The first probe beam 120_pr_-1 may be used to measure the Raman signal 160, and the second probe beam 120_pr_-2 may be used to measure the pump beam 120_pu_.

The frequency $v_3$ of first probe beam 120_pr_-1 overlaps the Raman signal 160 and is relatively close to the frequency $v_2$ of the Stokes beam 120S (e.g., $v_3$ may be within 200 GHz of $v_2$). The probe beam 120_pr_-1 and a spectral portion of the Raman signal 160 may be coherently mixed at a detector 220 to produce an electronic signal, from which a signal characteristic 162 may be determined. Additionally, the frequency $v_3$ of the probe beam 120_pr_-1 may be tuned across at least a portion of the Raman signal 160 to measure multiple signal characteristics 162 associated with the Raman signal.

The frequency $v_4$ of the second probe beam 120_pr_-2 is relatively close to the frequency $v_1$ of the pump beam 120_pu_ (e.g., $v_4$ may be within 50 GHz of $v_1$). For example, the frequency $v_4$ of the second probe beam 120_pr_-2 may be offset from the frequency $v_1$ of the pump beam 120_pu_ by approximately 10 GHz, 5 GHz, or 1 GHz. Alternatively, the frequency $v_4$ of the second probe beam 120_pr_-2 may be approximately equal to the frequency $v_1$ of the pump beam 120_pu_. After the pump beam 120_pu_ has interacted with the sample, the probe beam 120_pr_-2 may be coherently mixed with the pump beam. For example, after the pump and Stokes beams have produced the Raman signal 160 and after the pump beam has exited the sample, the pump and probe beams may be coherently mixed together at a detector 220 to produce an electronic signal, from which a signal characteristic may be determined.

Figure 17:
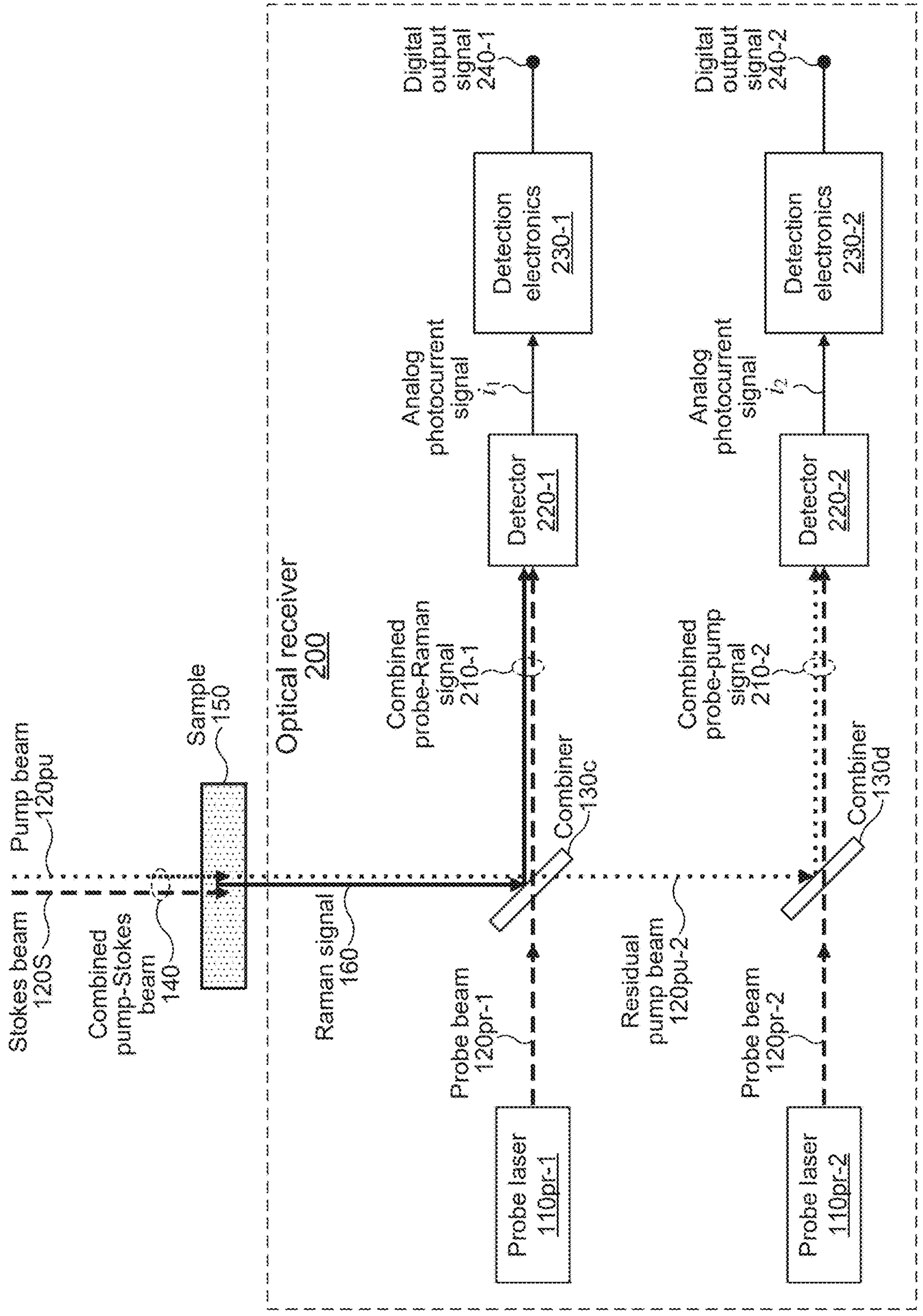
FIG. 17 illustrates an example optical receiver for measuring the Raman signal and pump beam of light from FIG. 16.

FIG. 17 illustrates an example optical receiver 200 for measuring the Raman signal 160 and pump beam of light 120_pu_ from FIG. 16. The combined pump-Stokes beam 140 (which includes pump beam 120_pu_ and Stokes beam 120S) is directed to a sample 150, which produces a Raman signal 160 in response to the pump and Stokes beams. The Raman signal 160 may be collected by one or more optical elements and directed to the optical receiver 200. Additionally, residual light from the pump beam 120_pu_ may be collected and directed to the optical receiver 200 as a residual pump beam 120_pu_-2. The residual pump beam 120_pu_-2 may include light from the pump beam 120_pu_ after the pump beam has interacted with and exited the sample 150. The optical receiver 200 in FIG. 17 may be referred to as a two-channel optical receiver that includes two parallel measurement channels for separately detecting and measuring the Raman signal 160 and the residual pump beam 120_pu_-2. The first measurement channel detects the Raman signal 160 and includes probe laser 110_pr_-1, detector 220-1, and detection electronics 230-1. The second measurement channel detects the residual pump beam 120$pu$-2 and includes probe laser 110$pr$-2, detector 220-2, and detection electronics 230-2.

The Raman signal 160 and the residual pump beam 120$pu$-2 are directed to the combiner 130$c$, which may be a dichroic beamsplitter, and the combiner 130$c$ reflects the Raman signal 160 and transmits the residual pump beam 120$pu$-2. The combiner 130$c$ also transmits at least a portion of the probe beam 120$pr$-1 produced by the probe laser 110$pr$-1 and combines the probe beam 120$pr$-1 with the Raman signal 160 to produce a combined probe-Raman signal 210-1. The probe-Raman signal 210-1 is sent to the detector 220-1, where the probe beam 120$pr$-1 and a spectral portion of the Raman signal 160 are coherently mixed to produce a photocurrent signal $i_1$. The detection electronics 230-1 receives the photocurrent signal $i_1$ and produces a digital output signal 240-1 that corresponds to the photocurrent signal $i_1$.

The combiner 130$d$ (which may be a dichroic or a non-dichroic beamsplitter) reflects at least a portion of the residual pump beam 120$pu$-2 and transmits at least a portion of the probe beam 120$pr$-2 produced by the probe laser 110$pr$-2. The combiner 130$d$ combines the probe beam 120$pr$-2 with the residual pump beam 120$pu$-2 to produce a combined probe-pump signal 210-2, which is sent to the detector 220-2. The probe beam 120$pr$-2 and the residual pump beam 120$pu$-2 are coherently mixed at the detector 220-2 to produce a photocurrent signal $i_2$, and the detection electronics 230-2 produces a digital output signal 240-2 that corresponds to the photocurrent signal $i_2$.

The two digital output signals 240-1 and 240-2 may be sent to a processor which determines a signal characteristic 162 of each of the photocurrent signals $i_1$ and $i_2$ based on the digital output signals. Additionally, the frequency of the first probe beam 120$pr$-1 may be tuned across at least a portion of the Raman signal 160 to measure multiple signal characteristics 162 associated with the Raman signal. If the frequency $v_1$ of the pump beam 120$pu$ remains fixed, the frequency $v_4$ of the second probe beam 120$pr$-2 may also remain fixed. Alternatively, if the frequency $v_1$ of the pump beam 120$pu$ is changed (e.g., to switch to a different frequency offset Ω), the frequency of the probe beam 120$pr$-2 may also be switched to maintain a particular frequency offset between the pump and probe frequencies.

Measurement of the residual pump beam 120$pu$-2 may be performed two or more times to determine how the power of the pump beam changes when the Raman signal 160 is produced. For example, the residual pump beam 120$pu$-2 may be measured once when the Stokes beam 120S is turned off (and no Raman signal 160 is produced) and another time when the Stokes beam is turned on (and the Raman signal 160 is produced). A processor may determine the change in the power of the residual pump beam 120$pu$-2 associated with the Stokes beam 120S being turned off and on. Since at least part of the Raman signal 160 may be produced by Stokes-shifted photons from the pump beam 120$pu$, a decrease in the power of the residual pump beam 120$pu$-2 may correspond to the power of the Raman signal.

In another embodiment of a two-channel optical receiver, the optical receiver may not include a second probe laser 110$pr$-2. Instead, the residual pump beam 120$pu$-2 may be sent to a detector 220 for direct detection without mixing the residual pump beam with another signal.

Figure 18:
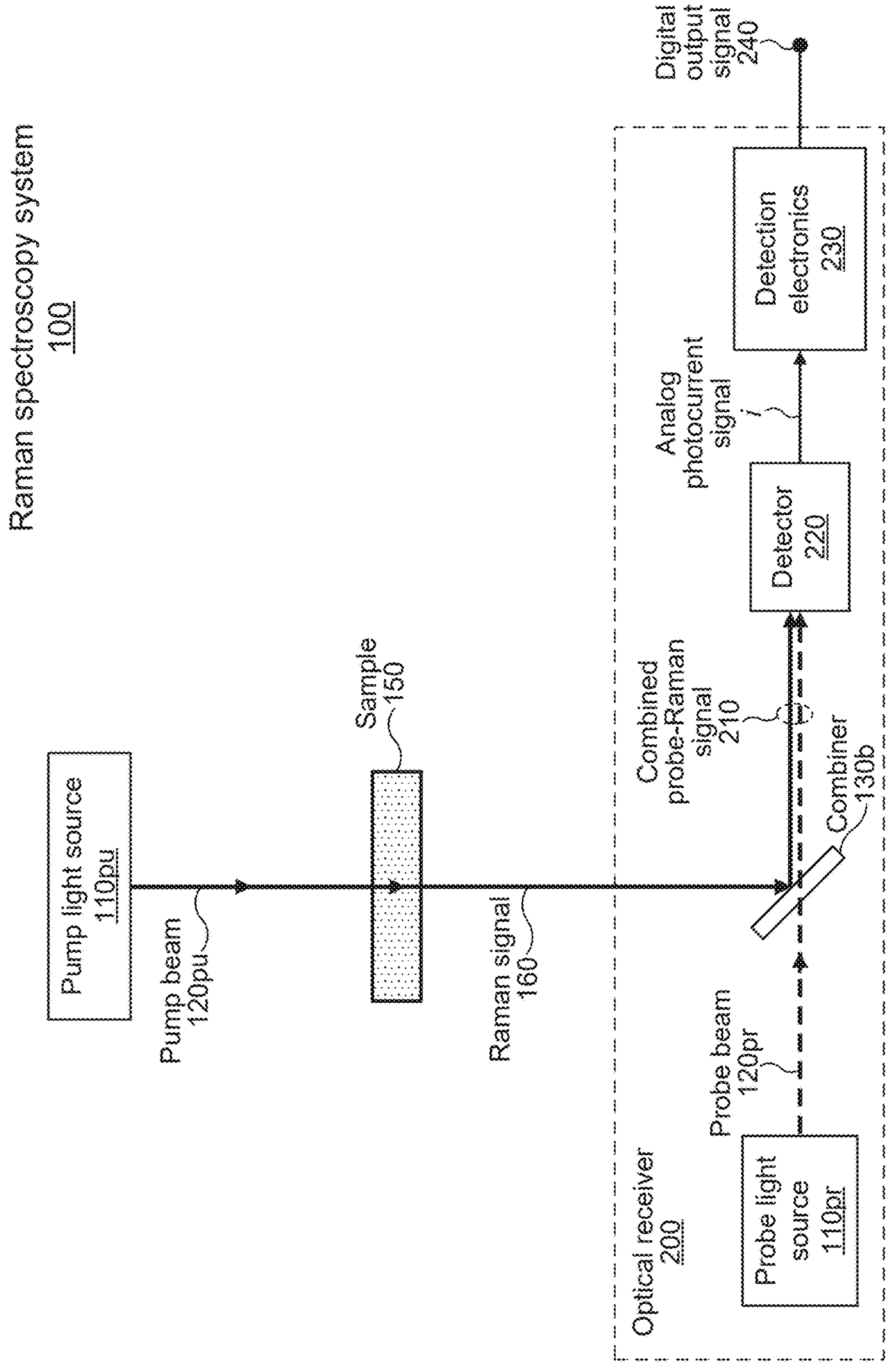
FIG. 18 illustrates an example Raman spectroscopy system for measuring a Raman signal produced by spontaneous Raman scattering.

FIG. 18 illustrates an example Raman spectroscopy system 100 for measuring a Raman signal 160 produced by spontaneous Raman scattering. Instead of producing a Raman signal by coherent Raman scattering of pump and Stokes beams within a sample (e.g., as illustrated in FIGS. 1-2), the Raman signal 160 in FIG. 18 is produced by spontaneous Raman scattering of the pump beam of light 120$pu$ within the sample 150. While the production of the Raman signal 160 in FIG. 18 is different from that of the Raman spectroscopy systems of FIGS. 1-2, the optical receiver 200 and the Raman-signal detection technique in FIG. 18 is similar to that of FIGS. 1-2. In FIG. 18, the Raman signal 160 is detected by coherently mixing the Raman signal with a probe beam of light 120$pr$.

The Raman spectroscopy system 100 in FIG. 18 includes a pump light source 110$pu$ that produces a pump beam of light 120$pu$ at a pump frequency $v_1$. The pump beam 120$pu$ is directed to a sample 150 (e.g., by one or more optical elements), and the sample 150 produces a Raman signal 160 by spontaneous Raman scattering of light from the pump beam. The spontaneous Raman signal 160 is collected (e.g., by one or more optical elements) and directed to the optical receiver 200. The optical receiver 200 includes a probe light source 110$pr$ that produces a probe beam of light 120$pr$ at a probe frequency $v_3$, where the probe frequency overlaps the Raman signal. The optical combiner 130$b$, which may be a dichroic or a non-dichroic beamsplitter, combines the Raman signal 160 and the probe beam 120$pr$ to produce a combined probe-Raman signal 210 that is directed to a detector 220. The detector 220 coherently mixes a spectral portion of the Raman signal 160 with the probe beam 120$pr$ to produce a photocurrent signal i. The detection electronics 230 may produce (i) an analog voltage signal that corresponds to the photocurrent signal i and (ii) a digital output signal 240 that corresponds to the photocurrent signal or the voltage signal. The digital output signal 240 may be sent to a processor, and the processor may determine a signal characteristic 162 of the photocurrent signal or voltage signal based on the digital output signal 240.

Figure 19:
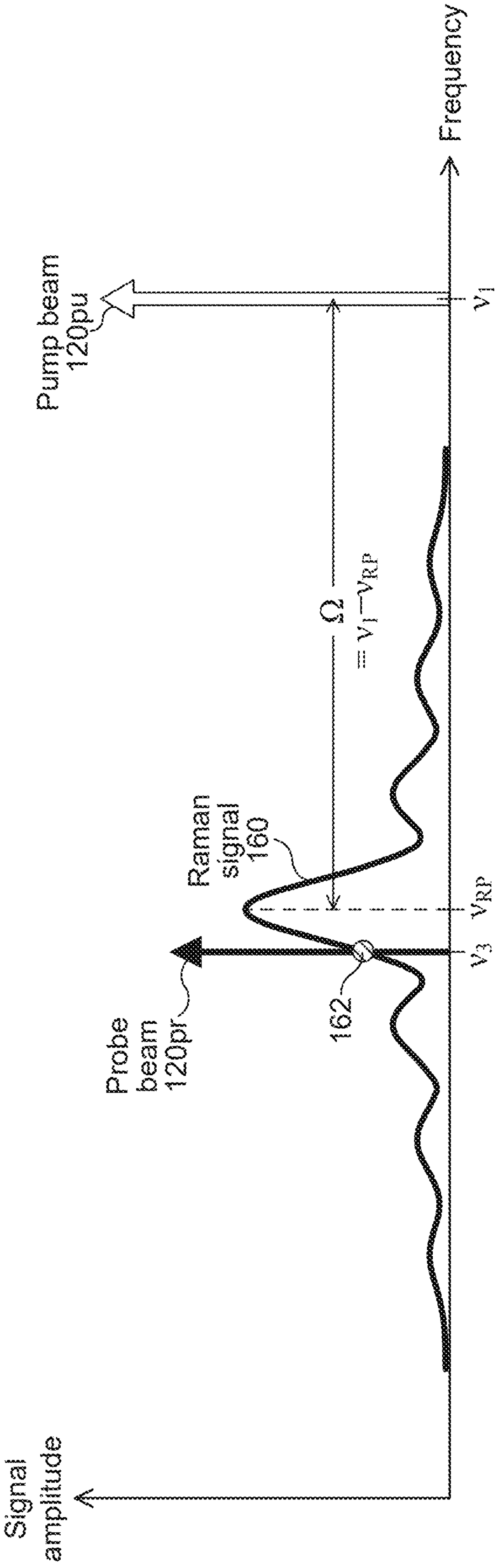
FIG. 19 illustrates an example Raman signal produced by the Raman spectroscopy system of FIG. 18.

FIG. 19 illustrates an example Raman signal produced by the Raman spectroscopy system of FIG. 18. The Raman signal 160 produced by spontaneous Raman scattering of the pump beam 120$pu$ has a peak frequency of $v_{RP}$. The frequency offset Ω between the pump beam and the peak frequency of the Raman signal equals $v_1 - v_{RP}$, and the frequency offset Ω may correspond to a vibrational frequency of a material that is part of the sample 150. In FIG. 19, the probe beam 120$pr$ may be coherently mixed with a spectral portion of the Raman signal 160 that is within a particular frequency range of the probe frequency $v_3$ to measure one signal characteristic 162. Additionally, the probe light source 110$pr$ in FIG. 18 may include a wavelength-tunable laser that tunes the probe beam 120$pr$ to multiple frequencies across at least a portion of the Raman signal 160, and the optical receiver 200 may measure multiple respective signal characteristics 162 associated with the Raman signal.

Figure 20:
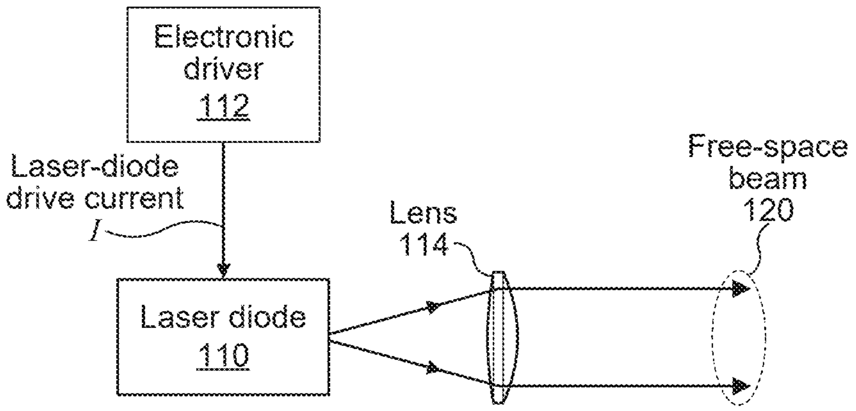
FIG. 20 illustrates an example laser diode that produces a free-space beam of light.

FIG. 20 illustrates an example laser diode 110 that produces a free-space beam of light 120. The laser diode 110 in FIG. 20 may be part of a pump light source 110$pu$, a Stokes light source 110S, or a probe light source 110$pr$, and the free-space beam 120 may be a pump beam 120$pu$, a Stokes beam 120S, or a probe beam 120$pr$. For example, the probe laser 110$pr$ in FIG. 2 may be similar to the laser diode 110 in FIG. 20, and the probe laser 110$pr$ may produce a free-space probe beam 120$pr$ that is combined with the Raman signal 160 by a free-space beam combiner 130$b$. In FIG. 20, the electronic driver 112 supplies laser-diode drive current I to the laser diode 110, and the laser diode produces output light that is collimated by a lens 114 to produce a collimated free-space beam 120. In other embodiments, a lens 114 may produce a focused free-space beam 120 (e.g., the lens may focus the free-space beam onto a sample 150). The laser current I supplied to the laser diode 110 may be a substantially constant DC current resulting in an output beam of light 120 having a substantially constant optical power. Additionally or alternatively, the laser current I may include pulses of current resulting in an output beam 120 that includes corresponding pulses of light.

The output beam of light 120 produced by the laser diode 110 may have a spectral linewidth of less than approximately 200 MHz, 100 MHz, 50 MHz, 10 MHz, 1 MHz, or 100 KHz. The laser diode 110 in FIG. 20 may be a wavelength-tunable laser diode where the wavelength of the output beam 120 is adjustable over a wavelength range having a width between approximately 10 nm and approximately 100 nm. For example, the operating wavelength of the laser diode 110 may be tunable over at least a portion of one of the following wavelength ranges: 1000 nm to 1100 nm; 1220 nm to 1450 nm; 1490 nm to 1570 nm; 1600 nm to 1690 nm. Alternatively, the laser diode 110 in FIG. 20 may be a fixed-wavelength laser diode. For example, the laser diode 110 in FIG. 20 may be a distributed feedback (DFB) laser diode with a spectral linewidth of less than 1 MHz, and the output beam 120 may have any suitable substantially fixed wavelength between approximately 600 nm and approximately 2000 nm.

Figure 21:
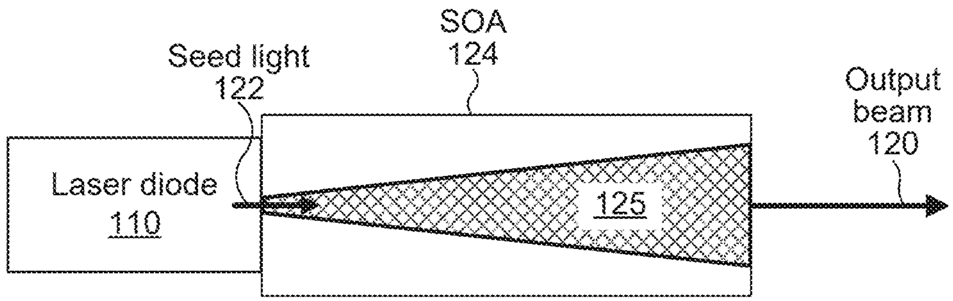
FIG. 21 illustrates an example laser diode that produces seed light that is amplified by a semiconductor optical amplifier (SOA).

FIG. 21 illustrates an example laser diode 110 that produces seed light 122 that is amplified by a semiconductor optical amplifier (SOA) 124. Instead of directly emitting an output beam 120 (e.g., as illustrated in FIG. 20), the light from a laser diode 110 may first be amplified by an optical amplifier. The laser diode 110 in FIG. 21 acts as a seed laser that produces seed light 122 that is coupled into the input end of the waveguide 125 of the SOA 124. The SOA waveguide 125 in FIG. 21 is indicated by the cross-hatched region within the SOA 124. The SOA 124 amplifies the seed light as it propagates within the waveguide from the input end to the output end, and the output beam of light 120 is emitted from the output end of the SOA. The optical gain provided by the SOA may come from electrical current that is supplied to the SOA by an electronic driver (not illustrated in FIG. 21). For example, an electronic driver 112 may supply substantially constant DC electrical current to the laser diode 110 and to the SOA 124, and the resulting output beam 120 may have substantially constant optical power. The output beam 120 may be a free-space beam, or the output beam 120 may be coupled into an optical fiber or into a waveguide of a photonic integrated circuit (PIC).

The laser diode 110 and the SOA 124 in FIG. 21 may be fabricated or integrated together on the same chip so that seed light 122 from the laser diode is directly coupled into the waveguide 125 of the SOA. The waveguide 125 of the SOA 124 may be a tapered optical waveguide (as illustrated in FIG. 21) with a width that increases along a lateral direction from the input end that receives the seed light 122 to the output end that emits the output beam 120. A light source that includes a seed laser diode 110 that supplies seed light 122 that is amplified by a SOA 124 (as illustrated in FIG. 21) may be referred to as a master-oscillator power-amplifier laser (MOPA laser). The seed laser diode 110 may be referred to as a master oscillator, and the SOA 124 may be referred to as a power amplifier. The MOPA laser in FIG. 21 may be part of a pump light source 110*pu*, a Stokes light source 110S, or a probe light source 110*pr*, and the output beam of light 120 may be a pump beam 120*pu*, a Stokes beam 120S, or a probe beam 120*pr*.

Figure 22:
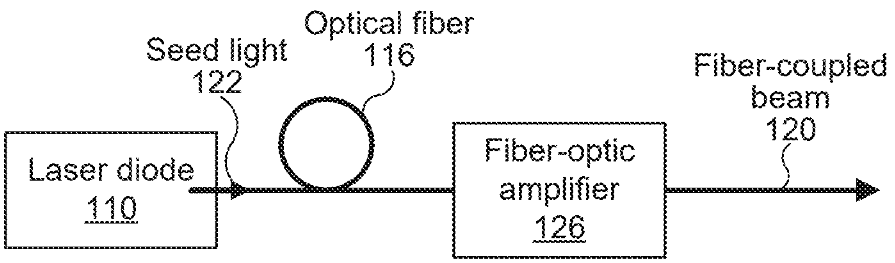
FIG. 22 illustrates an example laser diode that produces seed light that is amplified by a fiber-optic amplifier.

FIG. 22 illustrates an example laser diode 110 that produces seed light 122 that is amplified by a fiber-optic amplifier 126. The laser diode 110 in FIG. 22 acts as a seed laser that produces seed light 122 that is coupled into an optical fiber 116. The optical fiber 116 directs the seed light 122 to the fiber-optic amplifier 126, and the fiber-optic amplifier amplifies the seed light as it propagates through an optical gain fiber of the fiber-optic amplifier. The optical gain fiber may be doped with rare-earth ions (e.g., neodymium, erbium, or ytterbium) or bismuth that provide the optical gain to the seed light. One or more pump lasers may optically pump the active material (e.g., rare-earth ions or bismuth ions) in the optical gain fiber, which in turn provide optical amplification to the seed light 122 propagating through the gain fiber. The amplified seed light produced by the fiber-optic amplifier 126 propagates in an optical fiber as a fiber-coupled output beam 120. The laser diode 110 and fiber-optic amplifier 126 in FIG. 22 may be part of a pump light source 110*pu*, a Stokes light source 110S, or a probe light source 110*pr*, and the fiber-coupled output beam 120 may be directed to an optical combiner 130, a sample 150, or a detector 220.

A pump light source 110*pu*, a Stokes light source 110S, or a probe light source 110*pr* may include a seed laser diode 110 followed by an optical amplifier. The seed laser diode 110 may produce seed light 122 that is amplified by the optical amplifier to produce an output beam of light 120. An optical amplifier may include a SOA 124 (e.g., as illustrated in FIG. 21) or a fiber-optic amplifier 126 (e.g., as illustrated in FIG. 22). In some embodiments, an optical amplifier may include a SOA 124 followed by a fiber-optic amplifier 126. For example, a seed laser diode 110 may produce seed light 122 that is first amplified by a SOA 124 and then further amplified by a fiber-optic amplifier 126.

In some embodiments, a pump light source 110*pu*, a Stokes light source 110S, or a probe light source 110*pr* may include a laser diode 110 and an optical fiber 116 and may not include a fiber-optic amplifier. For example, light produced by a laser diode 110 may be coupled into an optical fiber 116 to produce a fiber-coupled beam 120, and the optical fiber may direct the laser-diode light to an optical combiner 130, a sample 150, or a detector 220. A laser diode 110 that produces a fiber-coupled beam 120 may be referred to as a fiber-coupled laser diode.

Figure 23:
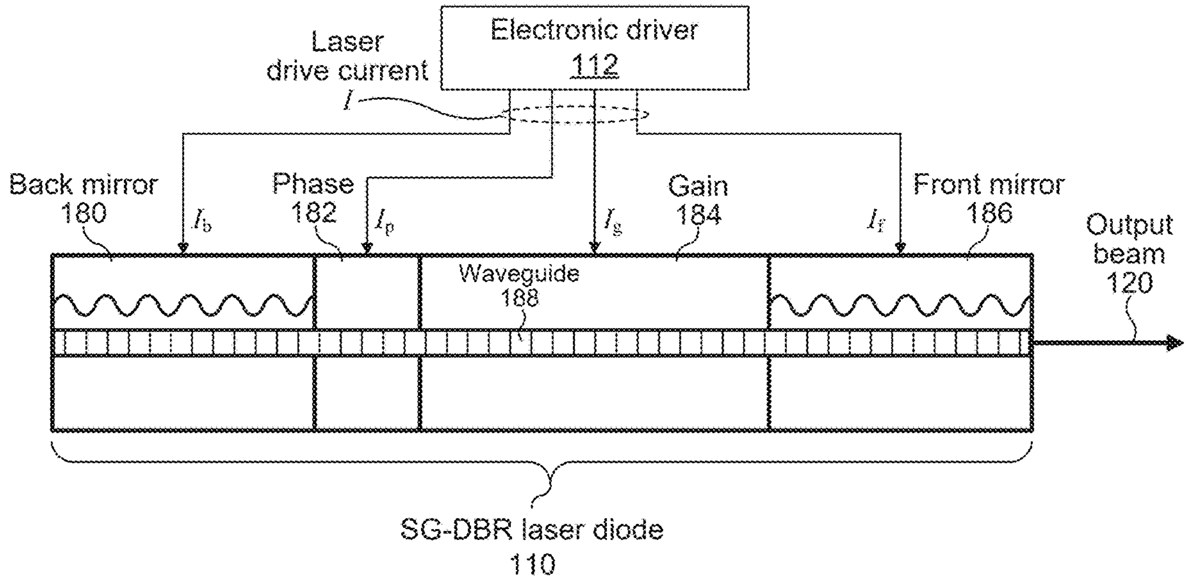
FIG. 23 illustrates an example sampled-grating distributed Bragg reflector (SG-DBR) laser.

FIG. 23 illustrates an example sampled-grating distributed Bragg reflector (SG-DBR) laser 110. An SG-DBR laser 110 is a wavelength-tunable laser diode that produces an output beam 120 that can be tuned over a wavelength range having a width of between 20 nm and 50 nm. For example, an SG-DBR laser 110 may have a 40-nm wavelength-tuning range from approximately 1530 nm to approximately 1570 nm or from approximately 1630 nm to approximately 1670 nm. The SG-DBR laser 110 in FIG. 23 may be part of a pump light source 110*pu*, a Stokes light source 110S, or a probe light source 110*pr*, and the output beam 120 may be a pump beam 120*pu*, a Stokes beam 120S, or a probe beam 120*pr*. For example, an SG-DBR laser 110 may be part of a probe light source 110*pr* that produces the probe beam 120*pr* in FIG. 6, and the SG-DBR laser may tune the frequency $v_3$ of the probe beam across at least a portion of the Raman signal 160. An SG-DBR laser 110 may produce a free-space beam 120, a fiber-coupled beam 120, or a beam that is coupled into a waveguide of a PIC. Alternatively, an SG-DBR laser 110 may be integrated with a SOA 124 that amplifies the light produced by the SG-DBR laser (e.g., as illustrated in FIG. 21).

The SG-DBR laser 110 in FIG. 23 includes a back mirror 180, a phase section 182, a gain section 184, and a front mirror 186, where the phase and gain sections are located between the front and back mirrors. The laser diode current I supplied to the SG-DBR laser 110 includes the following: current $I_b$ supplied to the back mirror 180, current $I_p$ supplied to the phase section 182, current $I_g$ supplied to the gain section 184, and current $I_f$ supplied to the front mirror 186. The gain current $I_g$ provides optical gain to the optical waveguide 188 of the SG-DBR laser 110, and the other currents may be used to set the wavelength of the output beam 120 produced by the SG-DBR laser. The electronic driver 112 may supply particular combinations of electrical currents to the back mirror 180, phase section 182, gain section 184, and front mirror 186, where each particular combination of electrical currents causes the SG-DBR laser 110 to produce an output beam 120 at a particular wavelength. For example, an SG-DBR laser 110 may be part of a wavelength-tunable probe light source 110*pr* that produces the probe beam 120*pr* in FIG. 11, and the electronic driver 112 may supply particular different combinations of the electrical currents $I_b$, $I_p$, $I_g$, and $I_f$ to produce the different probe frequencies $v_{3\text{-}1}$, $v_{3\text{-}2}$, $v_{3\text{-}3}$, . . . and $v_{3\text{-}n}$ to tune the probe beam across at least a portion of the Raman signal 160 in FIG. 11.

Figure 24:
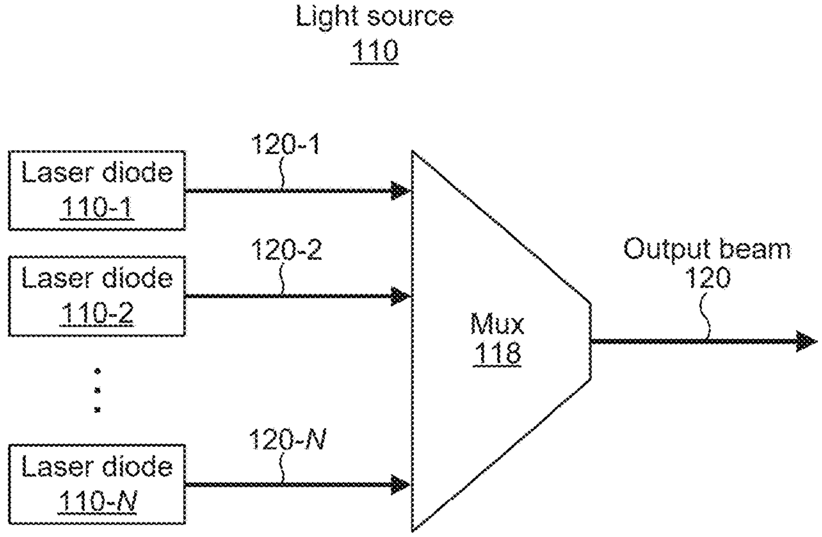
FIG. 24 illustrates an example light source with multiple laser diodes and an optical multiplexer that combines light produced by the laser diodes into a single output beam of light.

FIG. 24 illustrates an example light source 110 with multiple laser diodes 110 and an optical multiplexer 118 that combines light produced by the laser diodes into a single output beam of light 120. Each of the laser diodes 110-1, 110-2, . . . 110-N produces a respective output beam 120-1, 120-2, . . . 120-N, and the optical multiplexer 118 combines the output beams into the output beam of light 120. The light source 110 may be configured to switch between operating the N laser diodes one at a time so that, at any given time, only one laser diode produces light, and the output beam 120 includes just the light produced by that one laser diode.

The optical multiplexer 118 may be a free-space device, a fiber-optic device, a waveguide-based device, or a metamaterial-based device, and the multiplexer may combine N different wavelengths of light from the N laser diodes into a single output beam 120. The optical multiplexer 118 may include one or more of the following: a free-space diffraction grating; an arrayed waveguide grating (AWG); a metamaterial that acts as a diffractive optical element; one or more optical filters; one or more optical combiners; one or more optical switches (e.g., thermo-optic switches, liquid crystal switches, electro-optic switches, mechanical optical switches, or microelectromechanical systems (MEMS) switches); a series of two or more fiber Bragg gratings with optical circulators.

The light source 110 in FIG. 24 may be a pump light source 110*pu*, a Stokes light source 110S, or a probe light source 110*pr*, and the output beam 120 may be a pump beam 120*pu*, a Stokes beam 120S, or a probe beam 120*pr*. The output beam 120 may be a free-space beam, or the output beam 120 may be coupled into an optical fiber or into a waveguide of a photonic integrated circuit (PIC). For example, each of the laser diodes 110-1, 110-2, . . . 110-N may produce a fiber-coupled beam 120-1, 120-2, . . . 120-N, and the optical multiplexer 118 may be a fiber-optic device that produces a fiber-coupled output beam 120. The output beam 120 may be sent to an optical combiner 130, a sample 150, or a detector 220. Alternatively, the light source 110 may include an optical amplifier (e.g., an SOA or a fiber-optic amplifier) located after the optical multiplexer 118, and the output beam 120 may be coupled from the multiplexer to an optical amplifier that provides optical amplification to the output beam.

The light source 110 in FIG. 24 includes N laser diodes 110-1, 110-2, . . . 110-N, where N is an integer greater than or equal to 2. Each of the N laser diodes 110 in FIG. 24 may be a wavelength-tunable laser diode or a fixed-wavelength laser diode. For example, the light source in FIG. 24 may include (i) N wavelength-tunable laser diodes, (ii) N fixed-wavelength laser diodes, or (iii) one or more wavelength-tunable laser diodes and one or more fixed-wavelength laser diodes. The light source 110 in FIG. 24 may be referred to as a wavelength-tunable light source, a frequency-tunable light source, or a tunable light source. A wavelength-tunable light source may include one or more continuously tunable laser diodes (e.g., SG-DBR laser diodes); multiple fixed-wavelength laser diodes (e.g., multiple DFB laser diodes), each laser diode operating at a different wavelength; or any combination thereof.

The light source 110 in FIG. 24 may be a pump light source 110*pu* or a Stokes light source 110S that includes N fixed-wavelength laser diodes, each laser diode having a different operating wavelength. The wavelength of the output beam 120 produced by the wavelength-tunable light source 110 in FIG. 24 may be adjustable to any wavelength of N different wavelengths by selecting one of the N fixed-wavelength laser diodes for operation. The frequency offset Ω between the pump beam 120*pu* and Stokes beam 120S may be adjustable by selecting one of the fixed-wavelength laser diodes for operation. For example, the Stokes beams 120S and 120S' in FIG. 14 may be produced by the light source 110 in FIG. 24. Laser diode 110-1 may be a fixed-wavelength laser diode operating at the frequency $v_2$, and laser diode 110-2 may be a fixed-wavelength laser diode operating at the frequency $$v_2'.$$

Selecting laser diode 110-1 for operation produces the frequency offset $\Omega_1$ in FIG. 14, and selecting laser diode 110-2 for operation produces the frequency offset $\Omega_2$.

The light source 110 in FIG. 24 may operate only one of the N laser diodes 110 at any given time. Each of the laser diodes 110 may operate at a particular wavelength or over a particular range of wavelengths, and one of the laser diodes may be selected for operation based on the wavelength that is needed to perform a particular measurement. For example, the pump beams 120*pu* and 120*pu*' in FIG. 15 may be produced by the light source 110 in FIG. 24. Laser diode 110-1 may be a fixed-wavelength laser diode operating at the frequency $v_1$, and laser diode 110-2 may be a fixed-wavelength laser diode operating at the frequency $$v_1'.$$

During a first measurement period, laser diode 110-1 may be operated to produce output beam 120-1 at the frequency $v_1$, and the other laser diodes 110-2 to 110-N may be turned off or otherwise configured to not produce light. The multiplexer 118 receives the output beam 120-1 from the laser diode 110-1 and directs it to the output of the multiplexer to produce the output beam 120 having a frequency $v_1$. During a second measurement period, the Raman signal 160*c* in FIG. 15 may be measured, and laser diode 110-2 may be operated to produce output beam 120-2 at the frequency $$v_1'.$$

The other laser diodes (i.e., laser diodes 110-1 to 110-N, excluding laser diode 110-2) may be turned off or otherwise configured to not produce light. The multiplexer 118 receives the output beam 120-2 from the laser diode 110-2 and directs it to the output of the multiplexer to produce the output beam 120 having a frequency $$v_1'.$$

The light source 110 in FIG. 24 may be a probe light source that includes N wavelength-tunable laser diodes. The probe light source may be configured to tune over one or more wavelength ranges having a total width between $p \cdot N \cdot \Delta\lambda_{av}$ and $N \cdot \Delta\lambda_{av}$, where $\Delta\lambda_{av}$ is an average wavelength-tuning range of the N laser diodes 110, and p is a wavelength-overlap parameter between 0.5 and 1. For example, if the overlap parameter p has a value of 0.7, then the combined wavelength-tuning range of the N wavelength-tunable laser diodes may be between $(0.7)N \cdot \Delta\lambda_{av}$ and $N \cdot \Delta\lambda_{av}$. The wavelength-overlap parameter p represents the amount of wavelength overlap between adjacent wavelength-tuning ranges (e.g., an overlap value p of 1 indicates that there is no wavelength overlap between the wavelength-tuning ranges). For example, the light source 110 in FIG. 24 may be a probe light source that includes three SG-DBR laser diodes having respective wavelength-tuning ranges of 1490-1530 nm, 1520-1560 nm, and 1550-1590 nm. Each of the SG-DBR laser diodes has a 40-nm tuning range with a 10-nm overlap between adjacent tuning ranges, which results in the light source 110 in FIG. 24 having a 100-nm wavelength-tuning range from 1490 nm to 1590 nm. In this case, the average wavelength-tuning range $\Delta\lambda_{av}$ of the three laser diodes is 40 nm, and the total wavelength-tuning range has a width of 100 nm, which corresponds to the wavelength-overlap parameter p having a value of approximately 0.83. The probe light source 110 may produce an output beam 120 having any wavelength from 1490 nm to 1590 nm by selecting one of the three SG-DBR laser diodes for operation and tuning the laser diode to the desired wavelength. As another example, the light source 110 in FIG. 24 may be a probe light source 110 that includes three SG-DBR laser diodes having respective wavelength-tuning ranges of 1490-1530 nm, 1530-1560, and 1640-1680 nm. Each of the SG-DBR laser diodes has a 40-nm tuning range with no wavelength overlap between adjacent tuning ranges. The average wavelength-tuning range $\Delta\lambda_{av}$ of the three laser diodes is 40 nm, and the total wavelength-tuning range has a width of 120 nm. This corresponds to the wavelength-overlap parameter p having a value of 1, indicating that there is no wavelength overlap between the tuning ranges of the three laser diodes.

Figure 25:
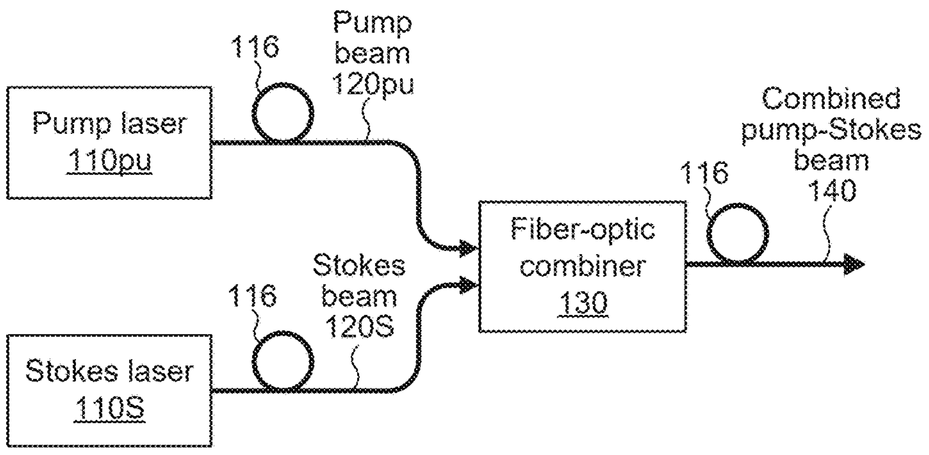
FIG. 25 illustrates an example pump laser and Stokes laser with a fiber-optic combiner that produces a combined pump-Stokes beam coupled into an optical fiber.

FIG. 25 illustrates an example pump laser 110*pu* and Stokes laser 110S with a fiber-optic combiner 130 that produces a combined pump-Stokes beam 140 coupled into an optical fiber 116. A Raman spectroscopy system 100 may include one or more optical elements that direct the pump and Stokes beams to a sample 150. The optical elements may include a combiner 130 that combines the pump beam 120*pu* and the Stokes beam 120S to produce a combined pump-Stokes beam 140 that is directed to a sample 150. In FIG. 1, the combiner 130*a* may be a free-space optical combiner, and the pump beam 120*pu*, Stokes beam 120S, and combined beam 140 may each be free-space beams. The combiner 130 in FIG. 25 is a fiber-optic combiner that receives the pump and Stokes beams via two input optical fibers 116 and combines the two beams into a combined pump-Stokes beam 140 that propagates in an output optical fiber 116. The pump laser 110*pu* may be a fiber-coupled laser diode that produces a pump beam 120*pu* that is directed to the fiber-optic combiner 130 via an input optical fiber 116. Similarly, the Stokes laser 110S may be a fiber-coupled laser diode that produces a Stokes beam 120S that is directed to the fiber-optic combiner 130 via another input optical fiber 116. The pump laser 110*pu* or the Stokes laser 110S may be followed by an optical amplifier (not illustrated in FIG. 25) that amplifies the pump beam 120*pu* or Stokes beam 120S prior to directing the light to the combiner 130. After the fiber-optic combiner 130 combines the pump and Stokes beams, the output optical fiber 116 may direct the combined pump-Stokes beam 140 to a sample 150.

The fiber-optic combiner 130 in FIG. 25 may include a fiber-optic wavelength division multiplexer (WDM) with two input optical fibers (for the pump and Stokes beam) and one output optical fiber for the output beam 120. The WDM may include a dichroic beamsplitter or a fused fiber coupler. Each of the input or output optical fiber 116 may be a single-mode optical fiber or a multi-mode optical fiber.

In some embodiments, instead of using a single pump laser or a single Stokes laser (as illustrated in FIG. 25), a Raman spectroscopy system may use a pump or Stokes light source 110 with multiple laser diodes and an optical multiplexer 118 (e.g., as illustrated in FIG. 24). For example, the light source 110 in FIG. 24 may be a pump light source that produces a fiber-coupled output beam 120 that is coupled to an input fiber of the fiber-optic combiner 130 in FIG. 25. One of the laser diodes of the pump light source may be selected for operation, and the light from the selected laser diode may be directed by the multiplexer 118 to an optical fiber that is coupled to the combiner 130. Additionally or alternatively, the light source 110 in FIG. 24 may be a Stokes light source that produces a fiber-coupled output beam 120 that is coupled to an input fiber of the fiber-optic combiner 130 in FIG. 25.

Figure 26:
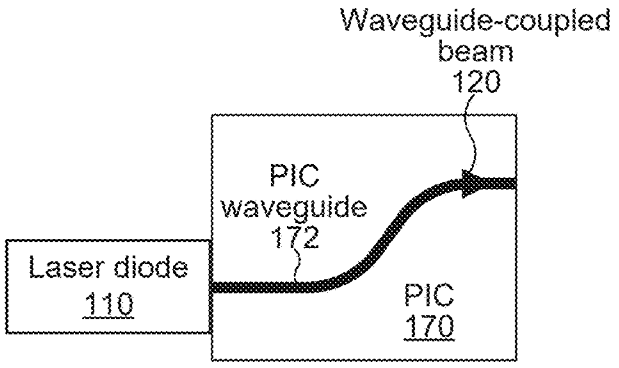
FIG. 26 illustrates an example laser diode coupled to a waveguide of a photonic integrated circuit (PIC).

FIG. 26 illustrates an example laser diode 110 coupled to a waveguide 172 of a photonic integrated circuit (PIC) 170. A PIC 170 (which may be referred to as a planar lightwave circuit (PLC), a waveguide-based device, an integrated-optic device, an integrated optoelectronic device, or a silicon optical bench) may be fabricated from a substrate that includes silicon, indium phosphide, glass (e.g., silica), a polymer, or an electro-optic material (e.g., lithium niobate ($LiNbO_3$) or lithium tantalate ($LiTaO_3$)). A PIC 170 may include one or more optical waveguides 172 that confine and guide a beam of light. An optical waveguide 172 that is part of a PIC 170 may be referred to as a PIC waveguide and may be a passive optical waveguide formed in the PIC, and the waveguide may convey light from one optical element to another with relatively low optical loss.

In FIG. 26, light from the laser diode 110 is coupled into the PIC waveguide 172 to produce a waveguide-coupled beam 120. The PIC waveguide 172 may convey the beam of light 120 from the laser diode 110 to another optical element (e.g., an optical combiner 130, a sample 150, or a detector 220). Light from the laser diode 110 in FIG. 26 may be coupled into the PIC waveguide 172 using one or more lenses, or the laser diode 110 may be butt-coupled to an input of the waveguide so that the light from the laser diode is directly coupled into the waveguide. The laser diode 110 may be mechanically attached or connected to the PIC 170 or to a substrate to which the PIC is also attached. For example, the laser diode 110 may be attached using epoxy, adhesive, or solder. Alternatively, the laser diode 110 in FIG. 26 may be located apart from the PIC 170, and the laser diode may send a beam of light 120 to the PIC 170 via optical fiber. An output end of the optical fiber may be attached or connected to the PIC 170 so that the light is coupled into the PIC waveguide 172. Light from the laser diode 110 may be amplified by an optical amplifier (not illustrated in FIG. 26) prior to being coupled into the PIC waveguide 172. For example, the laser diode 110 in FIG. 26 may be a MOPA laser similar to that illustrated in FIG. 21, and the output beam 120 produced by the MOPA laser may be directly coupled into the PIC waveguide 172.

Figure 27:
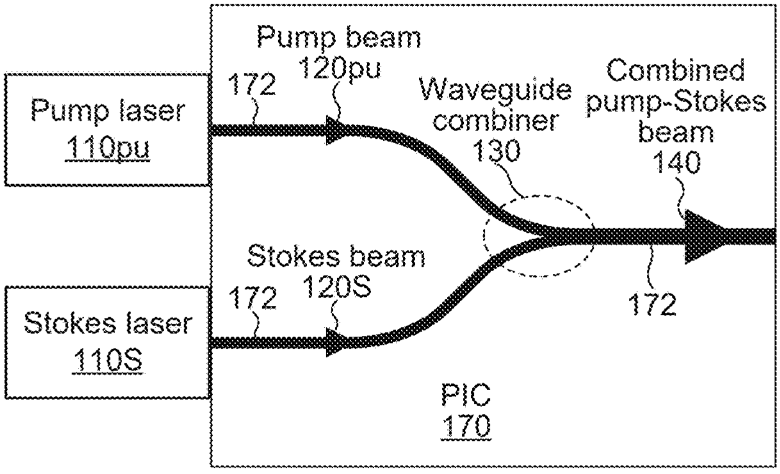
FIG. 27 illustrates an example pump laser and Stokes laser with a photonic integrated circuit (PIC) that produces a combined pump-Stokes beam coupled into an optical waveguide of the PIC.

FIG. 27 illustrates an example pump laser 110*pu* and Stokes laser 110S with a photonic integrated circuit (PIC) 170 that produces a combined pump-Stokes beam 140 coupled into an optical waveguide 172 of the PIC. The PIC 170 includes a waveguide combiner 130 and three PIC waveguides 172 (two input waveguides for the pump and Stokes beams and one output waveguide for the combined pump-Stokes beam 140). The waveguide combiner 130 is a waveguide-based optical combiner that combines the pump beam 120*pu* and the Stokes beam 120S to produce a combined pump-Stokes beam 140. The combined pump-Stokes beam 140 is coupled to an output PIC waveguide 172 of the PIC 170, and the output waveguide may direct the beam to a sample 150. The pump laser 110*pu* or the Stokes laser 110S may be a laser diode that is mechanically attached or connected to the PIC 170 or to a substrate to which the PIC is also attached. Alternatively, the pump laser 110*pu* or the Stokes laser 110S may be a fiber-coupled laser diode that sends a beam of light to the PIC via optical fiber (e.g., an output end of the optical fiber may be attached to the PIC so that the light is coupled into an input PIC waveguide 172).

In some embodiments, instead of using a single pump laser or a single Stokes laser (as illustrated in FIG. 27), a Raman spectroscopy system may use a pump or Stokes light source 110 with multiple laser diodes and an optical multiplexer 118 (e.g., as illustrated in FIG. 24). For example, the light source 110 in FIG. 24 may be a pump or Stokes light source that produces a fiber-coupled output beam 120 that is coupled to an input PIC waveguide 172 of the PIC 170 in FIG. 27. Alternatively, the multiplexer 118 in FIG. 24 may be a waveguide-based device and the output beam 120 may propagate in a PIC waveguide that directs the light to an input optical waveguide 172 of the PIC 170 in FIG. 27.

Figure 28:
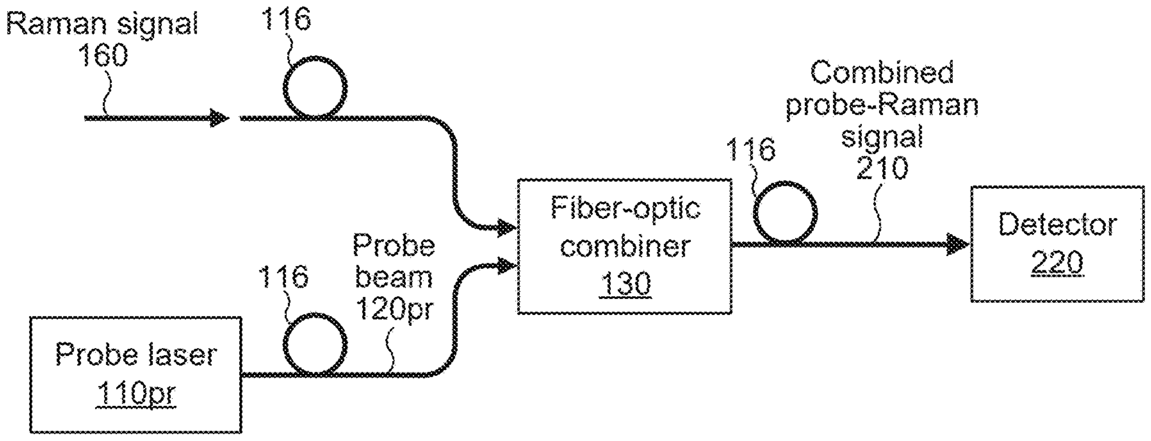
FIG. 28 illustrates an example fiber-optic combiner that combines a Raman signal with a probe beam.

FIG. 28 illustrates an example fiber-optic combiner 130 that combines a Raman signal 160 with a probe beam 120*pr*. An optical receiver 200 may include an optical combiner 130 that combines a Raman signal 160 and a probe beam of light 120*pr* to produce one or more combined probe-Raman signals 210 that are each directed to a detector 220. In FIG. 1, the combiner 130*b* may be a free-space optical combiner, and the Raman signal 160, probe beam 120*pr*, and the combined probe-Raman signal 210 may each be free-space beams. The combiner 130 in FIG. 28 is a fiber-optic combiner that receives the Raman signal 160 and the probe beam 120*pr* via two input optical fibers 116 and combines the two beams into a combined probe-Raman signal 210 that is directed to a detector 220 via an output optical fiber 116. Each of the input or output optical fiber 116 in FIG. 28 may be a single-mode optical fiber or a multi-mode optical fiber.

The Raman signal 160 in FIG. 28 may be a free-space beam that is coupled into an input optical fiber 116 using one or more lenses. The probe laser 110*pr* may be a fiber-coupled laser diode that directs the probe beam 120*pr* to the fiber-optic combiner 130 via optical fiber 116. The probe beam 120*pr* may be amplified by an optical amplifier (not illustrated in FIG. 28) prior to being directed to the combiner 130. In some embodiments, instead of using a single probe laser 110*pr* (as illustrated in FIG. 28), an optical receiver 200 may use a light source 110 with multiple laser diodes and an optical multiplexer 118 (e.g., as illustrated in FIG. 24). For example, the light source 110 in FIG. 24 may be a probe light source that produces a fiber-coupled output beam 120 that is coupled to an input optical fiber 116 of the fiber-optic combiner 130 in FIG. 28.

Figure 29:
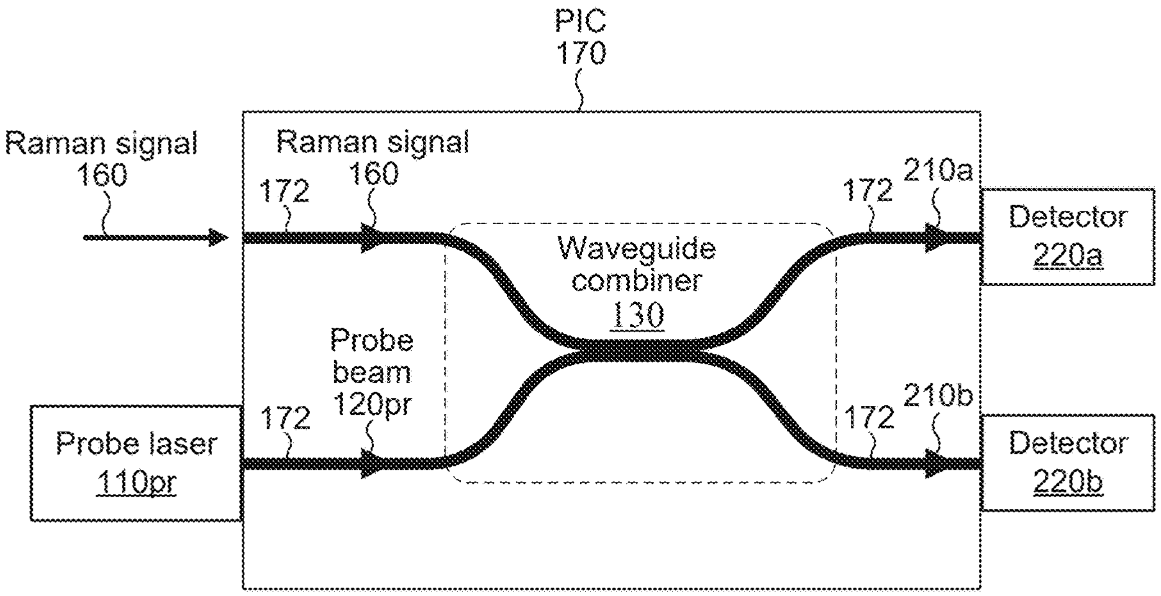
FIG. 29 illustrates an example photonic integrated circuit (PIC) with a waveguide combiner that combines a Raman signal with a probe beam.

FIG. 29 illustrates an example photonic integrated circuit (PIC) 170 with a waveguide combiner 130 that combines a Raman signal 160 with a probe beam 120*pr*. An optical combiner 130 may be a waveguide combiner 130 that is part of a PIC 170 and may combine a Raman signal 160 and a probe beam of light 120*pr* to produce one or more combined probe-Raman signals 210 that are each directed to a detector 220. The waveguide combiner 130 in FIG. 29 receives the Raman signal 160 and the probe beam 120*pr* via two input PIC waveguides 172. A waveguide combiner 130 may produce 1, 2, or 4 combined output beams 210. The waveguide combiner 130 in FIG. 29 combines the Raman signal 160 and the probe beam 120*pr* to produce two combined probe-Raman signals 210*a* and 210*b* which are each directed to a respective detector 220*a* and 220*b* via two output PIC waveguides 172. The PIC 170 in FIG. 29 may be part of an optical receiver 200.

The Raman signal 160 in FIG. 29 may be a free-space beam that is coupled into an input PIC waveguide 172 using one or more lenses. The probe laser 110*pr* may be a laser diode that is mechanically attached or connected to the PIC 170 or to a substrate to which the PIC is also attached. Alternatively, the probe laser 110*pr* may be a fiber-coupled laser diode that sends the probe beam 120*pr* to the PIC 170 via optical fiber (e.g., an output end of the optical fiber may be attached to the PIC so that the light is coupled into an input PIC waveguide 172). The probe beam 120*pr* may be amplified by an optical amplifier (not illustrated in FIG. 29) prior to being coupled into an input PIC waveguide 172. In some embodiments, instead of using a single probe laser 110*pr* (as illustrated in FIG. 29), an optical receiver 200 may use a light source 110 with multiple laser diodes and an optical multiplexer 118 (e.g., as illustrated in FIG. 24), and the probe beam 120*pr* may be delivered from the multiplexer to the PIC 170 via optical fiber or via a waveguide 172 of the PIC.

A Raman spectroscopy system 100 may include one or more optical elements that (i) direct a pump beam 120*pu* and a Stokes beam 120S to a sample 150 and (ii) direct a Raman signal 160 and a probe beam 120*pr* to one or more detectors 220. The optical elements may include one or more PICs 170 that each include one or more optical waveguides 172. One or more of the PIC waveguides 172 may direct the pump beam 120 and the Stokes beam 120*s* to the sample 150. For example, a PIC 170 may include an optical combiner 130 that produces a combined pump-Stokes beam 140 that is directed to the sample by an optical waveguide 172 of the PIC 170. One or more other PIC waveguides 172 may direct the Raman signal 160 and the probe beam 120*pr* to one or more detectors 220. For example, a PIC 170 may include an optical combiner 130 that combines the Raman signal 160 and the probe beam 120*pr* to produce one or more combined probe-Raman signals 210 that are each directed to a detector 220 by an optical waveguide 172 of the PIC 170.

FIGS. 30-35 each illustrate example frequency ranges of a pump beam 120_pu_ and a Stokes beam 120S. The pump beam 120_pu_ may be produced by a pump light source 110_pu_, and the Stokes beam 120S may be produced by a Stokes light source 110S. The pump and Stokes light sources may each include one or more fixed wavelength laser diodes or one or more wavelength-tunable laser diodes. In each of FIGS. 30-35, the pump beam 120_pu_ and the Stokes beam 120S each have one or more fixed frequencies or one or more frequencies that are adjustable over a particular frequency range. The corresponding frequency offset Ω between the pump and Stokes beams is indicated as a range of frequencies or a set of discrete frequencies that the frequency offset can be set to, based on the frequencies that are available to the pump and Stokes beams. The frequency offset Ω is determined from $v_1-v_2$, where $v_1$ is the range or set of fixed frequencies for the pump beam 120_pu_, and $v_2$ is the range or set of fixed frequencies for the Stokes beam 120S. The frequency offsets $\Omega_1$, $\Omega_2$, $\Omega_3$, and $\Omega_4$ in FIGS. 30-35 may have any suitable value between approximately 5 THz and approximately 100 THz. The frequency range ΔΩ over which a frequency offset may be varied may have any suitable value between approximately 5 THz and approximately 80 THz.

Figure 30:
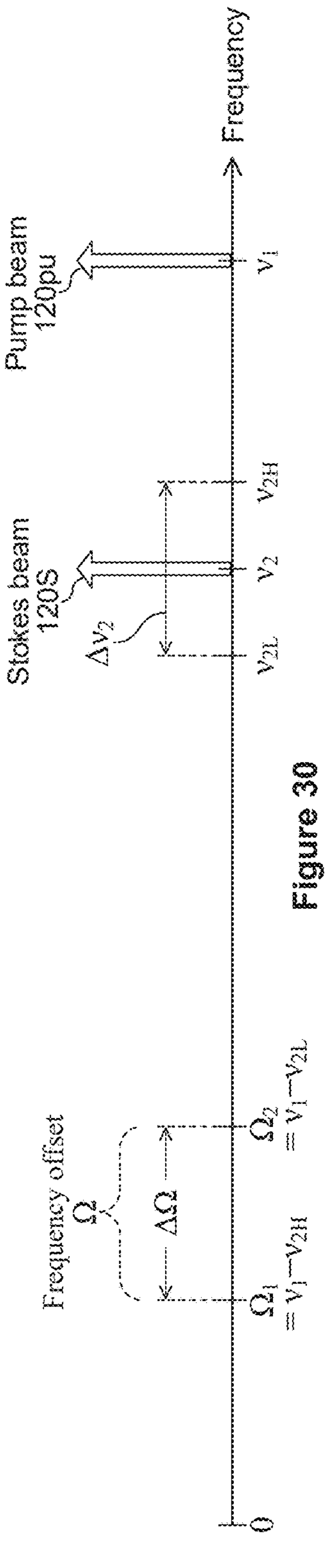
FIGS. 30-35 each illustrate example frequency ranges of a pump beam and a Stokes beam.

In FIG. 30, the pump beam 120_pu_ has a single fixed frequency $v_1$, and the Stokes beam 120S has a frequency $v_2$ that is adjustable over a frequency range of width $\Delta v_2$. The adjustable frequency range $\Delta v_2$ of the Stokes beam 120S extends from a low frequency $v_{2L}$ to a high frequency $v_{2H}$, where $\Delta v_2=v_{2H}-v_{2L}$. The pump laser 110_pu_ that produces the pump beam 120_pu_ in FIG. 30 may be a fixed-wavelength laser diode, and the Stokes laser 110S that produces the Stokes beam 120S may be a wavelength-tunable laser diode. The frequency offset Ω between the pump and Stokes beams may be set to any value between $\Omega_1$ and $\Omega_2$, and the frequency range ΔΩ of the frequency offset is $\Omega_2-\Omega_1$. In FIG. 30, the frequency range ΔΩ is also equal to the frequency range $\Delta v_2$ of the Stokes beam 120S. When the Stokes beam 120S is set to the lower frequency $v_{2L}$, the frequency offset between the pump and Stokes beams is $v_1-v_{2L}$, which is equal to $\Omega_2$. Similarly, when the Stokes beam 120S is set to the upper frequency $v_{2H}$, the frequency offset between the pump and Stokes beams is $v_1-v_{2H}$, which is equal to $\Omega_1$.

For example, the pump beam 120_pu_ in FIG. 30 may have a frequency $v_1$ of 250 THz (corresponding to a wavelength of approximately 1200 nm), and the Stokes beam 120S may be adjustable from a low frequency $v_{2L}$ of 195 THz to a high frequency $v_{2H}$ of 200 THz. This corresponds to a frequency-tuning range $\Delta v_2$ of the Stokes beam 120S of 5 THz (167 $cm^{-1}$ in wavenumbers) and a 38-nm wavelength-tuning range from approximately 1499 nm to approximately 1537 nm. The resulting frequency offset Ω between the pump and Stokes beams may be set to a value between the lower value $\Omega_1$ of 50 THz (1668 $cm^{-1}$ in wavenumbers) and the upper value $\Omega_2$ of 55 THz (1835 $cm^{-1}$ in wavenumbers), corresponding to a frequency range ΔΩ of 5 THz (167 $cm^{-1}$ in wavenumbers).

Figure 31:
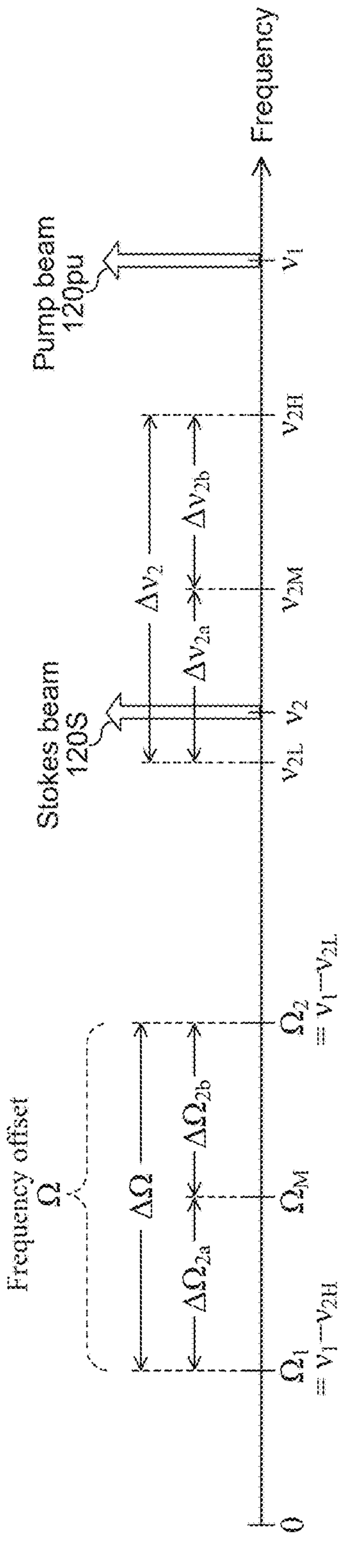

In FIG. 31, the pump beam 120_pu_ has a single fixed frequency $v_1$, and the Stokes beam 120S has a frequency $v_2$ that is adjustable over a frequency range of width $\Delta v_2$. The adjustable frequency range $\Delta v_2$ of the Stokes beam 120S extends from a low frequency $v_{2L}$ to a high frequency $v_{2H}$, where $\Delta v_2=v_{2H}-v_{2L}$. The pump laser 110_pu_ that produces the pump beam 120_pu_ in FIG. 31 may be a fixed-wavelength laser diode. The Stokes light source 110S that produces the Stokes beam 120S may include two wavelength-tunable laser diodes. For example, the Stokes light source 110S may be similar to the light source in FIG. 24 where two wavelength-tunable laser diodes are combined by a multiplexer 118. A first wavelength-tunable laser diode may operate from frequency $v_{2L}$ to frequency $v_{2M}$, and a second wavelength-tunable laser diode may operate from frequency $v_{2M}$ to frequency $v_{2H}$. The total tuning range $\Delta v_2$ of the Stokes laser 110S equals the sum of the tuning ranges $\Delta v_{2a}$ and $\Delta v_{2b}$ of the two wavelength-tunable laser diodes. In other embodiments, if the tuning ranges of the two wavelength-tunable laser diodes overlap, the total tuning range $\Delta v_2$ of the Stokes light source 110S will be reduced by the amount of frequency overlap between the two lasers.

In FIG. 31, the frequency offset Ω between the pump and Stokes beams may be set to any value between $\Omega_1$ and $\Omega_2$, and the frequency range ΔΩ of the frequency offset is $\Omega_2-\Omega_1$. When the first wavelength-tunable laser diode (with a frequency range from $v_{2L}$ to $v_{2M}$) is selected to operate, the frequency offset Ω may be set to any value between $\Omega_M$ and $\Omega_2$. For example, when the Stokes beam 120S is set to the lower frequency $v_{2L}$, the frequency offset between the pump and Stokes beams is $v_1-v_{2L}$, which is equal to 02. When the second wavelength-tunable laser diode (with a frequency range from $v_{2M}$ to $v_{2H}$) is selected to operate, the frequency offset Ω may be set to any value between $\Omega_1$ and $\Omega_M$. For example, when the Stokes beam 120S is set to the upper frequency $v_{2H}$, the frequency offset between the pump and Stokes beams is $v_1-v_{2H}$, which is equal to $\Omega_1$. The total frequency range ΔΩ of the frequency offset Ω is equal to the sum of the two frequency ranges $\Delta\Omega_{2a}$ and $\Delta\Omega_{2b}$. The frequency range ΔΩ is also equal to the overall frequency range $\Delta v_2$ of the Stokes beam 120S.

Figure 32:
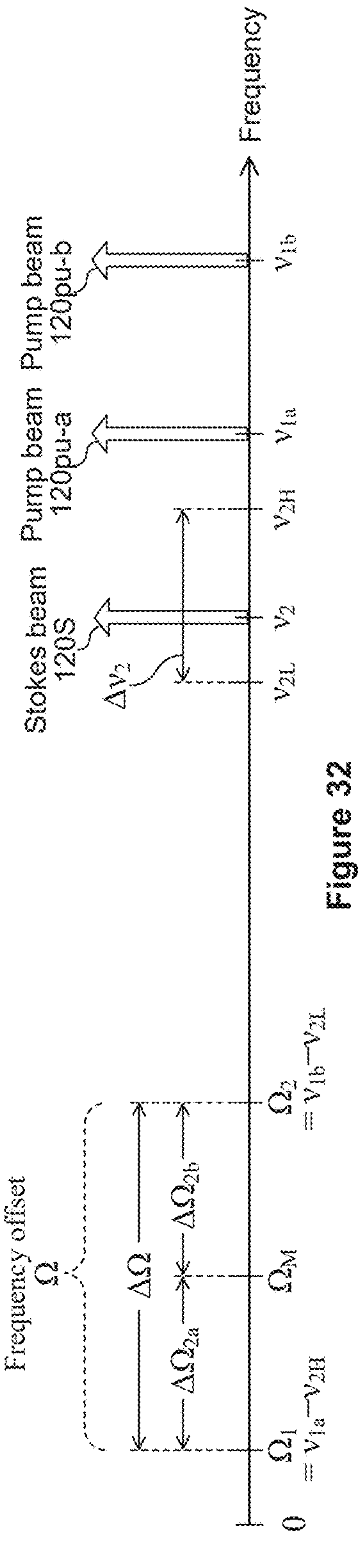

In FIG. 32, the pump beam 120_pu_ can be set to two fixed frequencies $v_{1a}$ and $v_{1b}$, and the Stokes beam 120S has a frequency $v_2$ that is adjustable over a frequency range of width $\Delta v_2$. The adjustable frequency range $\Delta v_2$ of the Stokes beam 120S extends from a low frequency $v_{2L}$ to a high frequency $v_{2H}$, where $\Delta v_2=v_{2H}-v_{2L}$. The pump light source 110_pu_ that produces the two pump beams 120_pu-a_ and 120_pu-b_ may include two fixed-wavelength laser diodes. For example, the pump light source 110_pu_ may be similar to the light source in FIG. 24 where two fixed-wavelength laser diodes are combined by a multiplexer 118. The Stokes laser 110S that produces the Stokes beam 120S may be a wavelength-tunable laser diode. The frequency offset Ω between the pump and Stokes beams may be set to any value between $\Omega_1$ and $\Omega_2$, and the frequency range ΔΩ of the frequency offset is $\Omega_2-\Omega_1$. When the pump laser 110_pu_ produces the pump beam 120_pu-a_ at frequency Via, the Stokes beam 120S may be tuned to a frequency between $v_{2L}$ and $v_{2H}$ to produce a frequency offset Ω between $\Omega_1$ and $\Omega_M$. For example, with the Stokes beam 120S set to the upper frequency $v_{2H}$, the frequency offset between the pump and Stokes beams is $v_{1a}$-$v_{2H}$, which is equal to $\Omega_1$. When the pump laser 110_pu_ produces the pump beam 120_pu-b_ at frequency $v_{1b}$, the Stokes beam 120S may be tuned to a frequency between $v_{2L}$ and $v_{2H}$ to produce a frequency offset Ω between $\Omega_M$ and $\Omega_2$. For example, with the Stokes beam 120S set to the lower frequency $v_{2L}$, the frequency offset between the pump and Stokes beams is $v_{1b}$-$v_{2L}$, which is equal to $\Omega_2$.

Figure 33:
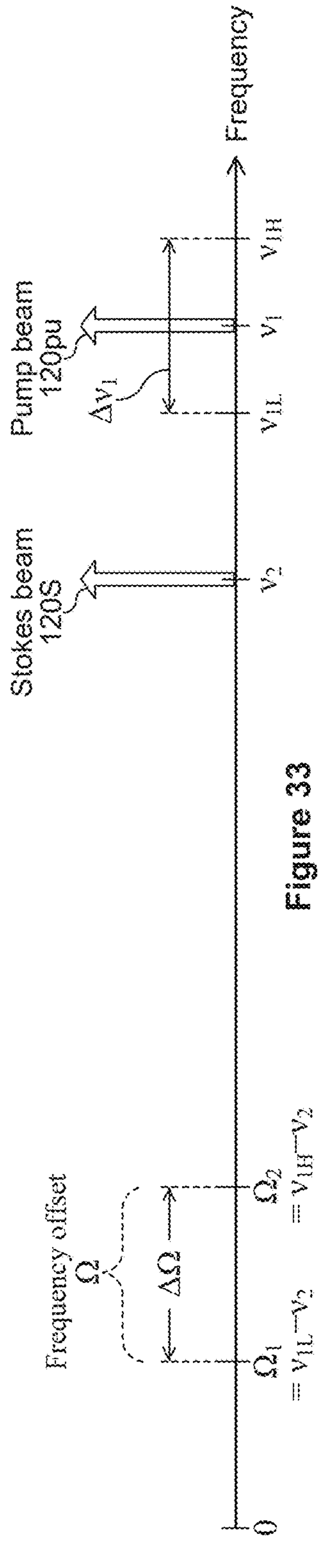

FIG. 33 is similar to FIG. 30, except in FIG. 33, the Stokes beam 120S has a fixed frequency $v_2$ and the frequency of the pump beam 120_pu_ is adjustable. The adjustable frequency range $\Delta v_1$ of the pump beam 120_pu_ extends from a low frequency $v_{1L}$ to a high frequency $v_{1H}$, where $\Delta v_1 = v_{1H} - v_{1L}$. The Stokes laser 110S that produces the Stokes beam 120*pu* in FIG. 33 may be a fixed-wavelength laser diode, and the pump laser 110*pu* that produces the pump beam 120*pu* may be a wavelength-tunable laser diode. The frequency offset $\Omega$ between the pump and Stokes beams may be set to any value between $\Omega_1$ and $\Omega_2$, and the frequency range $\Delta\Omega$ of the frequency offset is $\Omega_2 - \Omega_1$. In FIG. 33, the frequency range $\Delta\Omega$ is also equal to the frequency range $\Delta v_1$ of the pump beam 120*pu*. When the pump beam 120*pu* is set to the lower frequency $v_{1L}$, the frequency offset between the pump and Stokes beams is $v_{1L} - v_2$, which is equal to $\Omega_1$. Similarly, when the pump beam 120*pu* is set to the upper frequency $v_{1H}$, the frequency offset between the pump and Stokes beams is $v_{1H} - v_2$, which is equal to $\Omega_2$.

Figure 34:
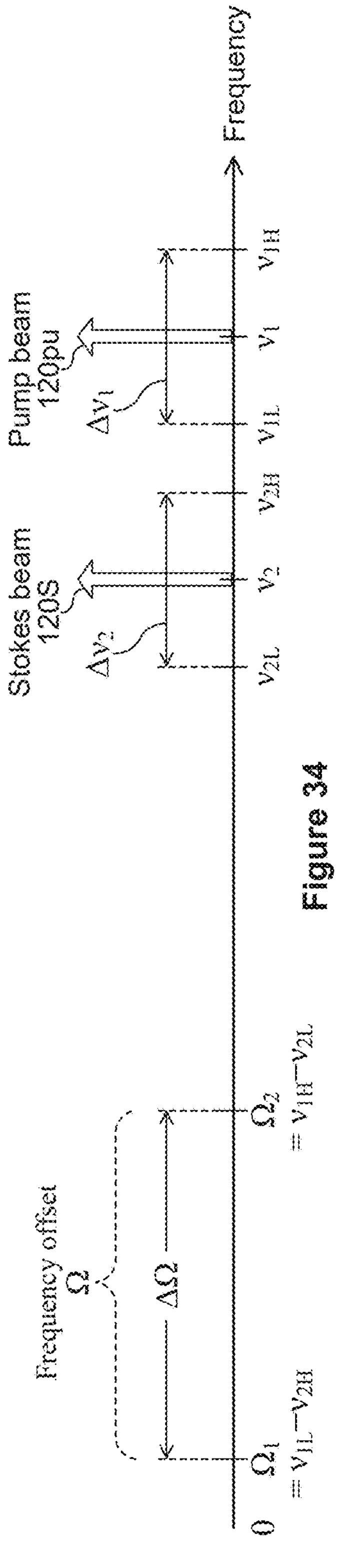

In FIG. 34, both the pump beam 120*pu* and the Stokes beam 120S have adjustable frequencies. The pump laser 110*pu* that produces the pump beam 120*pu* and the Stokes laser 110S that produces the Stokes beam 120S may each include a wavelength-tunable laser diode. The adjustable frequency range $\Delta v_1$ of the pump beam 120*pu* extends from a low frequency $v_{1L}$ to a high frequency $v_{1H}$, where $\Delta v_1 = v_{1H} - v_{1L}$. The adjustable frequency range $\Delta v_2$ of the Stokes beam 120S extends from a low frequency $v_{2L}$ to a high frequency $v_{2H}$, where $\Delta v_2 = v_{2H} - v_{2L}$. The frequency offset $\Omega$ between the pump and Stokes beams may be set to any value between $\Omega_1$ and $\Omega_2$, and the frequency range $\Delta\Omega$ of the frequency offset is $\Omega_2 - \Omega_1$. When the Stokes beam 120S is set to the lower Stokes frequency $v_{2L}$ and the pump beam 120*pu* is set to the upper pump frequency $v_{1H}$, the frequency offset between the pump and Stokes beams is $v_{1H} - v_{2L}$, which is equal to $\Omega_2$. When the Stokes beam 120S is set to the upper Stokes frequency $v_{2H}$ and the pump beam 120*pu* is set to the lower pump frequency $v_{1L}$, the frequency offset between the pump and Stokes beams is $v_{1L} - v_{2H}$, which is equal to $\Omega_1$.

Figure 35:
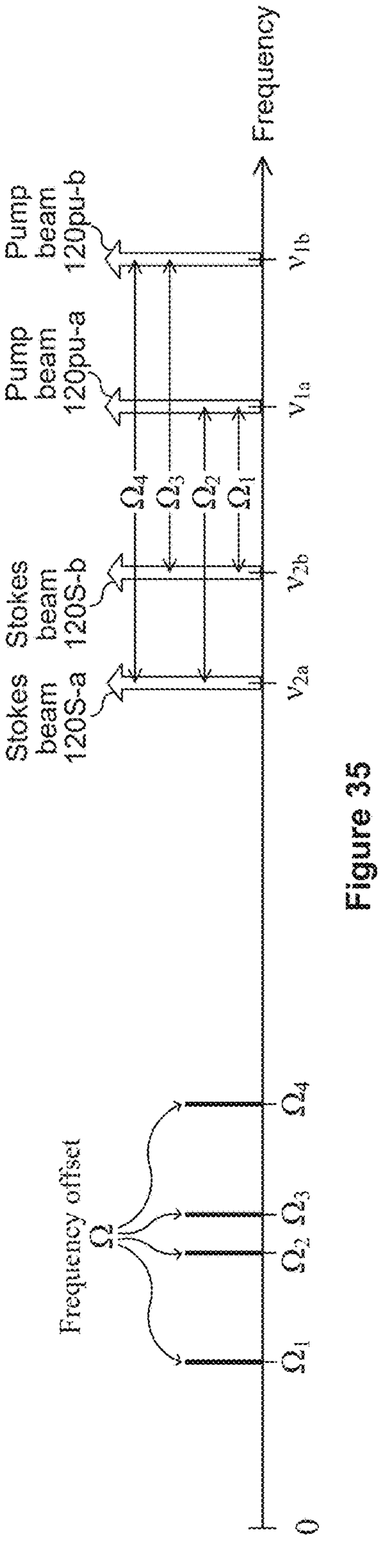

In FIG. 35, both the pump beam 120*pu* and the Stokes beam 120S can be set to two different fixed frequencies. A pump light source 110*pu* and a Stokes light source 110S may each include two or more fixed wavelength laser diodes, and each light source may be similar to the light source in FIG. 24 where multiple fixed-wavelength laser diodes are combined by a multiplexer 118. In FIG. 35, the pump light source 110*pu* that produces the two pump beams 120*pu-a* and 120*pu-b* may include two fixed-wavelength laser diodes, and the Stokes light source 110S that produces the two Stokes beams 120S-a and 120S-b may include two fixed-wavelength laser diodes. The frequencies of the pump and Stokes beams may be selected to produce four different frequency offsets $\Omega_1$, $\Omega_2$, $\Omega_3$, and $\Omega_4$. For example, selecting Stokes beam 120S-b at frequency $v_{2b}$ and pump beam 120*pu-a* at frequency Via produces a frequency offset $\Omega_1$, which is equal to $v_{1a} - v_{2b}$. As another example, selecting Stokes beam 120S-a at frequency $v_{2a}$ and pump beam 120*pu-b* at frequency $v_{1b}$ produces a frequency offset $\Omega_4$, which is equal to $v_{1b} - v_{2a}$. The frequency offset $\Omega_2$ may be produced by selecting Stokes beam 120S-a at frequency $v_{2a}$ and pump beam 120*pu-a* at frequency $v_{1a}$, and the frequency offset $\Omega_3$ may be produced by selecting Stokes beam 120S-b at frequency $v_{2b}$, and pump beam 120*pu-b* at frequency $v_{1b}$.

Figure 36:
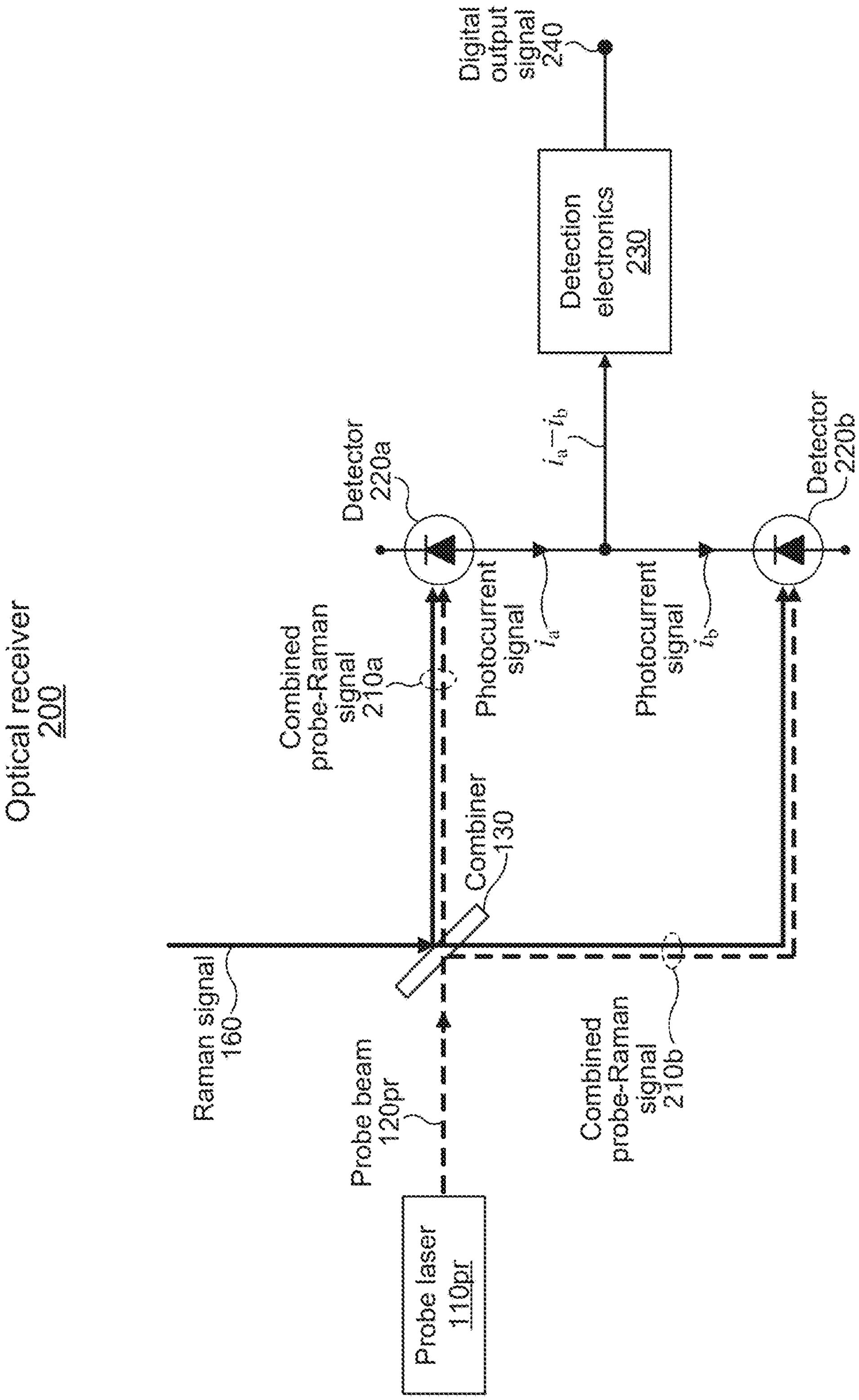
FIG. 36 illustrates an example optical receiver with two detectors.

FIG. 36 illustrates an example optical receiver 200 with two detectors 220*a* and 220*b*. The optical receivers 200 in FIGS. 29 and 36 are similar, except one difference is that the optical receiver in FIG. 29 is a waveguide-based optical receiver, while the optical receiver in FIG. 36 is a free-space optical receiver 200. The optical combiner 130 in FIG. 36 may be a 50/50 free-space beamsplitter that reflects approximately 50% of an incident beam of light and transmits approximately 50% of the beam. The optical combiner 130 splits the Raman signal 160 and the probe beam 120*pr* into two beams to produce two combined probe-Raman signals 210*a* and 210*b*. The combined probe-Raman signal 210*a* is directed to detector 220*a* and includes a transmitted portion of the probe beam 120*pr* and a reflected portion of the Raman signal 160 (e.g., approximately 50% of the probe beam and approximately 50% of the Raman signal). Similarly, the combined probe-Raman signal 210*b* is directed to detector 220*b* and includes a reflected portion of the probe beam 120*pr* and a transmitted portion of the Raman signal 160. The portions of the probe beam 120*pr* and the Raman signal 160 that make up the combined probe-Raman signal 210*a* may be coherently mixed at detector 220*a* to produce the photocurrent signal $i_a$. Similarly, the portions of the probe beam 120*pr* and the Raman signal 160 that make up the combined probe-Raman signal 210*b* may be coherently mixed at detector 220*b* to produce the photocurrent signal $i_b$.

The two detectors 220*a* and 220*b* are arranged so that their respective photocurrents $i_a$ and $i_b$ are subtracted. The anode of detector 220*a* is electrically connected to the cathode of detector 220*b*, and the subtracted photocurrent signal $i_a - i_b$ from the anode-cathode connection is sent to the detection electronics 230, which produces a digital output signal 240 that corresponds to the subtracted photocurrent signal. The subtracted photocurrent signal may be expressed as $i_a - i_b = 2E_R E_{pr} \cos[2\pi(v_R - v_3)t + \Delta\phi]$, which corresponds to the coherent-mixing term discussed herein. The subtracted photocurrent signal does not include the terms $$E_R^2 \text{ and } E_{pr}^2$$

corresponding to the respective optical powers of the Raman signal 160 and the probe beam 120*pr*. By subtracting the two photocurrents $i_a$ and $i_b$, the common-mode terms $$E_R^2 \text{ and } E_{pr}^2$$

(as well as common-mode noise) that appear in each of the photocurrent signals $i_a$ and $i_b$ are substantially removed, leaving the coherent-mixing term, which is the quantity of interest. Since subtraction may remove common-mode noise, the subtracted photocurrent signal $i_a - i_b$ may have a reduced noise compared to each of the photocurrent signals $i_a$ and $i_b$ alone. The dual-detector arrangement in FIG. 36 in which the photocurrents are subtracted may be referred to as a balanced optical detector. A balanced detector may be implemented as a free-space device, a fiber-optic-based device, or a waveguide-based device.

Figure 37:
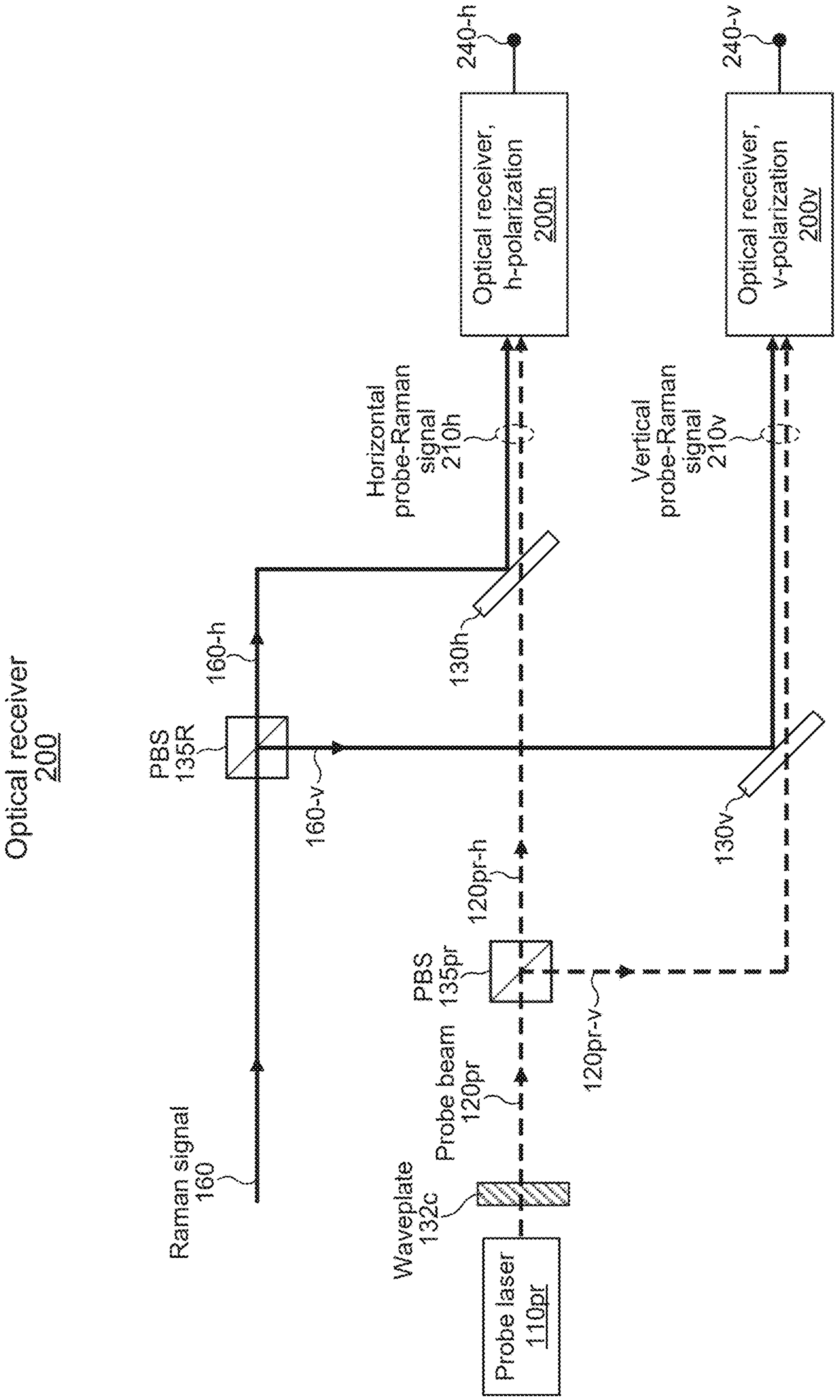
FIG. 37 illustrates an example optical receiver configured for polarization-sensitive detection of a Raman signal.

FIG. 37 illustrates an example optical receiver 200 configured for polarization-sensitive detection of a Raman signal 160. A polarization-sensitive optical receiver 200 may be used to determine the polarization of a Raman signal 160. The polarization of a Raman signal 160 may be determined by a processor based on one or more digital output signals 240 produced by the polarization-sensitive optical receiver 200. Determining the polarization of a Raman signal 160 may include determining a relative size or ratio of two orthogonal polarization components of the Raman signal (e.g., horizontal and vertical polarization components of the Raman signal). For example, if the ratio of the horizontal and vertical polarization components of a Raman signal 160 is 100:1, then the Raman signal may be determined to be substantially horizontally polarized. As another example, if the ratio of the horizontal and vertical polarization components of a Raman signal 160 is 1:1, then the horizontal and vertical polarization components of the Raman signal may be determined to be approximately equal (e.g., the Raman signal may be circularly polarized or linearly polarized at a 45-degree angle to the horizontal and vertical directions).

A polarization-sensitive optical receiver 200 may include a polarization beamsplitter (PBS) 135 that splits an input beam into two output beams, where one output beam is horizontally polarized, and the other output beam is vertically polarized. The horizontally polarized output beam includes the horizontal polarization component of the input beam, and the vertically polarized output beam includes the vertical polarization component of the input beam. The Raman signal 160 in FIG. 37 is directed to a Raman-signal PBS 135R that splits the Raman signal into a horizontal-polarization Raman signal 160-*h* and a vertical-polarization Raman signal 160-*v*. Similarly, the probe beam 120*pr* is directed to a probe-beam PBS 135*pr* that splits the probe beam into a horizontal-polarization probe beam 120*pr-h* and a vertical-polarization probe beam 120*pr-v*.

A polarization-sensitive optical receiver 200 may include a waveplate 132 that changes the polarization of the probe beam 120*pr* so that the probe beam is split into two polarization components. The two polarization components may each have approximately one-half the power of the probe beam 120*pr*. The waveplate 132*c* in FIG. 37 may be (i) a half-wave plate that rotates the polarization of the probe beam 120*pr* or (ii) a quarter-wave plate that converts the probe beam 120*pr* to a circular or elliptical polarization. For example, the probe laser 110*pr* may produce a probe beam 120*pr* that is vertically polarized, and the waveplate 132*c* may be a half-wave plate that rotates the probe-beam polarization by 45 degrees so that the horizontal-polarization and vertical-polarization probe beams 120*pr-h* and 120*pr-v* each have approximately equal optical powers.

The optical combiner 130*h* in FIG. 37 combines the horizontal-polarization Raman signal 160-*h* and the horizontal-polarization probe beam 120*pr-h* to produce a horizontal probe-Raman signal 210*h* that is directed to a horizontal-polarization optical receiver 200*h*. Similarly, the optical combiner 130*v* combines the vertical-polarization Raman signal 160-*v* and the vertical-polarization probe beam 120*pr-v* to produce a vertical probe-Raman signal 210*v* that is directed to a vertical-polarization optical receiver 200*v*. The horizontal-polarization optical receiver 200*h* may include one or more optical detectors 200, where each detector is configured to coherently mix at least a portion of the horizontal-polarization Raman signal 160-*h* and at least a portion of the horizontal-polarization probe beam 120*pr-h* to produce a horizontal-polarization electronic signal. Similarly, the vertical-polarization optical receiver 200*v* may include one or more optical detectors 200, where each detector is configured to coherently mix at least a portion of the vertical-polarization Raman signal 160-*v* and at least a portion of the vertical-polarization probe beam 120*pr-v* to produce a vertical-polarization electronic signal. The horizontal-polarization optical receiver 200*h* and the vertical-polarization optical receiver 200*v* may each include: (i) a single detector 220 (e.g., similar to the optical receiver 200 in FIG. 2), (ii) two detectors 220 (e.g., similar to the balanced optical detector arrangement in FIG. 36), or (iii) four detectors 220 (e.g., similar to the arrangement in FIG. 39). The electronic signals may include a photocurrent signal i, and each optical receiver may include an electronic amplifier 232 that produces a corresponding voltage signal 234. The h-polarization optical receiver 200*h* may produce a digital output signal 240-*h* corresponding to the horizontal-polarization electronic signal, and the v-polarization optical receiver 200*v* may produce a digital output signal 240-*v* corresponding to the vertical-polarization electronic signal.

A processor may determine one or more characteristics of the horizontal-polarization and vertical-polarization electronic signals based on the digital output signals 240-*h* and 240-*v*. Additionally, a processor may determine a polarization of the Raman signal 160 based on the characteristics of the horizontal-polarization and vertical-polarization electronic signals. For example, the characteristics of the electronic signals may include an amplitude or an area associated with the electronic signals, and the polarization of the Raman signal 160 may be expressed as a relative size or ratio of the amplitudes or areas associated with the horizontal and vertical polarization components of the Raman signal. If the horizontal digital output signal 240-*h* includes an amplitude characteristic with value 100 and the vertical digital output signal 240-*v* includes a corresponding amplitude characteristic with value 1, then the Raman signal 160 may be determined to be substantially horizontally polarized. If the horizontal and vertical digital output signals each include amplitude characteristics having approximately equal values, then the Raman signal 160 may be determined to have approximately equal horizontal and vertical polarization components.

A polarization-sensitive optical receiver 200 as illustrated in FIG. 37 may be implemented with free-space optical elements, fiber-optic components, waveguide-based optical elements, a metamaterial-based device, or any suitable combination thereof. For example, the two PBSs 135 in FIG. 37 may be free-space polarization beamsplitter cubes, and the Raman signal 160 and the probe beam 120*pr* may be free-space optical beams. Alternatively, the two PBSs 135 may be fiber-optic components, and the Raman signal 160 and the probe beam 120*pr* may be conveyed to the PBSs 135 via optical fiber (e.g., single-mode optical fiber or polarization-maintaining optical fiber). Additionally, the horizontally and vertically polarized probe-Raman signals 210*h* and 210*v* may be conveyed to the respective h-polarization and v-polarization optical receivers via polarization-maintaining optical fiber. The h-polarization and v-polarization optical receivers may each preserve the polarization of the respective horizontally and vertically polarized probe-Raman signals. For example, the h-polarization and v-polarization optical receivers may each include polarization-maintaining optical fiber that maintains the polarization of the beams. Alternatively, the h-polarization and v-polarization receivers may each include a PIC with optical waveguides configured to maintain the polarization of the beams.

Figure 38:
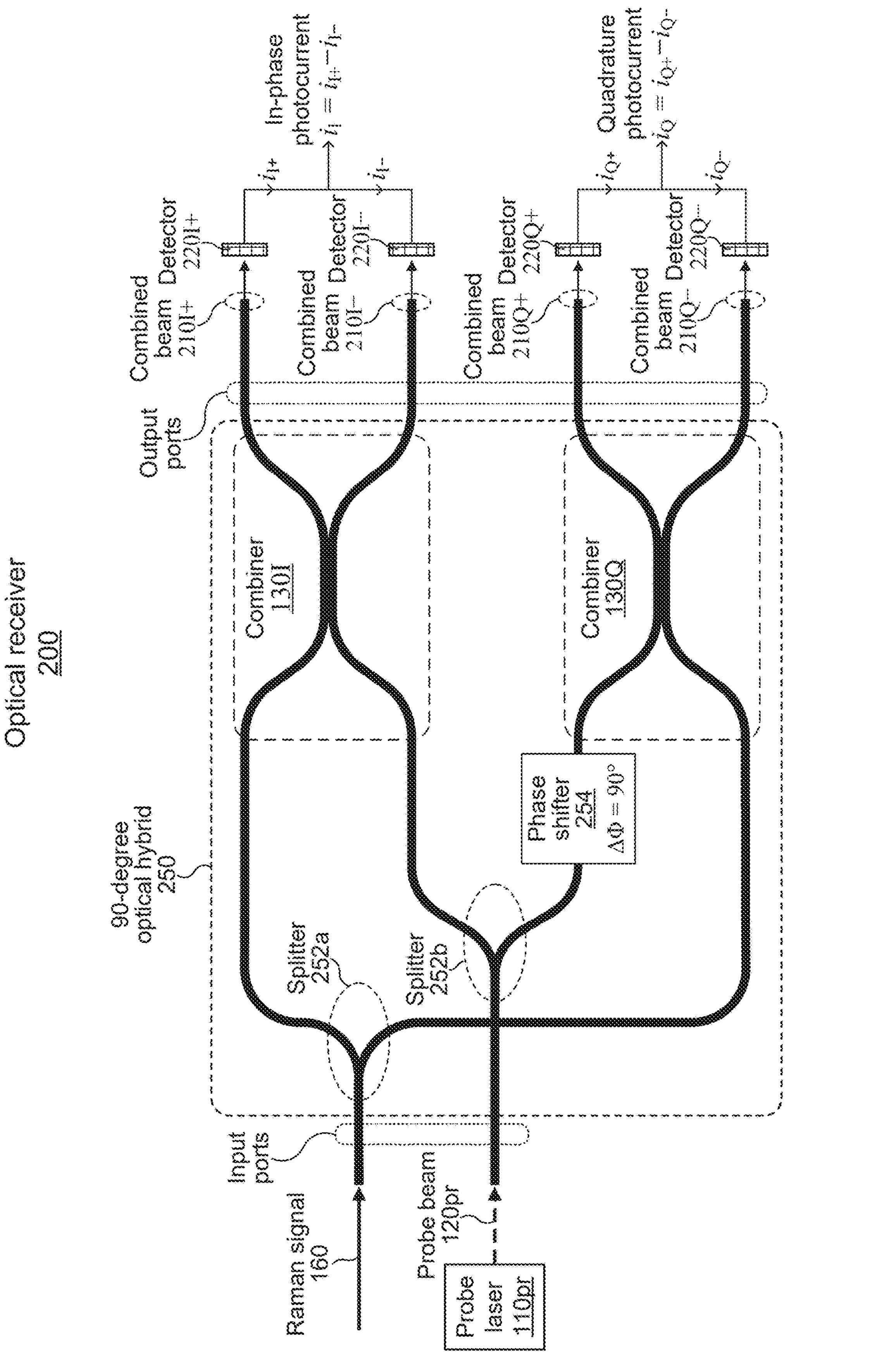
FIG. 38 illustrates an example optical receiver configured to detect in-phase and quadrature components of a Raman signal.

FIG. 38 illustrates an example optical receiver 200 configured to detect in-phase and quadrature components of a Raman signal 160. The optical receiver 200 includes a 90-degree optical hybrid 250 and four detectors 220I+, 220I−, 220Q+, and 220Q−. A 90-degree optical hybrid 250 is an optical-combiner component with two input ports and four output ports. Input light received at each of the two input ports is split, combined, and directed to each of the four output ports, and a 90-degree phase shift is imparted to one of the split beams before the Raman signal 160 and probe beam 120*pr* are combined. The 90-degree optical hybrid 250 in FIG. 38 combines a Raman signal 160 and a probe beam 120*pr* to produce four combined output beams: two in-phase combined beams 210I+ and 210I−, and two quadrature combined beams 210Q+ and 210Q−. Each of the four combined beams 210 may include a portion of the Raman signal 160 and a portion of the probe beam 120*pr*, and each of the combined beams is directed to one of the four detectors of the optical receiver 200. In FIG. 38, each of the four detectors produces a photocurrent signal that corresponds to the coherent mixing of a portion of the Raman signal 160 and a portion of the probe beam 120*pr*.

A 90-degree optical hybrid 250 may be configured so that the combined beams directed to each of the output ports have approximately the same optical power or energy. For example, the 90-degree optical hybrid 250 in FIG. 38 may split the Raman signal 160 into four approximately equal portions and direct each of the Raman-signal portions to one of the detectors. Similarly, the probe beam 120*pr* may be split into four approximately equal portions directed to each of the four detectors. In the example of FIG. 38, the combined beam 210I+, which is directed to detector 220I+, may include approximately one-quarter of the power of the Raman signal 160 and approximately one-quarter of the power of the probe beam 120*pr*. Similarly, each of the three other combined beams (210I−, 210Q+, 210Q−) in FIG. 38 may also include approximately one-quarter of the Raman signal 160 and approximately one-quarter of the probe beam 120*pr*.

A 90-degree optical hybrid 250 may be implemented as a waveguide-based device in a PIC. The 90-degree optical hybrid 250 in FIG. 38 is a waveguide-based optical device that includes two waveguide-based optical splitters (252*a*, 252*b*) and two waveguide-based optical combiners (130I, 130Q). Splitter 252*a* may split the Raman signal 160 into two portions having substantially equal optical power, a first portion directed to combiner 130I and a second portion directed to combiner 130Q. Similarly, splitter 252*b* may split the probe beam 120*pr* into two portions having substantially equal power, a first portion directed to combiner 130I and a second portion directed to combiner 130Q. Each optical combiner 130 combines a portion of the Raman signal 160 with a portion of the probe beam 120*pr*, and the combined portions are split into a first combined beam (e.g., combined beam 210I+) and a second combined beam (e.g., combined beam 210I−). The combined beam 210I+ is directed to detector 220I+ and includes portions of the Raman signal 160 and the probe beam 120*pr* (e.g., approximately 25% of the Raman signal 160 and approximately 25% of the probe beam 120*pr*). The combined beam 210I− is directed to detector 220I− and may include approximately 25% of the Raman signal 160 and approximately 25% of the probe beam 120*pr*.

In other embodiments, all or part of a 90-degree optical hybrid 250 may be implemented as a free-space optical device. For example, a free-space 90-degree optical hybrid 250 may include one or more free-space beamsplitters or combiners that receive the Raman signal 160 and probe beam 120*pr* as free-space beams and produce four free-space combined beams (210I+, 210I−, 210Q+, 210Q−). Alternatively, all or part of a 90-degree optical hybrid 250 may be implemented as a fiber-optic device. For example, a 90-degree optical hybrid 250 may be contained in a package with two input optical fibers that direct the Raman signal 160 and probe beam 120*pr* into the package and four output optical fibers that direct the four combined beams to four respective detectors.

A 90-degree optical hybrid 250 may include an optical phase shifter 254 that imparts a 90-degree phase change ($\Delta\phi$) to a portion of the probe beam 120*pr* or to a portion of the Raman signal 160. The phase shifter 254 may apply the 90-degree phase change after a beam of light is split by an optical splitter 252 and prior to combining the Raman signal with the probe beam at an optical combiner 130. For example, a splitter 252*a* may split the Raman signal 160 into two portions, and a phase shifter 254 may impart a 90-degree phase change to one portion of the Raman signal with respect to the other portion, after which the two portions are sent to two different optical combiners. As another example, a splitter 252*b* may split the probe beam 120*pr* into two portions, and a phase shifter 254 may impart a 90-degree phase change to one portion of the probe beam with respect to the other portion. In FIG. 38, the phase shifter is located after the splitter 252*b* and before the combiner 130Q. The splitter 252*b* splits the probe beam 120*pr* into two portions, and the phase shifter 254 imparts a 90-degree phase change to the probe-beam portion directed to combiner 130Q. The other portion of the probe beam 120*pr* directed to combiner 130I does not pass through the phase shifter 254 and does not receive a phase shift from the phase shifter 254.

An optical phase shifter 254 may be implemented as a part of a waveguide-based 90-degree optical hybrid 250. For example, a phase shifter 254 may be implemented as part of an optical waveguide that only one portion of the probe beam 120*pr* propagates through. That part of the optical waveguide may be temperature controlled to adjust the refractive index of the waveguide and produce a relative phase delay of approximately 90 degrees between two portions of the probe beam 120*pr*. Additionally or alternatively, the 90-degree optical hybrid 250 as a whole may be temperature controlled to set and maintain a 90-degree phase delay. As another example, a phase shifter 254 may be implemented by applying an external electric field to part of an optical waveguide to change the refractive index of the waveguide and produce a 90-degree phase delay. In other embodiments, a phase shifter 254 may be implemented as a part of a free-space or fiber-coupled 90-degree optical hybrid 250. For example, the input and output beams in a free-space 90-degree optical hybrid 250 may be reflected by or transmitted through the optical surfaces of a free-space optical hybrid 250 so that a relative phase shift of 90 degrees is imparted to one portion of the probe beam 120*pr* with respect to another portion of the probe beam.

In FIG. 38, each of the four detectors produces a photocurrent signal that corresponds to the coherent mixing of a portion of the Raman signal 160 and a portion of the probe beam 120*pr*. The photocurrents are subtracted in a manner similar to that illustrated in FIG. 36. The photocurrents $i_{I+}$ and $i_{I-}$ from detectors 220I+ and 220I− are subtracted to produce the subtracted in-phase photocurrent signal i which is equal to $i_{I+}-i_{I-}$. Similarly, the photocurrents $i_{Q+}$ and $i_{Q-}$ from detectors 220Q+ and 220Q− are subtracted to produce the subtracted quadrature photocurrent signal $i_Q$ which is equal to $i_{Q+}-i_{Q-}$. Each of the subtracted photocurrent signals represents a coherent-mixing term corresponding to the coherent mixing of a portion of the Raman signal 160 and a portion of the probe beam 120*pr*. The two subtracted photocurrent signals $i_I$ and $i_Q$ are similar, except the in-phase photocurrent signal $i_I$ includes a cosine function, while the quadrature photocurrent signal $i_Q$ includes a sine function. This difference between the two subtracted photocurrent signals arises from the 90-degree phase shift provided by the phase shifter 254. Because a 90-degree phase shift is imparted to the probe beam 120*pr* directed to the combiner 130Q, the subtracted quadrature photocurrent signal $i_Q$ includes a sine function (which has a 90-degree phase offset with respect to a cosine function).

Each of the subtracted photocurrent signals $i_I$ and $i_Q$ may be sent to detection electronics 230 that produce voltage signals and digital output signals corresponding to the subtracted photocurrent signals. Based on the digital output signals (which result from the four photocurrent signals $i_{I+}$, $i_{I-}$, $i_{Q+}$, and $i_{Q-}$), a processor may determine an in-phase portion IP associated with the Raman signal 160 and a quadrature portion Q associated with the Raman signal. Additionally or alternatively, the processor may determine a phase associated with the Raman signal 160. For example, the processor may determine a phase difference Δϕ between the Raman signal 160 and the probe beam 120*pr*. A phase difference may be referred to as a phase offset or a relative phase between the Raman signal 160 and the probe beam 120*pr*.

The in-phase portion IP associated with the Raman signal 160 may be determined from a characteristic (e.g., an amplitude or an area) of an electronic signal associated with the in-phase photocurrent signal $i_I$, and the quadrature portion Q may be determined from a characteristic associated with the quadrature photocurrent signal $i_Q$. The in-phase portion IP may correspond to an amount of the Raman signal 160 that is in-phase with the probe beam 120*pr*, and the quadrature portion Q may represent an amount of the Raman signal that is out of phase (i.e., 90-degrees phase-shifted) with the probe beam. For example, the in-phase portion IP and the quadrature portion Q, may each have values from −1 to 1. If the Raman signal 160 is in-phase with the probe beam 120*pr*, then the in-phase portion IP may have a value of approximately 1, and the quadrature portion Q may have a value of approximately 0. Similarly, if the Raman signal 160 is out of phase by ±90 degrees with respect to the probe beam 120*pr*, then the in-phase portion IP may have a value of 0, and the quadrature portion Q may have a value of ±1. The phase difference Δϕ between the Raman signal 160 and the probe beam 120*pr* may be determined from the expression Δϕ=arctan (Q/IP). For example, if Q is 0 and IP is 1, then the Raman signal and the probe beam are substantially in phase, with a phase difference Δϕ of 0 degrees. As another example, if Q is 1 and IP is 0, then the Raman signal and the probe beam are substantially out of phase, with a phase difference Δϕ of 90 degrees.

Figure 39:
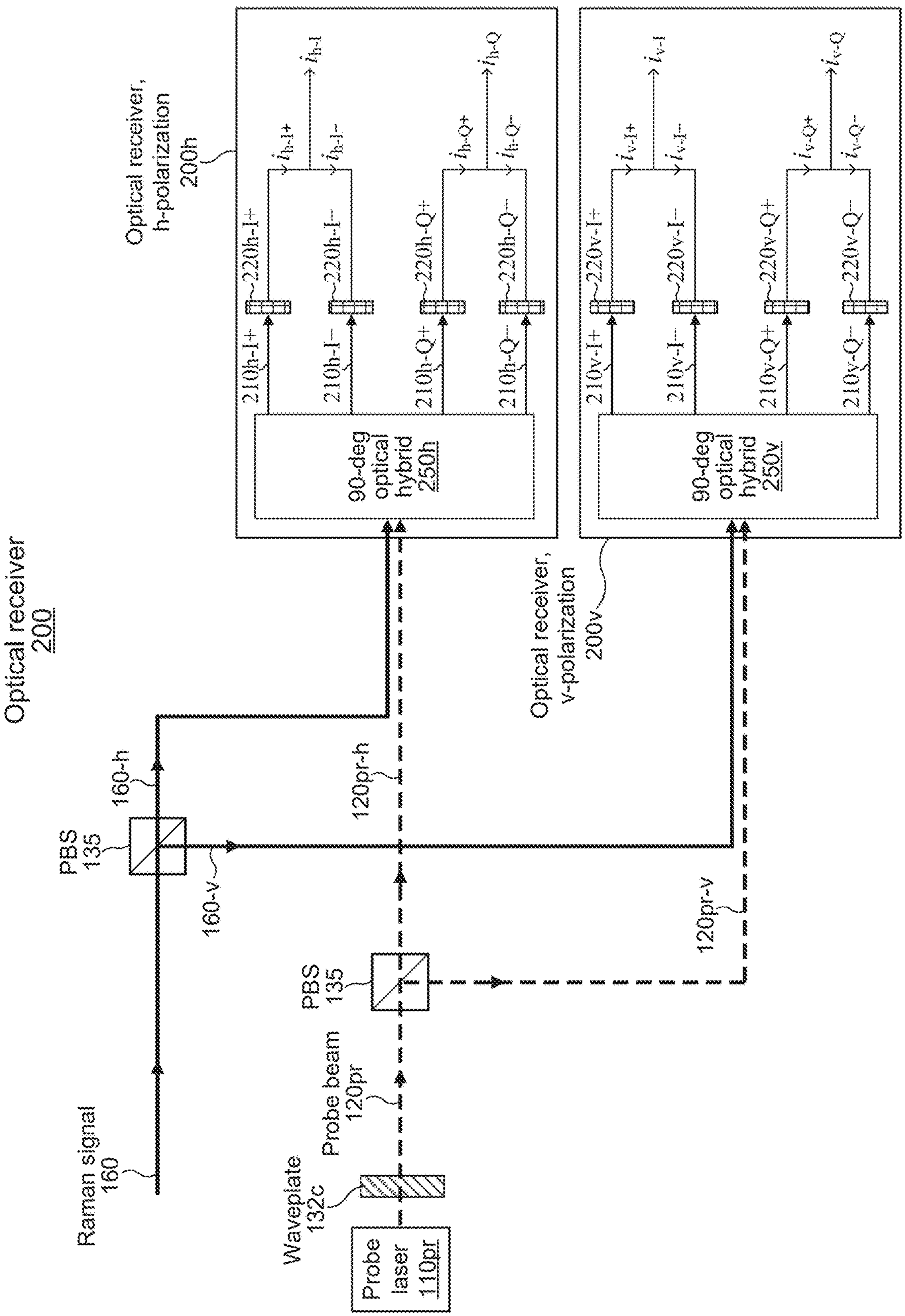
FIG. 39 illustrates an example optical receiver configured to detect polarization as well as in-phase and quadrature components of a Raman signal.

FIG. 39 illustrates an example optical receiver 200 configured to detect polarization as well as in-phase and quadrature components of a Raman signal 160. The optical receiver 200 in FIG. 39 is similar the optical receiver 200 in FIG. 37, where the horizontal-polarization optical receiver 200*h* and the vertical-polarization optical receiver 200*v* each includes a 90-degree optical hybrid 250. Each of the 90-degree optical hybrids in FIG. 39 may be similar to the 90-degree optical hybrid 250 in FIG. 38. In FIG. 39, the horizontal-polarization Raman signal 160-*h* and the horizontal-polarization probe beam 120*pr-h* are directed to a horizontal-polarization optical receiver 200*h* that includes a 90-degree optical hybrid 250*h* and four detectors 220*h*-I+, 220*h*-I−, 220*h*-Q+, and 220*h*-Q−. The vertical-polarization Raman signal 160-*v* and the vertical-polarization probe beam 120*pr-h* are directed to a vertical-polarization optical receiver 200*v* that includes a 90-degree optical hybrid 250*v* and four detectors 220*v*-I+, 220*v*-I−, 220*v*-Q+, and 220*v*-Q−. The h-polarization optical receiver 200*h* may be used to determine the relative size of the horizontal-polarization Raman signal 160-*h* as well as the in-phase and quadrature components of the horizontal-polarization Raman signal 160-*h*. Similarly, the v-polarization optical receiver 200*h* may be used to determine the relative size of the vertical-polarization Raman signal 160-*v* as well as the in-phase and quadrature components of the vertical-polarization Raman signal 160-*v*.

The 90-degree optical hybrid 250*h* in FIG. 39 combines the horizontal-polarization Raman signal 160-*h* and the horizontal-polarization probe beam 120*pr-h* to produce four horizontally polarized combined output beams: two in-phase combined beams 210*h*-I+ and 210*h*-I−, and two quadrature combined beams 210*h*-Q+ and 210*h*-Q−. Each of the four horizontally polarized combined beams includes a portion of the horizontal-polarization Raman signal 160-*h* and a portion of the horizontal-polarization probe beam 120*pr-h*. The four combined beams are directed to four respective detectors (220*h*-I+, 220*h*-I−, 220*h*-Q+, 220*h*-Q−), and each detector produces a respective photocurrent signal ($i_{h\text{-}I+}$, $i_{h\text{-}I-}$, $i_{h\text{-}Q+}$, $i_{h\text{-}Q-}$) that corresponds to the coherent mixing of a portion of the horizontal Raman signal 160-*h* and a portion of the horizontal probe beam 120*pr-h*. Each of the four photocurrents $i_{h\text{-}I+}$, $i_{h\text{-}I-}$, $i_{h\text{-}Q+}$, and $i_{h\text{-}Q-}$ may be referred to as a horizontal-polarization electronic signal. The photocurrents from the detectors are subtracted to produce a subtracted horizontal in-phase photocurrent signal $i_{h\text{-}I}$ which is equal to $i_{h\text{-}I+}-i_{h\text{-}I-}$ and a subtracted horizontal quadrature photocurrent signal $i_{h\text{-}Q}$ which is equal to $i_{h\text{-}Q+}-i_{h\text{-}Q-}$.

The 90-degree optical hybrid 250*v* in FIG. 39 combines the vertical-polarization Raman signal 160-*v* and the vertical-polarization probe beam 120*pr-v* to produce four vertically polarized combined output beams: two in-phase combined beams 210*v*-I+ and 210*v*-I−, and two quadrature combined beams 210*v*-Q+ and 210*v*-Q−. Each of the four vertically polarized combined beams includes a portion of the vertical-polarization Raman signal 160-*v* and a portion of the vertical-polarization probe beam 120*pr-v*. The four combined beams are directed to four respective detectors (220*v*-I+, 220*v*-I−, 220*v*-Q+, 220*v*-Q−), and each detector produces a respective photocurrent signal ($i_{v\text{-}I+}$, $i_{v\text{-}I-}$, $i_{v\text{-}Q+}$, $i_{v\text{-}Q-}$) that corresponds to the coherent mixing of a portion of the vertical Raman signal 160-*v* and a portion of the vertical probe beam 120*pr-v*. Each of the four photocurrents $i_{v\text{-}I+}$, $i_{v\text{-}I-}$, $i_{v\text{-}Q+}$, and $i_{v\text{-}Q-}$ may be referred to as a vertical-polarization electronic signal. The photocurrents from the detectors are subtracted to produce a subtracted vertical in-phase photocurrent signal $i_{v\text{-}I}$ which is equal to $i_{v\text{-}I+}-i_{v\text{-}I-}$ and a subtracted vertical quadrature photocurrent signal $i_{v\text{-}Q}$ which is equal to $i_{v\text{-}Q+}-i_{v\text{-}Q-}$.

Each of the subtracted photocurrent signals $i_{h\text{-}I}$, $i_{h\text{-}Q}$, $i_{v\text{-}I}$, and $i_{v\text{-}Q}$ may be sent to detection electronics 230 that produces voltage signals and digital output signals corresponding to the subtracted photocurrent signals. Based on the digital output signals (which are determined from the four horizontal-polarization electronic signals and the four vertical-polarization electronic signals), a processor may determine (i) the polarization of the Raman signal 160 and (ii) a phase associated with the Raman signal (e.g., a phase difference Δϕ between the Raman signal 160 and the probe beam 120*pr*). Determining the polarization of a Raman signal 160 may include determining a relative size or ratio of the horizontal and vertical polarization components of the Raman signal. For example, the relative size of the horizontal polarization component of the Raman signal 160 may be determined by adding characteristics (e.g., areas or amplitudes) associated with the two horizontal photocurrent signals $i_{h\text{-}I}$ and $i_{h\text{-}Q}$. Similarly, the relative size of the vertical polarization component of the Raman signal 160 may be determined by adding characteristics associated with the two vertical photocurrent signals $i_{v\text{-}I}$ and $i_{v\text{-}Q}$. As an example, if the relative size of the horizontal polarization component of the Raman signal 160 is 1 and the relative size of the vertical polarization component of the Raman signal 160 is 100, then the Raman signal 160 may be determined to be substantially vertically polarized.

Based on the digital output signals, a processor may determine a phase associated with the Raman signal. For example, the processor may determine (i) a phase difference $\Delta\phi_h$ between the horizontal Raman signal 160-*h* and the horizontal probe beam 120*pr-h* and (ii) a phase difference $\Delta\phi_v$ between the vertical Raman signal 160-*v* and the vertical probe beam 120*pr-v*. Based on the digital output signals, a processor may determine in-phase and quadrature portions associated with each of the horizontal Raman signal 160-*h* and vertical Raman signal 160-*v*. The phase difference $\Delta\phi_h$ between the horizontal Raman signal 160-*h* and the horizontal probe beam 120*pr-h* may be determined from the expression $\Delta\phi_h=\arctan(Q_h/IP_h)$, where $Q_h$ and $IP_h$ are the quadrature and in-phase portions associated with the horizontal Raman signal. The phase difference $\Delta\phi_v$ between the vertical Raman signal 160-*v* and the vertical probe beam 120*pr-v* may be determined from the expression $\Delta\phi_h=\arctan(Q_v/IP_v)$, where $Q_v$ and $IP_v$ are the quadrature and in-phase portions associated with the vertical Raman signal.

An optical receiver 200 may include one or more detectors 220. An optical receiver 200 may include one detector 220 (e.g., as illustrated in FIGS. 1, 2, and 18), or an optical receiver 200 may include multiple detectors 220 (e.g., as illustrated in FIGS. 17, 36, 38, and 39). An optical receiver 200 with multiple detectors 220 may include 2, 3, 4, 8, 16, or any other suitable number of detectors. For example, an optical receiver 200 may include two detectors 220 arranged so that their respective photocurrents are subtracted (e.g., as illustrated in FIG. 36). As another example, an optical receiver 200 may include four detectors 220 (e.g., as illustrated in FIG. 38) or eight detectors 220 (e.g., as illustrated in FIG. 39). In an optical receiver 200 with multiple detectors 220, portions of a probe beam 120*pr* and a Raman signal 160 may be coherently mixed together at one or more of the multiple detectors 220, and each of these one or more detectors may produce a photocurrent signal i corresponding to the coherent mixing of the probe beam and the Raman signal. Any of the optical receivers 200 described herein as having a single detector 220 may also be configured to have two or more detectors. For example, the optical receiver in FIG. 1 (which includes one detector 220) may include a second detector (not illustrated in FIG. 1), and the detection electronics 230 may be configured to receive and process photocurrent signals from each of the two detectors.

FIGS. 40-45 each illustrate an example Raman spectroscopy system 100 that includes one or more optical fibers 116. Each of the optical fibers 116 in FIGS. 40-45 may be referred to as an optical-fiber extension, a fiber-optic extension, or an external optical fiber. Additionally, each of the Raman spectroscopy systems may be referred to as a Raman spectroscopy system with optical-fiber extension, a Raman spectroscopy system with fiber-optic extension, or a Raman spectroscopy system with external optical fiber. An optical-fiber extension refers to one or more optical fibers 116 that transmit light to or from an enclosure 101 of a Raman spectroscopy system 100. The optical fibers 116 in each of FIGS. 40-45 direct the combined pump-Stokes beam 140 from the enclosure 101 to a sample 150 and direct the resulting Raman signal 160 back to the enclosure. An optical-fiber extension allows the Raman signal 160 of a sample 150 located external to a Raman spectroscopy system 100 and some distance away from the system to be measured.

Each of the Raman spectroscopy systems 100 in FIGS. 40-45 includes an enclosure 101 and one or more optical fibers 116, where at least a portion of the optical fibers is located external to the enclosure. The enclosure 101 of a Raman spectroscopy system 100 may be referred to as a chassis or housing and may be made from metal (e.g., aluminum), plastic, or any other suitable substantially rigid material. An enclosure 101 may substantially enclose or contain one or more parts of a Raman spectroscopy system 100 and may include a feedthrough or a fiber-optic adapter that allows one or more optical fibers to exit from or connect to the enclosure. In each of FIGS. 42-45, the enclosure 101 contains a pump light source 110*pu*, Stokes light source 110S, and optical receiver 200. An enclosure 101 may also contain all or part of a processor. For example, an enclosure 101 may contain a processor that receives a digital output signal 240 from detection electronics 230, and the processor may analyze the digital output signal to determine a characteristic of a corresponding photocurrent signal i. In some embodiments, a processor or a portion of a processor may be located in the detection electronics 230 of a Raman spectroscopy system.

An optical fiber 116 (which may be referred to as a fiber-optic cable, fiber optic, or fiber) refers to a flexible glass or plastic fiber that transmits light with relatively low optical loss (e.g., less than 1 dB of optical-power loss per kilometer of fiber length). Light that propagates in an optical fiber 116 may travel primarily through a fiber-optic core that is surrounded by a cladding. The fiber-optic core (which may be referred to as a fiber core or as a core) may have a higher refractive index than the cladding, which provides optical confinement and guidance for light that propagates within an optical fiber. The optical fiber 116 in each of FIGS. 40-45 may include any suitable type of optical fiber. For example, an optical fiber 116 may be a single-mode (SM) optical fiber (e.g., with a core diameter of approximately 4 to 14 μm) or a muti-mode (MM) optical fiber (e.g., with a core diameter of approximately 50 to 100 μm). As another example, an optical fiber 116 may be a polarization-maintaining (PM) optical fiber, which is a type of SM fiber having two propagation axes that each allow linearly polarized light to propagate along the fiber and substantially maintain the linear polarization. As another example, an optical fiber 116 may be a hollow-core optical fiber where light propagates primarily along a hollow region of the fiber. A hollow-core optical fiber may provide lower optical loss, reduced optical nonlinearities, a higher optical damage threshold, or a larger optical bandwidth as compared to an optical fiber having a solid core made from glass or plastic. As another example, an optical fiber 116 may be a multi-core optical fiber having two or more cores along which light may propagate (e.g., the input and output optical fibers in FIG. 41 may be replaced by a single dual-core optical fiber in which the pump-Stokes beam 140 propagates along one core and the Raman signal propagates along the other core). The optical fiber 116 in each of FIGS. 40-45 may have any suitable length, such as for example a length of approximately 1 m, 2 m, 5 m, 10 m, 100 m, 1 kilometer (km), or 10 km. For example, a Raman spectroscopy system with optical-fiber extension that is used in a medical clinic or hospital may have an optical fiber 116 with a length of less than 10 m, while a Raman spectroscopy system with optical-fiber extension that is used to investigate an oil well may have an optical fiber with a length of 1-10 km.

Figure 40:
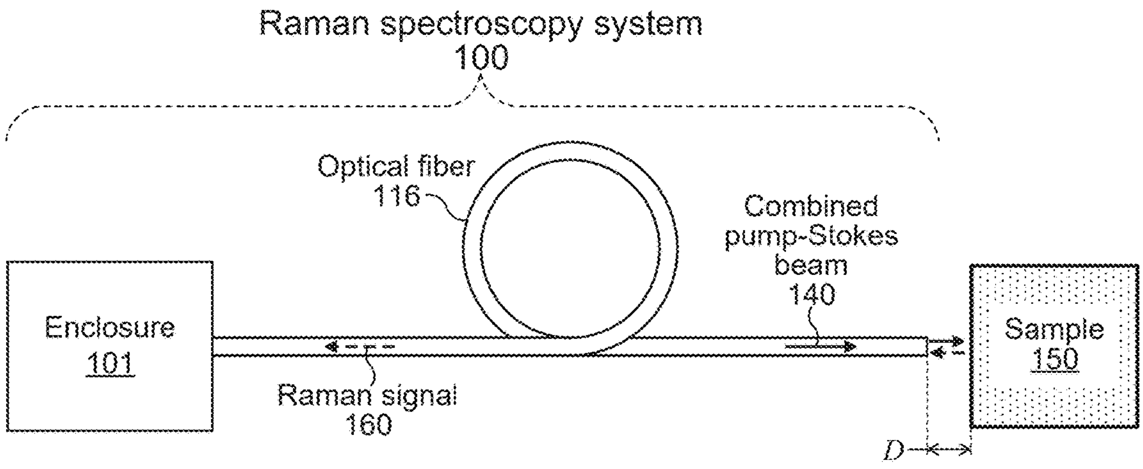
FIGS. 40-45 each illustrate an example Raman spectroscopy system that includes one or more optical fibers.
Figure 41:
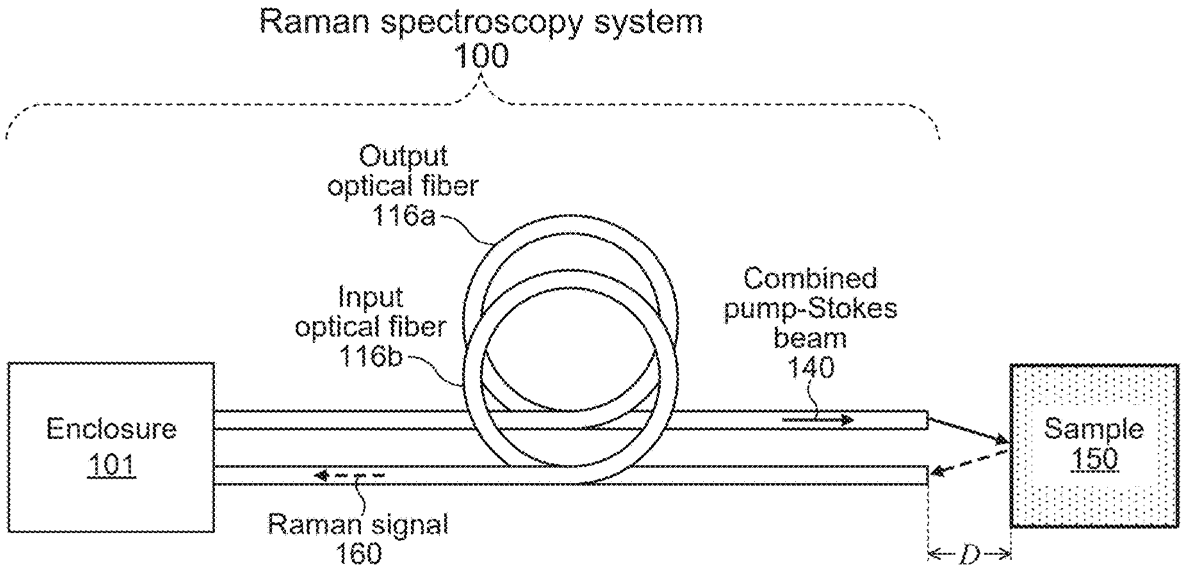

In each of FIGS. 40-41, a combined pump-Stokes beam 140 (which includes a pump beam 120*pu* and a Stokes beam 120S and which may be referred to as a pump-Stokes beam)

is directed by an optical fiber 116 from the enclosure 101 of a Raman spectroscopy system 100 to a sample 150. A Raman signal 160 is produced by coherent Raman scattering of the pump and Stokes beams of light at the sample 150, and the Raman signal is directed by an optical fiber 116 from the sample to the enclosure 101. A Raman spectroscopy system with optical-fiber extension may include 1, 2, 3, 4, 5, 10, or any other suitable number of optical fibers 116. In FIG. 40, the pump-Stokes beam 140 and the Raman signal 160 are directed to and from the sample 150 by a single optical fiber 116, and in FIG. 41, the pump-Stokes beam 140 and the Raman signal 160 are directed to and from the sample 150 separately by two optical fibers 116. The Raman spectroscopy system 100 in FIG. 40 includes one optical fiber 116 that (i) directs the combined pump-Stokes beam 140 to the sample 150 and (ii) directs the Raman signal 160 back to the enclosure 101 of the Raman spectroscopy system. The Raman spectroscopy system 100 in FIG. 41 includes two optical fibers: an output optical fiber 116*a* that directs the combined pump-Stokes beam 140 to the sample 150, and an input optical fiber 116*b* that directs the Raman signal 160 back to the enclosure 101 of the Raman spectroscopy system. In other embodiments, a Raman spectroscopy system 100 may include two or more optical fibers that direct the pump and Stokes beams to a sample or two or more optical fibers that direct the Raman signal back to the enclosure of the system. For example, one output optical fiber that directs a pump-Stokes beam to a sample may have two or more input optical fibers positioned around the output optical fiber, where each of the input optical fibers is configured to direct a portion of a Raman signal back to a Raman spectroscopy system.

In FIGS. 40-45, the pump-Stokes beam 140 may be emitted as a free-space optical beam directly from the output end of an optical fiber 116, and the resulting free-space pump-Stokes beam 140 may be a diverging beam. Alternatively, a lens may be located near the output end of an optical fiber 116, and the lens may produce a free-space pump-Stokes beam 140 that is focused or collimated. The sample 150 in FIGS. 40-41 is located a distance D from the end of the optical fiber 116. The distance D may have any suitable value, such as for example a value of approximately 1 mm, 2 mm, 5 mm, 10 mm, 100 mm, 1 m, 5 m, 10 m, 100 m, or 1 km. For example, the distance D may be between 0 mm and 10 mm for a Raman spectroscopy system with optical-fiber extension that is used to measure a person's skin for indications of skin cancer. As another example, the distance D may be between 1 m and 1 km for a Raman spectroscopy system used for remote measurement of a package, a person, a vehicle, or a manufacturing process.

In each of FIGS. 42-45, the Raman spectroscopy system 100 includes an enclosure 101 that contains a pump light source 110*pu*, a Stokes light source 110S, and an optical receiver 200 (which includes a probe light source 110*pr*, detector 220, and detection electronics 230). The pump light source 110*pu* produces a pump beam of light 120*pu* at a pump frequency (which may be referred to as a first frequency and may be represented by $v_{pu}$, $v_1$, $\omega_{pu}$, or $\omega_1$), and the Stokes light source 110S produces a Stokes beam of light 120S at a Stokes frequency (which may be referred to as a second frequency and may be represented by $v_S$, $v_2$, $\omega_S$, or $\omega_2$). The pump and Stokes frequencies may be offset by a frequency offset Ω, where Ω equals $v_{pu}-v_S$ (or equivalently, $\Omega=v_1-v_2$). The pump light source 110*pu* may be referred to as a first light source, and the pump beam of light 120*pu* may be referred to as a first beam of light. The Stokes light source 110S may be referred to as a second light source, and the Stokes beam of light 120S may be referred to as a second beam of light.

In each of FIGS. 42-45, the pump and Stokes beams are directed to a sample 150 by an optical fiber 116, and the sample produces a Raman signal 160 in response to the pump and Stokes beams. The Raman signal 160 may be produced by coherent Raman scattering of the pump and Stokes beams at the sample 150. For example, the Raman signal 160 may be produced by coherent Raman scattering that occurs within the sample 150 or at the surface of the sample. At least a portion of the Raman signal 160 produced by the sample 150 is coupled into an optical fiber 116 and directed to an optical receiver 200 that detects the Raman signal. The optical receiver 200 detects the Raman signal 160 using an optical heterodyne technique in which the Raman signal 160 is coherently mixed with a probe beam of light 120*pr* at an optical detector 220. An optical receiver 200 may include one or more optical detectors 220, where each detector is configured to coherently mix a portion of a Raman signal 160 with at least a portion of a probe beam 120*pr* to produce an electronic signal. The optical receiver 200 in each of FIGS. 42-45 includes one optical detector 220 that coherently mixes the Raman signal 160 with the probe beam 120*pr* to produce a photocurrent signal i. In other embodiments, an optical receiver 200 may include two or more optical detectors 220, where each detector is configured to coherently mix a portion of a Raman signal 160 with a portion of a probe beam 120*pr* to produce a corresponding photocurrent signal.

In each of FIGS. 42-45, the probe light source 110*pr* produces a probe beam of light 120*pr* at a probe frequency (which may be referred to as a third frequency and may be represented by $v_{pr}$, $v_3$, $\omega_{pr}$, or $\omega_3$). The probe beam 120*pr* is combined with the Raman signal 160, and the combined probe-Raman signal 210 is directed to an optical detector 220. The Raman signal 160 and the probe beam 120*pr* are coherently mixed at the detector 220 to produce a corresponding photocurrent signal i. Coherent mixing of the Raman signal 160 and the probe beam 120*pr* may refer to coherently mixing at least a portion of the Raman signal 160 with at least a portion of the probe beam 120*pr*. For example, an optical receiver 200 may include multiple detectors 220, and each detector may coherently mix a portion of a Raman signal with a portion of a probe beam 120*pr*. As another example, a detector 220 may coherently mix at least a portion of a probe beam 120*pr* with a spectral portion of a Raman signal 160, where the spectral portion of the Raman signal that is coherently mixed includes optical frequency components of the Raman signal that are located within a particular frequency range of the frequency $v_{pr}$ of the probe beam (e.g., the particular frequency range may depend on the electronic bandwidth of the detector 220).

In each of FIGS. 42-45, the detection electronics 230 (which may include or may be referred to as an electronic circuit) produces a digital output signal 240 corresponding to the photocurrent signal i. An electronic circuit 230 may include an electronic amplifier 232 and a digitizer 236 (e.g., like that illustrated in FIG. 2). The electronic amplifier 232 may amplify the photocurrent signal i to produce a voltage signal 234 that corresponds to the photocurrent signal, and the digitizer 236 may produce a digital representation of the voltage signal. The digital representation of the voltage signal 234 may include digital values that approximate the shape of the voltage signal. The digital representation of the voltage signal 234 may be sent to a processor as part of the digital output signal 240. The digital output signal 240 may be referred to as corresponding to the photocurrent signal i, since the digital output signal 240 includes a digital representation of the voltage signal 234, and the voltage signal corresponds to the photocurrent signal i.

The digital output signal 240 in each of FIGS. 42-45 may be sent to a processor, and the processor may determine a characteristic 162 of the photocurrent signal i based on the digital output signal. For example, the digital output signal may include a digital representation of a voltage signal 234. The processor may determine a characteristic of the digital representation of the voltage signal 234, and that characteristic may be referred to as being a characteristic of the corresponding photocurrent signal i. The characteristic 162 of a photocurrent signal may include one or more of: a peak amplitude, an average amplitude, an amplitude at a particular frequency, an amplitude at a particular time, an amplitude at a frequency center, an amplitude at a temporal center, a DC offset, an area, a frequency, a phase, and a polarization. Additionally, a processor may associate a Raman frequency shift with a determined characteristic 162 of a photocurrent signal i. The Raman frequency shift may equal $v_{pu}-v_{pr}$, where $v_{pu}$ is the pump frequency, and $v_{pr}$ is the probe frequency.

The probe light source 110*pr* in each of FIGS. 42-45 may include a wavelength-tunable laser configured to sequentially change the probe-beam frequency $v_{pr}$ to multiple different frequencies. At each of the different probe-beam frequencies, the optical detector 220 may coherently mix the probe beam 120*pr* and the Raman signal 160 to produce a corresponding photocurrent signal, and a processor may determine a characteristic of each of the photocurrent signals. In some embodiments, the frequency offset Ω between the pump and Stokes frequencies may be approximately equal to a vibrational frequency of a particular material, and a processor may determine, based on a determined characteristic 162 of a photocurrent signal i, (i) whether the particular material is present in a sample 150 or (ii) an amount or a concentration of the particular material in the sample. A processor of a Raman spectroscopy system 100 may include or may be referred to as a computer system, a controller, a computing device, a computing system, a computer, or a data-processing apparatus. A processor may be similar to the computer system 1000 illustrated in FIG. 122 and described herein. In some embodiments, a processor or a portion of a processor may be located in the detection electronics 230 of a Raman spectroscopy system.

Figure 42:
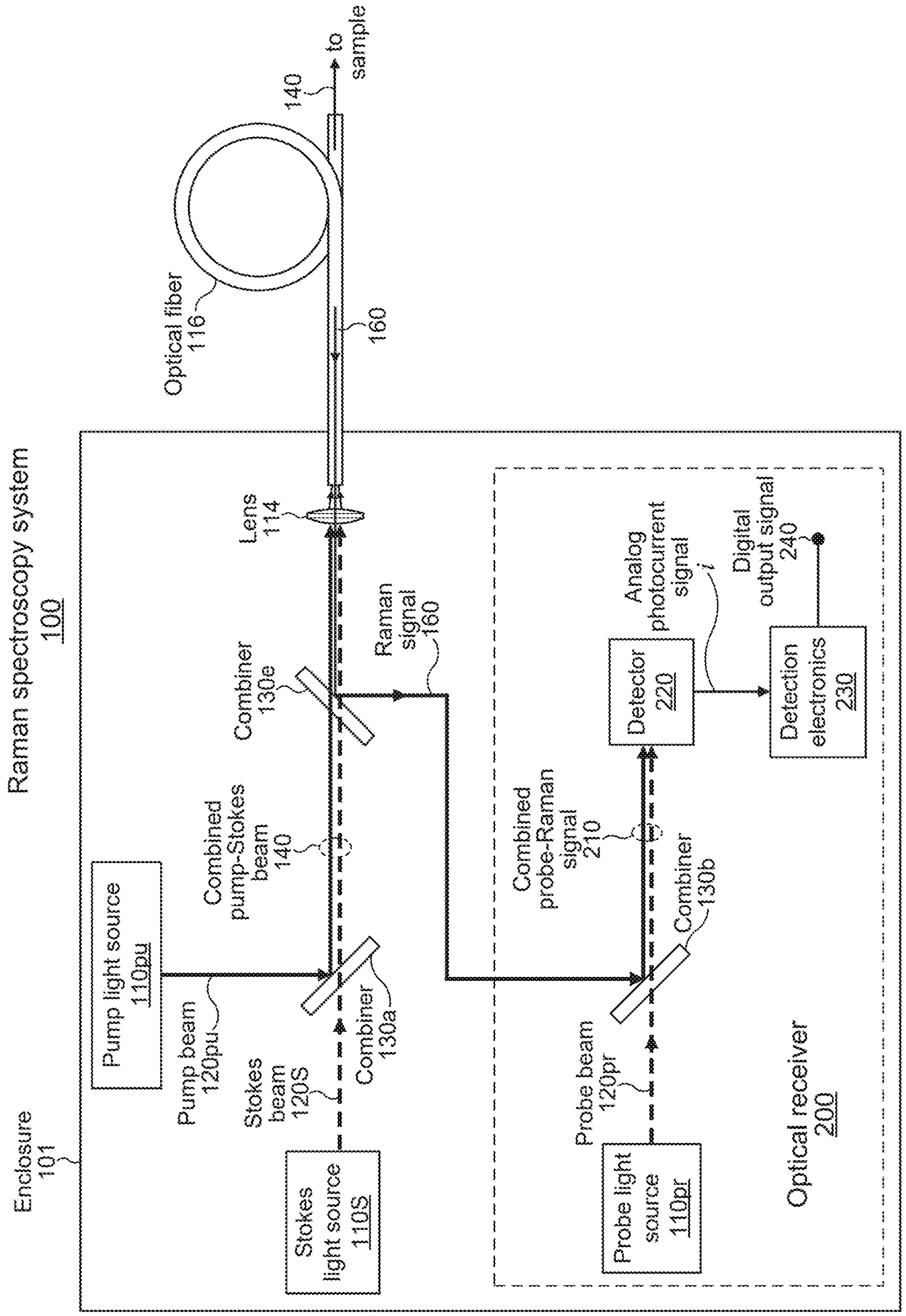
Figure 43:
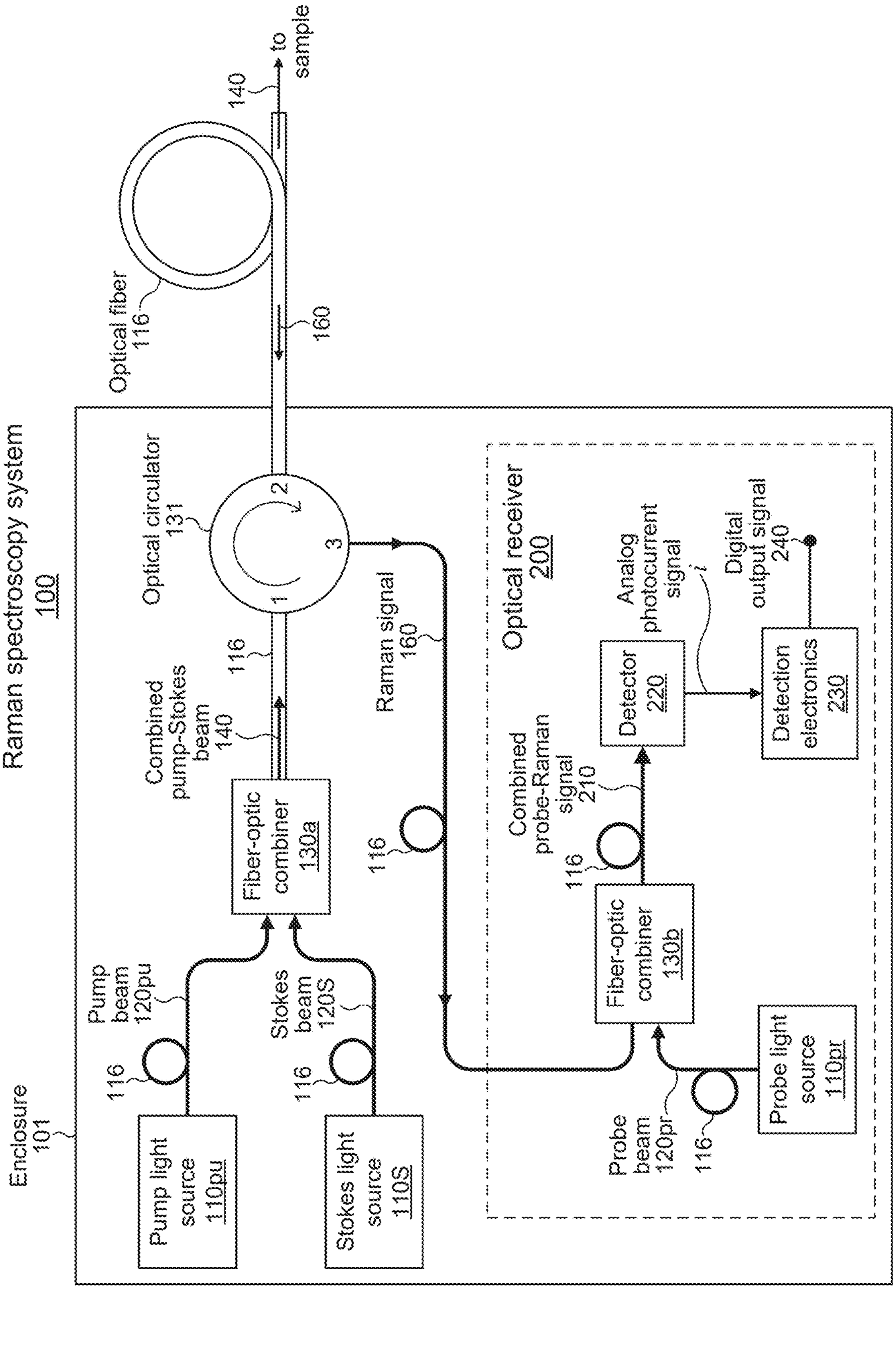

The Raman spectroscopy system 100 in each of FIGS. 42 and 43 includes one optical fiber 116 that (i) directs a pump beam 120*pu* and a Stokes beam 120S to a sample 150 and (ii) directs a Raman signal 160 back to the enclosure 101 of the system. The combined pump-Stokes beam 140 and the Raman signal 160 propagate in opposite directions within the same optical fiber 116. The Raman spectroscopy system 100 in each of FIGS. 44 and 45 includes two optical fibers: an output optical fiber 116*a* that directs a pump beam 120*pu* and a Stokes beam 120S to a sample 150, and an input optical fiber 116*b* that directs a Raman signal 160 back to the enclosure 101 of the system.

The optical beams within the enclosure 101 of a Raman spectroscopy system 100 may be free-space optical beams, fiber-coupled optical beams, or waveguide-coupled optical beams (e.g., a beam that propagates in an optical waveguide of a PIC), or any combination thereof. In FIG. 42, the optical beams within the enclosure 101 are primarily free-space optical beams, while in FIG. 43, the optical beams within the enclosure 101 are primarily fiber-coupled optical beams. In FIG. 42, the pump beam 120*pu* and the Stokes beam 120S are combined at a free-space optical combiner 130*a* to produce a free-space combined pump-Stokes beam 140 that is coupled into the optical fiber 116 by a lens 114. The Raman signal 160 produced by a sample is coupled into the opposite end of the optical fiber 116 and propagates along the optical fiber to the enclosure 101 of the Raman spectroscopy system 100. The Raman signal 160 is emitted from the optical fiber 116 and collimated by the lens 114. The optical combiner 130*e* (which may be a dichroic or non-dichroic beamsplitter or a polarization beamsplitter) splits off at least a portion of the Raman signal 160, which is directed to the optical receiver 200. The free-space optical combiner 130*b* combines the probe beam 120*pr* with the Raman signal 160 to produce a free-space probe-Raman signal 210 that is directed to a detector 220.

In FIG. 43, the fiber-coupled pump beam 120*pu* and Stokes beam 120S are combined at a fiber-optic combiner 130*a* to produce a fiber-coupled pump-Stokes beam 140 that is directed to an optical circulator 131 by an optical fiber. The optical circulator 131 is a three-port fiber-optic component that receives input light at one port and directs that light to exit the circulator from another port. For example, light that enters the optical circulator 131 at port 1 is directed to exit the circulator from port 2, and light that enters the circulator at port 2 is directed to exit the circulator from port 3. The optical circulator 131 in FIG. 43 receives the combined pump-Stokes beam 140 at port 1 and directs the combined pump-Stokes beam to the optical fiber 116, which is coupled to port 2. Additionally, the optical circulator 131 receives the Raman signal 160 from the optical fiber 116 at port 2 and directs the Raman signal to the optical receiver 200 via an optical fiber coupled to port 3. The fiber-optic combiner 130*b* combines the fiber-coupled probe beam 120*pr* with the fiber-coupled Raman signal 160 to produce a fiber-coupled probe-Raman signal 210 that is directed to a detector 220. In other embodiments, instead of using a fiber-optic circulator 131 (as illustrated in FIG. 43), a Raman spectroscopy system may use a fiber-optic combiner as an optical splitter that splits off at least a portion of a Raman signal and directs the split-off Raman signal to an optical receiver.

Figure 44:
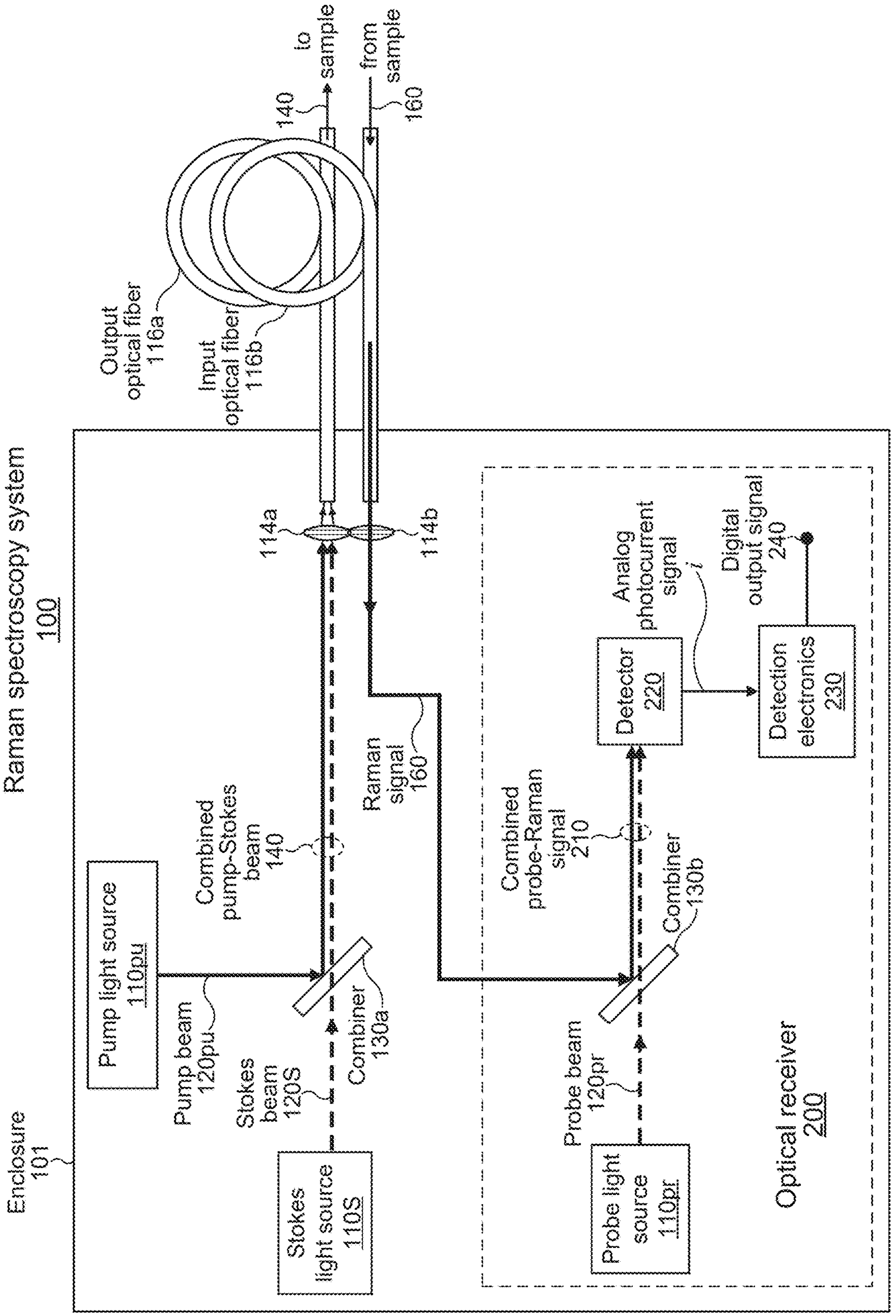
Figure 45:
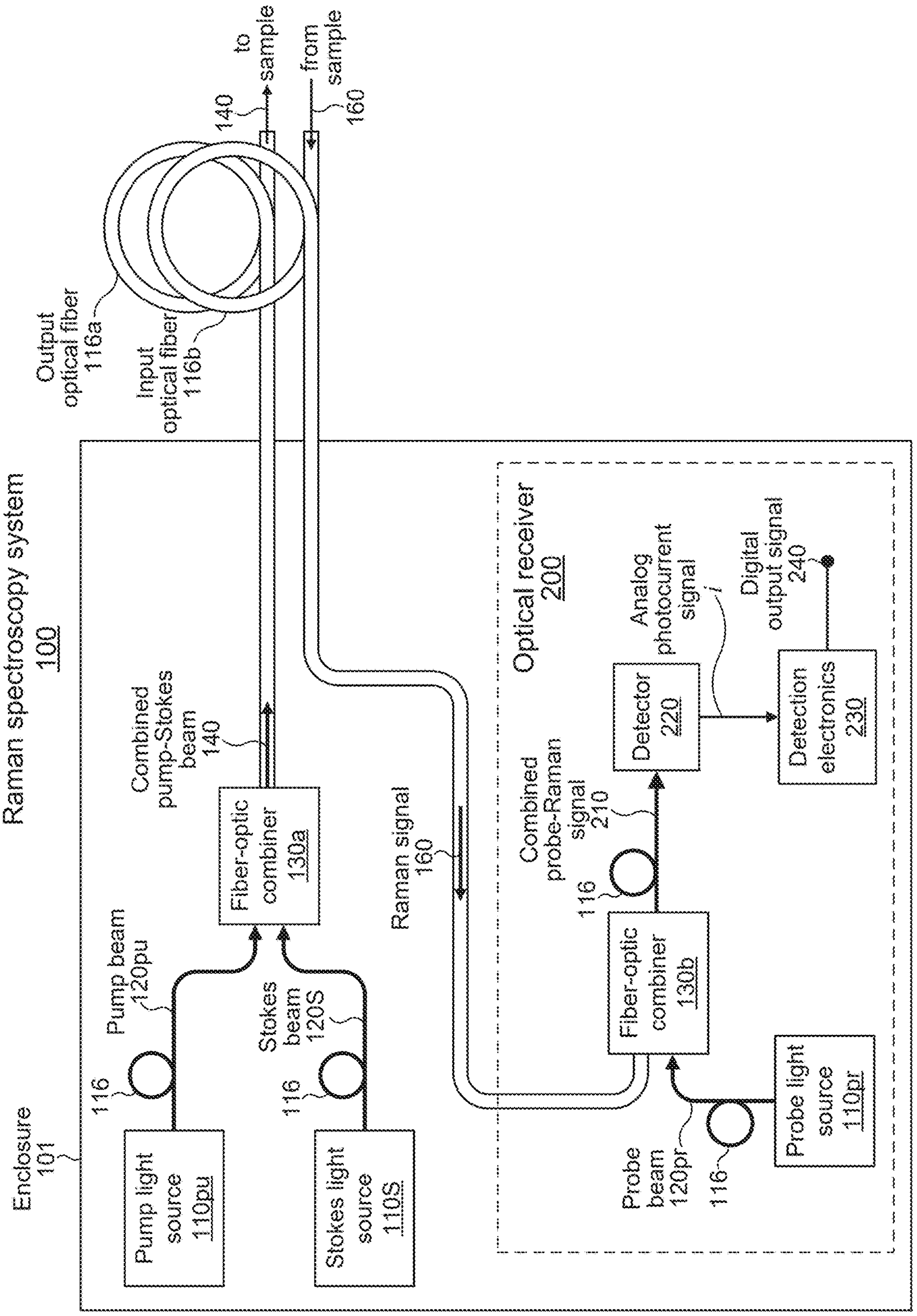

In FIG. 44, the optical beams within the enclosure 101 are primarily free-space optical beams, while in FIG. 45, the optical beams within the enclosure 101 are primarily fiber-coupled optical beams. In FIG. 44, the pump beam 120*pu* and the Stokes beam 120S are combined at a free-space optical combiner 130*a* to produce a free-space combined pump-Stokes beam 140 that is coupled into an output optical fiber 116*a* by a lens 114*a*. The Raman signal 160 produced by a sample is coupled into an input optical fiber 116*b* and propagates along the input fiber to the enclosure 101 of the Raman spectroscopy system 100. The Raman signal 160 is emitted from the optical fiber 116 and collimated by a lens 114*b* to produce a free-space Raman signal 160 that is directed to an optical receiver 200. The free-space optical combiner 130*b* combines the probe beam 120*pr* with the Raman signal 160 to produce a free-space probe-Raman signal 210 that is directed to a detector 220.

In FIG. 45, the fiber-coupled pump beam 120*pu* and Stokes beam 120S are combined at a fiber-optic combiner 130*a* to produce a fiber-coupled pump-Stokes beam 140 that propagates along an output optical fiber 116*a* and is directed to a sample. The fiber-optic combiner 130*a* in each of FIGS. 43 and 45 is similar to the fiber-optic combiner 130 illustrated in FIG. 25. In FIG. 45, the Raman signal 160 produced by the sample is coupled into an input optical fiber 116*b* and propagates along the input fiber into the enclosure 101 of the Raman spectroscopy system 100 and to a fiber-optic combiner 130*b*. The fiber-optic combiner 130*b* combines the fiber-coupled probe beam 120*pr* with the fiber-coupled Raman signal 160 to produce a fiber-coupled probe-Raman signal 210 that is directed to a detector 220. The fiber-optic combiner 130*b* in each of FIGS. 43 and 45 is similar to the fiber-optic combiner 130 illustrated in FIG. 28.

A technical advantage of a Raman spectroscopy system 100 with optical-fiber extension is the ability to measure a sample 150 located outside of the system. A Raman spectroscopy system with optical-fiber extension allows a sample 150 to be measured in place instead of having to first collect a sample that is then put inside a system for measurement. Additionally, since an optical fiber 116 is typically flexible and relatively lightweight, an operator of the system may direct the optical fiber to a particular location with relative ease while the enclosure 101 and its contents remain fixed in place. The flexible optical fiber 116 may allow an operator to make measurements by positioning the end face of the optical fiber to direct a combined pump-Stokes beam 140 at an object of interest (e.g., a person's skin, water, wastewater, or a manufacturing process). For example, a Raman spectroscopy system with optical-fiber extension may be used during a medical procedure, such as for example, to identify tumor margins during surgery, diagnose skin cancer, identify issues during a colonoscopy, or measure interstitial fluid located under the skin. The relatively low optical loss of an optical fiber 116 may allow the measurement of objects that are located a relatively long distance from the enclosure 101 of a Raman spectroscopy system 100. Additionally, the relatively small size of an optical fiber 116 may allow the measurement of objects located in relatively hard-to-reach places. For example, an optical fiber 116 inserted into an oil well may allow the measurement of materials located deep underground.

Figure 46:
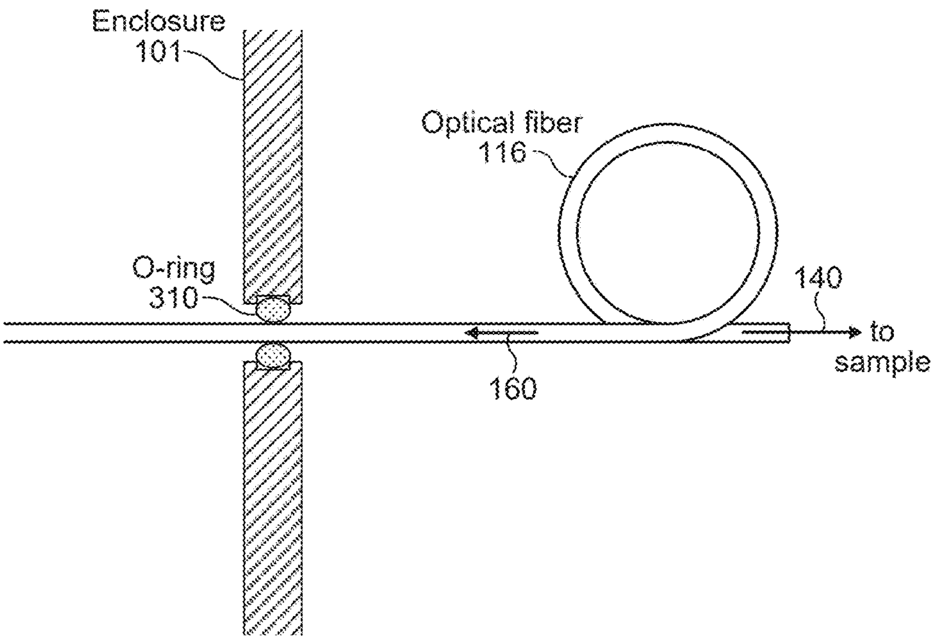
FIGS. 46-47 each illustrate a cross-section of a portion of an enclosure with an example fiber-optic feedthrough.
Figure 47:
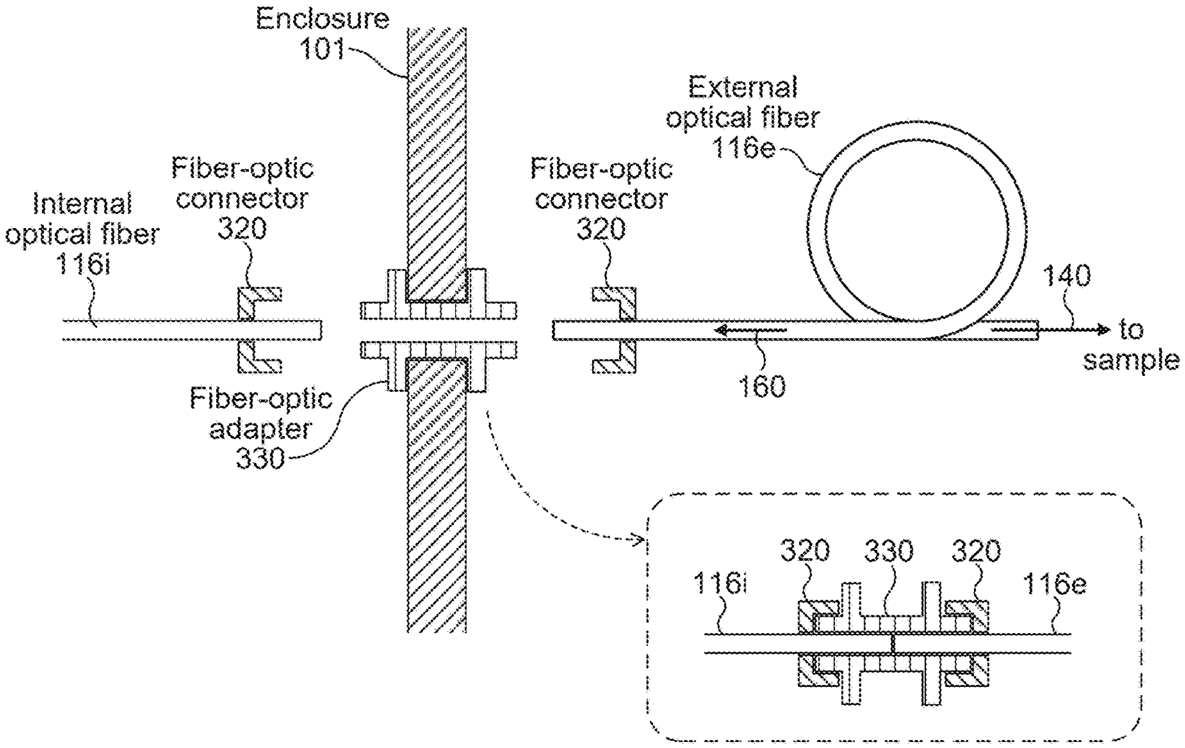

FIGS. 46-47 each illustrate a cross-section of a portion of an enclosure 101 with an example fiber-optic feedthrough. A fiber-optic feedthrough allows light propagating in an optical fiber 116 to be delivered (i) from inside the enclosure 101 of a Raman spectroscopy system 100 to outside the enclosure or (ii) from outside the enclosure to inside the enclosure. In FIG. 46, a fiber-optic feedthrough for an optical fiber 116 is provided by an opening in the enclosure 101 and an O-ring 310. The optical fiber 116 passes through a hole in the enclosure 101 and into the interior of the enclosure (located on the left side of FIG. 46). The O-ring 310 provides for a feedthrough that mechanically secures the optical fiber 116 and prevents movement or damage to the optical fiber. In FIG. 47, a fiber-optic feedthrough is provided by a fiber-optic adapter 330. An internal optical fiber 116*i* located in the interior of the enclosure 101 is connected to an external optical fiber 116*e* by a fiber-optic adapter 330. The internal and external optical fibers each have a fiber-optic connector 320 that is secured to the fiber-optic adapter 330 (e.g., by screwing the connector to mating threads on the adapter). The dashed-line inset in FIG. 47 illustrates the fiber-optic connectors 320 connected to the fiber-optic adapter 330 so that the ends of the optical fibers 116*i* and 116*e* are in contact and light may be coupled from one fiber to the other. The fiber-optic adapter 330 provides for an optical connection between the ends of the two optical fibers so that the combined pump-Stokes beam 140 and the Raman signal 160 are transmitted between the fibers with low optical loss (e.g., less than 0.5 dB of optical loss). The internal optical fiber 116*i* couples the combined pump-Stokes beam 140 to the external optical fiber 116*e*, which directs the pump-Stokes beam to a sample 150. Additionally, the external optical fiber 116*e* directs a Raman signal 160 from the sample 150 back to the enclosure 101 and couples the Raman signal to the internal optical fiber 116*i*. Any of the example Raman spectroscopy systems 100 in FIGS. 40-45 may include (i) an optical fiber 116 that enters the interior of the enclosure 101 through a hole in the enclosure (e.g., as illustrated in FIG. 46) or (ii) an external optical fiber 116*e* that is optically connected to an internal optical fiber 116*i* by a fiber-optic adapter 330 (e.g., as illustrated in FIG. 47).

Each of the optical fibers 116 in FIGS. 40-47 may be a passive optical fiber that transmits light with relatively low optical loss and does not provide optical amplification. In other embodiments, an optical fiber 116 may include a fiber-optic amplifier 126 that provides optical amplification to light traveling along the optical fiber. The fiber-optic amplifier may include an optical gain fiber doped with rare-earth materials (e.g., neodymium, erbium, or ytterbium) or bismuth. For example, a portion of the output optical fiber 116*a* in FIG. 45 that is located within the enclosure 101 may include a fiber-optic amplifier that amplifies the pump beam 120*pu* or the Stokes beam 120S. As another example, a portion of the input optical fiber 116*b* in FIG. 45 that is located within the enclosure 101 may include a fiber-optic amplifier that amplifies the Raman signal 160. As another example, the internal optical fiber 116*i* in FIG. 47 may include a fiber-optic amplifier that amplifies the pump or Stokes beam before exiting the enclosure 101 or amplifies the Raman signal 160 before the Raman signal is directed to an optical receiver 200. As another example, the pump light source 110*pu* or the Stokes light source 110S in any of FIGS. 42-45 may include a seed laser diode followed by an optical amplifier (e.g., a SOA 124 or a fiber-optic amplifier 126).

Figure 48:
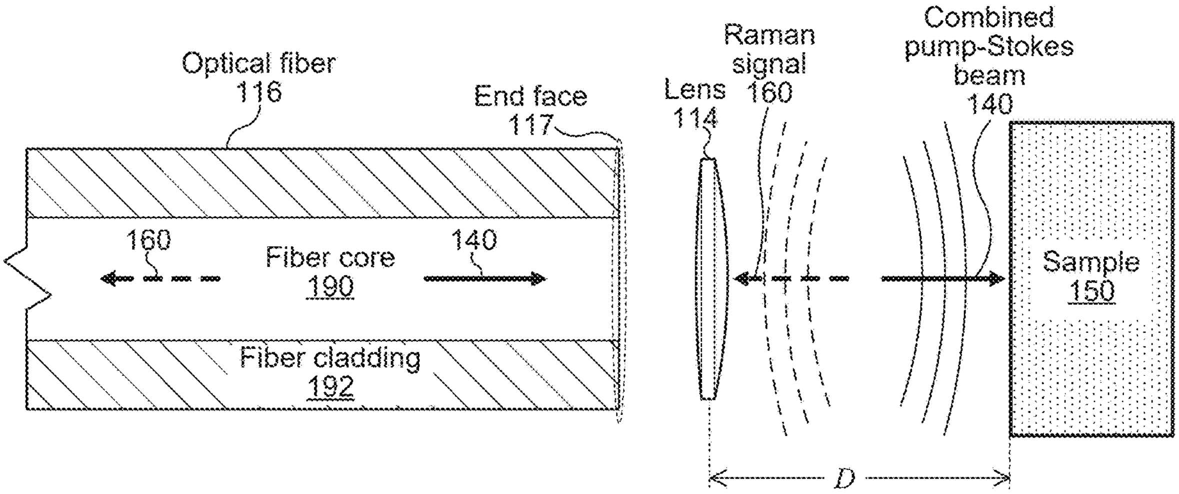
FIG. 48 illustrates the end face of an example optical fiber along with a lens.

FIG. 48 illustrates the end face 117 of an example optical fiber 116 along with a lens 114. The end face 117 of an optical fiber 116 (which may be referred to as a terminal end of an optical fiber) refers to an end of the optical fiber where light is coupled into the fiber or light is emitted from the fiber. The end face 117 may have a polished surface that provides an optical interface with low optical scattering. Additionally, an anti-reflection coating may be deposited onto the surface of the end face 117 to reduce the optical-reflection loss of light that is coupled into or out of the optical fiber 116. A combined pump-Stokes beam 140 emitted from the end face 117 of an optical fiber 116 may propagate as a free-space optical beam that includes the pump and Stokes beams. The free-space optical beam may be a diverging beam, or a lens 114 may be positioned near the end face 117 to produce a collimated or focused free-space beam.

The optical fiber 116 in FIG. 48 (which may correspond to the optical-fiber extension 116 in FIG. 40, 42, 43, 46, or 47) directs a combined pump-Stokes beam 140 to a sample 150 and directs the associated Raman signal 160 back to the enclosure 101 of a Raman spectroscopy system 100. The combined pump-Stokes beam 140 and the Raman signal 160 may propagate along the optical fiber 116 primarily through the fiber-optic core 190 which is surrounded by a fiber-optic cladding 192. In FIG. 48, the combined pump-Stokes beam 140 is emitted from the end face 117 of the optical fiber 116 as a free-space optical beam that includes the pump and Stokes beams. The lens 114, which is located near the end face 117, receives the pump-Stokes beam 140 emitted from the end face and produces a free-space pump-Stokes beam 140 that is directed to the sample 150. Additionally, the lens 114 in FIG. 48 receives the Raman signal 160 produced by the sample 150 in response to the pump and Stokes beams.

The lens 114 may focus the Raman signal 160 to couple the Raman signal into the optical fiber 116 via the end face 117.

In FIG. 48, the free-space pump-Stokes beam 140 emitted from the end face 117 may be a diverging free-space optical beam, and the lens 114 may be configured to produce a free-space pump-Stokes beam that is collimated or focused. For example, the lens 114 may produce a collimated pump-Stokes beam 140, and the distance D from the lens to the sample 150 may be any suitable distance from 0 mm to 1 km (e.g., the distance D may be approximately 0 mm, 1 mm, 2 mm, 5 mm, 10 mm, 0.1 m, 1 m, 10 m, 100 m, or 1 km). As another example, the lens 114 may be configured to focus the pump-Stokes beam 140 onto the sample 150. In this case, the distance D from the lens to the sample 150 may be between approximately f and 4f, where f is the focal length of the lens (e.g., for a lens with a 10-mm focal length, the distance to the sample may be 10-40 mm).

In other embodiments, the end face 117 of an optical fiber 116 may directly emit a combined pump-Stokes beam 140 without having a lens positioned near the end face, and the pump-Stokes beam may be emitted as a diverging free-space optical beam that is directed to a sample 150. Additionally, a Raman signal 160 produced by the sample 150 may be directly coupled into the optical fiber 116 without first being focused by a lens. For example, an optical fiber 116 without a lens may be used to investigate a sample 150 located between 0 mm and 10 mm from the end face 117.

A lens 114 may be attached to or integrated into the end face 117 of an optical fiber 116, or a lens may be located some distance from the end face 117. For example, the end face 117 of an optical fiber 116 may include a gradient refractive index or a lensed tip (which may be referred to as a fiber lens) that is integrated into the end face and that acts as a lens. As another example, a lens 114 may be a spherical lens, an aspheric lens, or a gradient-index (GRIN) lens, and the lens may be located some distance from the end face 117 or may be attached to the end face. The distance from the end face 117 to the lens 114 may be less than approximately 4f, where f is the focal length of the lens. For example, the distance from the end face 117 to the lens 114 may be approximately equal to for 2f. For a lens 114 that is attached to an end face 117, the distance from the end face to the lens may be referred to as being 0 mm.

Figure 49:
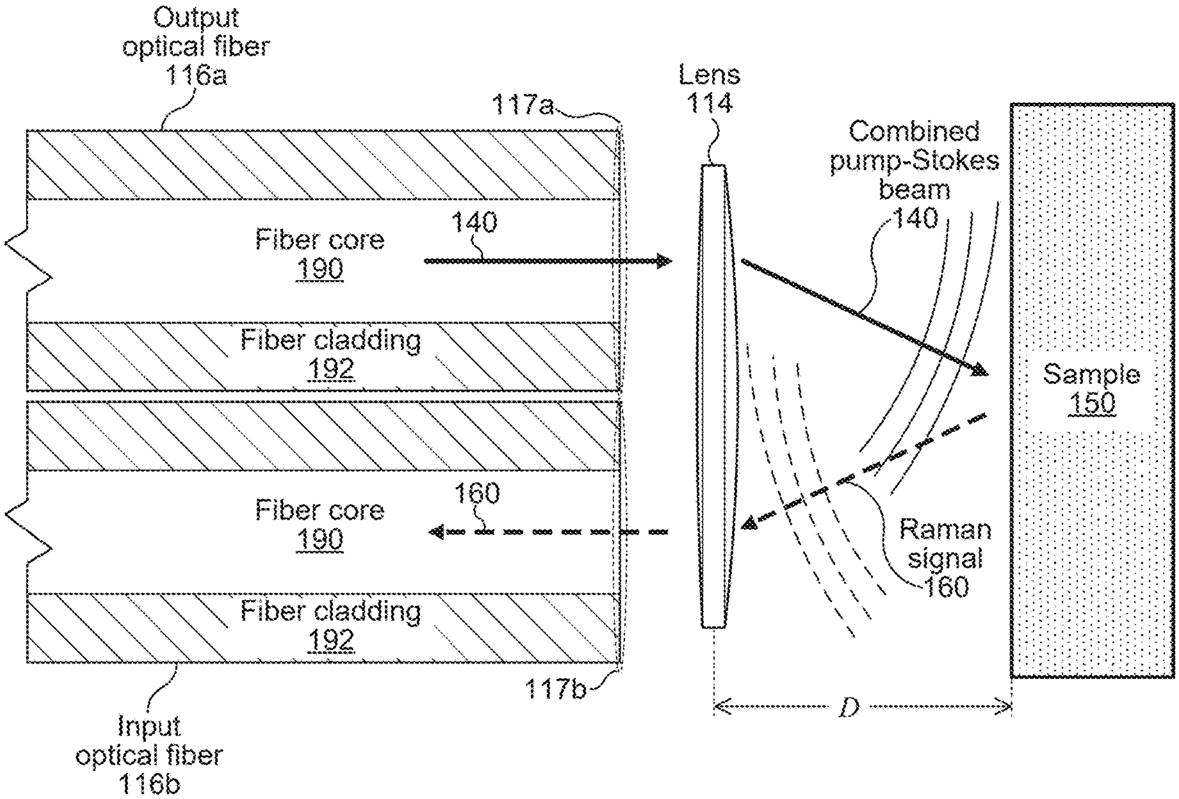
FIG. 49 illustrates example input and output optical fibers along with a lens.

FIG. 49 illustrates example input and output optical fibers 116*b* and 116*a* along with a lens 114. The input and output optical fibers 116*b* and 116*a* in FIG. 49 may correspond to the input and output optical fibers 116*b* and 116*a* in FIG. 41, 44, or 45. The output optical fiber 116*a* in FIG. 49 directs the combined pump-Stokes beam 140 to a sample 150, and the input optical fiber 116*b* directs the associated Raman signal 160 back to the enclosure 101 of a Raman spectroscopy system 100. The combined pump-Stokes beam 140 is emitted from the end face 117*a* of the output optical fiber 116*a* as a free-space optical beam that includes the pump and Stokes beams. The lens 114 receives the pump-Stokes beam 140 emitted from the end face 117*a* and produces a free-space pump-Stokes beam 140 that is directed to the sample 150. The free-space pump-Stokes beam 140 produced by the lens 114 may be a collimated or focused free-space beam. Additionally, the lens 114 in FIG. 49 receives the Raman signal 160 produced by the sample 150 in response to the pump and Stokes beams and couples the Raman signal into the input optical fiber 116*b*. The lens 114 may focus the Raman signal 160 to couple the signal into the input optical fiber 116*b* via the end face 117*b*.

In FIG. 49, a single lens 114 is used to (i) receive the pump-Stokes beam 140 from the output optical fiber 116*a* and direct the pump-Stokes beam to the sample 150 and (ii) receive the Raman signal 160 from the sample and couple the Raman signal into the input optical fiber 116*b*. In other embodiments, a Raman spectroscopy system 100 that includes multiple input or output optical fibers may include multiple lenses 114. For example, a Raman spectroscopy system 110 that includes one input optical fiber and one output optical fiber may include two lenses 114: an output lens located near the end face 117*a* of the output optical fiber 116*a*, and an input lens located near the end face 117*b* of the input optical fiber 116*b*. The output lens may receive the pump-Stokes beam 140 emitted from the end face 117*a* and produce a free-space pump-Stokes beam 140 that is directed to the sample 150. The free-space pump-Stokes beam 140 produced by the output lens may be a collimated or focused free-space beam. The input lens may receive the Raman signal 160 produced by the sample 150 in response to the pump and Stokes beams and couple the Raman signal into the input optical fiber 116*b* via the end face 117*b*. The input lens may focus the Raman signal 160 to couple the Raman signal into the input optical fiber 116*b*.

Figure 50:
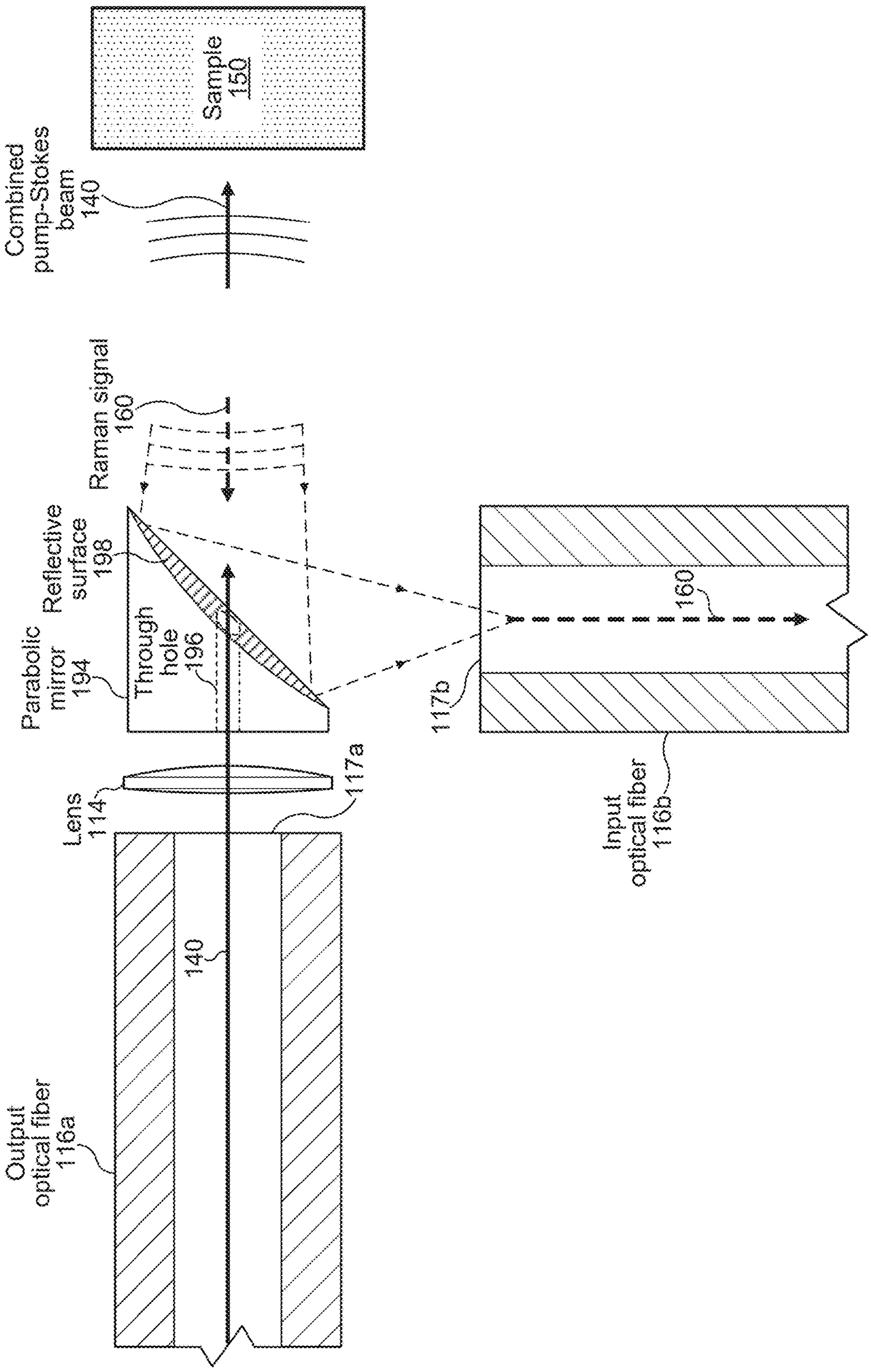
FIG. 50 illustrates example input and output optical fibers along with a parabolic mirror.

FIG. 50 illustrates example input and output optical fibers 116*b* and 116*a* along with a parabolic mirror 194. The input and output optical fibers 116*b* and 116*a* in FIG. 50 may correspond to the input and output optical fibers 116*b* and 116*a* in FIG. 41, 44, or 45. The output optical fiber 116*a* in FIG. 50 directs a combined pump-Stokes beam 140 to a sample 150, and the input optical fiber 116*b* directs the associated Raman signal 160 back to the enclosure 101 of a Raman spectroscopy system 100. The combined pump-Stokes beam 140 is emitted from the end face 117*a* of the output optical fiber 116*a* as a free-space optical beam that includes the pump and Stokes beams. The output lens 114 receives the pump-Stokes beam 140 emitted from the end face 117*a* and produces a combined pump-Stokes beam 140 that is directed to the sample 150. The free-space pump-Stokes beam 140 produced by the lens 114 may be a collimated or focused free-space beam.

The mirror 194 includes a through hole 196 that the free-space pump-Stokes beam 140 propagates through while traveling to the sample 150. The through hole 194 may be a circular or conical hole having a diameter greater than the beam diameter of the pump-Stokes beam 140. For example, the lens 114 may produce a collimated pump-Stokes beam 140 having a 2-mm beam diameter, and the through hole 194 may have a diameter of approximately 4 mm. The mirror 194 has a reflective surface 198 that receives the Raman signal 160 produced by the sample 150 in response to the pump and Stokes beams and reflects the Raman signal to direct the signal to the end face 117*b* of the input optical fiber 116*b*. The reflective surface 198 may be substantially flat, and a lens (not illustrated in FIG. 50) located between the reflective surface and the end face 117*b* may focus the Raman signal 160 into the optical fiber 116*b*. Alternatively, the reflective surface 198 may have a curved shape that focuses the Raman signal 160. For example, as illustrated in FIG. 50, the mirror 194 may be an off-axis parabolic mirror where the reflective surface 198 has a parabolic shape. The parabolic reflective surface 198 may focus the Raman signal 160 so that it is coupled into the input optical fiber 116*b* via the end face 117*b*.

Figure 51:
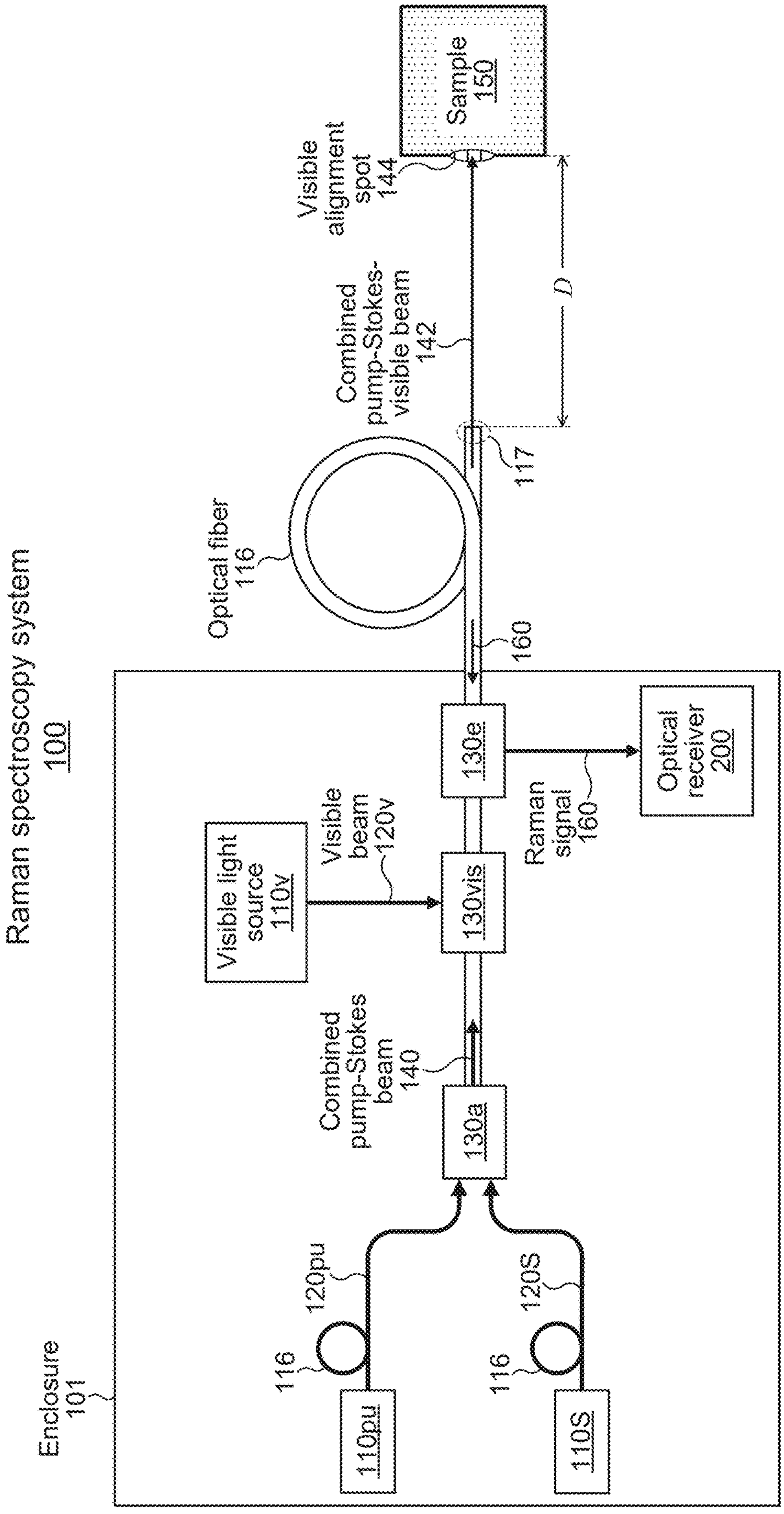
FIG. 51 illustrates an example Raman spectroscopy system that includes a visible light source.

FIG. 51 illustrates an example Raman spectroscopy system 100 that includes a visible light source 110*v*. The visible light source 110*v* produces a visible beam of light 120*v* that is combined at an optical combiner 130*v* is with the combined pump-Stokes beam 140 to produce a combined pump-Stokes-visible beam 142. The combined pump-Stokes-visible beam 142 (which includes the pump beam 120*pu*, the Stokes beam 120S, and the visible beam 120*v*) travels through an optical fiber 116 and is emitted as a free-space optical beam that is directed to a sample 150. The sample produces a Raman signal 160 in response to the pump and Stokes beams, and at least a portion of the Raman signal is coupled into the optical fiber 116 and propagates along the fiber to the enclosure 101 of the Raman spectroscopy system 100. The optical combiner 130*e* splits off at least a portion of the Raman signal 160, which is directed to the optical receiver 200 for detection. In other embodiments, an optical circulator 131 (e.g., as illustrated in FIG. 43) may be used in place of the optical combiner 130*e* in FIG. 51.

The pump beam 120*pu* and the Stokes beam 120S may each have wavelengths that are not visible to the human eye (e.g., the pump and Stokes wavelengths may be greater than approximately 900 nm), and the pump and Stokes beams may not produce a visible spot of light at the sample 150. The visible beam 120*v* may have a wavelength that is visible to the human eye. For example, the visible light source 110*v* may include a laser that produces a visible beam of light 120*v* having a wavelength between approximately 380 nm (blue) and approximately 780 nm (red). As another example, the visible light source 110*v* may include (i) a laser diode with an operating wavelength of approximately 450-490 nm or 635 nm or (ii) a solid-state laser with an operating wavelength of approximately 532 nm.

In FIG. 51, the visible beam 120*v* is directed to the sample 150 along with the pump and Stokes beams. The visible beam 120*v* produces a visible alignment spot 144 at a location where the combined pump-Stokes-visible beam 142 is incident on the sample 150. The visible alignment spot 144 includes light from the visible beam 120*v* that is scattered or reflected from the sample 150. The visible alignment spot 144 indicates the location of the pump and Stokes beams at the sample 150 and may be used by an operator of the system 100 to aim the combined pump-Stokes beam 140 to the sample. For example, an operator may position the end face 117 of the optical fiber 116 to direct the combined pump-Stokes-visible beam 142 to the sample 150 using the location of the visible alignment spot 144 as an alignment aid. Any of the Raman spectroscopy systems 100 illustrated in FIGS. 40-45 may include a visible light source 110*v* that produces a visible beam of light 120*v*, similar to that illustrated in FIG. 51.

In FIG. 51, the visible beam 120*v* propagates to the sample 150 in an optical fiber 116 along with the pump and Stokes beams. In other embodiments, a visible beam 120*v* produced by a visible light source 110*v* may propagate in a different optical fiber 116 from the pump and Stokes beams. For example, in FIG. 45, a visible beam 120*v* may be coupled into the input optical fiber 116*b* and directed to propagate to the sample (and in the opposite direction of the Raman signal 160). As another example, a Raman spectroscopy system 100 may include a separate optical fiber configured to direct a visible beam 120*v* to a sample 150. The pump-Stokes beam 140 may propagate in a first output optical fiber, and the visible beam 120*v* may propagate in a second output fiber. The first and second output optical fibers may be aligned so that the free-space pump-Stokes beam 140 and the free-space visible beam 120*v* propagate together and the visible alignment spot 144 produced at the sample 150 is substantially overlapped with or directly adjacent to the location of the pump and Stokes beams at the sample. For example, the free-space visible beam 120*v* may propagate along an optical axis that is approximately parallel to and directly adjacent to the optical axis along which the combined pump-Stokes beam 140 propagates.

Figure 52:
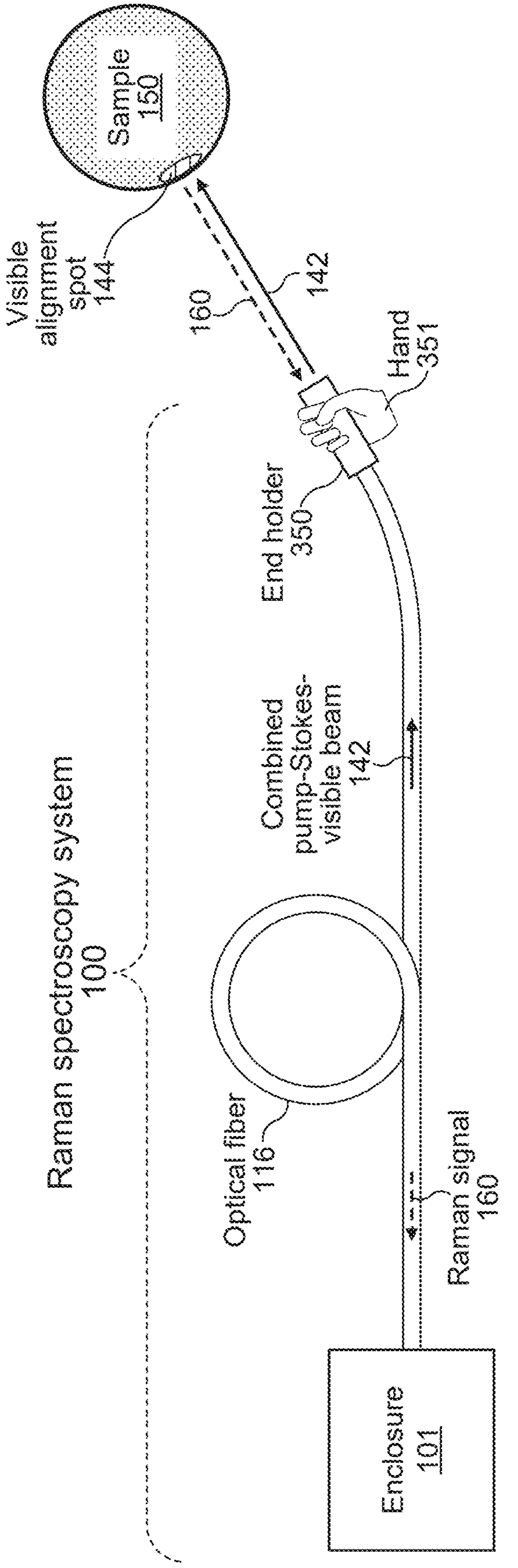
FIG. 52 illustrates an example Raman spectroscopy system with a moveable end holder.

FIG. 52 illustrates an example Raman spectroscopy system 100 with a moveable end holder 350. The end holder 350 may include a mechanical housing that contains the end face 117 of one or more optical fibers 116 along with one or more lenses 114 or a mirror 194 with a through hole 196. For example, the end face 117 and lens 114 in FIG. 48 may be contained within an end holder, or the end faces 117*a* and 117*b* and the lens 114 in FIG. 49 may be contained within an end holder. The end holder 350 may allow an operator of the Raman spectroscopy system 100 to position the end face 117 of an optical fiber 116 to direct a free-space pump-Stokes beam 140 to a sample 150. For example, an operator may grasp the end holder 350 in their hand 351, as illustrated in FIG. 52, and move or rotate the end holder to aim the pump-Stokes beam 140 to a particular location. Additionally, the Raman spectroscopy system 100 may include a visible light source 110*v* that produces a visible beam 120*v*. The visible beam 120*v* may propagate to the sample 150 along with the pump and Stokes beams, and the operator may use the visible alignment spot 144 as an alignment aid for directing the pump and Stokes beams.

The Raman spectroscopy system 100 in FIG. 51 or 52 may operate so that initially the visible light source 110*v* is turned on and the pump and Stokes light sources are turned off. When the pump and Stokes light sources are turned off, the pump and Stokes beams may include little to no light. With the visible light source 110*v* turned on, an operator may position the end holder 350 in FIG. 52 to direct the visible beam 120*v* to a desired location (as indicated by the location of the visible alignment spot 144). Then, the pump and Stokes light sources may be turned on to produce the combined pump-Stokes beam 140 and the resulting Raman signal 160 may be measured by the system. The end holder 350 may include a switch or a button that allows an operator to turn on or off the pump and Stokes light sources.

Figure 53:
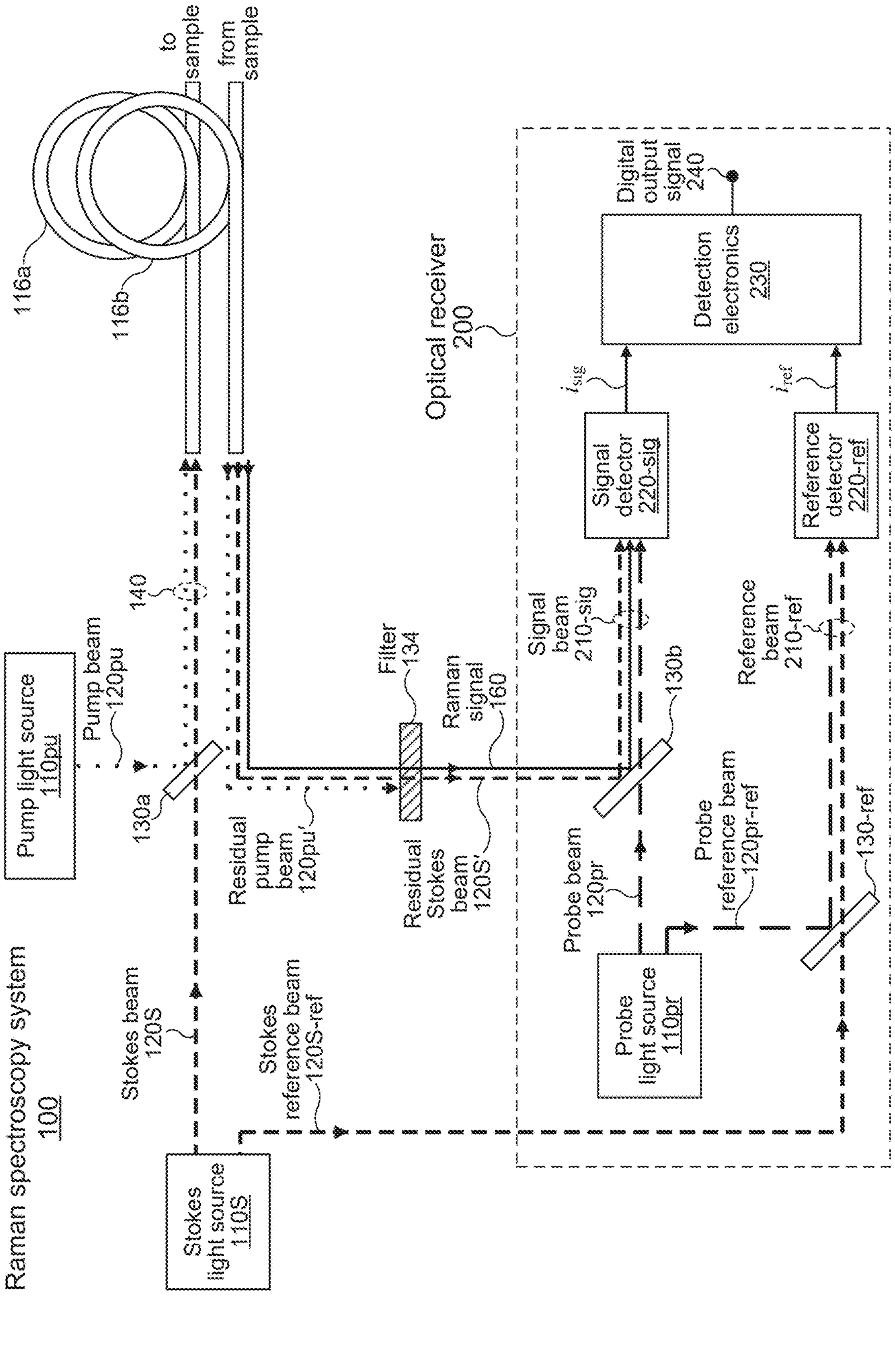
FIG. 53 illustrates an example Raman spectroscopy system with a balanced-detection optical receiver.

FIG. 53 illustrates an example Raman spectroscopy system 100 with a balanced-detection optical receiver 200. The optical receiver 200 includes two detectors (signal detector 220-*sig* and reference detector 220-*ref*) arranged in a balanced-detection configuration. The Raman spectroscopy system 100 in FIG. 53 may detect a Raman signal 160 by coherently mixing the Raman signal 160 with the probe beam of light 120*pr* at the signal detector 220-*sig*. Additionally, the reference detector 220-*ref* may be used to reduce or remove common-mode noise that is present in both the signal beam 210-*sig* and the reference beam 210-*ref*. The Raman spectroscopy system 100 in FIG. 53 is similar to the Raman spectroscopy systems in FIGS. 42-45, except the optical receiver 200 in FIG. 53 includes two detectors arranged for balanced detection. Additionally, the system in FIG. 53 is configured to produce a Stokes reference beam 120S-ref and a probe reference beam 120*pr*-*ref* that are detected by the reference detector 220-*ref*. The light directed to and from a sample in FIG. 53 may be delivered via one or more optical fibers 116 (e.g., similar to the systems illustrated in FIGS. 40-45), and the Raman spectroscopy system 100 in FIG. 53 may be referred to as a Raman spectroscopy system with optical-fiber extension and balanced detection.

In FIG. 53, the combined pump-Stokes beam 140 is directed to a sample 150 by an output optical fiber 116*a*. The light that returns from the sample 150 (which includes a Raman signal 160 as well as residual light from the pump beam 120*pu* and Stokes beam 120S) is directed back to the system by an input optical fiber 116*b*. The residual pump light 120*pu*' and the residual Stokes light 120S' refers to light that is "leftover" after the pump and Stokes beams have interacted with the sample 150 to produce the Raman signal 160. The residual pump beam of light 120*pu*' may be produced by light from the pump beam 120*pu* that is reflected from, transmitted through, or scattered by the sample 150. Similarly, the residual Stokes beam of light 120S' may be produced by light from the Stokes beam 120S that is reflected from, transmitted through, or scattered by the sample 150. The optical filter 134 blocks the light from the residual pump beam 120*pu*' and transmits the Raman signal 160 and the residual Stokes light 120S'. The Raman signal 160 and the residual Stokes beam of light 120S' are combined with the probe beam 120*pr* at the optical combiner 130*b* to produce the combined signal beam 210-*sig*, which is directed to the signal detector 220-*sig*.

In addition to producing the Stokes beam of light 120S, the Stokes light source 110S in FIG. 53 produces a Stokes reference beam of light 120S-ref. Similarly, in addition to producing the probe beam of light 120*pr*, the probe light source 110*pr* produces a probe reference beam of light 120*pr-ref*. The probe and Stokes reference beams are combined at the optical combiner 130-*ref* to produce the reference beam 210-*ref*, which is directed to the reference detector 220-*ref*. The probe and Stokes reference beams may each be produced by splitting off a portion of a primary beam. For example, the Stokes light source 110S may include a laser that produces a primary output beam of light, and a small portion (e.g., between 1% and 10%) of light from the primary output beam may be split off to produce the Stokes reference beam of light 120S-ref. The Stokes beam of light 120S may be produced from the remaining portion (e.g., between 90% and 99%) of light from the primary output beam that is not split off.

The signal detector 220-*sig* in FIG. 53 receives the signal beam 210-*sig* (which includes the Raman signal 160, probe beam 120*pr*, and residual Stokes beam 120S') and produces a signal photocurrent $i_{sig}$ corresponding to the Raman signal, probe beam, and residual Stokes beam, where a portion of the signal photocurrent corresponds to coherent mixing between the Raman signal and the probe beam. The reference detector 220-*ref* receives the reference beam 210-*ref* (which includes the probe reference beam 120*pr-ref* and the Stokes reference beam 120S-ref) and produces a reference photocurrent $i_{ref}$ corresponding to the probe and Stokes reference beams.

The detection electronics 230 in FIG. 53 receives the signal photocurrent $i_{sig}$ and the reference photocurrent $i_{ref}$ and produces a digital output signal 240 that corresponds to the two photocurrents. For example, the detection electronics 230 may include a subtraction module that determines a subtraction signal that corresponds to or that equals a difference between (i) a signal corresponding to the signal photocurrent $i_{sig}$ and (ii) a signal corresponding to the reference photocurrent $i_{ref}$. The detection electronics 230 may include two electronic amplifiers 232, where each electronic amplifier is configured to produce a voltage signal corresponding to one of the photocurrents. The subtraction signal may be determined as the difference between a first voltage signal corresponding to the signal photocurrent $i_{sig}$ and a second voltage signal corresponding to the reference photocurrent $i_{ref}$. The detection electronics 230 may include a digitizer that produces a digital representation of the subtraction signal, and the digital output signal 240 may include the digital representation of the subtraction signal. The digital output signal 240 may be sent to a processor, and the processor may determine a characteristic 162 of the subtraction signal based on the digital output signal 240. In other embodiments, the detection electronics 230 may include: two electronic amplifiers 232; a first digitizer that produces a first digital signal corresponding to the signal photocurrent $i_{sig}$; and a second digitizer that produces a second digital signal corresponding to the reference photocurrent $i_{ref}$. For example, the first digital signal may include a digital representation of a first voltage signal that corresponds to the signal photocurrent $i_{sig}$, and the second digital signal may include a digital representation of a second voltage signal that corresponds to the reference photocurrent $i_{ref}$. The digital output signal 240 may include the two digital signals corresponding to the two photocurrents. A processor may determine a digital subtraction signal from the two digital signals, and a characteristic 162 of a subtraction signal may be determined from the digital subtraction signal.

The balanced-detection configuration in FIG. 53 uses two detectors to substantially reduce or remove intensity noise that may be present in the probe beam 120*pr* or the Stokes beam 120S. The signal beam 210-*sig* detected by the signal detector 220-*sig* includes the Raman signal 160 along with the probe beam 120*pr* and the residual Stokes beam 120S'. The reference beam 210-*ref* detected by the reference detector 220-*ref* includes the probe reference beam 120*pr-ref* and the Stokes reference beam 120S-ref. Since the probe beam 120*pr* and probe reference beam 120*pr-ref* may be derived from the same light source, the two beams may each include correlated (or, common-mode) noise signals. Similarly, the residual Stokes beam 120S' and the Stokes reference beam 120S-ref may each include correlated noise signals. In a balanced-detection optical receiver 200, a signal corresponding to the reference photocurrent $i_{ref}$ may be subtracted from a signal corresponding to the signal photocurrent $i_{sig}$ to produce a subtraction signal. The subtraction signal may include a signal associated with the Raman signal 160, while the common-mode noise present in the probe beam and the Stokes beam may be substantially removed by the subtraction operation that produces the subtraction signal. As a result, the subtraction signal may have a reduced noise compared to each of the photocurrent signals $i_{sig}$ and $i_{ref}$ alone.

Figure 54:
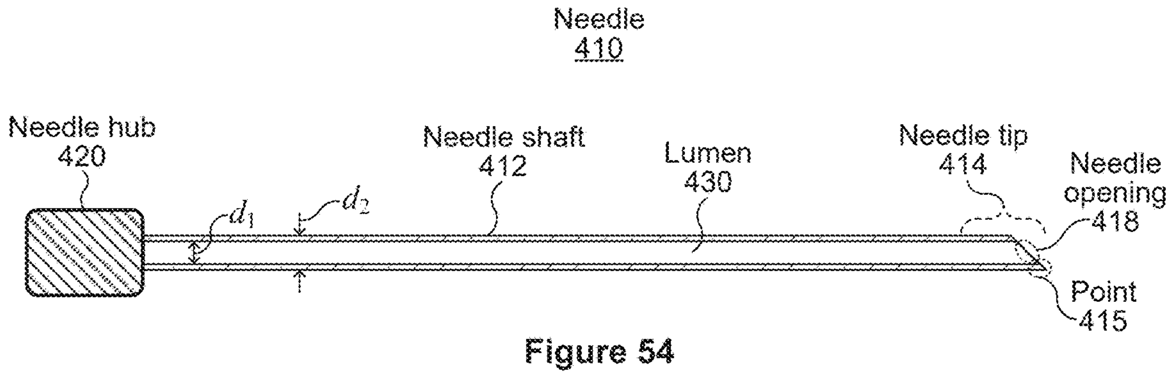
FIG. 54 illustrates an example needle.

FIG. 54 illustrates an example needle 410. The needle 410, which may be referred to as a hypodermic needle, includes a hub 420, shaft 412, lumen 430, and tip 414. The needle shaft 412 is a substantially cylindrical tube with a hollow space (referred to as the lumen 430) located within the tube. The needle shaft 412 may be made from stainless steel, niobium, or other suitable metal. The needle hub 420 is attached to the shaft 412 at one end of the shaft, which may be referred to as the proximal end of the shaft. The hub 420 may be used for grasping or handling the needle (e.g., with a person's finger's), or the hub may include a connector or fitting used to connect the needle to a syringe, catheter tubing, or other medical apparatus. The needle tip 414 is located at the end of the shaft 412 opposite the hub 420 (which may be referred to as the distal end of the shaft) and includes an opening 418 and a point 415. The needle tip 414 refers to the portion of the shaft 412 that includes the opening 418 and the point 415, and the tip may have a length of less than approximately 10 mm. The needle opening 418 refers to a hole in the shaft 412 that allows for (i) a fluid to flow into or out of the lumen 430 or (ii) light to propagate into or out of the needle shaft 412. The point 415 refers to a sharp end of the needle shaft 412 that may be used to insert at least the needle tip 414 into the body of a subject (e.g., a human or animal). For example, a portion of the needle shaft 412 including the tip 414 may be inserted into the body of a subject by using the point 415 to (i) pierce through the skin of the subject or (ii) pierce into an organ or another part of the subject's body. The end of the needle 410 that includes the needle hub 420 may be referred to as the proximal end, and the end of the needle 410 that includes the needle tip 414 may be referred to as the distal end.

A needle shaft 412 may be referred to as having a shape that is substantially cylindrical. A substantially cylindrical shaft may refer to a tube-like shape with a hollow interior, where the inner and outer dimensions of the shaft are substantially constant along the length of the shaft. For example, the size or diameter of a cross-sectional dimension of the shaft may vary by less than 10% along the length of the shaft. A needle shaft 412 may have a cross-sectional shape that is circular, elliptical, or any other suitable shape. The needle shaft 412 in FIG. 54 has a circular cross-sectional shape with an inner diameter of $d_1$ (which corresponds to the diameter of the lumen 430) and an outer diameter of $d_2$, and the inner and outer diameters may vary by less than 10% along the length of the shaft. The inner and outer diameters may each have any suitable value between approximately 0.1 mm and approximately 2.5 mm. For example, the needle 410 may be a 22-gauge needle with an inner diameter $d_1$ of 0.41 mm and an outer diameter $d_2$ of 0.72 mm.

Figure 55:
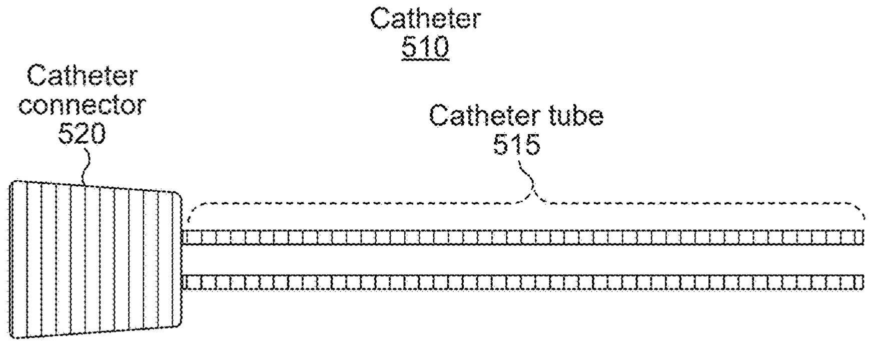
FIG. 55 illustrates an example catheter.

FIG. 55 illustrates an example catheter 510. The catheter 510 includes a catheter connector 520 and a catheter tube 515. The catheter tube 515 is a flexible tube with a substantially cylindrical shape and a hollow space located within the tube. A catheter tube 515 may be made from a plastic or rubber material (e.g., polyurethane or silicone). The catheter connector 520 is attached to the catheter tube 515 at one end of the tube. The catheter connector 520 may be used to connect the catheter 510 to a medical apparatus, such as a syringe or catheter tubing to introduce medication or fluids intravenously to a patient or to withdraw blood or another fluid from a patient. A catheter connector 520 may include a male or female fitting configured to connect to a mating connector. For example, the catheter connector 520 in FIG. 55 may be a female-type connector that can be connected to catheter tubing having a male-type connector. A catheter connector 520 may be a screw-on connector (e.g., LUER-LOK) that connects by screwing the threads of two mating connectors together or may be a press-fit connector (e.g., LUER-SLIP) that connects by pressing two mating connectors together. Catheter tubing, which may be referred to as extension tubing or as a fluid line, may include a length of plastic tubing with a catheter connector located at each end of the tubing.

Figure 56:
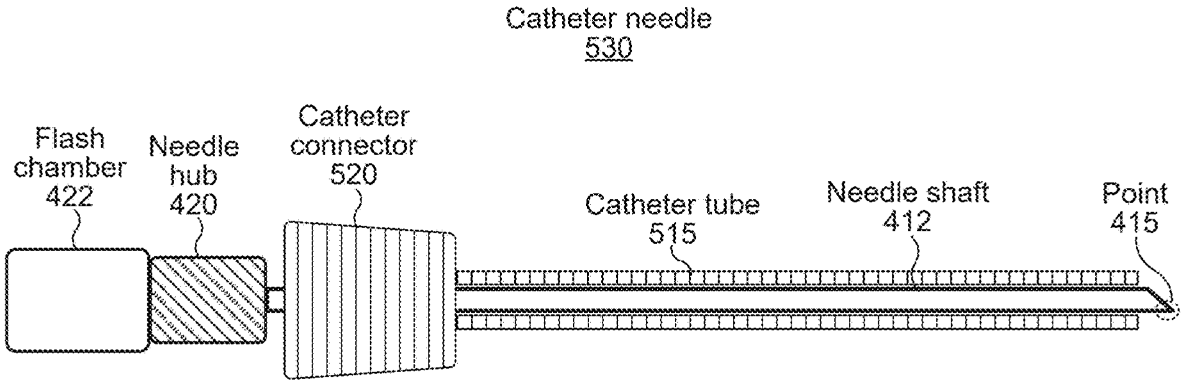
FIG. 56 illustrates an example catheter needle.

FIG. 56 illustrates an example catheter needle 530. The catheter needle 530 includes the needle 410 of FIG. 54 inserted into the catheter 510 of FIG. 55. The needle shaft 412 is sleeved into the catheter tube 515 so that the catheter tube surrounds at least a portion needle shaft, with at least the point 415 extending beyond the end of the catheter tube. The catheter tube 515 may be made from flexible or elastic material having an inner diameter approximately equal to the outer diameter $d_2$ of the needle shaft 412 so that the needle shaft 412 can be inserted into or withdrawn from the catheter tube. A catheter needle 530 may be used to install a catheter 510 into the body of a subject (e.g., a human or animal) by using the point 415 of the needle 410 to pierce through skin or pierce into an organ or another part of the body. Once the end of the catheter tube 515 reaches the desired location, the needle 410 may be removed (e.g., by grasping the hub 420 and withdrawing the needle from the catheter), which leaves the catheter tube inserted into the body of the subject. Once a catheter 510 is installed into a part of a body, at least the end portion of the catheter tube 515 is located inside the body, while another portion of the catheter tube and the connector 520 are located external to the body. For example, a catheter needle 530 may be used to install a catheter 510 into a blood vessel, and once installed, the end portion of the catheter tube 515 may be located in the blood vessel, and another portion of the catheter tube and the connector 520 are located external to the body. The catheter connector 520 may be connected to a syringe or catheter tubing to supply a therapeutic, diagnostic, medication, or other fluid or to withdraw blood or another fluid. The catheter needle 530 in FIG. 56 includes a flash chamber 422 that provides a visual indication when the needle tip 414 enters a blood vessel by producing a "flash" of blood that can be seen by a person directing the needle to the blood vessel.

Figure 57A:
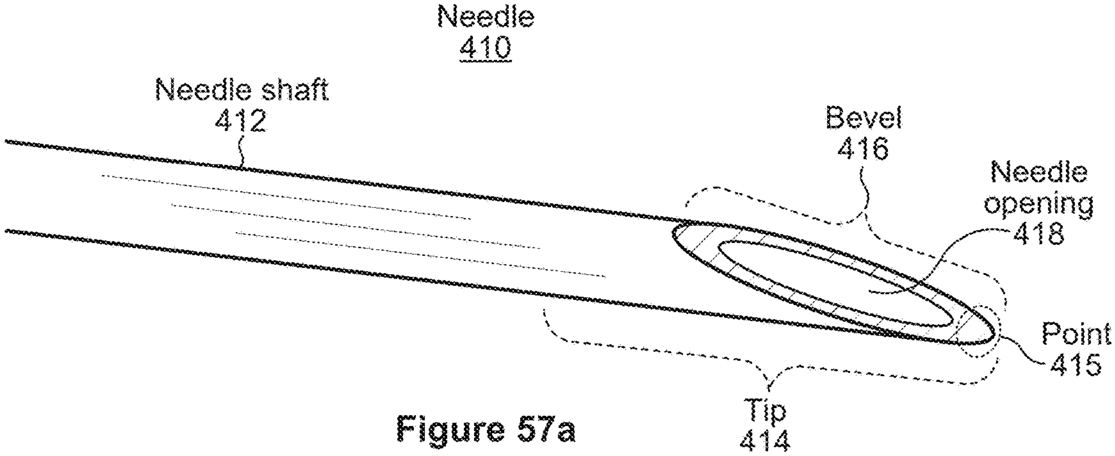
FIGS. 57*a*-57*c* illustrate three views of an example needle.
Figure 57B:
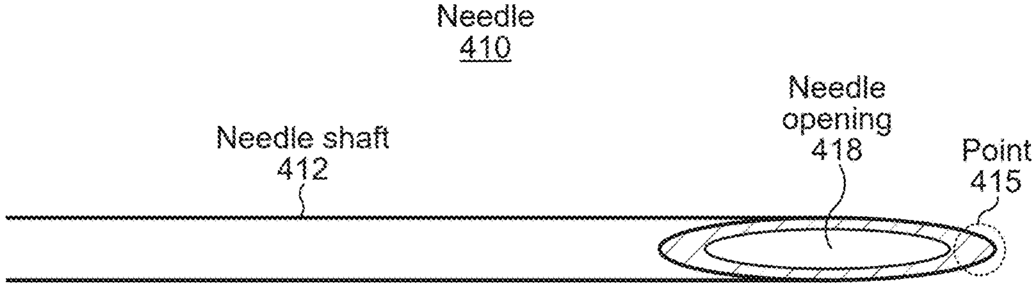
Figure 57C:
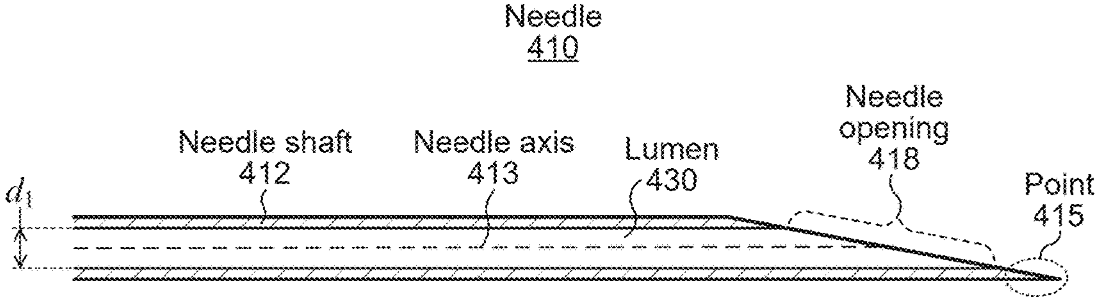
Figure 58A:
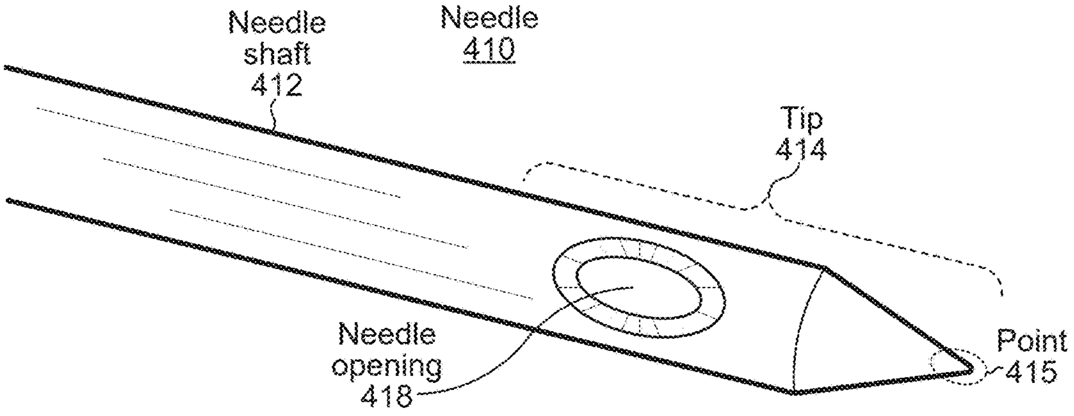
FIGS. 58*a*-58*c* illustrate three views of another example needle.
Figure 58B:
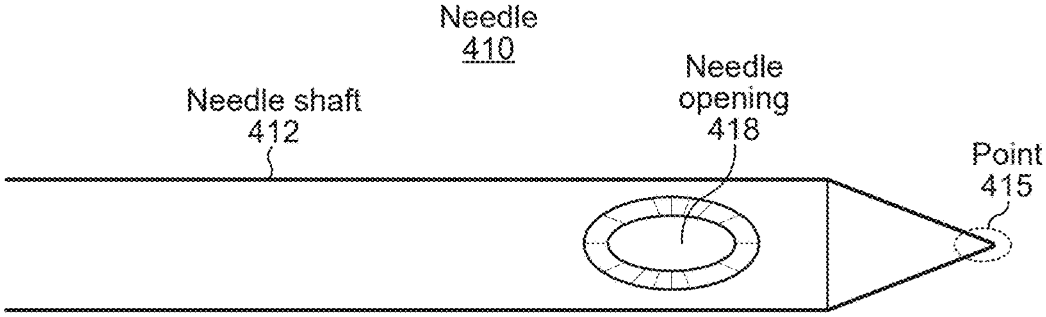
Figure 58C:
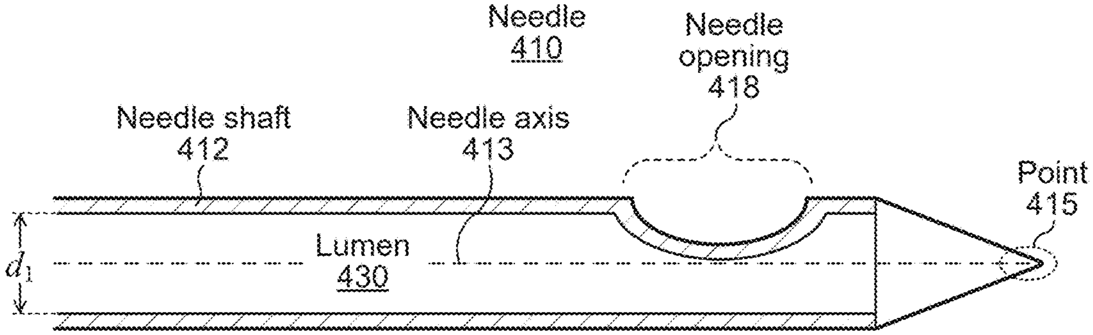

FIGS. 57*a*-57*c* illustrate three views of an example needle 410, and FIGS. 58*a*-58*c* illustrate three views of another example needle 410. The figures illustrate a perspective view (FIGS. 57*a* and 58*a*), a top view (FIGS. 57*b* and 58*b*), and a cross-sectional side view (FIGS. 57*c* and 58*c*) of a portion of a needle 410 (the needle hub is not shown in FIGS. 57*a*-57*c* and 58*a*-58*c*). The needle 410 in FIGS. 57*a*-57*c*, which may be referred to as a Quincke-type needle, has a tip 414 that is terminated by a bevel 416 that forms the needle opening 418 and the point 415. The needle 410 in FIGS. 58*a*-58*c*, which may be referred to as a Whitacre-type needle or a pencil-point needle, has an opening 418 located on the side of the needle tip 414 (rather than the opening being located at the end of the tip, as illustrated in FIGS. 57*a*-57*c*). The end of the needle tip 414 in FIGS. 58*a*-58*c* includes a conical shape that tapers to form a point 415. In each of FIGS. 57*c* and 58*c*, the needle axis 413 (which may be referred to as the central axis of the needle) represents a line that runs along the length the needle 410 and through the approximate center of the needle shaft 412. Any of the needles discussed herein may be a Quincke-type needle (as illustrated in FIGS. 57*a*-57*c*), a Whitacre-type needle (as illustrated in FIGS. 58*a*-58*c*), or any other suitable type of hypodermic needle.

Figure 59:
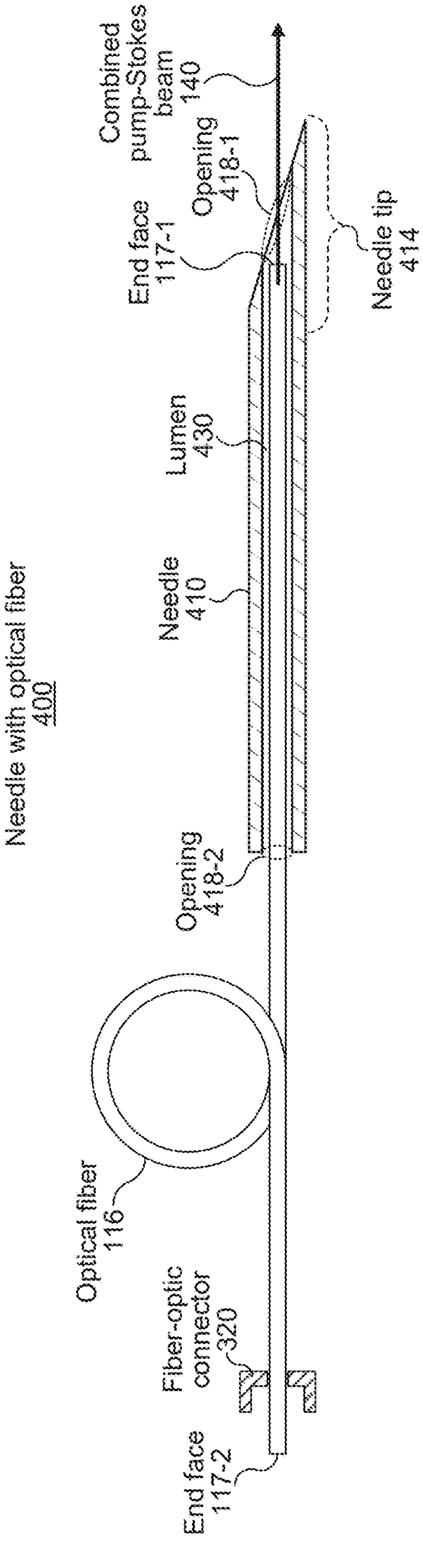
FIGS. 59-61 each illustrate an example needle with optical fiber.
Figure 60:
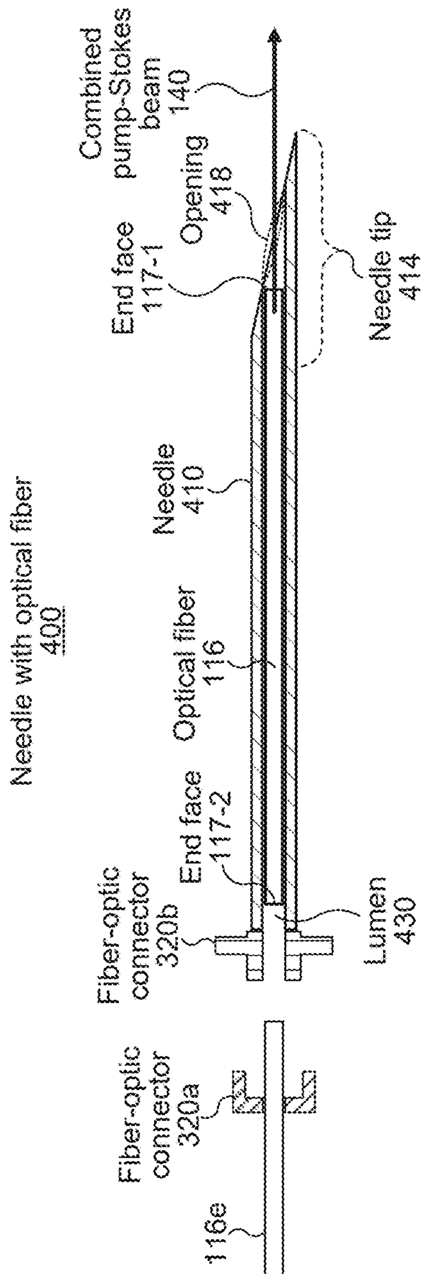
Figure 61:
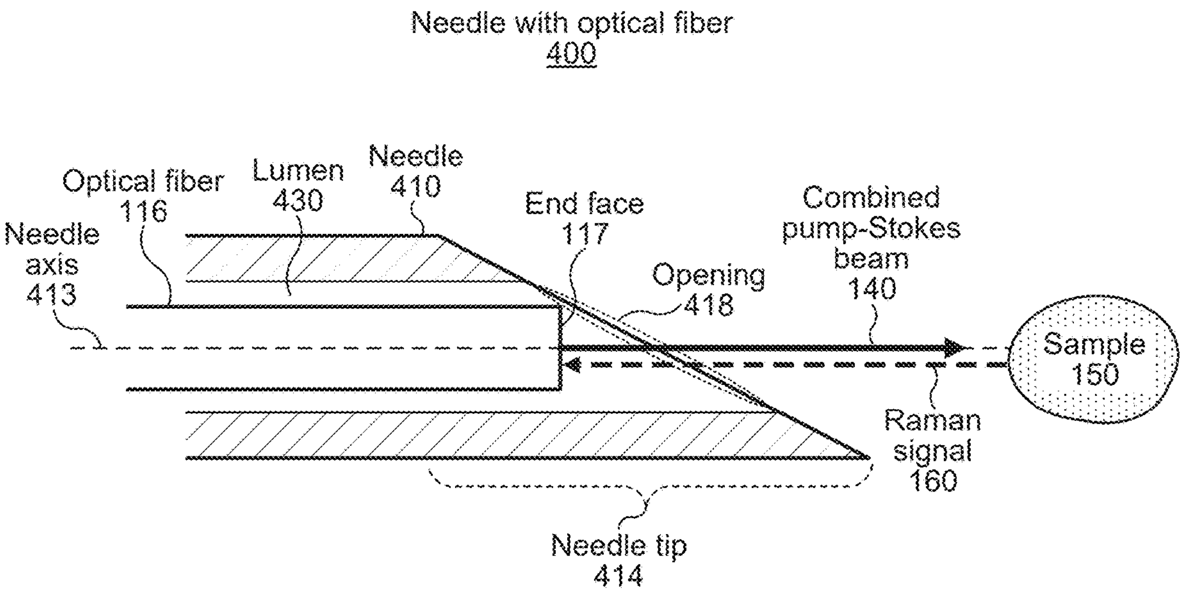

FIGS. 59-61 each illustrate an example needle with optical fiber 400. A needle with optical fiber 400 includes a needle 410 and one or more optical fibers 116 and may be referred to as a needle apparatus, a needle-fiber apparatus, or a needle-with-optical-fiber apparatus. The needle 410 may be a Quincke-type needle (as illustrated in FIGS. 57*a*-57*c*), a Whitacre-type needle (as illustrated in FIGS. 58*a*-58*c*), or any other suitable type of hypodermic needle. Each of the one or more optical fibers 116 may be a single-mode optical fiber, a multi-mode optical fiber, a polarization-maintaining optical fiber, a hollow-core optical fiber, a multi-core optical fiber, or any other suitable type of optical fiber. An optical fiber 116 of each of the needles with optical fiber 400 described herein may be coupled to an optical fiber of a Raman spectroscopy system with optical-fiber extension. Additionally, an optical fiber 116 of each of the needles with optical fiber 400 described herein may transmit a pump-Stokes beam 140 along the fiber toward the needle tip 414 or may transmit a Raman signal 160 along the fiber in a direction away from the needle tip.

In FIG. 59, a portion of the optical fiber 116 is located within the lumen 430 of the needle 410, and another portion of the optical fiber is located outside the needle. The portion of the optical fiber 116 in the lumen 430 is terminated by a first end face 117-1, which is also located within the lumen 430. The optical fiber 116 extends outside the needle 410 through another opening 418-2 located at the proximal end of the needle 410 opposite the tip 414, and that portion of the optical fiber is terminated by a second end face 117-2. The fiber-optic connector 320 located at the end face 117-2 may be used to couple the optical fiber 116 to another optical fiber. For example, the optical fiber 116 in FIG. 59 may be coupled to a Raman spectroscopy system with optical-fiber extension. The Raman spectroscopy system 100 may produce a combined pump-Stokes beam 140, and the optical fiber 116 in FIG. 59 may be coupled to the Raman spectroscopy system via one or more additional optical fibers. For example, the optical fiber 116 in FIG. 59 may be coupled to the optical fiber 116 in FIG. 42 or 43 (e.g., the fiber-optic connector 320 in FIG. 59 may be coupled to another optical fiber having a mating fiber-optic connector or using a fiber-optic adapter). A combined pump-Stokes beam 140, which includes a pump beam 120*pu* and a Stokes beam 120S, may be referred to as a pump-Stokes beam. A fiber-optic connector 320 may be a male-type or female-type SC connector, ST connector, FC connector, LC connector, or any other suitable type of fiber-optic connector. The optical fiber 116 in FIG. 59 may receive the pump-Stokes beam 140 produced by a Raman spectroscopy system 100 via the end face 117-2 and may transmit the pump-Stokes beam along the fiber toward the needle tip 414 and to the end face 117-1. The pump-Stokes beam 140 is emitted from the end face 117-1 and directed through the opening 418-1 of the needle 410. For example, the pump-Stokes beam 140 may be directed through the opening 418-1 and to a sample 150.

In FIG. 60, the needle with optical fiber 400 includes a needle 410 and an optical fiber 116, where the optical fiber is fully contained within the lumen 430 of the needle. The optical fiber 116 includes two end faces 117-1 and 117-2, both of which are located within the lumen 430. Additionally, the needle with optical fiber 400 includes a fiber-optic connector 320*b* that is coupled to the proximal end of the needle 410 opposite the tip 414. The fiber-optic connector 320*b* may be used to couple the optical fiber 116 within the lumen 430 to another optical fiber located external to the needle 410. In FIG. 60, the optical fiber 116*e* includes a fiber-optic connector 320*a* configured to connect to the mating fiber-optic connector 320*b*. The optical fiber 116*e* may be coupled to a Raman spectroscopy system with optical-fiber extension, and the Raman spectroscopy system may produce a pump-Stokes beam 140 that is sent to the needle with optical fiber 400 by the optical fiber 116*e*. The optical fiber 116 in FIG. 60 receives the pump-Stokes beam 140 produced by the Raman spectroscopy system 100 via the end face 117-2, and the optical fiber transmits the pump-Stokes beam along the fiber toward the needle tip 414 and to the end face 117-1. The pump-Stokes beam 140 is emitted from the end face 117-1 and directed through the opening 418 of the needle 410. For example, the pump-Stokes beam 140 may be directed through the opening 418 and to a sample 150.

The optical fiber 116 in FIG. 61 may extend outside the needle 410 (e.g., as illustrated in FIG. 59), or the optical fiber may be fully contained within the lumen 430 of the needle (e.g., as illustrated in FIG. 60). The optical fiber 116 may be coupled to an optical fiber from a Raman spectroscopy system 100. The optical fiber 116 may receive a pump-Stokes beam 140 produced by the Raman spectroscopy system 100 and transmit the pump-Stokes beam along the fiber toward the needle tip 414 and to the end face 117. In FIG. 61, the pump-Stokes beam 140 is emitted from the end face 117 and directed through the opening 418 of the needle 410 to a sample 150. The pump-Stokes beam of light 140 includes a pump beam of light 120*pu* and a Stokes beam of light 120S, where the pump and Stokes frequencies are offset by a frequency offset Ω. The pump-Stokes beam 140 may produce a Raman signal 160 by coherent Raman scattering of the pump and Stokes beams of light at the sample 150. At least a portion of the Raman signal 160 produced at the sample 150 may be directed to the optical fiber 116 and coupled into the optical fiber via the end face 117. The optical fiber 116 may transmit the received Raman signal 160 along the optical fiber in a direction away from the needle tip 414 and opposite the direction of the pump-Stokes beam 140. For example, the optical fiber 116 in FIG. 61 may be coupled to the optical fiber 116 in FIG. 42 or 43, and the Raman signal 160 may be transmitted to the Raman spectroscopy system 100 for measurement. The pump-Stokes beam 140 emitted from the optical fiber 116 and the Raman signal 160 that is coupled into the optical fiber may propagate in opposite directions along approximately the same optical axis. In FIG. 61, the pump-Stokes beam 140 and the Raman signal 160 are offset laterally for clarity to allow each beam to be visualized. Other figures described herein may include similar lateral offsets between optical beams for clarity to allow the beams to be visualized.

A free-space optical beam refers to a beam of light that propagates through a medium (e.g., air, liquid, or a dielectric material) without being optically confined within a physical waveguiding structure like an optical fiber or optical waveguide. In each of FIGS. 59-61, the pump-Stokes beam 140 propagates in the optical fiber 116 as a confined or guided optical beam, and when the pump-Stokes beam is emitted from end face 117 of the optical fiber, it propagates as a free-space optical beam. The free-space pump-Stokes beam 140 in each of FIGS. 59-61 may be directed to propagate through air, a liquid (e.g., water, blood, urine, saliva), or any other suitable material. The Raman signal 160 in FIG. 61 propagates from the sample 150 to the end face 117 of the optical fiber 116 as a free-space optical beam. After the Raman signal is coupled into the optical fiber 116 via the end face 117, the Raman signal propagates along the optical fiber as a guided optical beam.

Figure 62:
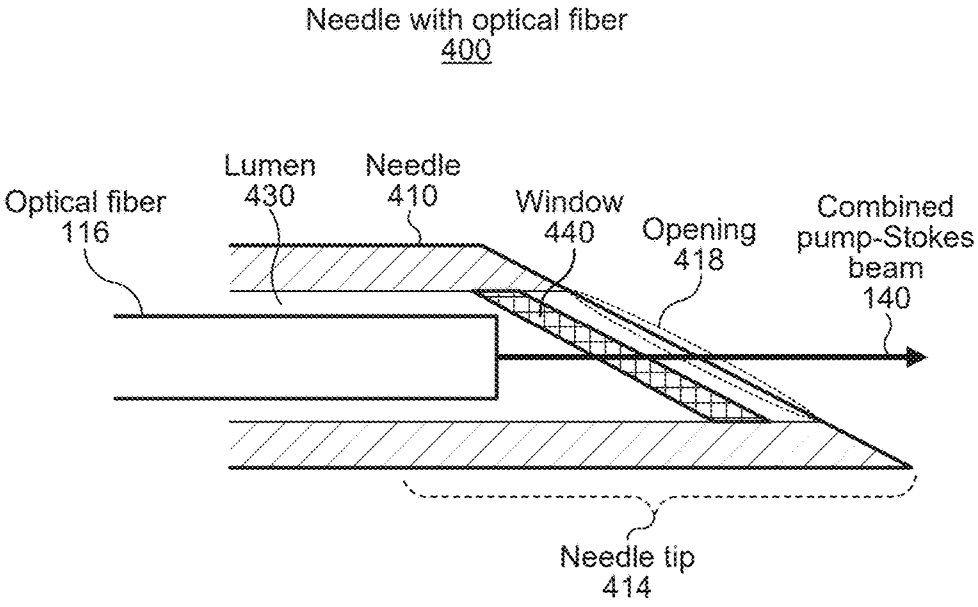
FIG. 62 illustrates an example needle with optical fiber that includes a window.

FIG. 62 illustrates an example needle with optical fiber 400 that includes a window 440. The window 440 (which may be referred to as an optical window) may be attached to the needle 410 at or near the needle opening 418. For example, the window 440 may be attached to an interior surface of the needle 410 using an adhesive, and the window may be located within 10 mm of the opening 418. The optical window 440 may be configured to (i) transmit a pump-Stokes beam 140 and (ii) prevent a fluid from flowing into the lumen 430 of the needle via the opening 418. For example, the window 440 may have an optical transmission of greater than 80% for light at the wavelengths of the pump and Stokes beams. Additionally, the window 440 may transmit light at the wavelength of a Raman signal 160 produced by the pump and Stokes beams. The optical window 440 may be made from glass (e.g., borosilicate or fused silica) or an optically transmissive plastic material, and the window may include an anti-reflection coating that reduces the optical reflectivity of the window. The window 440 may be attached to the needle 410 (e.g., using adhesive) that forms a seal between the outer edge of the window and an interior surface of the needle, and the sealed window may prevent fluid from flowing into the lumen 430. For example, the needle tip 414 in FIG. 62 may be inserted into a blood vessel to make a measurement of blood using the optical fiber 116, and the window 440 may allow the pump-Stokes beam 140 to propagate to the blood (and the resulting Raman signal to propagate back to the fiber) while preventing blood from flowing into the lumen 430. As another example, in FIG. 59, a window located near the front opening 418-1 may prevent fluid from flowing into the needle lumen 430 and leaking out the proximal end of the needle through the back opening 418-2.

Figure 63:
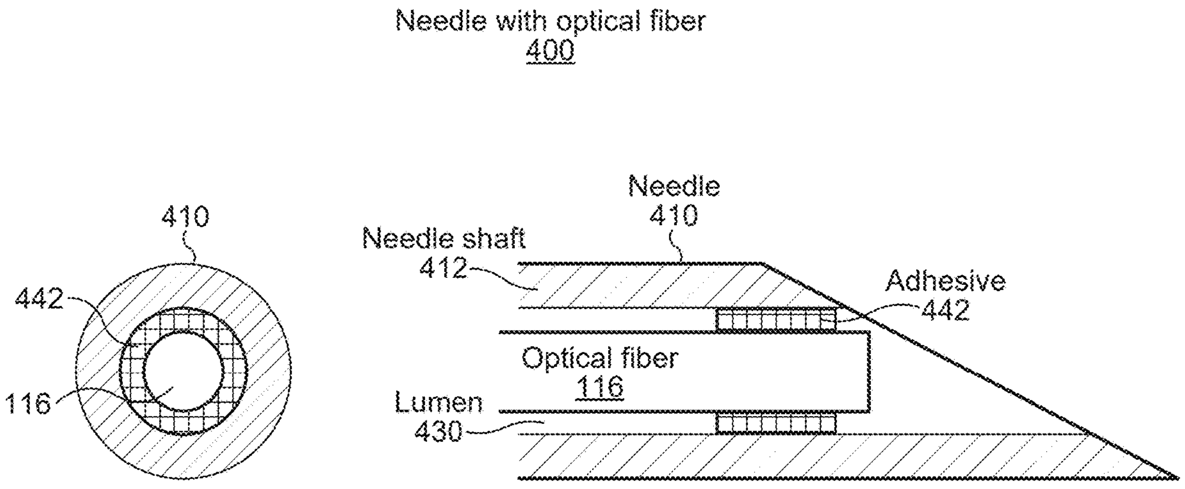
FIGS. 63-64 each illustrate an example needle with optical fiber in which the optical fiber is attached to the needle by an adhesive.
Figure 64:
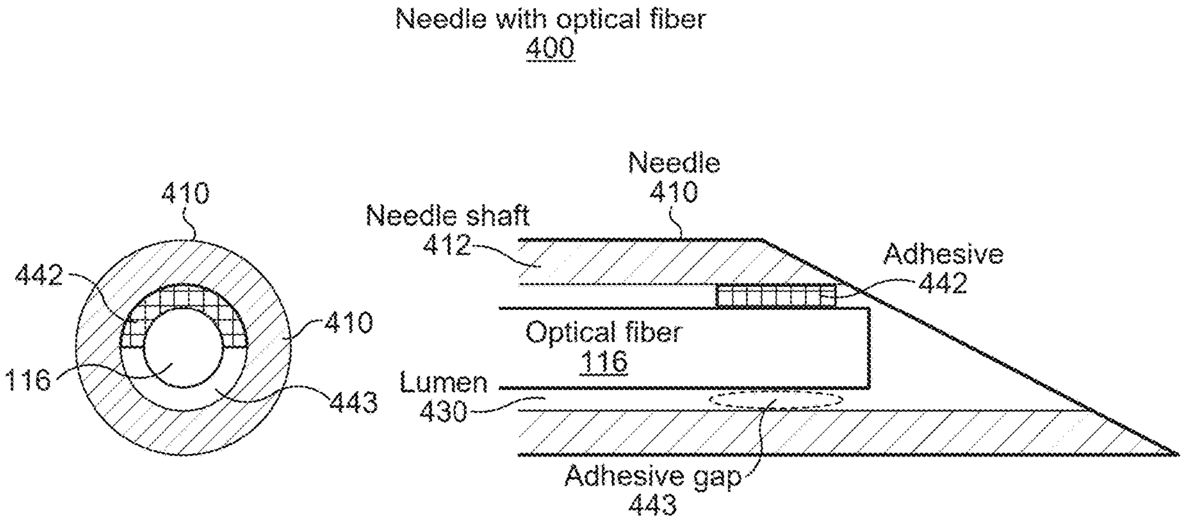

FIGS. 63-64 each illustrate an example needle with optical fiber 400 in which the optical fiber 116 is attached to the needle 410 by an adhesive 442. The right portion of each figure illustrates a cross-sectional side view, and the left portion illustrates a cross-section as viewed from an end of the needle 410. In each of FIGS. 63-64, the optical fiber 116 is attached to the interior surface of the needle shaft 412 by an adhesive 442. Herein, an adhesive refers to an epoxy, adhesive, solder, or any other suitable material configured to attach two or more items together (e.g., to attach an optical fiber to a needle) or to form a seal. In FIG. 63, the adhesive 442 extends around the circumference of the optical fiber 116 and forms a seal between the optical fiber and the interior surface of the needle shaft 412. The seal formed by the adhesive 442 may prevent a fluid from flowing into or through the needle lumen 430. The needle-fiber apparatus 400 in FIG. 63 may be used to prevent a fluid from flowing into the needle and leaking out the back opening of the needle. In FIG. 64, the adhesive 442 provides an adhesive gap 443 that allows a fluid to flow into and through the needle lumen 430. The adhesive 442 in FIG. 64 extends around half of the circumference of the optical fiber 116, and the adhesive gap 443 leaves the remaining space between the fiber and the interior surface of the needle shaft 412 unblocked. In other embodiments, an adhesive 442 may be applied in two or more locations around an optical fiber 116, which provides two or more corresponding adhesive gaps 443. For example, an adhesive 442 may be applied in three spots around an optical fiber 116, which leaves three adhesive gaps 443 that allow for fluid to flow through the lumen 430. The needle-fiber apparatus 400 in FIG. 64 may be used for introducing a fluid into a patient's body or withdrawing a fluid from a patient by allowing the fluid to flow through the adhesive gap 443.

Figure 65:
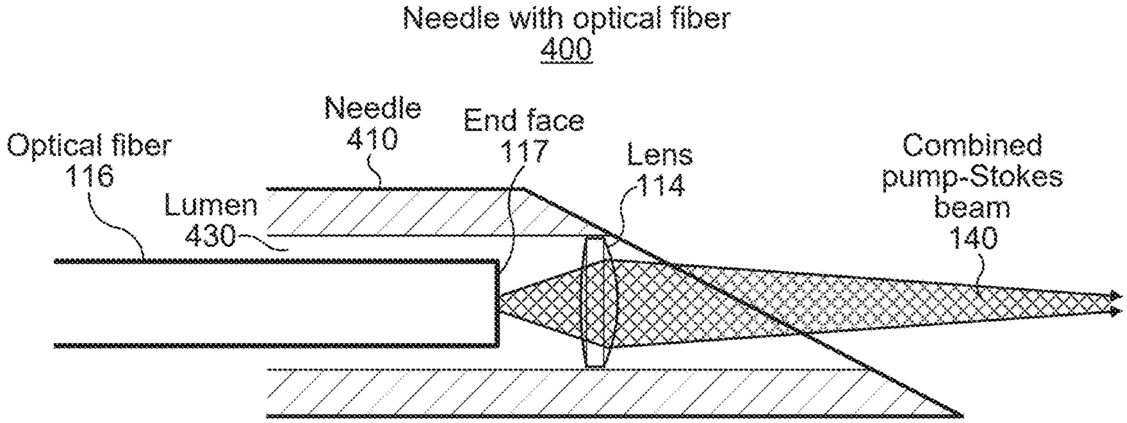
FIGS. 65-67 each illustrate an example needle with optical fiber that includes a lens.
Figure 66:
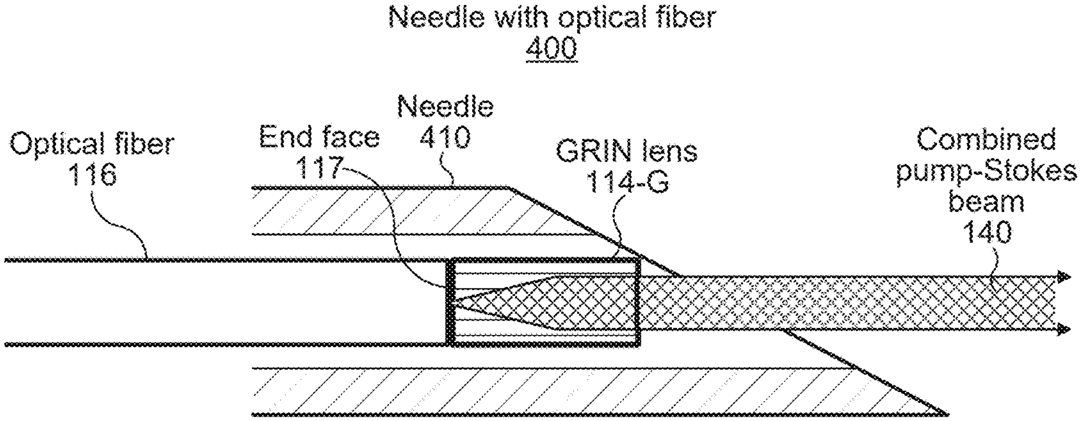
Figure 67:
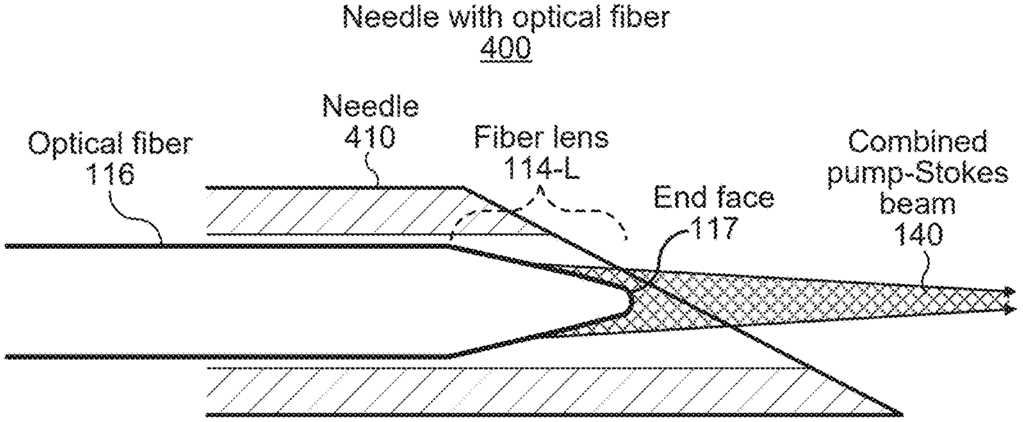

FIGS. 65-67 each illustrate an example needle with optical fiber 400 that includes a lens 114. The lens 114 in each of FIGS. 65-67 receives a pump-Stokes beam 140 from an optical fiber 116 and produces a free-space pump-Stokes beam 140. The free-space pump-Stokes beam 140 produced by a lens 114 may be a collimated optical beam (e.g., as illustrated in FIG. 66) or a focused optical beam (e.g., as illustrated in FIGS. 65 and 67). The free-space pump-Stokes beam 140 may be directed to a sample (not illustrated in FIGS. 65-67), and a Raman signal 160 may be produced by coherent Raman scattering of the pump and Stokes beams of light at the sample 150. At least a portion of the Raman signal 160 produced at the sample 150 may be directed to the lens 114, and the lens 114 may focus the received Raman signal 160 to couple the Raman signal into the optical fiber 116 via the end face 117.

The lens 114 in FIG. 65 is a free-space lens (which may be referred to as a bulk lens) that receives a diverging free-space pump-Stokes beam 140 emitted from the end face 117 of the optical fiber 116 and produces a focused free-space pump-Stokes beam. In other embodiments, a free-space lens 114 may produce a collimated free-space pump-Stokes beam 140. The free-space lens 114 in FIG. 65 may be attached to the interior surface of the needle 410 (e.g., using an adhesive). For example, the lens 114 may be attached to the needle 410 using an adhesive that forms a seal between the lens and the interior surface of the needle, and the sealed lens may prevent a fluid from flowing through the needle opening and into the lumen 430. In other embodiments, in addition to or instead of being attached to the interior surface of a needle 410, a free-space lens 114 may be attached to the end face 117 of an optical fiber 116.

The lens 114-G in FIG. 66 is a gradient-index (GRIN) lens that is attached to the end face 117 of the optical fiber 116. For example, the GRIN lens 114-G may be attached to the end face 117 using an optically clear adhesive that is substantially transparent to light at the wavelengths of the pump and Stokes beams. The pump-Stokes beam 140 in FIG. 66 is directly coupled from the optical fiber 116 to the GRIN lens 114-G, and the GRIN lens produces a collimated free-space pump-Stokes beam 140. In other embodiments, a GRIN lens 114-G may produce a focused free-space pump-Stokes beam 140.

The lens 114-L in FIG. 67 is a fiber lens (which may be referred to as a lensed tip or a lensed fiber). A fiber lens 114-L may be formed at the end face 117 of an optical fiber 116, and the fiber lens may be referred to as being integrated into the end face of the optical fiber. The fiber lens 114-L may be formed by tapering or shaping the end of an optical fiber 116 to produce a lens-like structure. The pump-Stokes beam 140 in FIG. 67 propagates through the fiber lens 114-L and is then emitted as a focused free-space pump-Stokes beam 140. In other embodiments, a fiber lens 114-L may produce a collimated free-space pump-Stokes beam 140.

Figure 68:
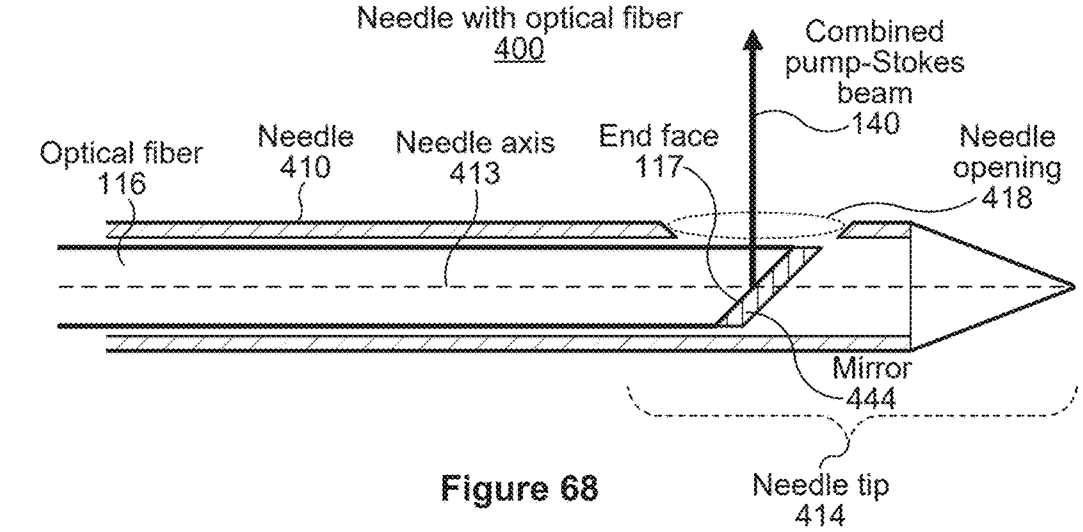
FIGS. 68-70 each illustrate an example needle with optical fiber that includes a mirror.
Figure 69:
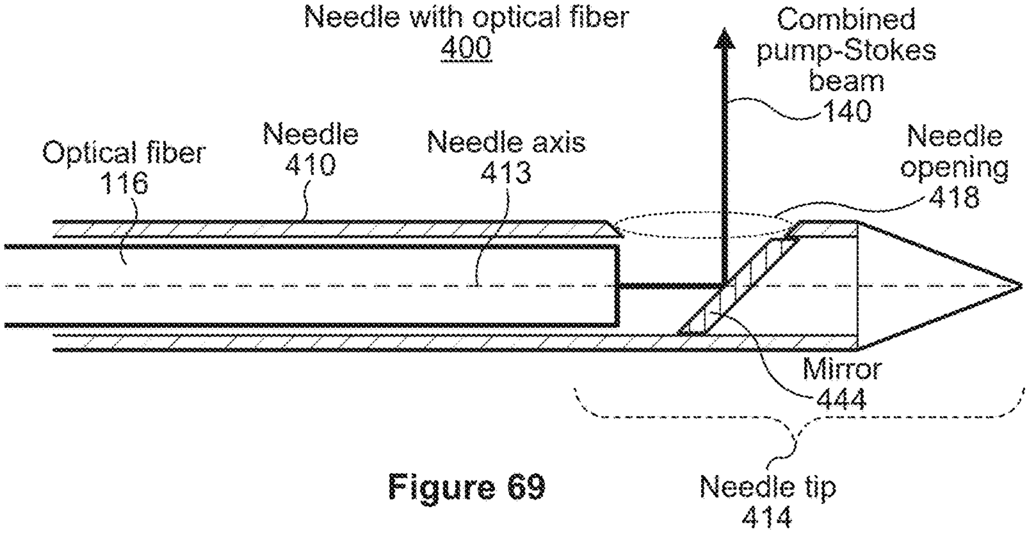
Figure 70:
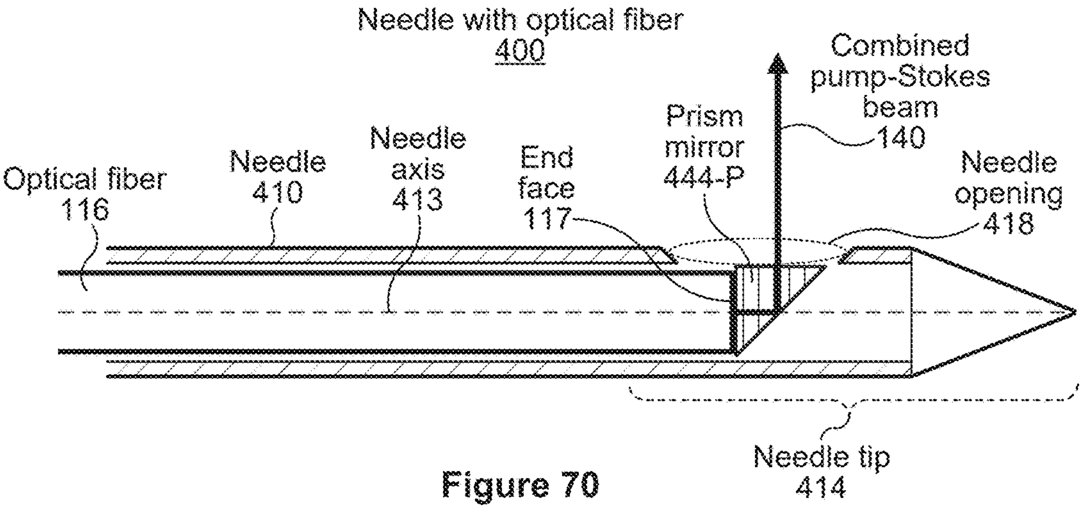

FIGS. 68-70 each illustrate an example needle with optical fiber 400 that includes a mirror 444. The needle 410 in each of FIGS. 68-70, which is similar to the Whitacre-type needle illustrated in FIGS. **58*a*-58*c*, has an opening 418 located on the side of the needle tip 414 (instead of the opening being located at the end of the tip). The needle with optical fiber 400 in each of FIGS. 68-70 includes a mirror 444 that receives a pump-Stokes beam 140 from the end face 117 of the optical fiber 116 and reflects the beam to direct the beam to the needle opening 418. The reflected pump-Stokes beam 140 exits the needle 410 through the opening 418 along a direction approximately orthogonal to the needle axis 413 (which may be referred to as the central axis of the needle). For example, the reflected pump-Stokes beam 140 may be directed through the opening 418 at an angle between 80 and 100 degrees with respect to the needle axis 413. Each of the mirrors 444 in FIGS. 68-70 may have a reflective surface that is oriented at approximately 45 degrees with respect to the needle axis 413 so that the pump-Stokes beam 140 is reflected at approximately 90 degrees with respect to the needle axis. In some embodiments, the reflective surface may be curved to produce a reflected pump-Stokes beam 140** that is focused or collimated.

In FIG. 68, the end face 117 of the optical fiber 116 is angled, and the mirror 444 is a reflective optical coating that is deposited onto the end face 117 of the optical fiber. For example, the mirror 444 may be produced by polishing the end face 117 at a 45-degree angle with respect to the needle axis 413 and then depositing a reflective metallic or dielectric optical coating onto the polished end face. In FIG. 69, the mirror 444 is a separate optical element that may be attached to the needle 410 by an adhesive. The mirror 444 has a reflective surface oriented at approximately 45 degrees with respect to the needle axis 413. In FIG. 70, the mirror 444-P is a prism mirror that includes a prism with a reflective surface. The prism mirror 444-P may be attached to the end face 117 of the optical fiber 116 using an optically clear adhesive. In other embodiments, a prism mirror 444-P may be located apart from the end face 117 and may be attached to the needle 410 by an adhesive. The prism mirror 444-P includes a right-angle prism made from a transparent material (e.g., a glass or plastic material that transmits light at the wavelengths of the pump and Stokes beams). The pump-Stokes beam 140 propagates along the optical fiber 116 and through the transparent prism of the prism mirror 444-P and is reflected at the hypotenuse surface of the prism mirror, which is oriented at 45 degrees with respect to the needle axis 413. The hypotenuse surface may reflect the pump-Stokes beam 140 by total internal reflection, or the surface may be coated with a reflective optical coating.

A needle with optical fiber 400 that includes a mirror 444 may be used to direct a pump-Stokes beam 140 to locations around the needle 410. For example, an operator of a Raman spectroscopy system 100 that is coupled to a needle with optical fiber 400 may rotate the needle 410 about the needle axis 413. By rotating the needle 410, the pump-Stokes beam 140 may be directed in a scanning motion around the needle, similar to a light beam that is scanned around a lighthouse. The tip 414 of the needle with optical fiber 400 that includes a mirror 444 may be inserted into a sample 150. As the needle 410 is rotated, the Raman spectroscopy system 100 may make measurements of Raman signals 160 produced by different parts of the sample 150.

One or more optical elements that are part of a needle apparatus may include a radiopaque material. For example, a portion of an optical fiber 116, window 440, lens 114, mirror 444, faceted optic 446, or other optical element that is part of a needle apparatus may include a radiopaque material. A radiopaque material is a substance that blocks or does not allow X-rays to pass through it, which makes the material appear white or bright on X-ray images or other radiographic scans. A radiopaque material may be referred to as a radiocontrast material and may include a metal (e.g., titanium or tungsten), barium sulfate, bismuth oxide, or zirconium oxide. A radiopaque material may be applied as a coating onto a surface of an optical element or may be incorporated into at least a portion of the volume of the optical element. Adding a radiopaque material to an optical element may allow the optical element to clearly show up as a bright spot in an X-ray. For example, if an optical element with a radiopaque material needs to be located or becomes detached from a needle apparatus, an X-ray image may allow the optical element to be located more readily than if the optical element did not include a radiopaque material.

Figure 71:
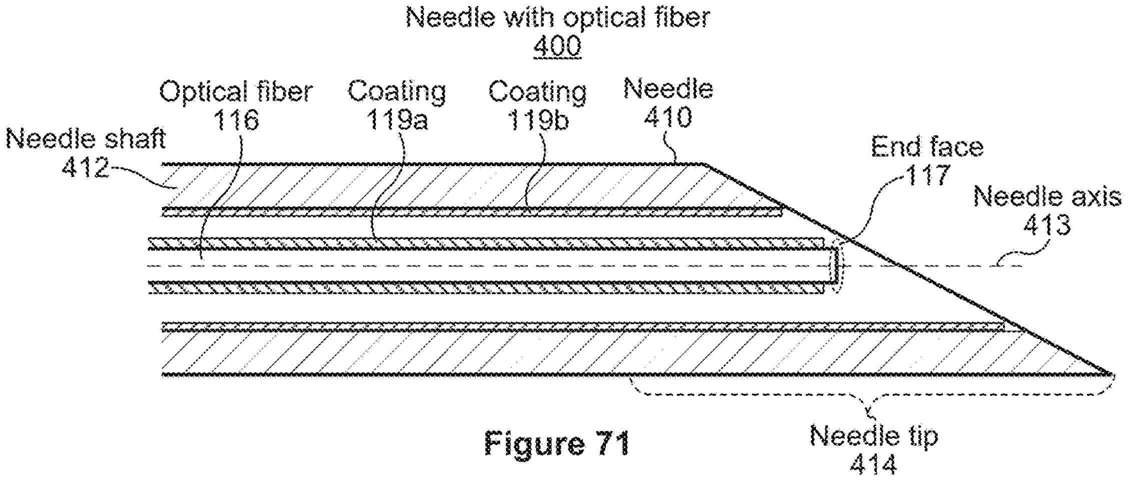
FIG. 71 illustrates an example needle with optical fiber that includes a coating on the optical fiber and a coating on the needle.

FIG. 71 illustrates an example needle with optical fiber 400 that includes a coating 119*a* on the optical fiber 116 and a coating 119*b* on the needle 410. One or more of the coatings 119 may include an anticoagulant substance or a stiffening material. For example, the exterior surface of the optical fiber 116 may be coated with an anticoagulant substance or a stiffening material, or the interior surface of the needle shaft 412 may be coated with an anticoagulant substance. The coating 119*a* on the optical fiber 116 may not extend over the end face 117 so that light may enter or exit the optical fiber via the end face.

In FIG. 71, coating 119*a* on the exterior surface of the optical fiber 116 may be an anticoagulant substance, or coating 119*b* on the interior surface of the needle shaft 412 may be an anticoagulant substance. An anticoagulant substance refers to a material or drug that prevents or reduces the coagulation of blood or coagulation of other fluids. Applying an anticoagulant coating 119 to the outer surface of the optical fiber 116 or the interior surface of the needle shaft 412 may allow blood to flow into or around the needle 410 without coagulation when the needle tip 414 is inserted into a blood vessel. Examples of anticoagulant substances include everolimus, sirolimus, zotarolimus, and paclitaxel. An anticoagulant may be applied as a liquid that is dried onto a surface or as a spray-coated material.

In FIG. 71, coating 119*a* may be a material that increases the bending stiffness or flexural rigidity of the optical fiber 116. For example, the stiffening material may include a plastic or polymer material, such as polyimide, or the stiffening material may include a metal (e.g., a metallic coating applied to the exterior surface of the optical fiber 116), such as chrome, nickel, aluminum, or gold. Coating 119*a* may include an anticoagulant in addition to a stiffening material. For example, after applying a stiffening material to the exterior surface of the optical fiber 116, an anticoagulant coating may be applied over the stiffening material. An optical fiber 116 with a coating 119*a* that includes a material that increases bending stiffness may allow the optical fiber to be moved along a longitudinal direction (e.g., back and forth along the direction of the needle axis 413). For example, the optical fiber 116 in FIG. 71 may not be attached to the needle 410, and pushing or pulling on the optical fiber from outside the needle may allow the location of the end face 117 to be adjusted. Without a stiffening material, the relatively high flexibility of the optical fiber 116 may make it difficult to move the fiber from left to right (as viewed in FIG. 71) by pushing on the fiber from outside the needle. A coating 119*a* that includes a material that increases the bending stiffness of the optical fiber 116 (or equivalently, increases the fiber's resistance to bending) may allow a force to be applied to the fiber from outside the needle so that the fiber may be moved from left to right.

Figure 72:
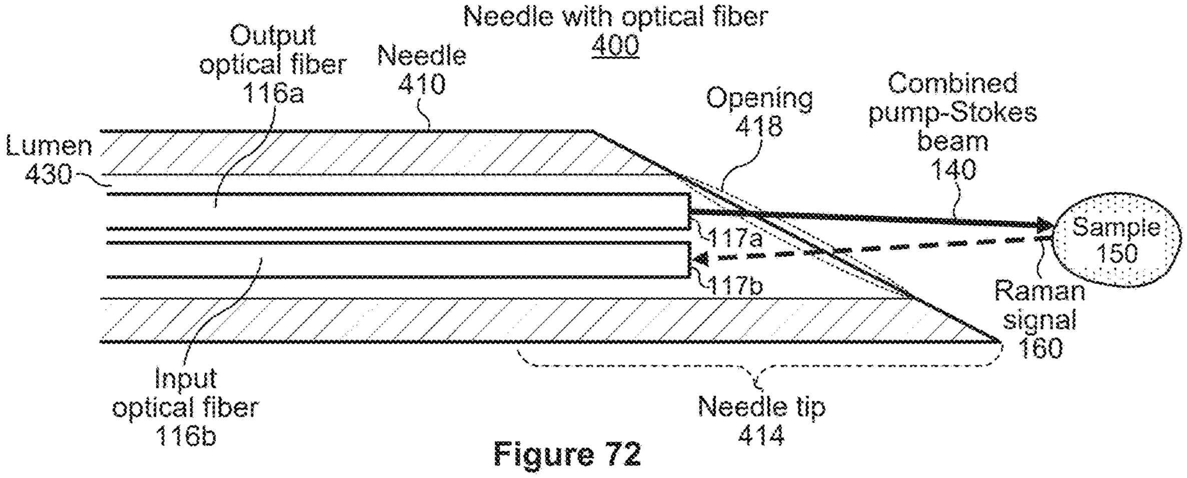
FIG. 72 illustrates an example needle with optical fiber that includes two optical fibers.

FIG. 72 illustrates an example needle with optical fiber 400 that includes two optical fibers 116. A needle with optical fiber 400 may include 1, 2, 3, 5, 10, or any other suitable number of optical fibers 116. The needle with optical fiber 400 in FIG. 61 includes one optical fiber 116 that (i) transmits a pump-Stokes beam 140 along the fiber 116 toward the needle tip 414 and to the end face 117 and (ii) transmits the received Raman signal 160 along the optical fiber in a direction away from the needle tip and opposite the direction of the pump-Stokes beam 140. The needle with optical fiber 400 in FIG. 72 includes two optical fibers: an output optical fiber 116*a* and an input optical fiber 116*b*. At least a portion of both optical fibers 116*a* and 116*b* as well as their end faces 117*a* and 117*b* are located within the lumen 430 of the needle 410. The output optical fiber 116*a* transmits a pump-Stokes beam 140 along the fiber toward the needle tip 414 and to the output-fiber end face 117*a*. The pump-Stokes beam 140 is emitted from the end face 117*a* and directed through the opening 418 of the needle 410 to a sample 150. The pump-Stokes beam 140 may produce a Raman signal 160 by coherent Raman scattering of the pump and Stokes beams of light at the sample 150. At least a portion of the Raman signal 160 produced at the sample 150 may be directed to and received by the input-fiber end face 117*b* of the input optical fiber 116*b*. The received Raman signal 160 is coupled into the input optical fiber 116*b* via the input-fiber end face 117*b*, and the input optical fiber 116*b* may transmit the received Raman signal along the fiber in a direction away from the needle tip 414. The needle with optical fiber 400 in FIG. 72 may be coupled to the Raman spectroscopy system 100 in FIG. 44 or 45 by the corresponding output and input optical fibers, and the Raman signal 160 may be transmitted to the Raman spectroscopy system for measurement. For example, the output optical fiber 116*a* in FIG. 44 or 45 may be coupled to the output optical fiber 116*a* in FIG. 72 (e.g., by a fiber-optic connector 320 or adapter 330 or by one or more intermediate optical fibers 116), and the input optical fiber 116*b* in FIG. 44 or 45 may be similarly coupled to the input optical fiber 116*b* in FIG. 72.

Figure 73:
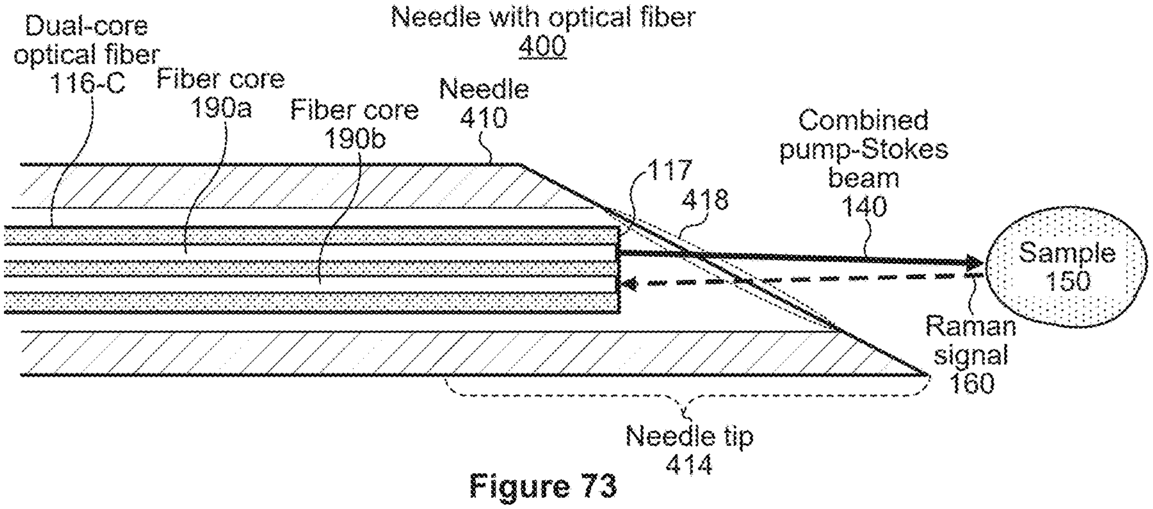
FIG. 73 illustrates an example needle with optical fiber that includes a dual-core optical fiber.

FIG. 73 illustrates an example needle with optical fiber 400 that includes a dual-core optical fiber 116-C. A needle with optical fiber 400 may include a multi-core optical fiber having two or more light-guiding cores in which light may propagate. The dual-core optical fiber 116-C in FIG. 73 has two fiber-optic cores: output fiber core 190*a* and input fiber core 190*b*. The pump-Stokes beam 140 propagates in fiber core 190*a*, and the Raman signal 160 propagates in fiber core 190*b*. The output fiber core 190*a* transmits the pump-Stokes beam 140 along the optical fiber 116-C toward the needle tip 414 and to the end face 117. The pump-Stokes beam 140 is emitted from the end face 117 and directed through the opening 418 of the needle 410 to a sample 150. The pump-Stokes beam 140 may produce a Raman signal 160 by coherent Raman scattering of the pump and Stokes beams of light at the sample 150. At least a portion of the Raman signal 160 produced at the sample 150 may be received by the end face 117 and coupled into the input fiber core 190*b*. The received Raman signal 160 propagates in fiber core 190*b* along the optical fiber 116-C in a direction away from the needle tip 414 and opposite the pump-Stokes beam 140. The needle with optical fiber 400 in FIG. 73 may be coupled to a Raman spectroscopy 100 by one or more optical fibers 116, and the Raman signal 160 may be transmitted to the Raman spectroscopy system for measurement. For example, the dual-core optical fiber 116-C may be coupled to a corresponding dual-core optical fiber from the Raman spectroscopy system 100, or the dual-core optical fiber 116-C may be split into two optical fibers that are coupled to corresponding output and input optical fibers from the system.

Figure 74:
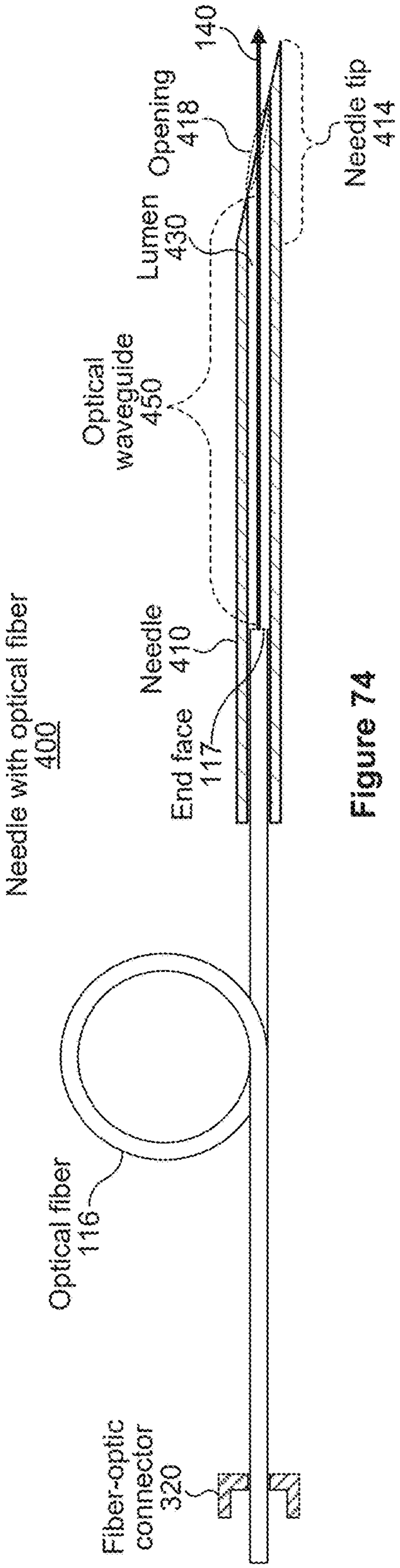
FIG. 74 illustrates an example needle with optical fiber that includes an optical waveguide.

FIG. 74 illustrates an example needle with optical fiber 400 that includes an optical waveguide 450. Part of the needle lumen 430 is occupied by a portion of the optical fiber 116 and the end face 117, and another part of the lumen is occupied by the optical waveguide 450. The optical waveguide 450 in FIG. 74 is an optical waveguide located within the needle 410 and may be referred to as a needle waveguide. The end face 117 of the optical fiber 116 is separated from the needle opening 418 by the needle waveguide 450. The pump-Stokes beam 140 is emitted from the end face 117 and propagates within the lumen 430 and along the optical waveguide 450 from the end face to the opening 418. At the end of the optical waveguide 450, the pump-Stokes beam 140 is directed through the opening 418. The pump-Stokes beam may be directed to a sample 150, and a Raman signal 160 may be produced by coherent Raman scattering of the pump and Stokes beams of light at the sample. At least a portion of the Raman signal 160 may be directed to the opening 418 and coupled into the optical waveguide 450. The Raman signal 160 may propagate along the optical waveguide 450 from the opening 418 to the end face 117 where it is coupled into the optical fiber 116.

The needle waveguide 450 in FIG. 74 (which may also be referred to as a metallic tube waveguide or a hollow metallic waveguide) includes the hollow space within the lumen 430 and the reflective interior surface of the needle 410. The needle waveguide may guide light by reflecting the light from the interior wall of the needle 410 as the light propagates along the waveguide. The needle 410 may be made from a metallic material, and the metallic surface of the interior wall may be reflective to light at the wavelengths of the pump and Stokes beams. Additionally or alternatively, the interior surface may be polished or a reflective metal or dielectric coating may be deposited onto the interior wall to increase the reflectivity of the wall.

The needle with optical fiber in FIG. 74 may include a lens located near the end face 117 or near the opening 418, and the lens may collimate or focus the pump-Stokes beam 140. For example, a first lens located near the end face 117 may produce a collimated pump-Stokes beam 140 that propagates along the optical waveguide 450, and a second lens located near the opening 418 may produce a focused pump-Stokes beam that is directed to a sample. The second lens may be attached to the needle 410 by an adhesive that forms a seal to prevent fluid from flowing into the lumen 430. Additionally or alternatively, the needle with optical fiber in FIG. 74 may include a window located near the opening 418 that transmits the pump-Stokes beam 140 and is sealed to prevent fluid from flowing into the lumen 430.

FIGS. 75-78 each illustrate an example needle with optical waveguide 400-W. A needle with optical waveguide 400-W includes a needle 410 with an optical waveguide 450 located within the needle and may be referred to as a needle apparatus, a needle-waveguide apparatus, or a needle-with-optical-waveguide apparatus. The needle 410 may be a Quincke-type needle (as illustrated in FIGS. 57*a*-57*c*), a Whitacre-type needle (as illustrated in FIGS. 58*a*-58*c*), or any other suitable type of hypodermic needle. Each needle with optical waveguide 400-W described herein may be coupled to a Raman spectroscopy system with optical-fiber extension via one or more optical fibers. For example, the extension optical fibers 116*e* in FIGS. 75-77 may be coupled to a Raman spectroscopy system, and the fiber-optic connector 320 in FIG. 78 may be used to couple the optical fiber 116 to another optical fiber that is coupled to a Raman spectroscopy system.

In each of FIGS. 75-78, the needle with optical waveguide 400-W includes an optical waveguide 450 located within the needle shaft 412 that extends along most of the length of the shaft. Instead of using an optical fiber to transmit light along all or part of the length of a needle 410 (e.g., as illustrated by the needles with optical fiber 400 in FIGS. 59-74), a needle with optical waveguide 400-W includes an optical waveguide 450 that transmits a pump-Stokes beam 140 or a Raman signal 160 along most of the length of a needle. In each of FIGS. 75-77, the optical fiber 116*e* may be connected to the needle with optical waveguide 400-W by coupling the fiber-optic connectors 320*a* and 320*b* together, and then light may be coupled from the optical fiber 116*e* into the optical waveguide 450 (or vice versa). In each of FIGS. 75-78, the optical waveguide 450 receives a pump-Stokes beam of light 140 emitted from the end face 117 of an optical fiber 116, where the end face is located at the proximal end of the needle shaft 412 opposite the tip 414. The optical waveguide 450 conveys the pump-Stokes beam 140 along the waveguide to the needle tip 414, where the pump-Stokes beam is emitted from the waveguide and directed through the opening 418 of the needle 410. The pump-Stokes beam may be directed to a sample 150, and a Raman signal 160 may be produced by coherent Raman scattering of the pump and Stokes beams of light at the sample. At least a portion of the Raman signal 160 may be directed to the opening 418 and coupled into the optical waveguide 450. The Raman signal 160 may propagate along the optical waveguide 450 from the opening 418 to the end face 117 where it is coupled into the optical fiber 116.

The optical waveguide 450 in each of FIGS. 75-78 includes the reflective interior surface of the needle 410. The optical waveguide 450 may guide light by reflecting the light from the interior wall of the needle 410 as the light propagates along the waveguide. The needle 410 may be made from a metallic material, and the metallic surface of the interior wall may be reflective to light at the wavelengths of the pump and Stokes beams. Additionally or alternatively, the interior surface may be polished or may include a reflective optical coating (e.g., a metallic or dielectric optical coating). The coating may have a relatively high reflectivity (e.g., reflectivity greater than 75%) at the wavelengths of the pump and Stokes beams and may reflect the pump-Stokes beam of light 140 as it propagates along the waveguide 450.

Figure 75:
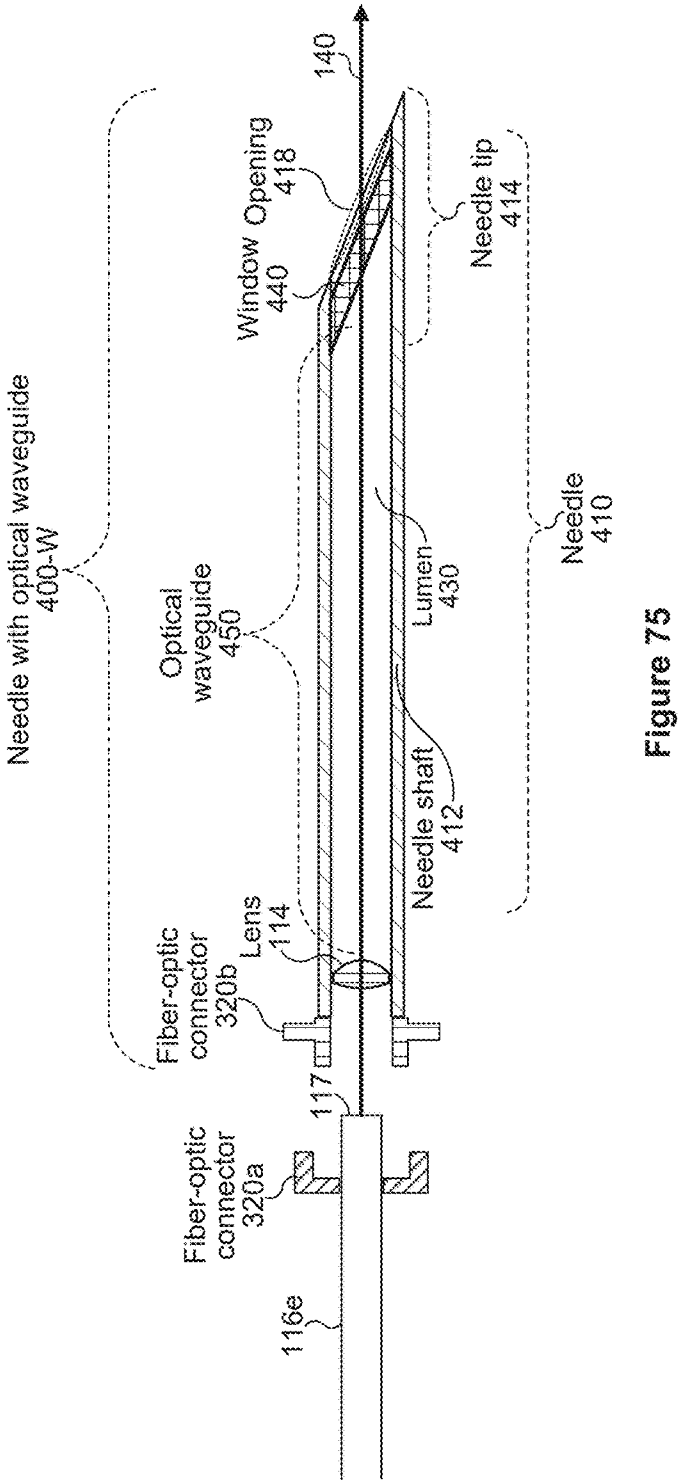
FIGS. 75-78 each illustrate an example needle with optical waveguide.
Figure 76:
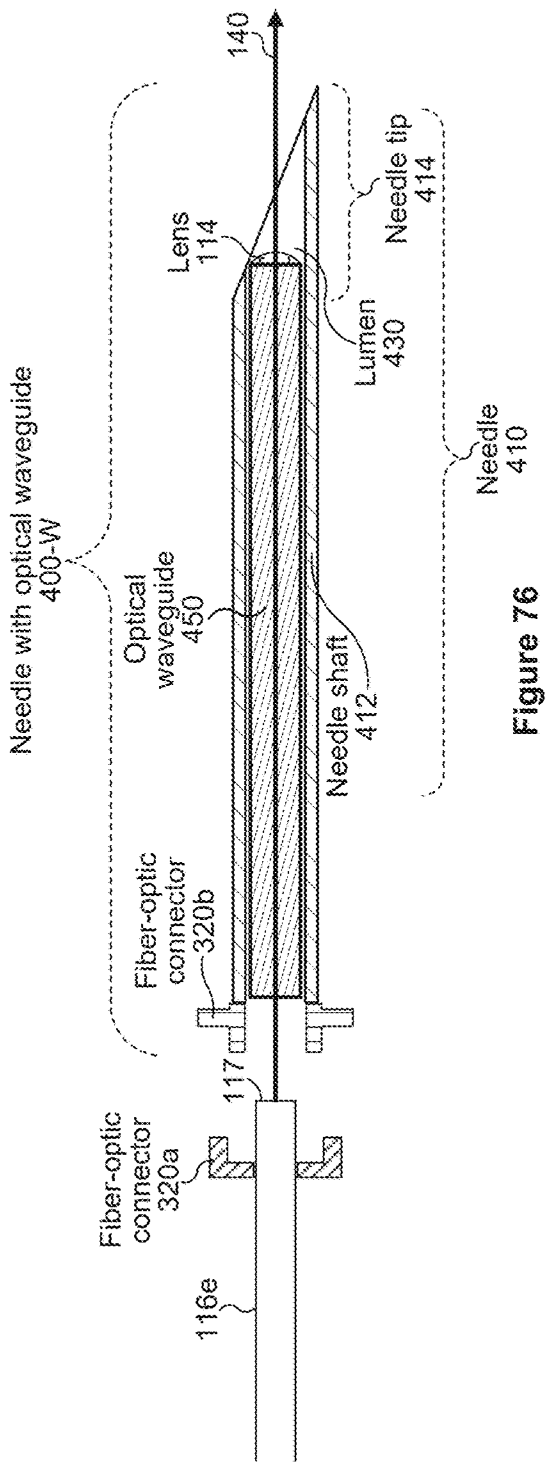
Figure 77:
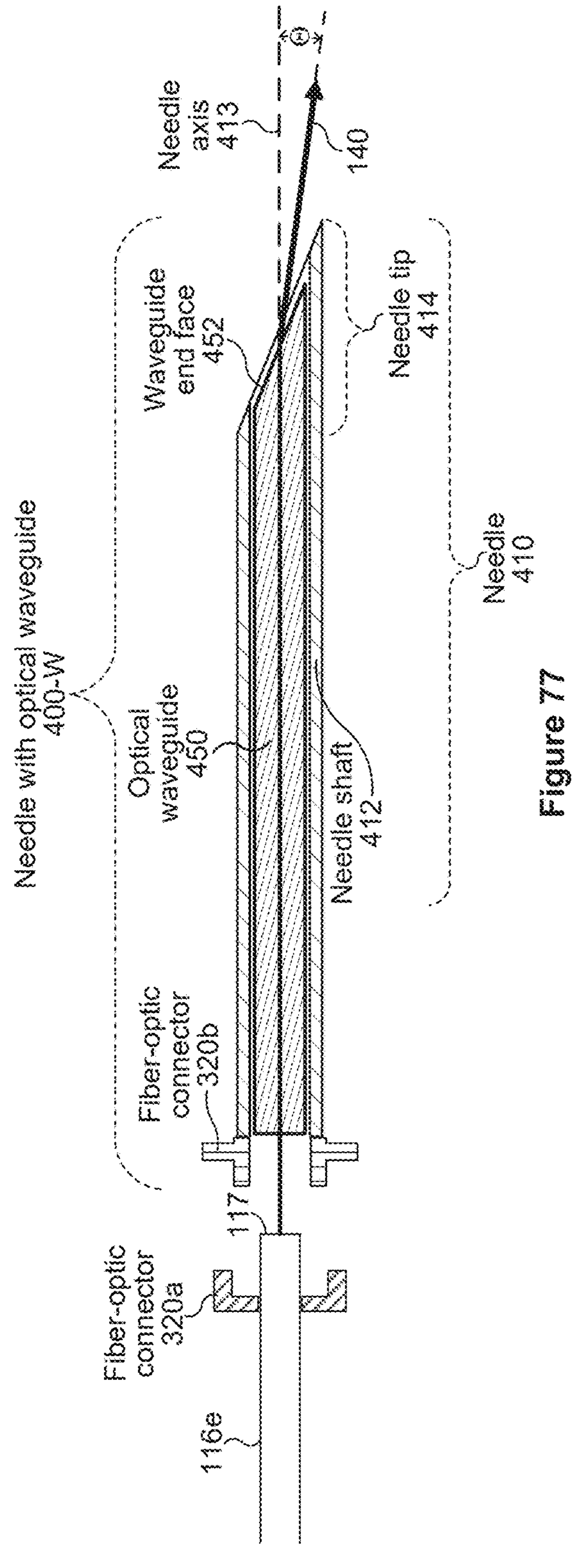
Figure 78:
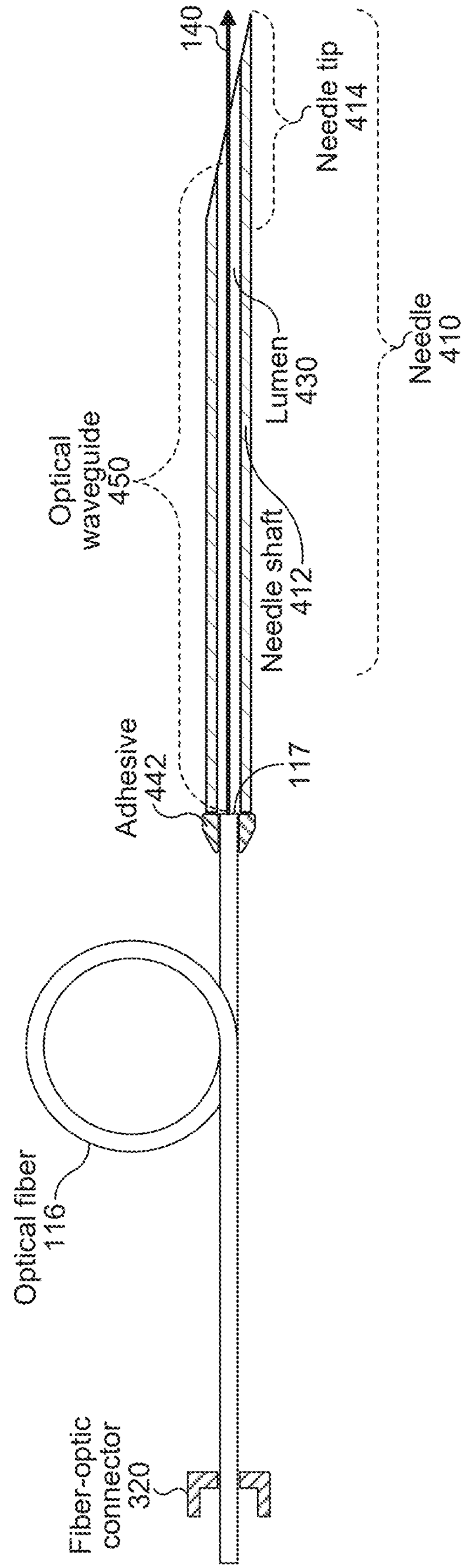

An optical waveguide 450 may be substantially hollow or may include an optically transparent material that transmits light at the wavelengths of the pump and Stokes beams. The optical waveguide 450 in each of FIGS. 75 and 78 is substantially hollow and includes the hollow space located within the needle shaft 412, where the hollow space corresponds to the lumen 430. In FIGS. 76-77, instead of having an optical waveguide with a hollow interior, the optical waveguide 450 includes a transparent material that transmits the pump-Stokes beam 140. For example, the optical waveguide 450 may include a transparent plastic, epoxy, or other dielectric material that fills most of the lumen, and the material may transmit light at the wavelengths of the pump and Stokes beams. The transparent material of the optical waveguide 450 may be injected into the needle 410 as a liquid and may be bonded to the interior surface of the needle 410 after curing. Alternatively, a solid optical waveguide 450 may be inserted into the needle 410 and then attached to the needle 410 by an adhesive. The transparent material of the optical waveguide 450 may be substantially uniform or may include a channel or core having a higher refractive index than the surrounding material for guiding light that propagates along the waveguide. As another example, the optical waveguide 450 may include a series of GRIN lenses cascaded one after the other along the length of the needle shaft 412. The GRIN lenses may guide light along the optical waveguide 450 by repeatedly focusing and collimating the light as it propagates from one end of the needle to the other.

In each of FIGS. 75-77, the needle with optical waveguide 400-W includes a fiber-optic connector 320*b* that is coupled to the needle 410 at the proximal end of the needle opposite the tip 414. The connector 320*b* may be attached to the needle 410 using an adhesive or by welding the two parts together. The needle with optical waveguide 400-W can be coupled to the optical fiber 116*e* by connecting the fiber-optic connector 320*a* to the mating fiber-optic connector 320*b*. When the optical fiber 116*e* is connected to the needle with optical waveguide 400-W, a pump-Stokes beam of light 140 may be coupled from the optical fiber into the optical waveguide 450, or a Raman signal 160 may be coupled from the optical waveguide into the optical fiber.

In FIG. 78, the needle with optical waveguide 400-W includes an optical fiber 116 that is attached to the needle 410 at the proximal end of the needle opposite the tip 414. The optical fiber 116 may be permanently attached to the needle using an adhesive 442. The optical fiber 116 may be coupled to a Raman spectroscopy system 100 using the fiber-optic connector 320. The optical fiber 116 may transmit a pump-Stokes beam 140 along the fiber to the needle 410, and the pump-Stokes beam may be emitted from the end face 117 and directed into the optical waveguide 450.

A needle with optical waveguide 400-W may include a lens 114 located at or near the proximal end of the needle 410. The lens 114 may be attached to the needle 410 using an adhesive, or the lens may be integrated into a fiber-optic connector 320*b* located at the proximal end of the needle.

The lens 114 in FIG. 75 receives a pump-Stokes beam 140 from the end face 117 of the optical fiber 116*e*, and the lens may produce a collimated or focused pump-Stokes beam 140 that is directed into the optical waveguide 450.

A needle with optical waveguide 400-W may include a lens 114 or optical window 440 attached to the needle 410 at or near the opening 418 of the needle. The needle with optical waveguide 400-W in FIG. 75 includes a window 440 located in the needle tip 414 near the opening 418. The window 440 may transmit light at the pump and Stokes wavelengths (as well as the wavelength of an associated Raman signal). Additionally, the window 440 may be attached to the needle 410 using an adhesive that forms a seal, and the sealed window may prevent fluid from flowing through the opening 418 and into the lumen 430. In other embodiments, a needle with optical waveguide 400-W may include a lens 114 located at or near the opening 418. For example, in FIG. 75, a lens 114 may be located in the needle tip 414 in place of the window 440 (e.g., similar to the lens 114 in FIG. 65). The lens 114 may transmit the pump-Stokes beam 140 and produce a collimated or focused pump-Stokes beam that may be directed to a sample 150. Additionally, the lens 114 may be attached to the needle 410 using an adhesive that forms a seal, and the sealed lens may prevent fluid from flowing through the opening 418 and into the lumen 430. As another example, a lens 114 may be integrated into an optical waveguide 450 that includes a transparent material, as illustrated in FIG. 76. The lens 114 in FIG. 76 may be a separate optical element that is attached to the end face of the optical waveguide 450, or the lens may be formed by shaping the end face of the optical waveguide to produce a lens.

A needle with optical waveguide 400-W may include an optical waveguide 450 with an angled end face. The optical waveguide 450 in FIG. 77 has an end face 452 that is angled, which causes the pump-Stokes beam 140 to be emitted from the optical waveguide at an angle Θ with respect to the central axis 413 of the needle 410. The needle with optical waveguide 400-W may be rotated about the needle axis 413 to change the propagation direction of the pump-Stokes beam 140. For example, an operator of a Raman spectroscopy system 100 that is coupled to the needle with optical waveguide 400-W in FIG. 77 may rotate the needle 410 about the needle axis 413 to direct the pump-Stokes beam 140 in different directions. The tip 414 of the needle with optical waveguide 400-W may be inserted into a sample 150. As the needle 410 is rotated, the Raman spectroscopy system 100 may make measurements of Raman signals 160 produced by different parts of the sample 150.

Figure 79:
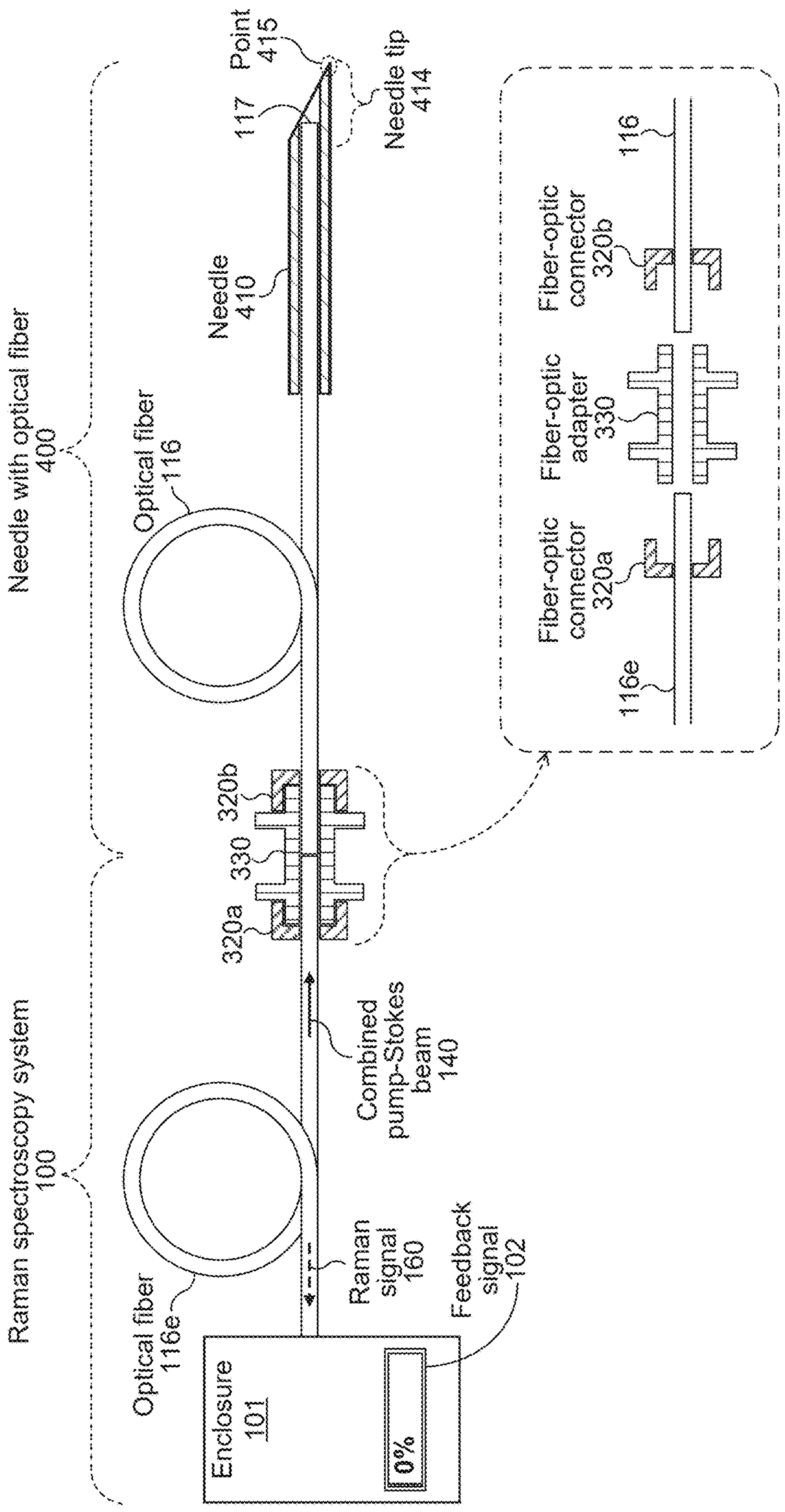
FIGS. 79-81 each illustrate an example needle with optical fiber coupled to a Raman spectroscopy system.
Figure 80:
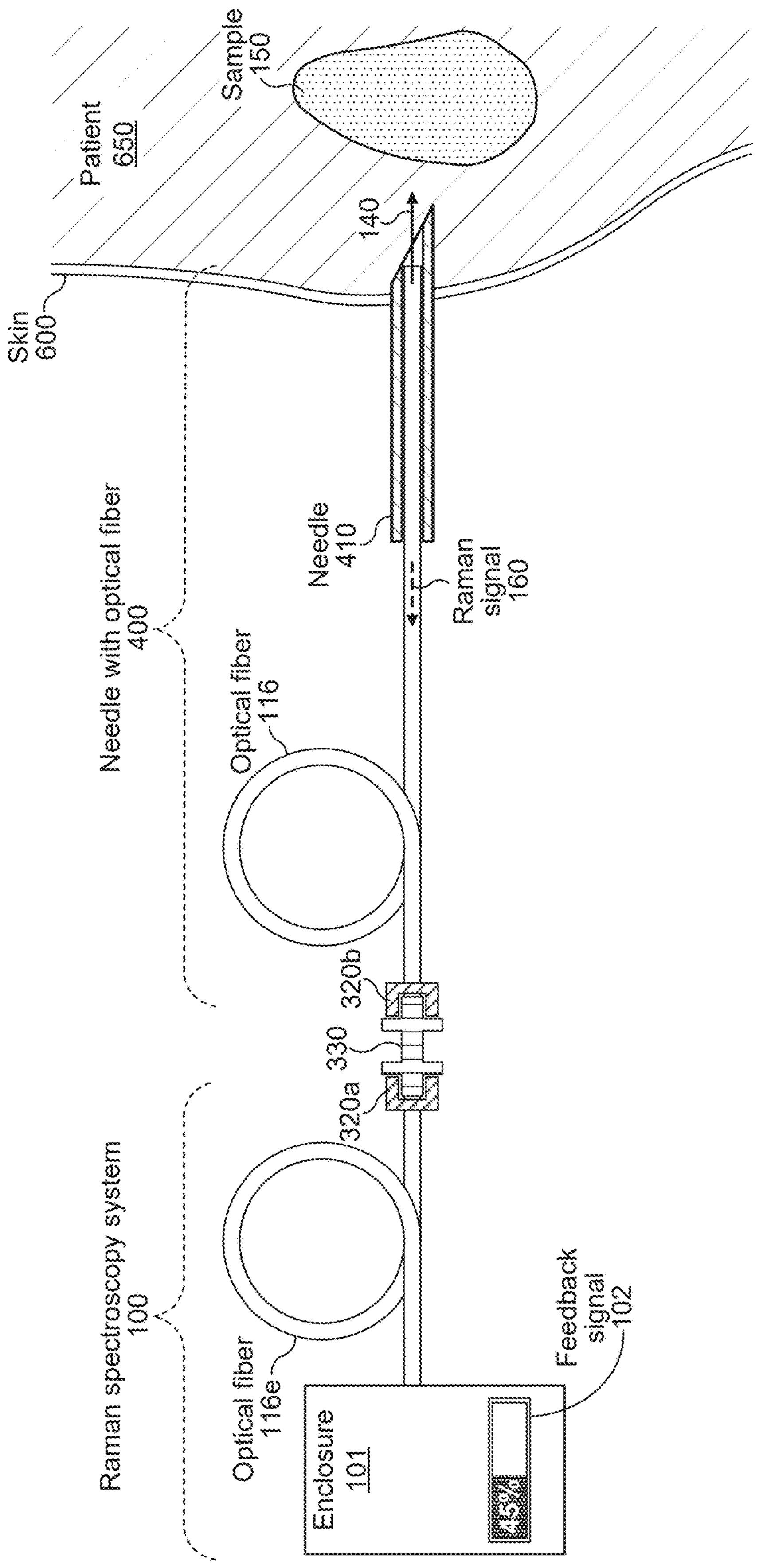
Figure 81:
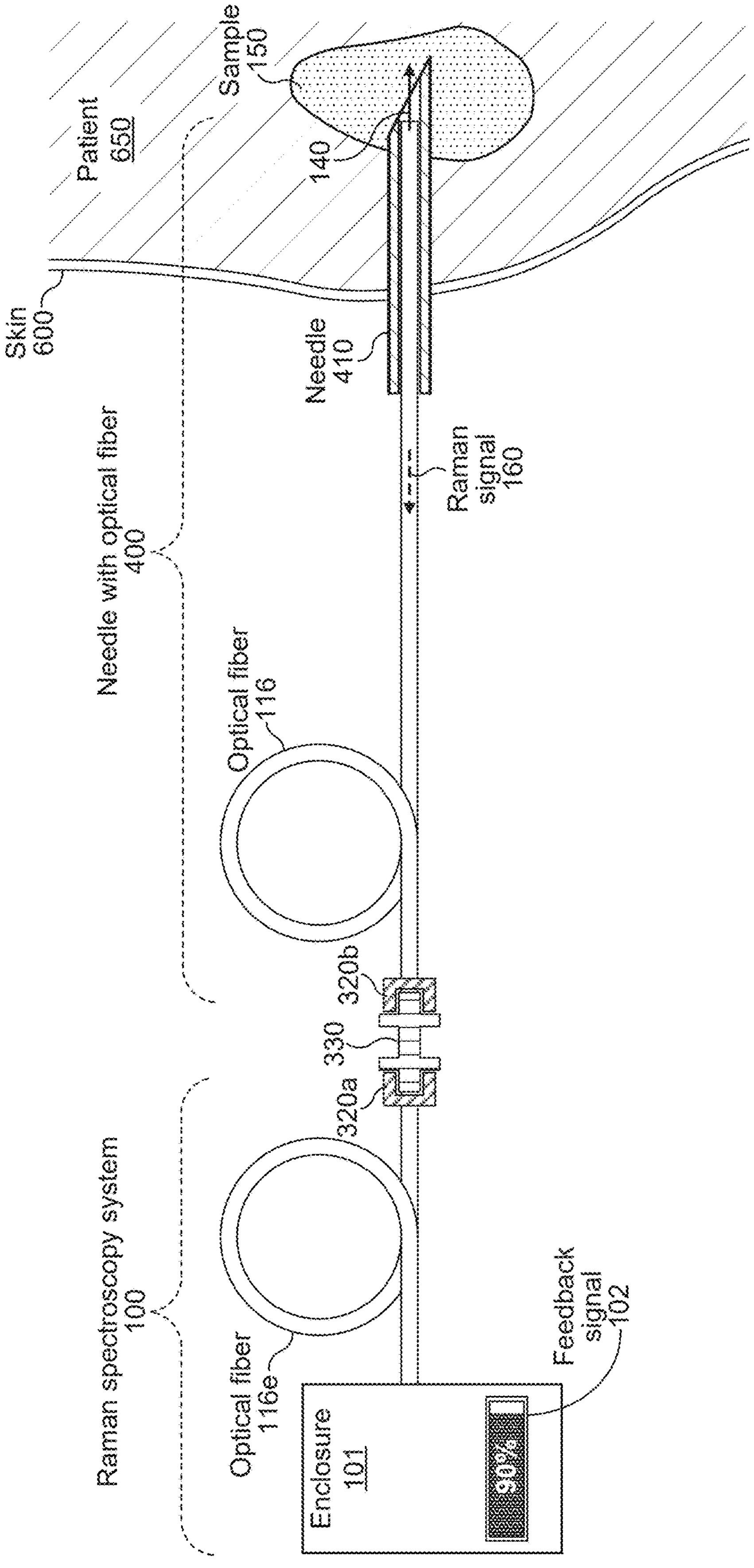

FIGS. 79-81 each illustrate an example needle with optical fiber 400 coupled to a Raman spectroscopy system 100. The Raman spectroscopy system 100 is a Raman spectroscopy system with optical-fiber extension and is similar to the system in FIG. 40, 42, or 43. The optical fiber 116*e* may be referred to as an optical-fiber extension, a fiber-optic extension, or an external optical fiber. The needle with optical fiber 400 in FIGS. 79-81 is similar to that in FIG. 59. While the arrangement in FIGS. 79-81 illustrates a needle with optical fiber 400 similar to that in FIG. 59, any suitable needle with optical fiber may be used in this type of arrangement. For example, any suitable needle with optical fiber 400 described herein may be used in the arrangement of FIGS. 79-81. Additionally, while the arrangement in FIGS. 79-81 illustrates a needle with optical fiber 400 coupled to a Raman spectroscopy system 100, a needle with optical waveguide 400-W or a catheter needle with optical fiber 500 may be used instead of the needle with optical fiber. For example, any suitable needle with optical waveguide 400-W described herein or any suitable catheter needle with optical fiber 500 described herein may be used in the arrangement of FIGS. 79-81 in place of the needle with optical fiber 400 illustrated in those figures.

In FIGS. 79-81, the optical fiber 116 of the needle with optical fiber 116 is coupled to the Raman spectroscopy system 100 via the optical fiber 116*e*. The dashed-line inset in FIG. 79 illustrates the optical fibers 116 and 116*e* prior to being connected together. To connect the optical fibers, the ends of the fibers are inserted into the adapter 330 and the fiber-optic connectors 320*a* and 320*b* are secured to the adapter 330, at which point the optical fibers 116*e* and 116 are connected together and light may be transmitted between the two fibers. In other embodiments, the two optical fibers may have mating optical connectors (e.g., similar to connectors 320*a* and 320*b* in FIG. 75) that may be connected together without a fiber-optic adapter 330.

The Raman spectroscopy system in FIGS. 79-81 produces a pump-Stokes beam of light 140 that is sent to a sample 150 via the optical fiber 116, and the pump-Stokes beam of light includes a pump beam of light 120*pu* and a Stokes beam of light 120S. For example, the Raman spectroscopy system 100 may include a pump light source 110*pu* that produces a pump beam of light 120*pu* at a pump frequency and a Stokes light source 110S that produces a Stokes beam of light 120S at a Stokes frequency, where the pump and Stokes frequencies are offset by a frequency offset Ω. The pump and Stokes beams may be combined together to produce a pump-Stokes beam of light 140 that is coupled into the optical fiber 116*e* and sent to the needle with optical fiber 400. The pump-Stokes beam 140 propagates along the optical fiber 116*e* and then is coupled into the optical fiber 116, which, in FIG. 80, directs the pump-Stokes beam to a sample 150. A Raman signal 160 may be produced by coherent Raman scattering of the pump and Stokes beams of light at the sample 150, and a portion of the Raman signal 160 may be coupled into the optical fiber 116. The Raman signal 160 is then directed along the optical fibers 116 and 116*e* to the Raman spectroscopy system 100 for measurement. For example, the Raman signal 160 may be directed to an optical receiver 200 where it is coherently mixed with a probe beam of light 120*pr* at a detector 220 to produce a corresponding photocurrent signal, and a characteristic of the photocurrent signal may be determined.

In FIGS. 79-81, the pump-Stokes beam 140 and the Raman signal 160 propagate along the same optical fibers 116 and 116*e* (e.g., similar to the arrangement in FIGS. 40, 42, and 43). In other embodiments, a needle with optical fiber 400 may include multiple optical fibers or a multi-core optical fiber, and the pump-Stokes beam 140 and the Raman signal 160 may propagate along separate optical fibers (e.g., similar to the arrangement in FIGS. 41, 44, and 45).

A portion of a needle 410 may be inserted into the body of a patient 650 to make a measurement of a Raman signal 160 produced by a part of the patient's body. For example, at least the tip 414 of a needle 410 may be inserted into a patient's body by using the point 415 to (i) pierce through the skin 600 of the patient 650 or (ii) pierce into an organ or another part of the patient's body. Herein, a patient 650 (which may be referred to as a subject) may include a human or an animal. In FIG. 80, the end portion of the needle with optical fiber 400 (which includes the needle tip 414 and the end face 117 of the optical fiber 116) is inserted into the body of a patient 650 by piercing through a layer of skin 600. In FIG. 81, the end portion of the needle with optical fiber 400 is directed into the sample 150. In other instances, instead of piercing through a layer of skin to direct a needle with optical fiber 400 to a sample 150, the end portion of a needle with optical fiber 400 may be inserted directly into an organ or another part of a patient's body. For example, a needle with optical fiber 400 may be inserted directly into an organ or another part of a patient's body during a surgical procedure via a body opening or a surgical incision. As another example, a needle with optical fiber 400 may be inserted ex vivo into an organ or tissue that has been removed from a patient's body.

The end portion of a needle with optical fiber 400 (which includes the needle tip 414) may be inserted into a sample 150 to perform a measurement of the sample using a Raman spectroscopy system 100 that is coupled to the needle with optical fiber 400. A sample 150 may include any suitable part of the body of a patient 650 or any suitable solid, liquid, or gas produced by a patient. For example, a sample 150 may include: cerebrospinal fluid, synovial fluid, pleural fluid, pericardial fluid, peritoneal fluid, a portion of a lymphatic system, a portion of a biliary system, blood, urine, tears, sputum, wound exudate, saliva, sweat, vaginal secretion, urethral secretion, nasal secretion, semicircular canal fluid, amniotic fluid, breast milk, interstitial fluid, pancreatic fluid, stool, gastric contents, aqueous humor, vitreous humor, or breath. As another example, a Raman spectroscopy system 100 may be used in a measurement to determine whether a cancer or other disease is present or whether a particular molecule is present, and the associated sample 150 that is measured may include: liver, kidney, spleen, skeletal muscle, skin or subcutaneous tissue, bone, marrow, brain, pancreas, lung, prostate, thyroid gland, salivary gland, mammary gland, breast, adrenal gland, bladder, intestinal mass, ovary, testicle, parathyroid gland, thymus, eye, lymph node, uterus, or endometrium.

During insertion of a needle 410 into a part of the body of a patient 650, a Raman spectroscopy system 100 may provide a feedback signal 102 to assist in directing the needle to a sample 150. The feedback signal 102 may represent the portion of a measured Raman signal 160 that is associated with the sample 150. For example, the feedback signal 102 may indicate a size or a relative amount of the Raman signal 160 that is produced by coherent Raman scattering of the pump and Stokes beams of light at the sample 150. In FIG. 79, prior to inserting the needle 410 of the needle with optical fiber 400 into a part of a patient's body, an operator of the Raman spectroscopy system 100 may provide an indication to the system of what type of sample is to be measured (e.g., blood, interstitial fluid, liver, or pancreas). The Raman spectroscopy system 100 may then refer to a library to determine the expected characteristics that a Raman signal 160 produced by that type of sample may exhibit. During insertion of the needle 410, the Raman spectroscopy system 100 may make multiple Raman-signal measurements by continually sending out a pump-Stokes beam 140 and then measuring the resulting Raman signal 160 that is collected. The Raman spectroscopy system may compare the measured Raman signal 160 with the expected characteristics of the sample 150 to determine the portion of the measured Raman signal 160 that is associated with the sample.

In FIGS. 79-81, the Raman spectroscopy system 100 provides a feedback signal 102 that may indicate how far the needle tip 414 (as well as the end face 117) is located from the sample 150. In FIG. 79, before the needle 410 is inserted, the feedback signal 102 reads "0%," indicating the presence of little or no Raman signal associated with the sample 150. In FIG. 80, while the needle 410 is being inserted, the feedback signal 102 reads "45%," which indicates that a portion of the received Raman signal 160 corresponds to the expected characteristics associated with the sample 150, which in turn indicates that the needle tip may be positioned near the sample. In FIG. 81, the feedback signal 102 reads "90%," which indicates that most of the received Raman signal 160 corresponds to the expected characteristics associated with the sample 150, which in turn indicates that the needle tip is located at or within the sample.

In a situation where a feedback signal is not provided during a needle insertion process, directing a needle to a particular location within a patient's body can be a difficult or time-consuming process and may cause unnecessary discomfort to the patient. These problems may be avoided or reduced significantly by providing a feedback signal 102 to help in guiding a needle to a desired location. By coupling a needle with optical fiber 400 to a Raman spectroscopy system, the process of inserting a needle may be improved by providing a feedback signal to help an operator quickly and successfully guide the needle to a desired location.

Figure 82:
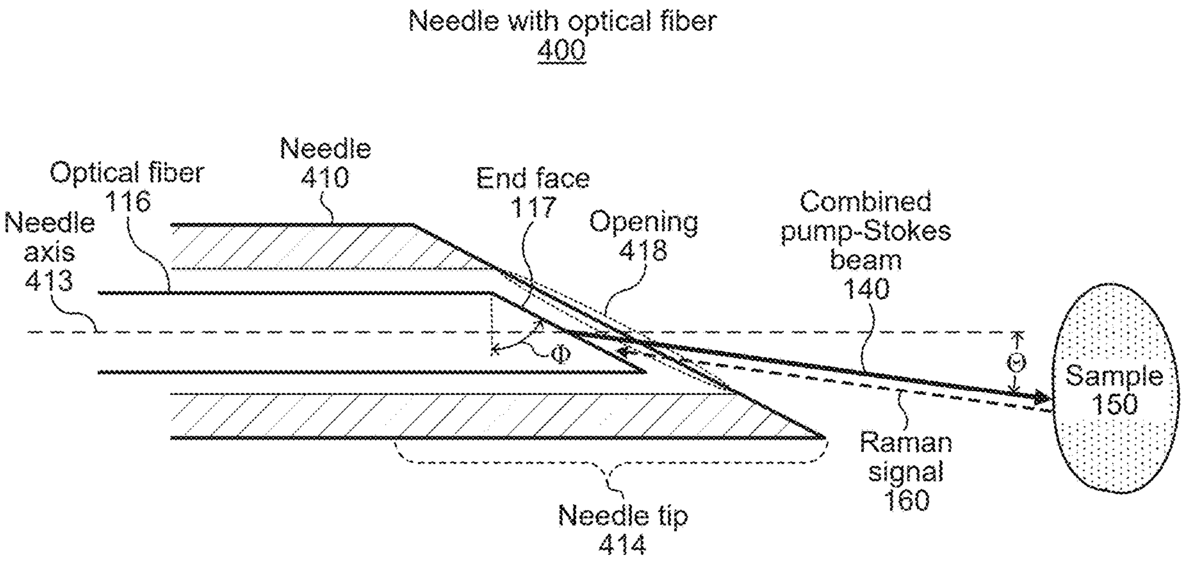
FIGS. 82-83 each illustrate an example needle with optical fiber where a pump-Stokes beam is directed at an angle with respect to the needle axis.
Figure 83:
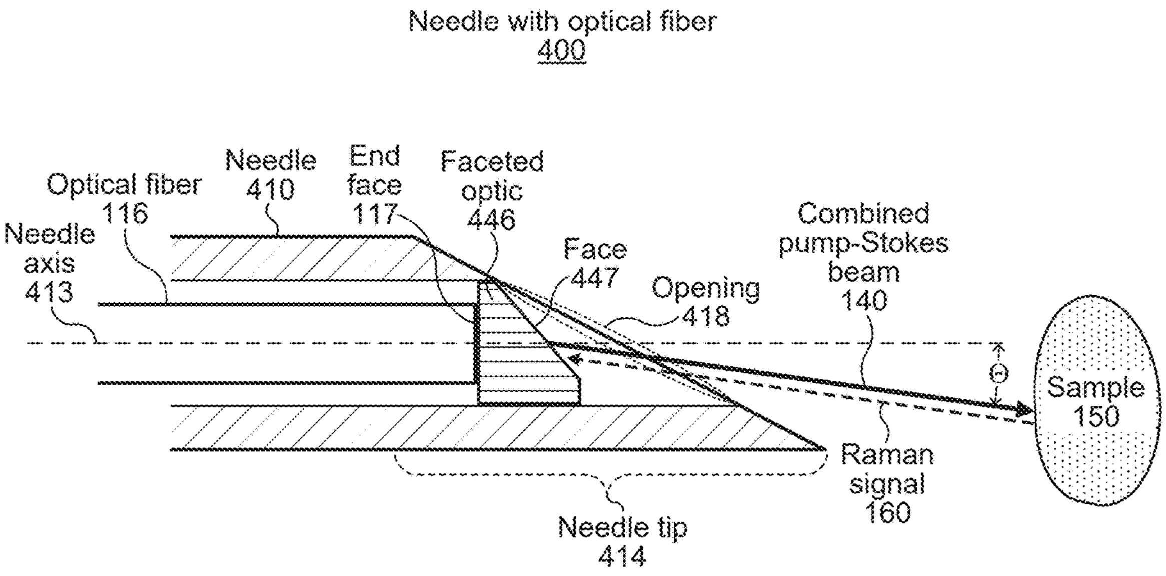

FIGS. 82-83 each illustrate an example needle with optical fiber 400 where a pump-Stokes beam 140 is directed at an angle Θ with respect to the needle axis 413. In each of FIGS. 82-83, the pump-Stokes beam 140 propagates along the optical fiber 116 in a direction that is approximately parallel to the needle axis 413. The pump-Stokes beam 140 is then emitted from the optical fiber 116 and directed through the needle opening 418 along a propagation direction that is at an angle Θ with respect to the needle axis 413. The propagation direction of each of the beams in FIGS. 82-83 corresponds to the direction of the arrow associated with the beam. The angle Θ along which a pump-Stokes beam 140 is directed may be any suitable nonzero angle, such as for example, an angle between 1 degree and 60 degrees. For example, the pump-Stokes beam 140 in each of FIGS. 82-83 is directed through the needle opening 418 at an angle Θ of approximately 8 degrees with respect to the needle axis 413.

A pump-Stokes beam 140 that is emitted at an angle Θ, may be used to perform a Raman-signal measurement along the propagation direction of the beam. For example, a pump-Stokes beam 140 may be directed along an angle to a part of a sample 150, and the beam may interact with that part of the sample to produce a Raman signal 160 that is measured by a Raman spectroscopy system 100. In each of FIGS. 82-83, the pump-Stokes beam 140 is directed at an angle Θ and to a sample 150. A Raman signal 160 may be produced by coherent Raman scattering of the pump and Stokes beams of light at the sample 150, and a portion of the Raman signal may be coupled into the optical fiber 116. The Raman signal 160 may propagate along the optical fiber 116 and to a Raman spectroscopy system 100 for measurement.

In FIG. 82, the end face 117 of the optical fiber 116 is angled, which causes the pump-Stokes beam 140 to be refracted and emitted from the optical fiber along an angle. The end face 117 being angled refers to the surface normal of the end face having a nonzero angle with respect to the propagation direction of the pump-Stokes beam 140 in the optical fiber 116. The angle ϕ of the end face 117 may have any suitable nonzero value, such as for example, an angle between 1 degree and 45 degrees. An angled end face 117 may be produced by polishing the end face of the optical fiber to the desired angle ϕ. The angle Θ along which the pump-Stokes beam 140 is directed corresponds to the angle ϕ of the end face 117. For example, the angles Θ and ϕ may be related by the Snell's law of refraction that relates the two angles and the refractive indices of the optical fiber 116 and the medium into which the pump-Stokes beam 140 is emitted.

In FIG. 83, the needle with optical fiber 400 includes a faceted optic 446 with a face 447 that is angled. The end face 117 of the optical fiber 116 is non-angled, and the angled pump-Stokes beam 140 is produced by the faceted optic 446. The face 447 of the faceted optic 446 being angled refers to the surface normal of the face having a nonzero angle with respect to the propagation direction of the pump-Stokes beam 140 in the optical fiber 116. The faceted optic 446 has a wedged shape with a first surface that is parallel to the end face 117 and a second surface (face 447) oriented at an angle. The first surface of the faceted optic 446 may be attached to the end face 117 using an optically clear adhesive. The pump-Stokes beam 140 travels through the two surfaces of the faceted optic 446, and refraction at the angled face 447 causes the beam to be directed along a propagation direction that is at an angle Θ with respect to the needle axis 413. In FIG. 83, the face 447 of the faceted optic 446 is flat. In other embodiments, a faceted optic 446 may have a face 447 that includes a lens that collimates or focuses the pump-Stokes beam of light 140. For example, a lens may be attached to the face 447 of the faceted optic 446, or a lens may be formed by shaping the face 447 to produce a lens.

Figure 84:
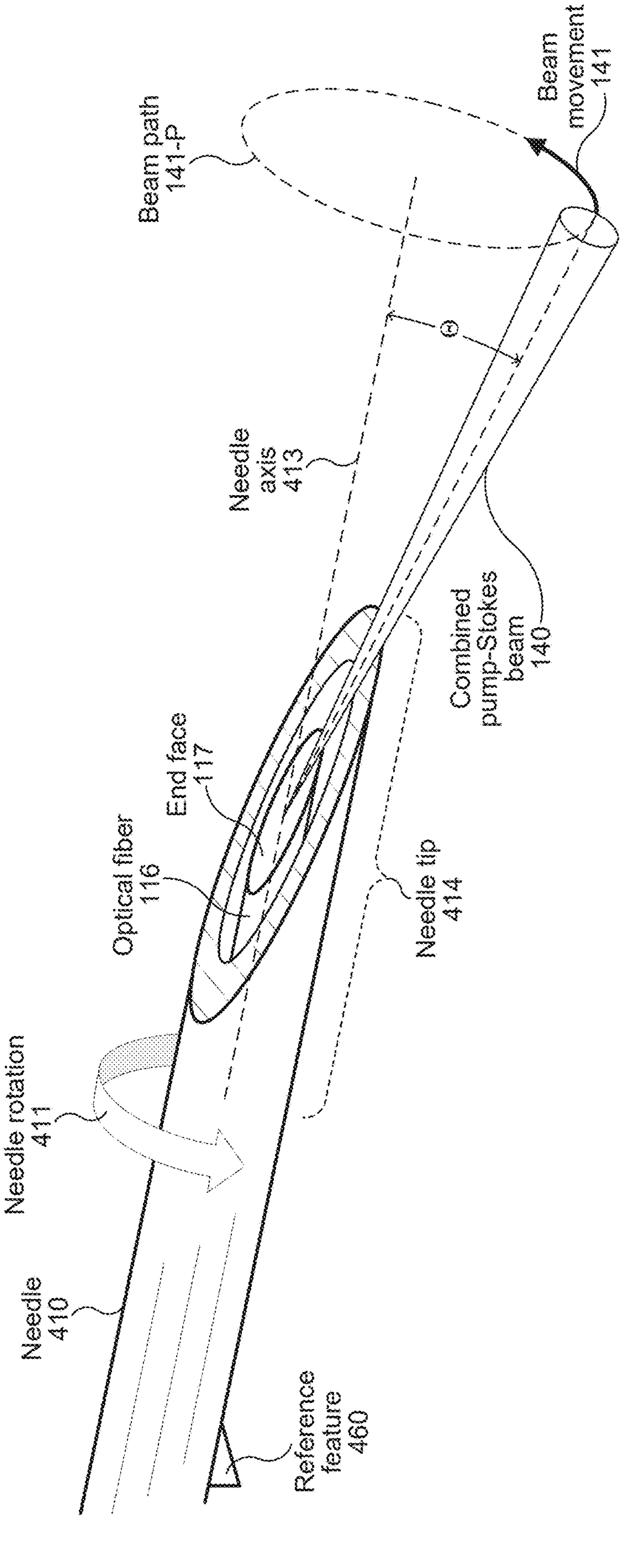
FIG. 84 illustrates an example needle with optical fiber that is rotated to sweep a pump-Stokes beam along a beam path.

FIG. 84 illustrates an example needle with optical fiber 400 that is rotated to sweep a pump-Stokes beam 140 along a beam path 141-P. The end face 117 of the optical fiber 116 in FIG. 84 is angled, and the pump-Stokes beam 140 is emitted at an angle θ with respect to the needle axis 413 (similar to the needle with optical fiber 400 in FIG. 82). In other embodiments, an angled pump-Stokes beam may be produced using a faceted optic 446 (e.g., as illustrated in FIG. 83) or using a mirror to direct the pump-Stokes beam at an angle. In FIG. 84, a needle rotation 411 is applied to the needle 410 to produce a corresponding beam movement 141 of the pump-Stokes beam 140 along the beam path 141-P. The beam path 141-P swept out by the pump-Stokes beam 140 may be approximately circular. The optical fiber 116 in FIG. 84 may be attached to the needle 410 so that as the needle is rotated, the optical fiber and the end face 117 are also rotated in a similar manner. When the needle 410 is rotated about the needle axis 413, the propagation direction of the pump-Stokes beam 140 is changed correspondingly. For example, the needle rotation 411 in FIG. 84 is in a clockwise direction as viewed along the needle axis 413 from the reference feature 460 toward the tip, and a 90-degree clockwise rotation of the needle may produce a corresponding clockwise beam movement 141 of 90 degrees along the beam path 141-P.

The needle with optical fiber 400 in FIG. 84 may be coupled to a Raman spectroscopy system 100, and the system may make multiple Raman-signal measurements along the different propagation directions of the pump-Stokes beam 140 as the needle 410 is rotated. For example, an operator may rotate the needle 410 as it is being directed to a sample 150, and the Raman spectroscopy system 100 may provide a feedback signal 102 to assist in directing the needle to the sample. By observing how the feedback signal 102 changes as the needle 410 is rotated about the needle axis 413, an operator may adjust the direction in which the needle is pointed to direct the needle to the sample 150. Additionally, the needle 410 may be rotated after reaching the sample 150 to make multiple measurements from different parts of the sample located along the beam path 141-P.

The needle 410 in FIG. 84 includes a reference feature 460 located on the outer surface of the needle 410, and the reference feature 460 corresponds to the propagation direction of the pump-Stokes beam 140. For example, the reference feature 460 in FIG. 84 is positioned to indicate or point in the direction along which the pump-Stokes beam 140 propagates. The reference feature 460 may be an indentation, a marking, a line, a protrusion (as illustrated in FIG. 84), or any other suitable visible or tactile feature that a person viewing or handling the needle may be able to see or feel. A reference feature 460 may be located on a part of a needle 410 that remains external to a patient's body during needle insertion, and the reference feature 460 may be used by an operator during needle insertion to indicate the direction in which the pump-Stokes beam 140 is emitted. For example, as the needle 410 is rotated, an operator may observe how a feedback signal 102 changes, and the reference feature 460 may be used to determine a direction in which the needle should be steered in order to reach a desired location.

Figure 85:
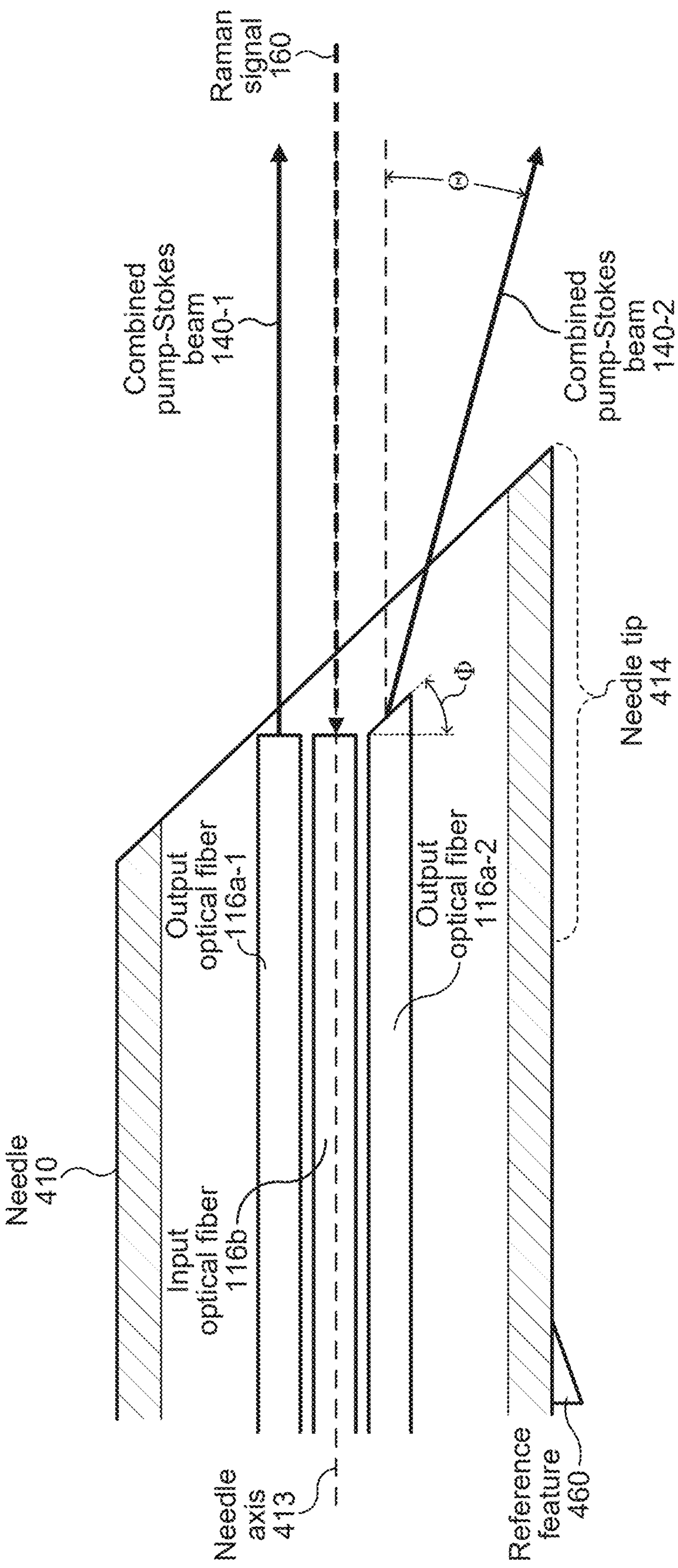
FIG. 85 illustrates an example needle with optical fiber that includes two output optical fibers and an input optical fiber.

FIG. 85 illustrates an example needle with optical fiber 400 that includes two output optical fibers 116*a*-1 and 116*a*-2 and an input optical fiber 116*b*. The output optical fiber 116*a*-1, which has a non-angled end face, produces a pump-Stokes beam 140-1 that is directed substantially parallel to the needle axis 413 (similar to the optical fiber 116 in FIG. 61). The output optical fiber 116*a*-2, which has an angled end face, produces a pump-Stokes beam 140 that is directed at a nonzero angle Θ with respect to the needle axis 413 (similar to the optical fiber 116 in FIG. 82). The needle with optical fiber 400 may be rotated about the needle axis 413 to change the propagation direction of the pump-Stokes beam 140-2 (similar to the rotation illustrated in FIG. 84). While the needle 410 is rotated, the pump-Stokes beam 140-1 that propagates substantially parallel to the needle axis 413 may not exhibit a significant change in its propagation direction. The needle with optical fiber 400 in FIG. 85 may be used to perform Raman-signal measurements in the forward direction using pump-Stokes beam 140-1 as well as along the angled direction using pump-Stokes beam 140-2. Additionally, the needle 410 may be rotated to continually perform measurements in the forward direction as well as along the different propagation directions of the pump-Stokes beam 140-2 as the needle is rotated.

Each of the pump-Stokes beams 140-1 and 140-2 in FIG. 85 may produce a Raman signal 160 by coherent Raman scattering, and the input optical fiber 116*b* may be configured to receive at least a portion of the Raman signal produced by each of the pump-Stokes beams. The input optical fiber 116*b* may transmit the received Raman signal 160 along the optical fiber in a direction away from the tip of the needle and to a Raman spectroscopy system 100 for measurement. In other embodiments, a needle with optical fiber 400 may include multiple output optical fibers and may not include any input optical fibers. In this embodiment, each of the output optical fibers, in addition to transmitting and emitting a pump-Stokes beam, may be configured to receive a Raman signal produced by coherent Raman scattering of the pump-Stokes beam and transmit the Raman signal along the optical fiber in a direction opposite the pump-Stokes beam.

Figure 86:
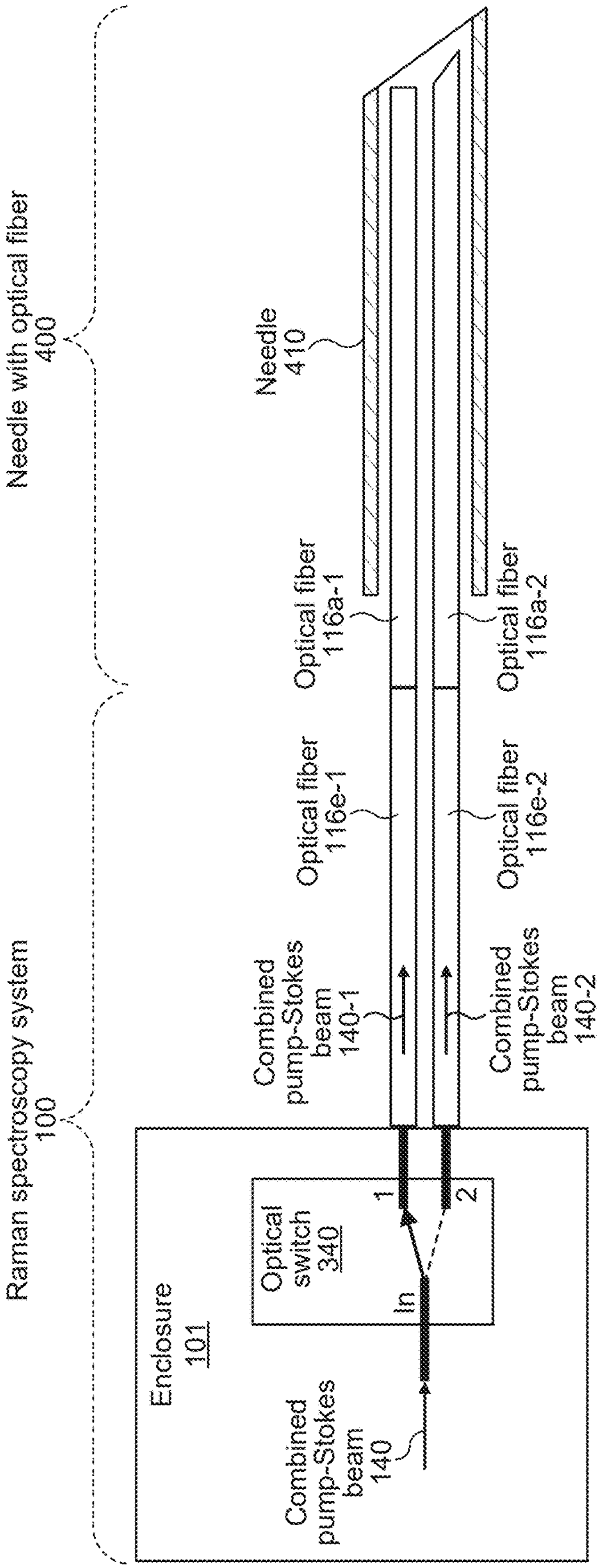
FIG. 86 illustrates an example needle with optical fiber coupled to a Raman spectroscopy system that includes an optical switch.

FIG. 86 illustrates an example needle with optical fiber coupled 400 to a Raman spectroscopy system 100 that includes an optical switch 340. A Raman spectroscopy system 100 may include a 1×N optical switch 340 that switches a beam of light to one of N output ports, where N is an integer greater than or equal to 2. The optical switch may include a thermo-optic switch, liquid crystal switch, electro-optic switch, mechanical optical switch, MEMS switch, or any other suitable type of optical switch. A Raman spectroscopy system 100 may use an optical switch 340 to couple light to a needle with optical fiber 400 that includes multiple input or output optical fibers. For example, a Raman spectroscopy system 100 may include a 1×N optical switch 340 to couple a pump-Stokes beam 140 to a needle with optical fiber 400 that includes N optical fibers 116. The optical switch 340 may switch between the N output ports one at a time in sequence so that the pump-Stokes beam 140 is directed successively to each of the N optical fibers 116. As the pump-Stokes beam 140 is directed to each of the N optical fibers 116, the Raman spectroscopy system 100 may perform a measurement of an associated Raman signal 160 produced by the pump-Stokes beam.

The optical switch 340 in FIG. 86 is a 1×2 optical switch that directs a pump-Stokes beam of light 140 to one of two output ports. When the optical switch 340 is set to direct the pump-Stokes beam 140 to output port 1, the beam (designated as pump-Stokes beam 140-1) is directed to optical fiber 116*e*-1 and then coupled to optical fiber 116*a*-1 of the needle with optical fiber 400. The pump-Stokes beam 140-1 may produce an associated Raman signal 160 that is directed to the Raman spectroscopy system 100 for measurement via optical fiber 116*a*-1 (or via a separate input optical fiber, similar to that illustrated in FIG. 85). The optical switch 340 may then be switched to direct the pump-Stokes beam 140 to output port 2, in which case the beam (designated as pump-Stokes beam 140-2) is directed to optical fiber 116*e*-2 and then coupled to optical fiber 116*a*-2. The pump-Stokes beam 140-2 may produce an associated Raman signal 160 that is directed to the Raman spectroscopy system 100 for measurement via optical fiber 116*a*-2 (or via a separate input optical fiber). The optical switch 340 may be switched back and forth between output ports 1 and 2 to allow the Raman spectroscopy system to make a series of successive Raman-signal measurements using each of the optical fibers 116*a*-1 and 116*a*-2. For example, the needle with optical fiber 400 in FIG. 85 may be coupled to a Raman spectroscopy system 100 with a 1×2 optical switch 340, and the system may continually switch between the two output optical fibers to make measurements in the forward direction using optical fiber 116*a*-1 and in the angled direction using optical fiber 116*a*-2.

Figure 87:
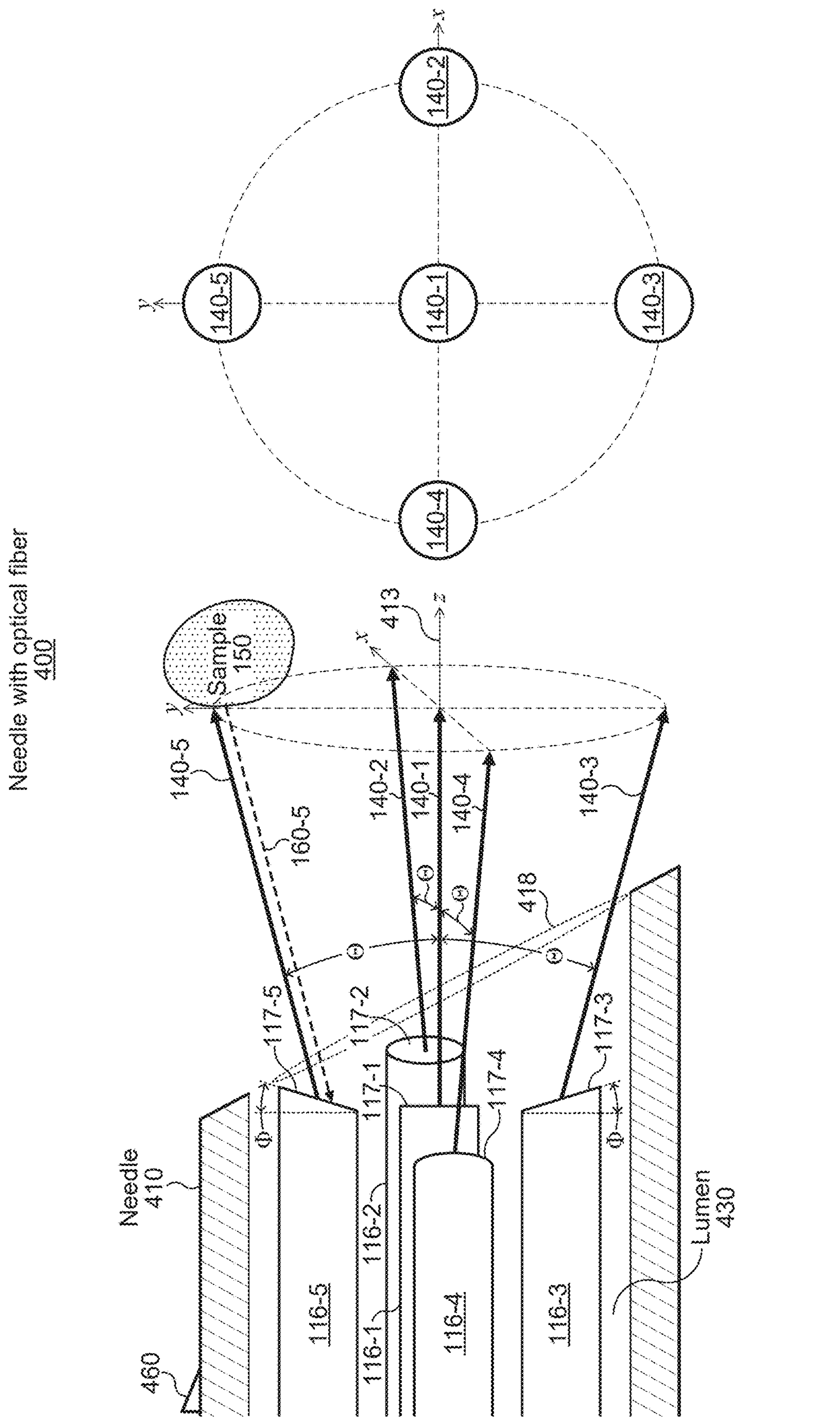
FIGS. 87-90 each illustrate an example needle with optical fiber that includes multiple optical fibers.
Figure 88:
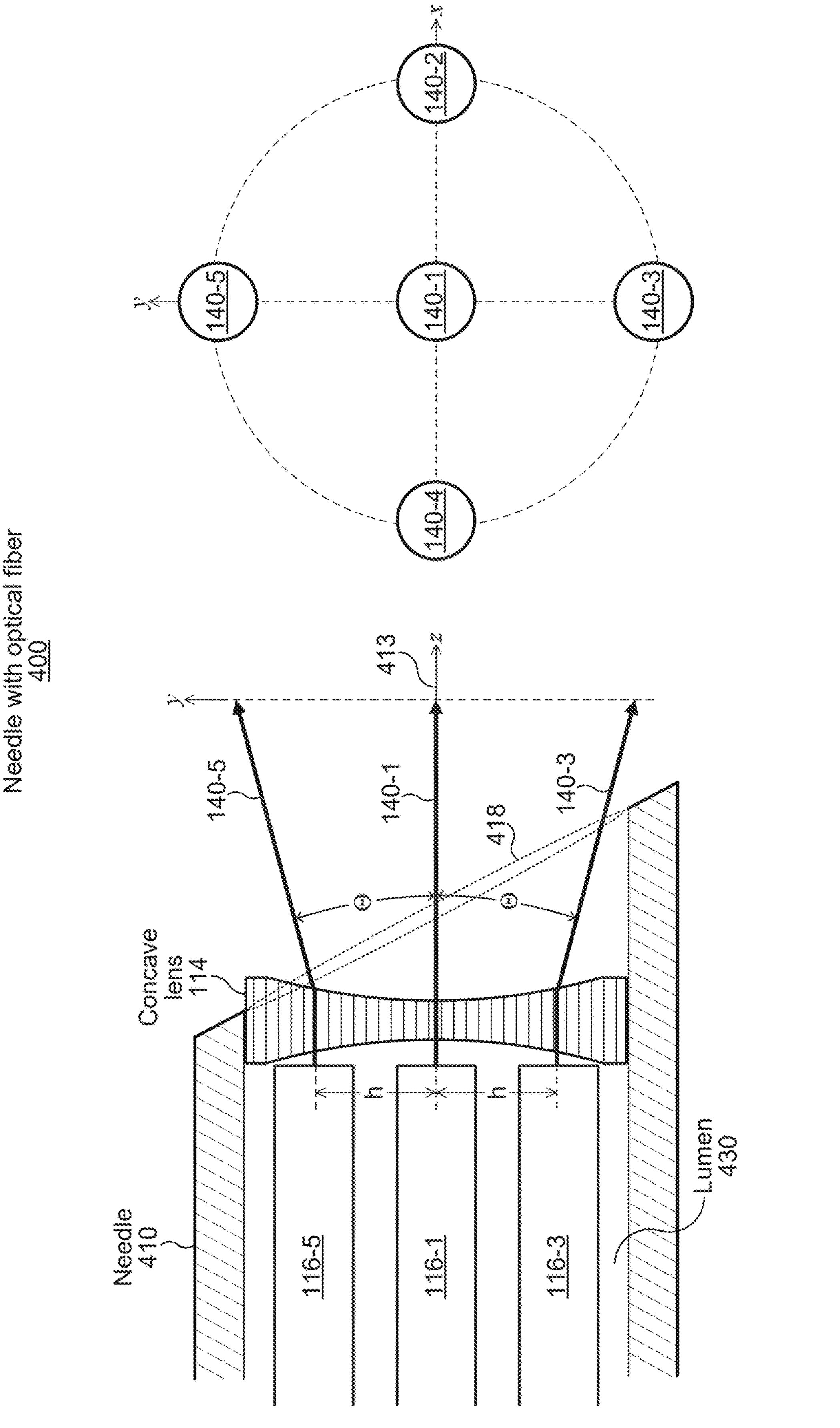
Figure 89:
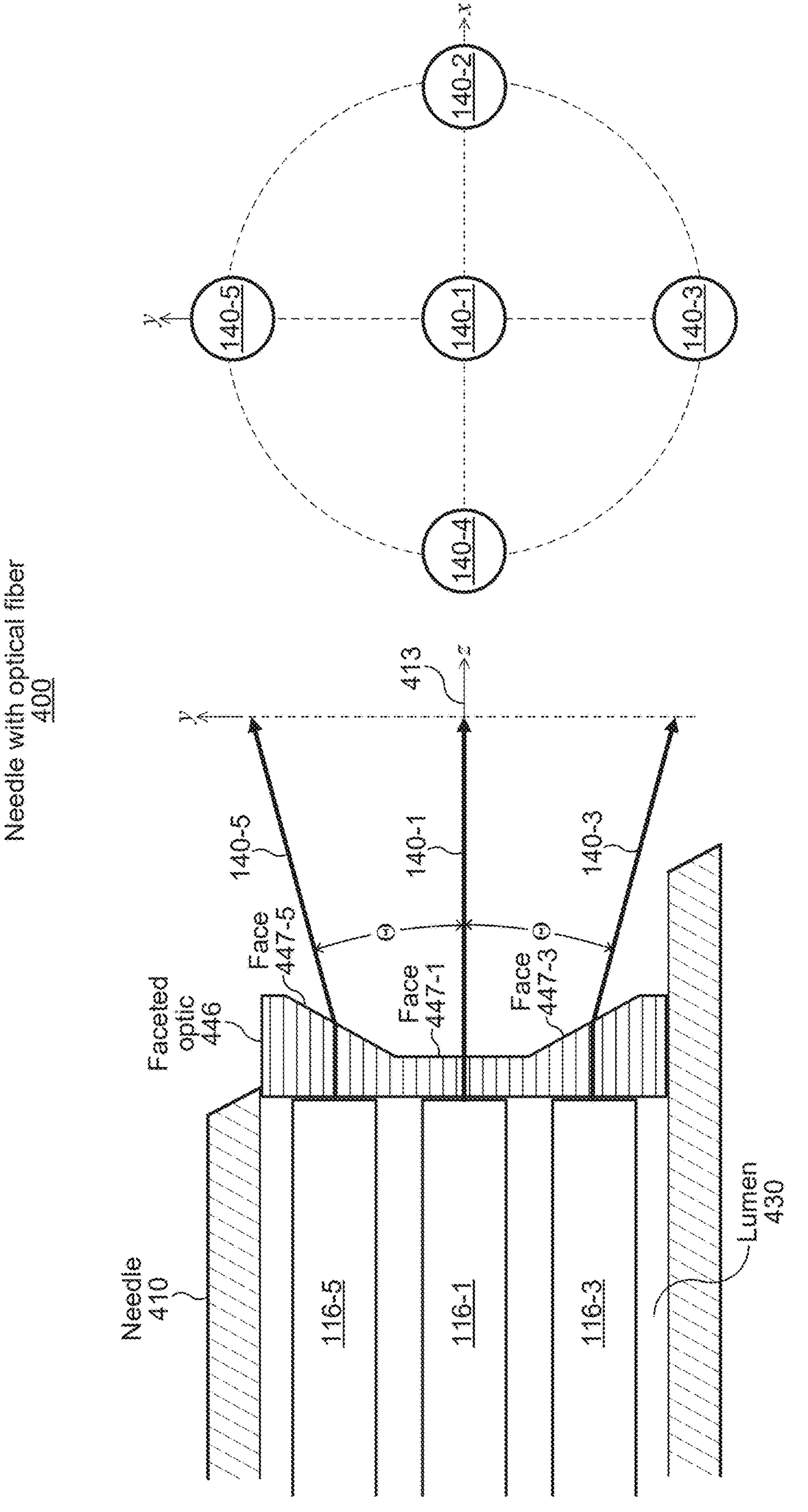
Figure 90:
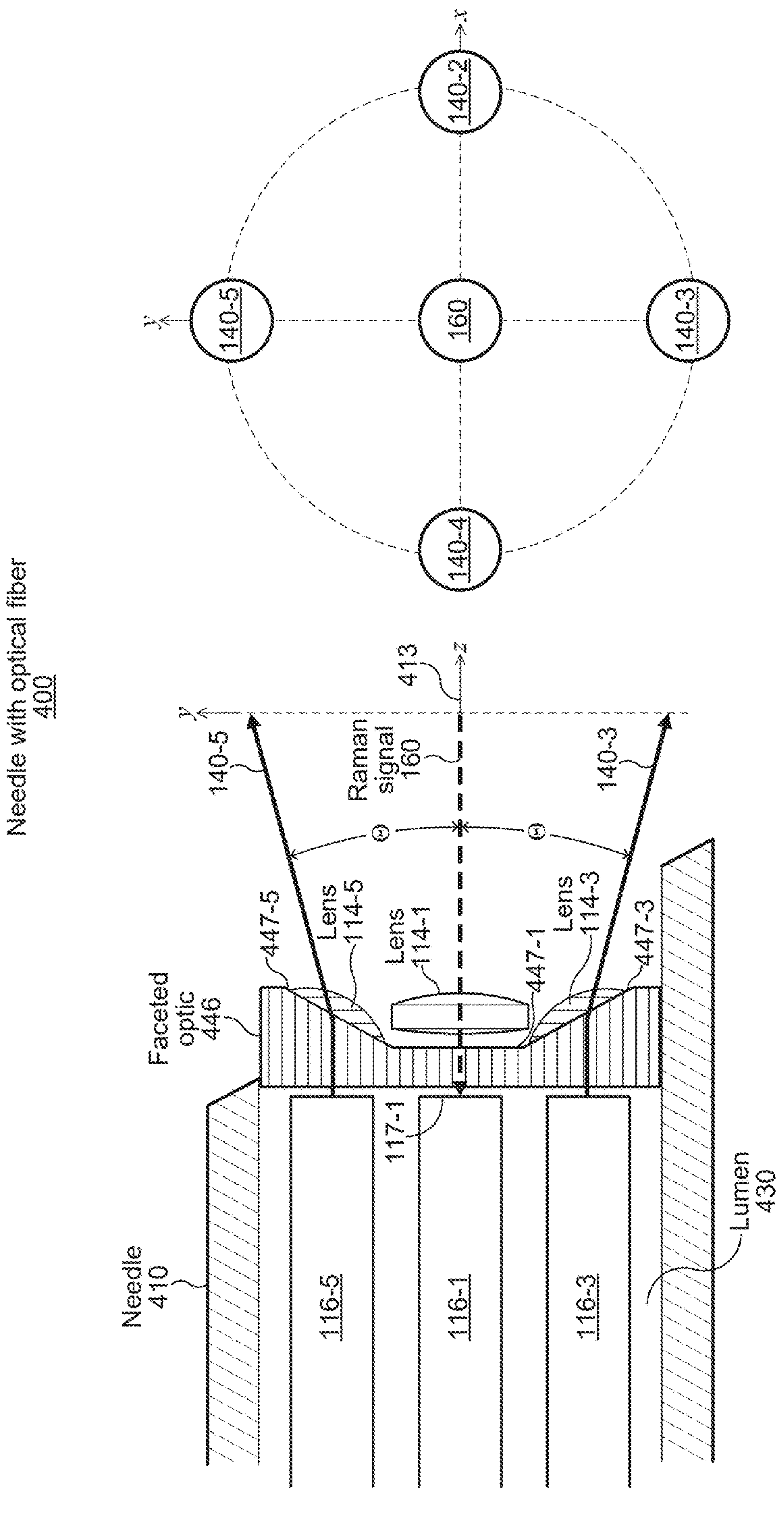

FIGS. 87-90 each illustrate an example needle with optical fiber 400 that includes multiple optical fibers 116. The end face 117 and at least a portion of each optical fiber 116 are located within the lumen 430 of the needle 410. A needle with optical fiber 400 that includes multiple optical fibers 116 may include 2, 5, 10, 20, or any other suitable number of optical fibers. Each of the needles with optical fiber 400 in FIGS. 87-90 includes five optical fibers 116. The left portion of FIG. 87 is a perspective view that shows each of the five optical fibers, while the left portion of FIGS. 88-90 is a cross-sectional side view that shows three of the five optical fibers (optical fibers 116-2 and 116-4 are not shown in FIGS. 88-90). The right portion of FIGS. 87-90 illustrates the pump-Stokes beams emitted from the optical fibers as viewed looking toward the needle (i.e., looking along the negative z direction). Pump-Stokes beams 140-2 through 140-5 are each directed along an angle with respect to the needle axis, and in FIGS. 87-89, pump-Stokes beam 140-1 is directed substantially parallel to the needle axis 413.

A needle with optical fiber 400 that includes multiple optical fibers 116 may include two or more optical fibers that each emit a pump-Stokes beam 140 that is directed at a nonzero angle with respect to the needle axis 413, and each of the pump-Stokes beams may be directed in a different propagation direction from the other pump-Stokes beams. For example, the needle with optical fiber 400 in each of FIGS. 87-89 includes five optical fibers, where four of the optical fibers (116-2, 116-3, 116-4, and 116-5) produce angled pump-Stokes beams, and one of the optical fibers (116-1) produces a non-angled pump-Stokes beam. Each of the five pump-Stokes beams 140-1 through 140-5 is directed along a different propagation direction. As another example, the needle with optical fiber 400 in FIG. 90 includes five optical fibers, where four of the optical fibers (116-2, 116-3, 116-4, and 116-5) produce angled pump-Stokes beams, and one of the optical fibers (116-1) does not produce a pump-Stokes beam (optical fiber 116-1 is configured to receive a Raman signal 160).

In each of FIGS. 87-90, the four optical fibers 116-2, 116-3, 116-4, and 116-5 emit four respective pump-Stokes beams 140-2, 140-3, 140-4, and 140-5 that are directed through the opening 418 of the needle 410 along a propagation direction that is at an angle Θ with respect to the needle axis 413, where the needle axis corresponds to the z-axis. Each of the four pump-Stokes beams 140-2, 140-3, 140-4, 140-5 is directed along a propagation direction that is different from the propagation directions of the other pump-Stokes beams. Optical fiber 116-2 emits a pump-Stokes beam 140-2 that is directed along the +x direction at an angle Θ with respect to the needle axis 413. Optical fiber 116-3 emits a pump-Stokes beam 140-3 that is directed along the −y direction at an angle Θ with respect to the needle axis 413. Optical fiber 116-4 emits a pump-Stokes beam 140-4 that is directed along the −x direction at an angle Θ with respect to the needle axis 413. Optical fiber 116-5 emits a pump-Stokes beam 140-5 that is directed along the +y direction at an angle Θ with respect to the needle axis 413. In FIGS. 87-89, in addition to the four angled pump-Stokes beams, optical fiber 116-1 emits a non-angled pump-Stokes beam 140-1 that is directed substantially parallel to the needle axis 413. The angle Θ along which a pump-Stokes beam 140 is directed may be any suitable nonzero angle, such as for example, an angle between 1 degree and 60 degrees. For example, each of the angled pump-Stokes beams in FIGS. 87-90 is directed through the needle opening 418 at an angle Θ of approximately 15 degrees with respect to the needle axis 413.

Each of the pump-Stokes beams emitted from a needle with optical fiber 400 that includes multiple optical fibers may be used to perform a Raman-signal measurement. For example, the needle with optical fiber 400 in each of FIGS. 87-89 may be coupled to a Raman spectroscopy system that includes a 1×5 optical switch 340. The Raman spectroscopy system 100 may produce a pump-Stokes beam 140, and the optical switch 340 may sequentially couple the pump-Stokes beam to each of the five optical fibers 116-1 through 116-5. The four optical fibers 116-2 through 116-5 may be used to perform Raman-signal measurements along each of the four angled-propagation directions, and the optical fiber 116-1 may be used to perform a Raman-signal measurement along the z-axis (which may be referred to as the forward direction). As another example, the needle with optical fiber 400 in FIG. 90 may be coupled to a Raman spectroscopy system that includes a 1×4 optical switch 340. The pump-Stokes beam 140 produced by the Raman spectroscopy system 100 may be coupled sequentially to each of the four optical fibers 116-2 through 116-5, and the four optical fibers may be used to perform Raman-signal measurements along each of the four angled-propagation directions.

An optical fiber 116 that emits a pump-Stokes beam 140 may also be configured to receive a Raman signal 160 produced by coherent Raman scattering of the pump-Stokes beam. For example, the needle with optical fiber 400 in each of FIGS. 87-89 may be coupled to a Raman spectroscopy system 100, and each of the five optical fibers 116-1 through 116-5 may be configured to (i) emit a pump-Stokes beam 140 and (ii) receive a Raman signal 160 produced by coherent Raman scattering of the pump-Stokes beam. In FIG. 87, the pump-Stokes beam 140-5 is emitted from the end face 117-5 of optical fiber 116-5 and propagates through the opening 418 at an angle Θ with respect to the needle axis 413. The pump-Stokes beam 140-5 produces a Raman signal 160-5 at the sample 150, and the optical fiber 116-5 receives at least a portion of the Raman signal. The received Raman signal 160-5 may be coupled into the optical fiber 116-5 and transmitted along the fiber in a direction opposite the pump-Stokes beam 140-5 and to a Raman spectroscopy system 100 for measurement.

A needle with optical fiber 400 that includes multiple optical fibers 116 may include multiple optical fibers with angled end faces 117. The needle with optical fiber 400 in FIG. 87 includes four optical fibers with angled end faces and one optical fiber with a non-angled end face. The end faces 117-2, 117-3, 117-4, 117-5 of the respective optical fibers 116-2, 116-3, 116-4, 116-5 are angled, and the end face 117-1 of optical fiber 116-1 is non-angled. The end faces 117-3 and 117-5 each have angles ϕ, where end face 117-3 may be referred to as being oriented at an angle ϕ along the +y direction, and end face 117-5 may be referred to as being oriented at an angle ϕ along the −y direction. The end faces 117-2 and 117-4 may also have angles ϕ, where end face 117-2 may be oriented at an angle ϕ along the −x direction, and end face 117-4 may be oriented at an angle ϕ along the +x direction. Each of the angled optical fibers emits a pump-Stokes beam at an angle Θ that corresponds to the angle ϕ of the end face of the optical fiber from which the beam is emitted. For example, the angles Θ and ϕ may be related by Snell's law of refraction according to the expression $n_1 \sin d = n_2 \sin(\Theta+\Phi)$, where $n_1$ is the refractive index of the optical fiber 116 and $n_2$ is the refractive index of the medium into which the pump-Stokes beam 140 is emitted.

A needle with optical fiber 400 that includes multiple optical fibers 116 may include one or more lenses 114. For example, a needle with optical fiber 400 may include a convex or concave lens that directs multiple pump-Stokes beams along different propagation directions. The needle with optical fiber 400 in FIG. 88 includes a concave lens 114 that directs the four pump-Stokes beams 140-2 through 140-5 along different propagation directions that are each at an angle Θ with respect to the needle axis 413. Each of the pump-Stokes beams 140-2 through 140-5 is offset from the center of the lens 114 by a distance h, and the angle Θ at which a beam is directed may be approximately equal to h/f, where f is the focal length of the lens. The pump-Stokes beam 140-1 emitted by the optical fiber 116-1 is directed approximately through the center of the lens 114 (so that h equals zero), and as a result, the beam is directed substantially parallel to the needle axis 413.

A needle with optical fiber 400 that includes multiple optical fibers 116 may include a faceted optic 446. The faceted optic 446 may include multiple angled faces 447, where each angled face directs a pump-Stokes beam 140 along a particular propagation direction. The needle with optical fiber 400 in each of FIGS. 89-90 includes a faceted optic 446 with multiple angled faces that direct the four pump-Stokes beams 140-2 through 140-5 along different propagation directions that are each at an angle Θ with respect to the needle axis 413. The pump-Stokes beam 140-3 emitted from optical fiber 116-3 propagates through the faceted optic 446 and is directed by angled face 447-3 along the −y direction at an angle Θ with respect to the needle axis 413. Similarly, face 447-5 is angled to direct the pump-Stokes beam 140-5 along the +y direction at an angle Θ with respect to the needle axis 413. In FIG. 89, face 447-1 is non-angled, and the pump-Stokes beam 140-1 is directed substantially parallel to the needle axis 413. The faceted optic 446 may also include two additional angled faces (not illustrated in FIGS. 89-90) configured to direct the pump-Stokes beams 140-2 and 140-4 along the +x and −x directions at an angle Θ with respect to the needle axis 413. A faceted optic 446 may be attached to the end face of one or more optical fibers using an optically clear adhesive. For example, the faceted optic 446 in FIG. 89 may be attached to the end faces of the optical fibers 116-1, 116-3, and 116-5.

In some embodiments, a faceted optic 446 may include multiple angled faces 447, where each angled face includes a lens 114. A lens may be attached to the face 447 of a faceted optic 446, or a lens may be formed by shaping the face 447 to produce a lens. Each lens 114 may receive a pump-Stokes beam 140 emitted from an optical fiber 116 and may collimate or focus the pump-Stokes beam. In FIG. 90, the pump-Stokes beam 140-3 emitted from optical fiber 116-3 is directed by the angled face 447-3 at an angle Θ with respect to the needle axis 413. Additionally, the angled face 447-3 includes a lens 114-3 which may collimate or focus the pump-Stokes beam 140-3. Similarly, the angled face 447-5 includes a lens 114-5 which may produce a collimated or focused pump-Stokes beam 140-5. The faceted optic 446 in FIG. 90 may also include two additional faces (not illustrated in FIG. 90) that each include a lens that collimates or focuses the pump-Stokes beams 140-2 and 140-4.

A needle with optical fiber 400 that includes multiple optical fibers 116 may include (i) two or more output optical fibers that each emit a pump-Stokes beam 140 that is directed at a nonzero angle with respect to the needle axis 413 and (ii) one or more input optical fibers configured to receive a Raman signal 160 produced by a pump-Stokes beam. For example, the needle with optical fiber 400 in FIG. 90 may include four output optical fibers that produce the pump-Stokes beams 140-2 through 140-5 and one input optical fiber 116-1. The input optical fiber 116-1 may receive a Raman signal 160 produced by a pump-Stokes beam, and the input optical fiber may transmit the received Raman signal along the fiber and to a Raman spectroscopy system for measurement. The needle with optical fiber 400 in FIG. 90 includes a lens 114-1 that may focus the received Raman signal 160 to couple the Raman signal into the optical fiber 116-1 via the input-fiber end face 117-1. The lens 114-1 may be a separate optical element or may be attached to or integrated into the face 447-1 of the faceted optic 446.

Figure 91:
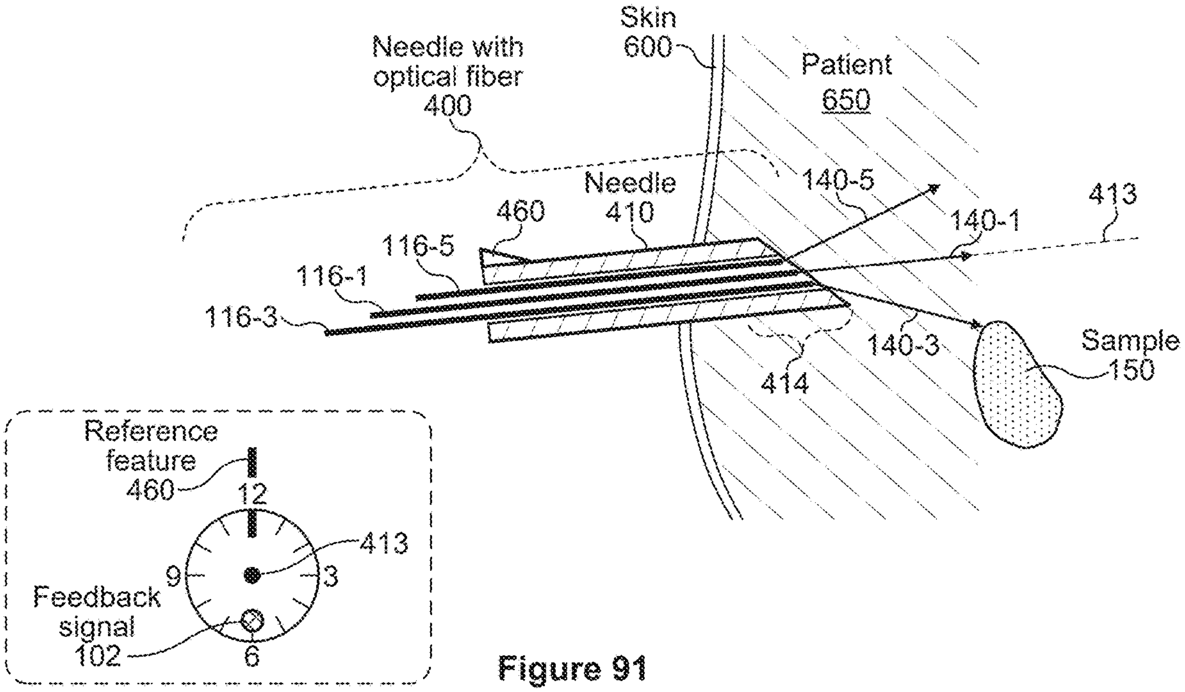
FIGS. 91-92 illustrate an example needle with optical fiber that is being directed to a sample.
Figure 92:
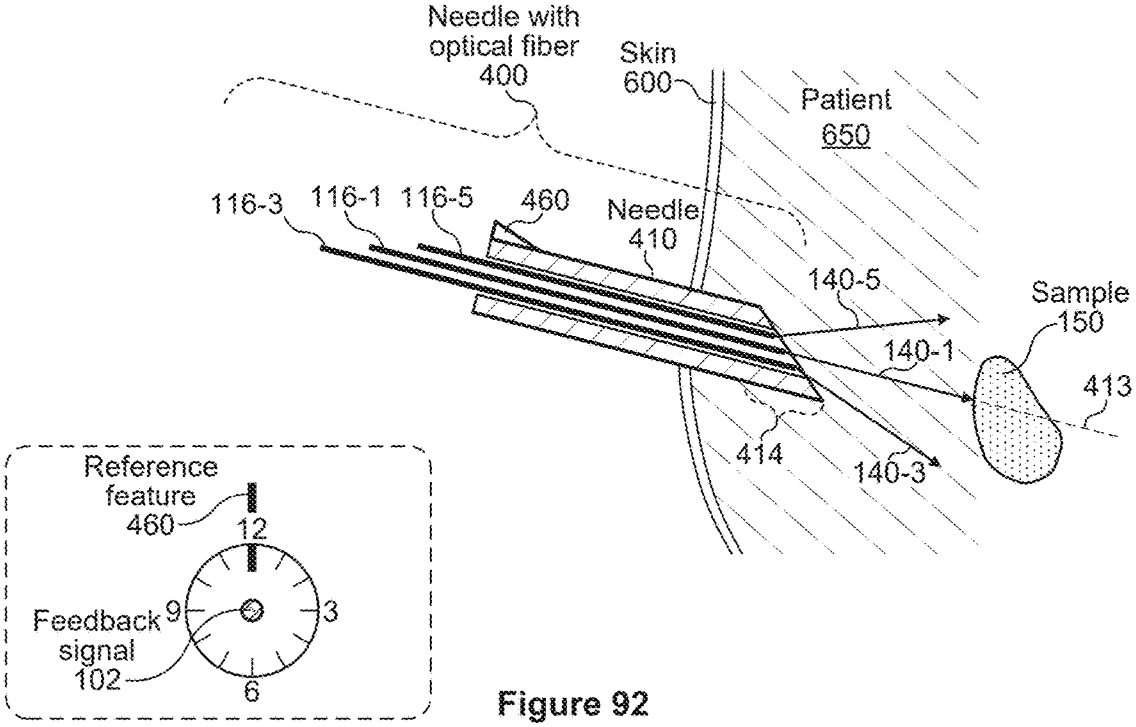

FIGS. 91-92 illustrate an example needle with optical fiber 400 that is being directed to a sample 150. The needle with optical fiber 400 in FIGS. 91-92 may be similar to any of the needles with optical fiber 400 illustrated in FIGS. 87-90. The needle with optical fiber 400 in FIGS. 91-92 includes multiple optical fibers 116 that produce pump-Stokes beams directed at a nonzero angle with respect to the needle axis 413. Optical fibers 116-3 and 116-5 produce the respective pump-Stokes beams 140-3 and 140-5 which are each directed at an angle with respect to the needle axis 413. Additionally, optical fiber 116-1 produces a pump-Stokes beam 140-1 that is directed substantially parallel to the needle axis 413. The needle with optical fiber 400 in FIGS. 91-92 may include two additional optical fibers (e.g., similar to optical fibers 116-2 and 116-4 in FIG. 87) that produce additional pump-Stokes beams directed at an angle with respect to the needle axis 413.

A needle with optical fiber 400 that includes multiple optical fibers 116 may additionally include a reference feature 460, and the reference feature may correspond to the propagation direction of one of the emitted pump-Stokes beams. The needle with optical fiber 400 in FIGS. 91-92 includes a reference feature 460 that corresponds to the propagation direction of pump-Stokes beam 140-5. The reference feature 460 may be used by an operator during insertion of the needle with optical fiber 400 into a patient's body to direct the needle 410 to a sample 150. For example, a feedback signal 102 provided to the operator may indicate an angle or direction with respect to the reference feature 460 in which the needle 410 should be pointed to direct the needle to the sample 150. The reference feature 460 in FIGS. 91-92, which is similar to the reference feature 460 in FIG. 87, is positioned on a part of the needle 410 that remains external to the patient's body and points in the propagation direction of pump-Stokes beam 140-5.

The needle with optical fiber 400 in FIGS. 91-92 may be coupled to a Raman spectroscopy system 100, and the Raman spectroscopy system may provide a feedback signal 102 to assist in directing the needle 410 to a sample 150. In FIGS. 91-92, the needle tip 414 of the needle with optical fiber 400 has been inserted into the body of a patient 650 by piercing through the patient's skin 600. As the needle with optical fiber 400 is inserted into the patient's body and directed to the sample 150, the Raman spectroscopy system 100 may make Raman-signal measurements along each of the different propagation directions of the pump-Stokes beams 140. Based on the Raman-signal measurements, the Raman spectroscopy system 100 may provide a feedback signal 102 to assist in directing the needle to the sample 150. The feedback signal 102 may (i) represent a portion of a Raman signal that is associated with the sample 150 or (ii) indicate an angle or a direction in which the needle 410 should be pointed to direct the needle to the sample 150. For example, a feedback signal 102 may indicate the angle or direction to point the needle 410 with respect to the reference feature 460. Herein, directing a needle 410 to a sample 150 may include or may refer to directing a needle toward a sample or directing a needle into a sample.

The dashed-line inset in FIGS. 91-92 illustrates an example feedback signal 102 that may be produced by a Raman spectroscopy system 100 coupled to the needle with optical fiber 400. The feedback signal 102 indicates a direction in which the needle 410 should be pointed to direct the needle to the sample 150. For example, while the tip 414 of the needle with optical fiber 400 is being directed to the sample 150, the Raman spectroscopy system 100 may measure and compare the Raman signals obtained from each of the pump-Stokes beams to determine the direction in which the sample is located. In FIG. 91, the Raman spectroscopy system 100 may measure the Raman signal produced by each of the pump-Stokes beams 140-1, 140-3, 140-5 and determine the portion of each Raman signal that is associated with the sample 150. Since pump-Stokes beam 140-3 is directed to the sample 150, the portion of the Raman signal produced by pump-Stokes beam 140-3 that is associated with the sample 150 may be relatively large compared to the Raman signals produced by pump-Stokes beams 140-1 and 140-5 (which are not directed to the sample). These Raman-signal measurements may then be used to determine that the sample 150 is located along the direction of pump-Stokes beam 140-3.

In FIGS. 91-92, the feedback signal 102 is presented on a clock-face background that represents different directions with respect to the needle axis 413, where the needle axis 413 corresponds to the center of the clock face. The reference feature 460, which corresponds to the propagation direction of pump-Stokes beam 140-5, is located in the 12 o'clock position, and the propagation direction of the pump-Stokes beam 140-3 corresponds to the 6 o'clock position. The needle with optical fiber 400 may produce additional pump-Stokes beams (not illustrated in FIGS. 91-92) with propagation directions that correspond, for example, to the 3 o'clock and 9 o'clock positions. In FIG. 91, the feedback signal 102 is located near the 6 o'clock position, which indicates that the sample 150 is located along a direction that corresponds approximately to the direction of pump-Stokes beam 140-3. In FIG. 92, the needle 410 has been turned in the 6 o'clock direction so that the needle points at the sample 150, and the feedback signal 102 is now located in the center of the clock face, which indicates that the needle is aimed at the sample. An operator may observe the feedback signal 102 in FIG. 91 and then steer the needle 410 in the direction indicated so that the needle is aimed at the sample, as illustrated in FIG. 92. Once the needle 410 is pointed toward the sample 150, the needle may be inserted further until the needle tip 414 is located at or in the sample.

A technical advantage of a needle with optical fiber 400 is the ability to guide a needle to a desired location in a patient's body with relative ease and with minimal discomfort to the patient, as compared to conventional techniques. A conventional technique for directing a needle to a sample 150 may include an operator using medical imaging guidance (e.g., ultrasound or fluoroscopy) or an operator using tactile feedback or visual inspection to guide the needle to the desired location (e.g., a vein or a part of the spine). These techniques may be difficult, expensive, or time-consuming and may cause discomfort to the patient. By using a needle with optical fiber 400 as described herein, the needle 410 may be guided to a sample 150 within a patient's body relatively quickly and with minimal discomfort to the patient. For example, the needle with optical fiber 400 may be coupled to a Raman spectroscopy system 100 that provides a feedback signal 102 to help an operator guide the needle 410 to a desired location with relative ease.

An additional technical advantage of a needle with optical fiber 400 is the ability perform a Raman measurement of a sample 150 in situ without having to remove a part of the sample from the patient's body. A conventional technique for performing a measurement or characterization of a sample 150 is to remove part of the sample from a patient's body and perform the measurement or characterization outside the patient's body. For example, a biopsy of an organ (e.g., liver, kidney, or prostate) may be performed by removing a sample of tissue from the organ, but this procedure may be difficult, expensive, or time-consuming. As another example, meningitis or other conditions may be diagnosed by performing a lumbar puncture to remove a sample of cerebrospinal fluid from a patient's spine, but this procedure can cause discomfort to the patient and may require some time for the patient to recover and restore the removed cerebrospinal fluid. Using a needle with optical fiber 400 as described herein may allow a sample 150 to be measured in situ and may eliminate the need to remove a part of the sample from the patient's body. For example, the needle with optical fiber 400 may be coupled to a Raman spectroscopy system 100, and once the needle with optical fiber 400 has been directed to a sample 150 within a patient's body, the Raman spectroscopy system may perform a Raman-signal measurement of the sample without having to remove any of the sample from the patient's body. Performing a Raman-signal measurement in situ using a needle with optical fiber 400 may be easier, less expensive, or relatively quick, as compared to a conventional technique, and the patient may experience less pain or discomfort during or after the procedure.

Figure 93:
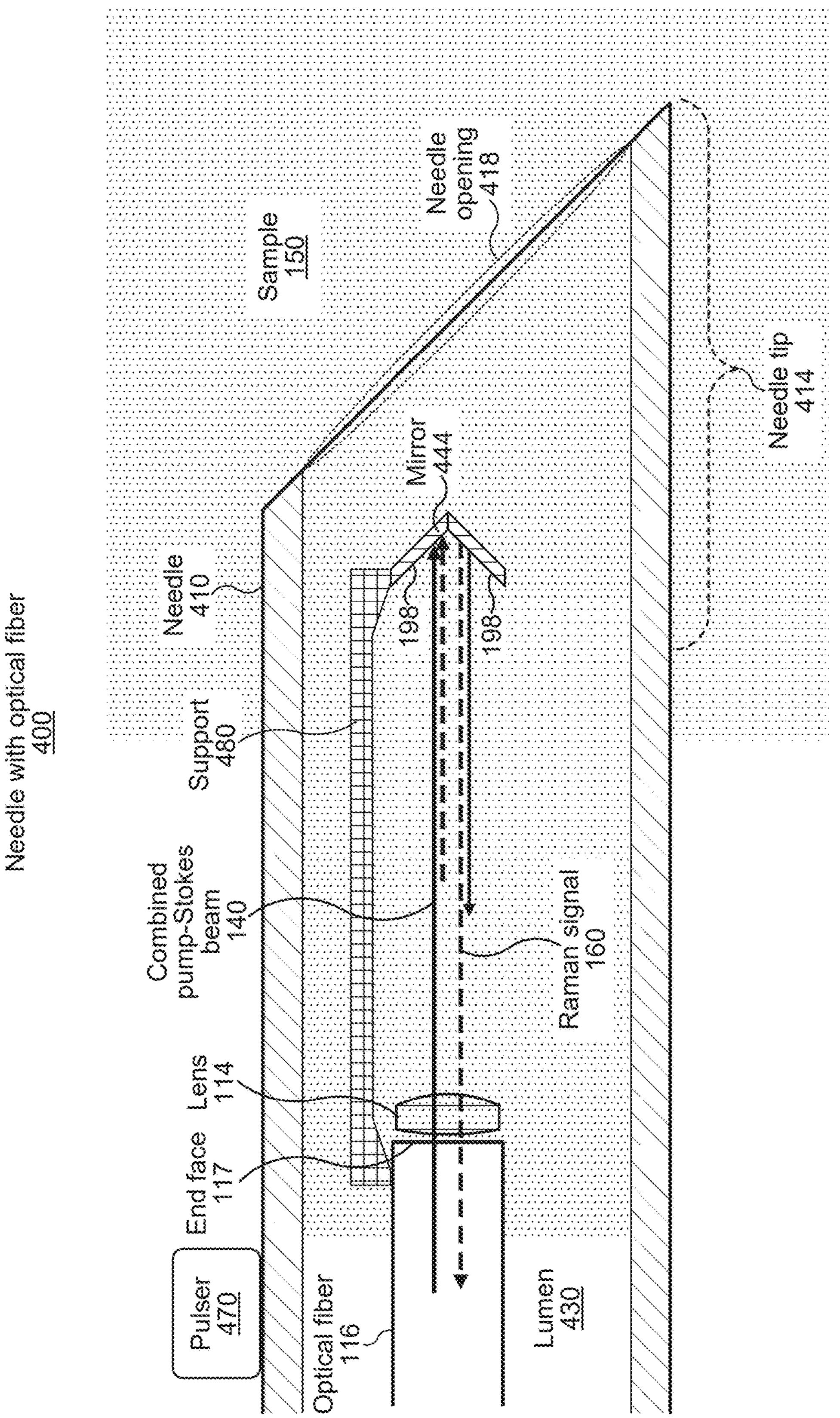
FIGS. 93-95 each illustrate an example needle with optical fiber in which a measurement is performed on a sample located in the lumen of the needle.
Figure 94:
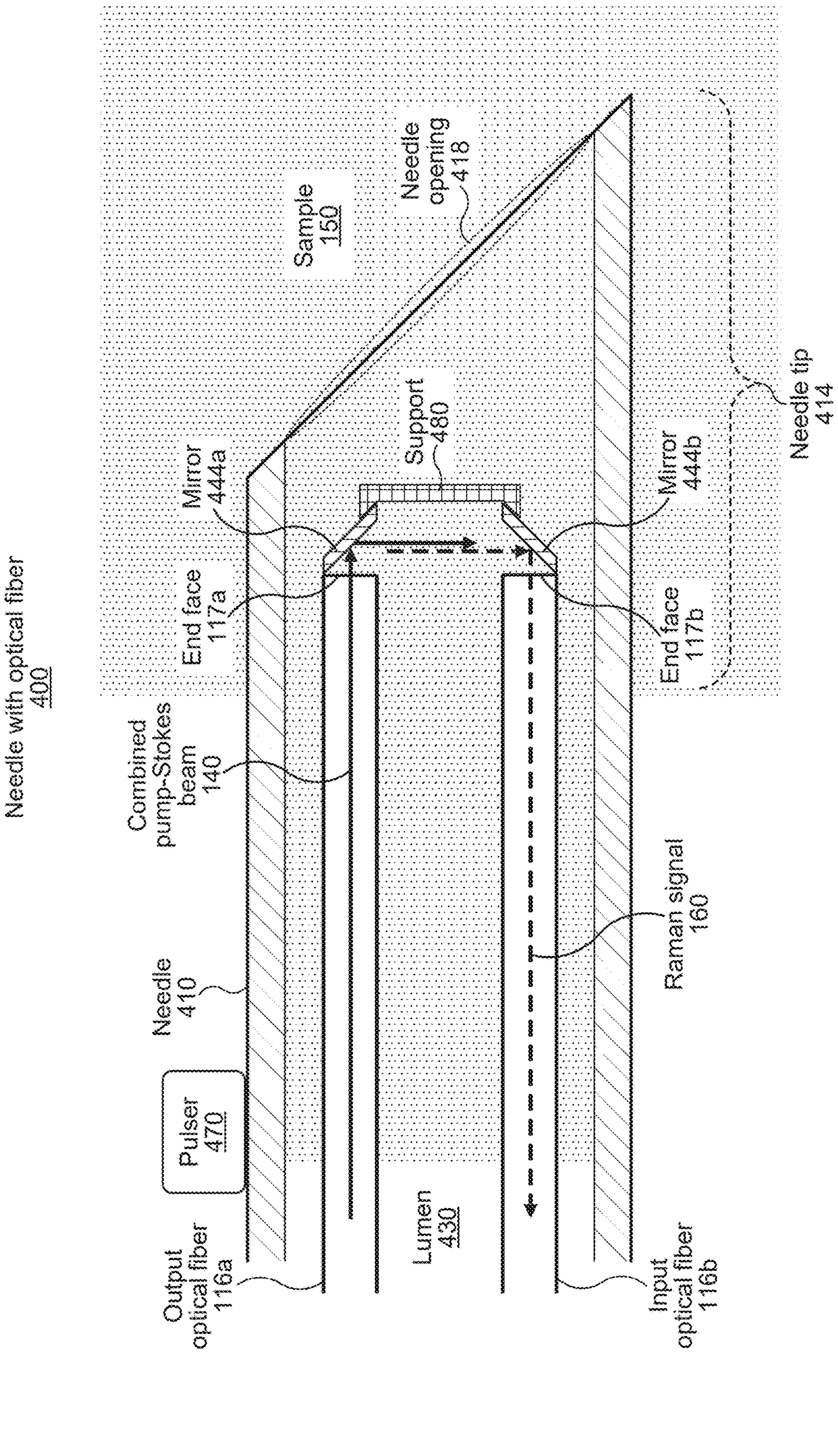
Figure 95:
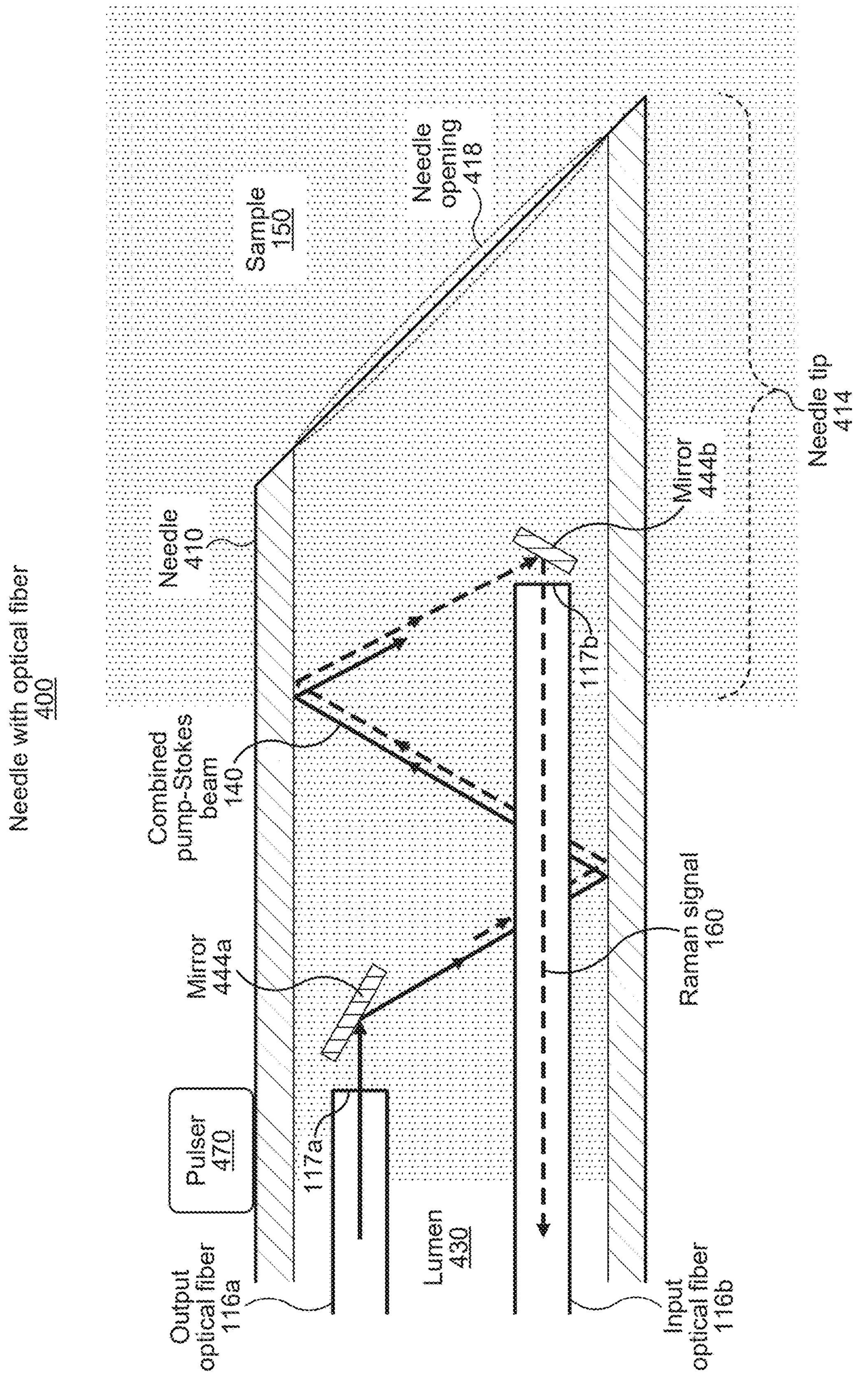

FIGS. 93-95 each illustrate an example needle with optical fiber 400 in which a measurement is performed on a sample 150 located in the lumen 430 of the needle 410. The sample 150 in each of FIGS. 93-95 may include a fluid that flows through the needle opening 418 and into at least part of the lumen 430. A portion of the needle 410 including the needle tip 414 may be inserted into a patient's body and directed to a sample 150 that includes a fluid. For example, the needle tip 414 may be inserted into a blood vessel and the sample 150 may include blood located in the blood vessel. As another example, the sample 150 may include urine, interstitial fluid, cerebrospinal fluid, synovial fluid, or any other suitable fluid. Each of the needles with optical fiber 400 in FIGS. 93-95 may be coupled to a Raman spectroscopy system 100 that supplies a pump-Stokes beam 140 and that receives and measures a Raman signal 160 produced by the pump-Stokes beam. Additionally, the Raman spectroscopy system 100 may produce a feedback signal 102 to assist in directing the needle 410 to a sample 150.

In each of FIGS. 93-95, at least the tip 414 of the needle 410 is inserted into a sample 150, and the sample flows through the opening 418 and into the lumen 430. The pump-Stokes beam 140 produces a Raman signal 160 while propagating through the sample 150. The pump-Stokes beam 140 and the Raman signal 160 may propagate together in approximately the same direction and along approximately the same optical axis. In FIGS. 93-95, the pump-Stokes beam 140 and the associated Raman signal 160 are illustrated as being offset laterally for clarity to allow each beam to be visualized.

The needle with optical fiber 400 in FIG. 93 includes a single optical fiber 116, where the end face 117 and at least a portion of the optical fiber are located within the lumen 430. The pump-Stokes beam 140 propagates along the optical fiber 116 toward the needle tip 414 and is emitted from the end face 117 and directed to a sample 150 located in the needle lumen 430. The pump-Stokes beam 140 may produce a Raman signal 160 by coherent Raman scattering of the pump and Stokes beams while propagating through the sample 150. The optical fiber 116 receives at least a portion of the Raman signal 160 via the end face 117 and transmits the received Raman signal along the optical fiber in a direction opposite the pump-Stokes beam 140. For example, the received Raman signal 160 may be directed via the optical fiber 116 to a Raman spectroscopy system 100 for measurement.

In each of FIGS. 94-95, the needle with optical fiber 400 includes two optical fibers: an output optical fiber **116*a* and an input optical fiber 116*b*. The end faces 117*a* and 117*b* and at least a portion of the optical fibers 116*a* and 116*b* are located within the lumen 430. The pump-Stokes beam 140 propagates along the output optical fiber 116*a* toward the needle tip 414 and is emitted from the output-fiber end face 117*a* and directed to a sample 150 located in the needle lumen 430. The pump-Stokes beam 140 may produce a Raman signal 160 by coherent Raman scattering of the pump and Stokes beams while propagating through the sample 150. The input optical fiber 116*b* receives at least a portion of the Raman signal 160** via the input-fiber end face 117*b* and transmits the received Raman signal along the optical fiber in a direction away from the needle tip 414. For example, the received Raman signal 160 may be directed via the input optical fiber 116*b* to a Raman spectroscopy system 100 for measurement.

A needle with optical fiber 400 may include one or more mirrors 444 configured to reflect at least a Raman signal 160. The mirrors may be located within the needle lumen 430 or located at or just outside the needle opening 418. The needles with optical fiber 400 in each of FIGS. 93-95 include one or more mirrors 444 located within the needle lumen 430 and configured to reflect a Raman signal 160 or a pump-Stokes beam 140. The needle with optical fiber 400 in FIG. 93 includes a mirror 444 that reflects the Raman signal 160 to direct the Raman signal to the end face 117 of the optical fiber 116. The mirror 444 may also reflect the pump-Stokes beam 140 so that the pump-Stokes beam interacts further with the sample 150 to increase the amount of Raman signal 160 that is produced.

A mirror 444 that is part of a needle with optical fiber 400 may have 1, 2, 3, or any other suitable number of reflective surfaces 198. The mirror 444 in FIG. 93 includes two reflective surfaces 198 oriented orthogonally and configured to reflect the incident Raman signal 160 to direct the Raman signal to the end face 117 of the optical fiber 116. Alternatively, the mirror 444 in FIG. 93 may be a retroreflector-type mirror having three reflective surfaces arranged orthogonally with respect to one another so that an incident Raman signal 160 is reflected and directed to the end face 117 of the optical fiber 116. A mirror 444 with three reflective surfaces 198 arranged orthogonally with respect to one another may be referred to as a retroreflector or a retroreflector mirror. In some embodiments, a mirror 444 may have a reflective surface that is curved. For example, a mirror with a curved reflective surface having a concave shape may be used in FIG. 93 instead of the mirror shown. The concave mirror may collimate or focus the reflected Raman signal 160 that is directed to the end face 117 of the optical fiber 116.

In each of FIGS. 94-95, the needle with optical fiber 400 includes two mirrors 444*a* and 444*b*. Mirror 444*a* reflects the pump-Stokes beam 140 emitted from the output-fiber end face 117*a* and directs the pump-Stokes beam to propagate through the sample 150. The mirror 444*a* may have a curved reflective surface that collimates or focuses the pump-Stokes beam 140 that is directed to propagate through the sample 150. The pump-Stokes beam 140 propagates through the sample 150 and interacts with the sample to produce a Raman signal 160 that may propagate in the same direction along with the pump-Stokes beam. In FIG. 95, the pump-Stokes beam 140 and the associated Raman signal are reflected from the interior surface of the needle as they propagate from mirror 444*a* to mirror 444*b*. In each of FIGS. 94-95, mirror 444*b* reflects the Raman signal 160 and directs the reflected Raman signal to the input-fiber end face 117*b*. The mirror 444*b* may have a curved reflective surface that focuses the Raman signal 160 to couple the Raman signal into the input optical fiber 116*b* via the end face 117*b*.

In some embodiments, a needle with optical fiber 400 that includes one or more mirrors that reflect a pump-Stokes beam 140 or a Raman signal 160 may include one or more prism mirrors (e.g., similar to the prism mirror 444-P in FIG. 70). For example, mirror 444*a* or 444*b* in FIGS. 94-95 may be a prism mirror.

In some embodiments, an optical fiber 116 may have an end face 117 that is angled, and a mirror may be produced by depositing a reflective optical coating onto the end face (e.g., similar to the optical fiber 116 and mirror 444 in FIG. 68). For example, instead of using two discrete mirrors 444*a* and 444*b* as illustrated in FIG. 94, the output-fiber end face 117*a* and the input-fiber end face 117*b* may be angled and a reflective optical coating may be deposited onto each end face. The pump-Stokes beam 140 may be reflected from the mirror on the angled end face 117*a* to direct the pump-Stokes beam to propagate through the sample 150, and the Raman signal 160 may be reflected from the mirror on the angled end face 117*b* to couple the Raman signal into the optical fiber 116*b*.

A mirror 444 may be attached to the interior surface of a needle 410 by an adhesive or one or more mechanical fasteners. For example, mirrors 444*a* and 444*b* in FIG. 95 may be attached to the interior surface of the needle 410 by an adhesive. Alternatively, a mirror 444 may be attached to a mirror support 480 (e.g., by an adhesive), and the mirror support may in turn be attached to (i) the interior surface of a needle 410 or (ii) an optical fiber 116. A mirror support 480 may refer to a mount for mechanically holding a mirror 444 and securing the mirror in place at some fixed location within a needle lumen 430.

In FIG. 93, one end of the mirror support 480 is attached to the mirror 444 and the other end of the mirror support is attached to the optical fiber 116 so that the mirror and the optical fiber are mechanically coupled together by the mirror support. The mirror support 480 may ensure that the mirror 444 and the end face 117 of the optical fiber 116 are located in a fixed position relative to one another so that the pump-Stokes beam 140 and the Raman signal 160 propagate between the mirror 444 and the end face 117 along a fixed optical path without experiencing misalignment. The mirror 444 and the optical fiber 116 in FIG. 93 may each be attached to the mirror support 480 by an adhesive. Additionally, the optical fiber 116 may be attached to the interior surface of the needle 410 by an adhesive, or the mirror support 480 may be attached to the interior surface of the needle 410 by an adhesive or one or more mechanical fasteners. In FIG. 94, each of the mirrors 444*a* and 444*b* are attached to a mirror support 480. Additionally, the mirror support 480 may be attached to the interior surface of the needle 410 or to the optical fibers 116*a* and 116*b*, or each of the mirrors 444*a* and 444*b* may be attached to the respective optical fibers 116*a* and 116*b*. The mirror support 480 in FIG. 94 may ensure that the mirrors 444*a* and 444*b* and the end faces 117*a* and 117*b* are located in a fixed position relative to one another.

A needle with optical fiber 400 may include one or more lenses 114 that (i) produce a collimated or focused pump-Stokes beam 140 or (ii) focus a Raman signal 160 into an optical fiber 116. The needle with optical fiber 400 in FIG. 93 includes a lens 114 that receives the pump-Stokes beam 140 emitted from the end face 117 of the optical fiber 116 and may collimate or focus the pump-Stokes beam that is directed to propagate through the sample 150. Additionally, the lens 114 in FIG. 93 may receive the Raman signal 160 and focus the Raman signal to couple the Raman signal into the optical fiber 116 via the end face 117. The lens in FIG. 93 may be attached to the end face 117 of the optical fiber 116, to the mirror support 480, or to the interior surface of the needle 410. In each of FIGS. 94-95, a lens (not illustrated in FIGS. 94-95) may be positioned (i) at or near the output-fiber end face 117*a* to collimate or focus the pump-Stokes beam 140 or (ii) at or near the input-fiber end face 117*b* to focus the Raman signal 160 into the input optical fiber 116*b*.

The needle with optical fiber 400 in each of FIGS. 93-95 includes a pulser 470. The pulser 470 may be mechanically coupled to the needle 410 using adhesive or one or more mechanical fasteners. A pulser 470 may be used to cause the needle 410 to vibrate and may include a piezoelectric transducer (PZT), a vibration motor (e.g., an eccentric rotating mass (ERM) motor or a linear resonant actuator (LRA)), an acoustic actuator (e.g., similar to an audio speaker), or any other suitable device configured to produce a vibration that is coupled to a needle 410. A pulser 470 attached to a needle 410 may impart a vibration to the needle to cause the sample 150 to be circulated in or around the needle tip 414. For example, the sample 150 may include a fluid, and the pulser 470 may produce a mechanical vibration that is coupled to the needle 410, causing the needle to move or vibrate. The motion or vibration of the needle 410 may cause fluid located within the lumen 430 to flow or circulate within the lumen. Additionally or alternatively, the motion or vibration of the needle 410 may cause a continuous circulation of fluid from outside the needle 410 into the lumen 430 and vice versa. A pulser 470 may allow for multiple portions of a fluid sample 150 to be measured by a Raman spectroscopy system 100 by causing the fluid to circulate and by preventing a small portion of the fluid from stagnating and remaining substantially still within the lumen 430. In FIG. 93, the pulser 470 may impart a mechanical vibration to the needle 410 that causes the sample to flow or circulate around or between the mirror 444 and the end face 117 of the optical fiber 116. In FIGS. 93-94, vibration from the pulser 470 may cause the sample 150 to flow or circulate around or between the mirrors **444*a* and 444*b*. Additionally, the pulser 470 in FIGS. 93-95 may cause the sample 150 to flow into the lumen 430 from outside the needle 410 and from the lumen to the region outside the needle. A pulser 470** may vibrate at any suitable frequency, such as for example, a frequency between approximately 10 Hz and 20 KHz.

The needle with optical fiber 400 in each of FIGS. 93-95 may include an anticoagulant substance. For example, the exterior surface of a portion of the optical fiber 116 in FIG. 93 may be coated with an anticoagulant substance, or the interior surface of the needle 410 may be coated with an anticoagulant substance. An anticoagulant applied to the optical fiber 116 or the needle 410 may allow blood or other fluids to flow or circulate within the needle lumen 430 without the fluid undergoing coagulation.

FIGS. 96-99 each illustrate an example catheter needle with optical fiber 500. A catheter needle with optical fiber 500 includes a needle 410, one or more optical fibers 116, and a catheter 510 and may be referred to as a needle apparatus, a catheter-needle-fiber apparatus, or a catheter-needle-with-optical-fiber apparatus. A catheter needle with optical fiber 500 may be similar to the catheter needle 530 in FIG. 56 with the addition of one or more optical fibers 116 located in the lumen 430 of the needle 410. A catheter needle with optical fiber 500 includes a needle 410 and one or more optical fibers 116, and the needle-and-optical-fiber portion of a catheter needle with optical fiber 500 may be similar to any of the needles with optical fiber 400 described herein. Additionally, any of the needles with optical fiber 400 described herein may be combined with a catheter 510 to produce a catheter needle with optical fiber 500. For example, the needle 410 in any of FIGS. 59-74 and 79-95 may be inserted into a catheter 510 to produce a catheter needle with optical fiber 500, and a pump-Stokes beam 140 may be emitted from an optical-fiber end face while the needle apparatus is being guided to a sample 150 in a patient's body. After the catheter needle with optical fiber 500 has been guided to the sample 150, the needle with optical fiber 400 may be withdrawn to leave the catheter 510 installed in the patient's body.

A catheter needle with optical waveguide may include a needle 410, an optical waveguide 450, and a catheter 510, and any of the needles with optical waveguide 400-W described herein may be combined with a catheter 510 to produce a catheter needle with optical waveguide. For example, the needle 410 in any of FIGS. 75-78 may be inserted into a catheter 510 to produce a catheter needle with optical waveguide, and a pump-Stokes beam 140 may be emitted from the optical waveguide 450 while the needle apparatus is being guided to a sample 150. A catheter needle with optical waveguide may be used in a manner similar to that of a catheter needle with optical fiber 500 as described herein. For example, after a catheter needle with optical waveguide has been guided to a sample 150 in a patient's body, the needle with optical waveguide 400-W may be withdrawn, which leaves the catheter 510 installed in the patient's body.

Figure 96:
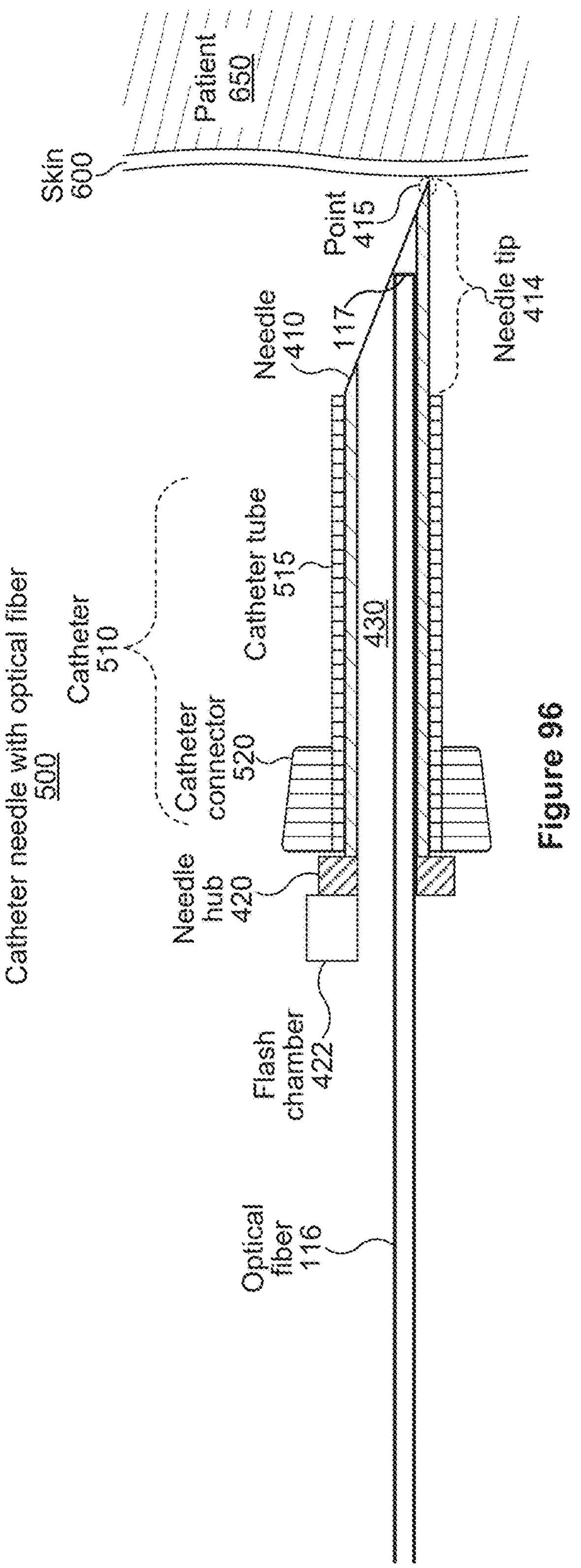
FIGS. 96-99 each illustrate an example catheter needle with optical fiber.
Figure 98:
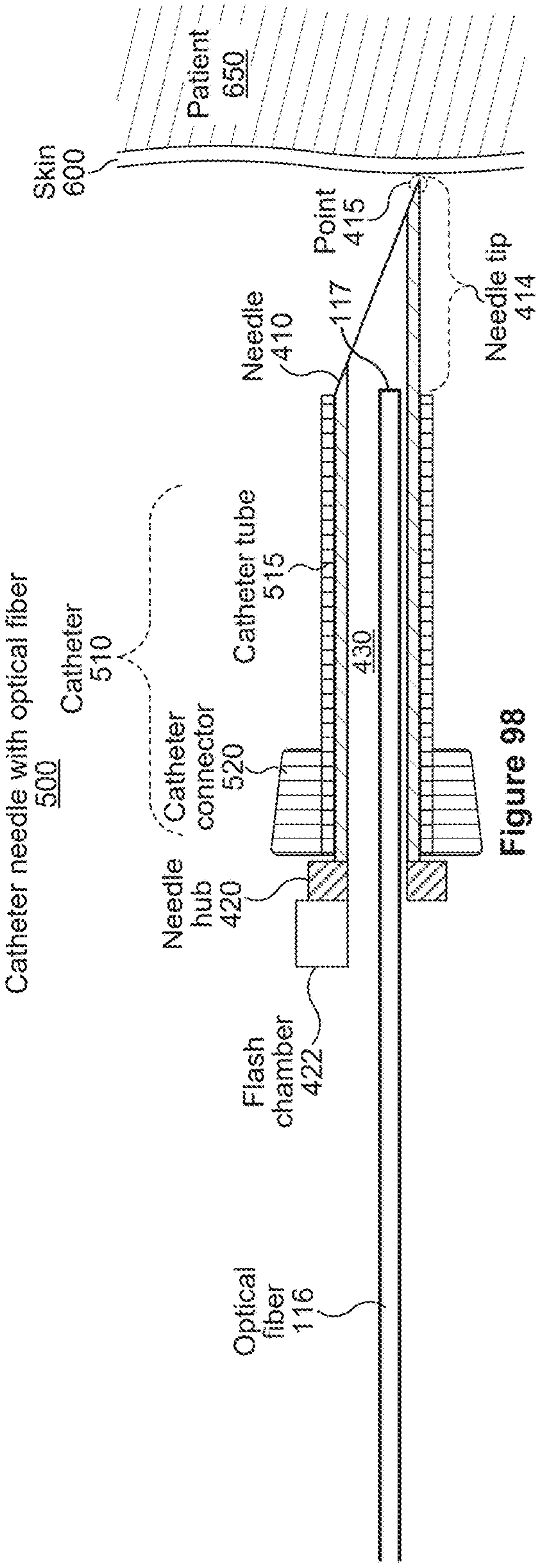

In each of FIGS. 96 and 98, the catheter needle with optical fiber 500 includes an optical fiber 116, where the end face 117 and at least a portion of the optical fiber are located within the lumen 430 of the needle 410. Additionally, the catheter needle with optical fiber 500 includes a catheter 510 that includes a catheter connector 520 and a catheter tube 515. The catheter 510 is combined with the needle 410 so that the catheter tube 515 surrounds at least a portion of the needle shaft 412. For example, the catheter tube 515, which may have a substantially cylindrical shape, may be sleeved onto the needle shaft 412 so that the catheter tube surrounds at least a portion of the needle shaft, with at least the point 415 of the needle 410 extending beyond the end of the catheter tube. The outer diameter $d_2$ of the needle shaft 412 may be approximately equal to the inner diameter of the catheter tube 515 so that when the needle 410 is inserted into the catheter 510, the outer surface of the needle shaft 412 and the inner surface of the catheter tube 515 may be in physical contact.

Figure 97:
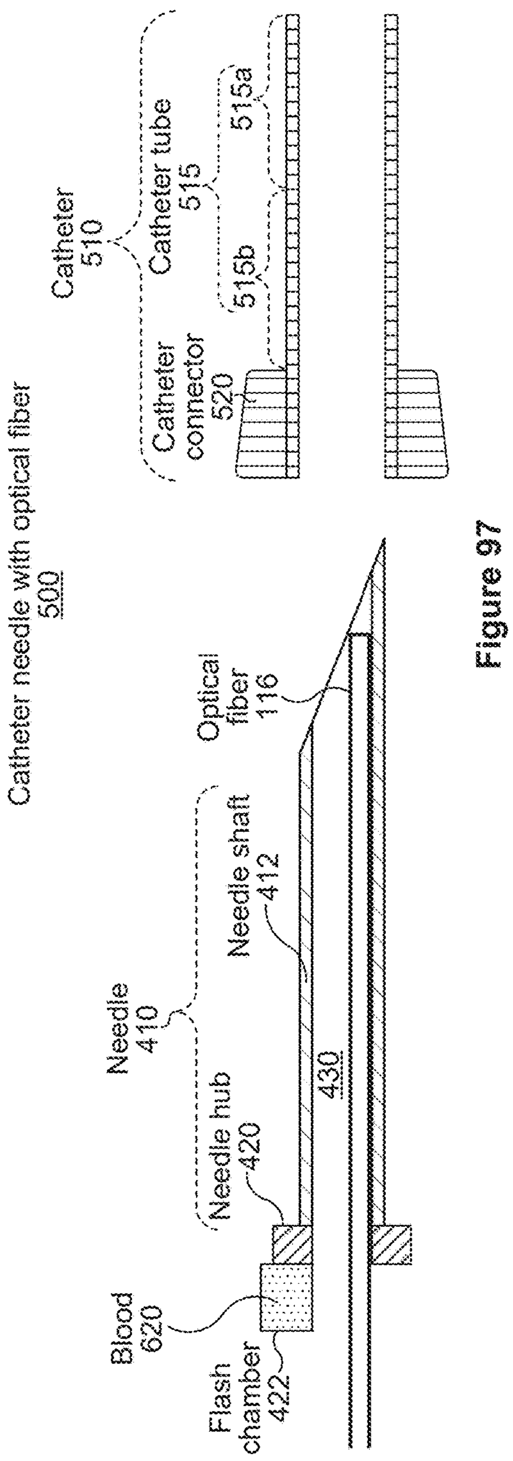
Figure 99:
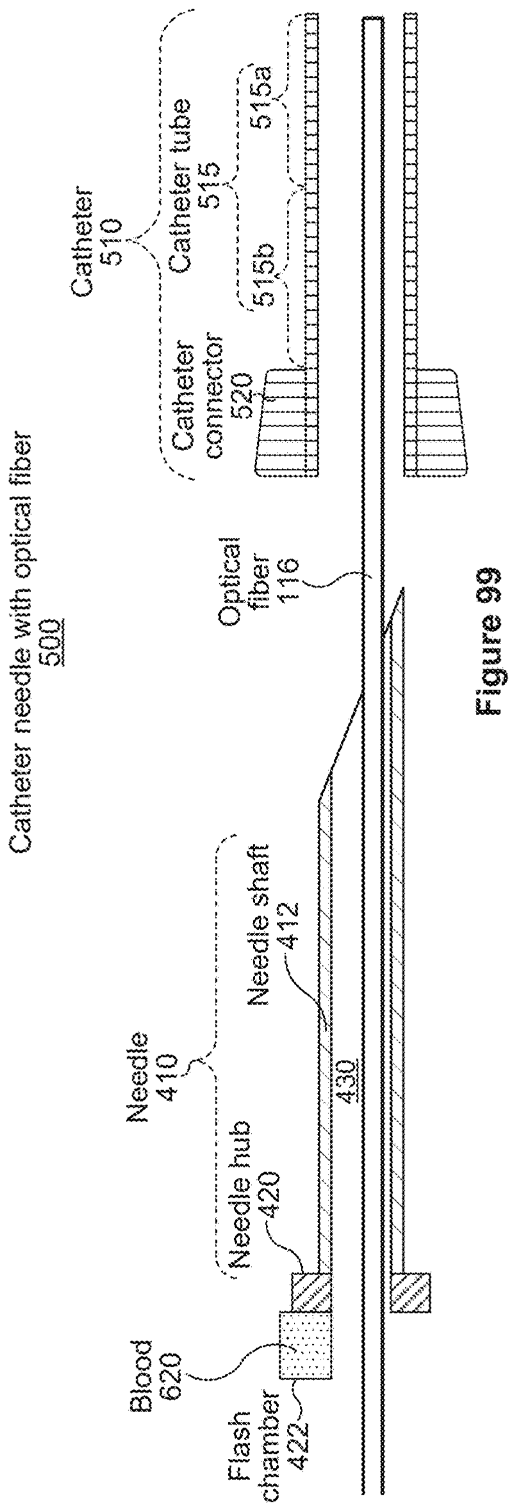

A catheter needle with optical fiber 500 may be used to install a catheter 510 into the body of a patient 650 by using the point 415 of the needle 410 to pierce through skin 600 (e.g., as illustrated in FIGS. 96 and 98) or to pierce into an organ or another part of the body. A catheter needle with optical fiber 500 may be at least partially inserted into a patient's body so that at least the tip 414 of the needle 410, the end face 117 of the optical fiber 116, and a portion of the catheter tube 515 are located within the patient's body. When a catheter needle with optical fiber 500 is inserted into a patient's body, the flash chamber 422, needle hub 420, catheter connector 520, and another portion of the catheter tube 515 may remain external to the patient's body. For example, the catheter-tube portion **515*a* in FIGS. 97 and 99 may be located inside the patient's body, and catheter-tube portion 515*b*, which is located closer to the catheter connector 520, may remain external to the patient's body. After a catheter needle with optical fiber 500 has been inserted into a patient's body and the end of the catheter tube 515 has reached the desired location, the needle 410 and optical fiber 116 may be removed (e.g., by grasping the needle hub 420 and withdrawing the needle and optical fiber from the catheter), which leaves a portion of the catheter tube 515 inserted into the patient's body. FIG. 97 illustrates the catheter needle with optical fiber 500 of FIG. 96 after the needle 410 and optical fiber 116 have been withdrawn from the catheter 510. Alternatively, once a catheter needle with optical fiber 500 has been inserted into a patient's body and the end of the catheter tube 515 has reached the desired location, the needle 410 may be removed, leaving the catheter 510 as well as the optical fiber 116 installed in place. The optical fiber 116 may be used to make ongoing Raman-signal measurements of a sample 150 in which the catheter 510 is installed. FIG. 99 illustrates the catheter needle with optical fiber 500 of FIG. 98 after the needle 410 has been withdrawn from the catheter 510. The optical fiber 116 in FIGS. 98-99 may not be attached to the needle 410 so that the needle may be removed while the optical fiber and catheter 510** remain in place.

Figure 100:
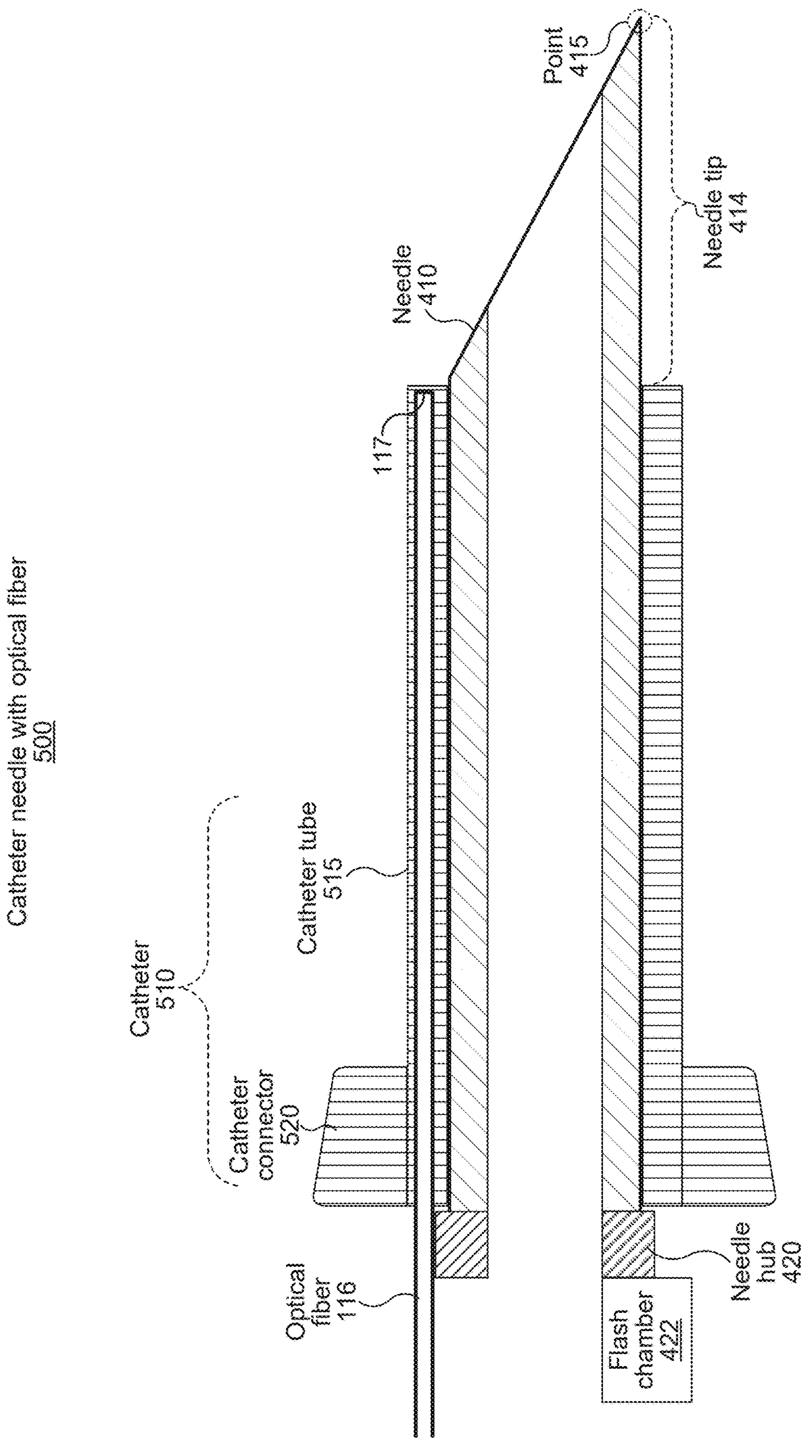
FIG. 100 illustrates an example catheter needle with optical fiber in which the optical fiber is located within the catheter tube.

FIG. 100 illustrates an example catheter needle with optical fiber 500 in which the optical fiber 116 is located within the catheter tube 515. Instead of an optical fiber 116 being located within the needle lumen 430 (e.g., as illustrated in FIGS. 96 and 98), a catheter needle with optical fiber 500 may include one or more optical fibers 116 that are located within the catheter tube 515. In FIG. 100, the optical fiber 500 is encased within the catheter tube 515 and extends along most of the length of the catheter tube. The end face 117 of the optical fiber 116 may be located at or near the end of the catheter tube 515 so that (i) a pump-Stokes beam 140 may be emitted from the end face and directed to a sample 150 or (ii) a Raman signal 160 may be coupled into the optical fiber. For example, the end face 117 may be located within 2 mm of the end of the catheter tube 515. After the catheter needle with optical fiber 500 in FIG. 100 has been inserted into a patient's body and the end of the catheter tube 515 has reached the desired location, the needle 410 may be removed, leaving the catheter 515 and the optical fiber 116 installed in place. The optical fiber 116 may be used to make ongoing Raman-signal measurements of a sample 150 in which the catheter 510 is installed.

The one or more optical fibers 116 of a catheter needle with optical fiber 500 may be coupled to a Raman spectroscopy system 100. For example, the catheter needle with optical fiber 500 in each of FIGS. 96-100 may be coupled to a Raman spectroscopy system 100 that supplies a pump-Stokes beam 140 and that receives and measures a Raman signal 160 produced by the pump-Stokes beam. In each of FIGS. 96, 98, and 100, a pump-Stokes beam 140 may be emitted from the end face 117 of the optical fiber 116 and an associated Raman signal 160 may be coupled into the optical fiber and directed to a Raman spectroscopy system 100 for measurement. Additionally, while the catheter needle with optical fiber 500 in FIGS. 96, 98, and 100 is being inserted into a patient's body, the Raman spectroscopy system 100 may measure one or more Raman signals 160 and may provide a feedback signal 102 to assist in directing the needle 410 to a sample 150. For example, the sample 150 may be blood 620 located in a blood vessel 610, and the feedback signal 102 may be used to direct the needle tip 414 to the blood vessel.

Figure 101:
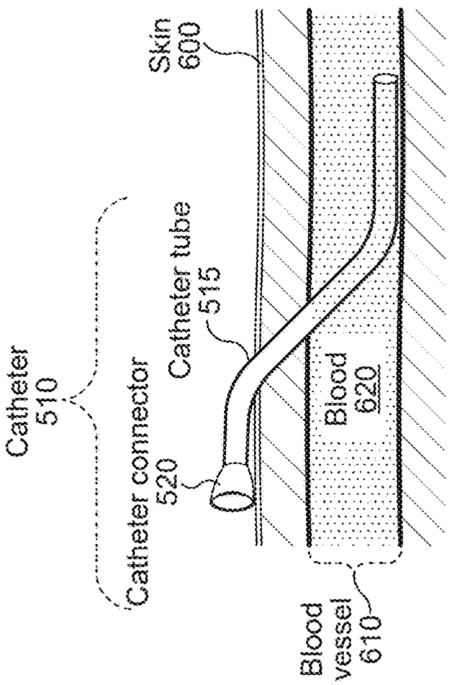
FIG. 101 illustrates an example catheter installed in a blood vessel.

FIG. 101 illustrates an example catheter 510 installed in a blood vessel 610. The catheter needle with optical fiber 500 in FIG. 96 may be used to install the catheter 510 into a blood vessel 610, as illustrated in FIG. 101. The catheter needle with optical fiber 500 in FIG. 96 may be inserted by using the point 415 to pierce through the skin 600. The optical fiber 116 in FIG. 96 may be coupled to a Raman spectroscopy system 100 that provides a feedback signal 102 to assist in directing the needle tip 414 to the blood vessel 610. For example, the Raman spectroscopy system 100 may determine a feedback signal 102 by measuring a Raman signal 160 and determining an amount of the Raman signal that is associated with blood 620. After the needle tip 414 and an end portion of the catheter tube 515 are inserted into the blood vessel 610 (which may be indicated by the appearance of blood 620 in the flash chamber 422), the needle 410 and optical fiber 116 may be removed. This leaves the catheter 510 installed in the blood vessel 610 with the end portion of the catheter tube 515 located within the blood vessel and the catheter connector 520 and another portion of the catheter tube 515 located outside the patient's body (e.g., as illustrated in FIG. 101). After the catheter 510 is installed in the blood vessel 610, the catheter connector 520 may be used to connect the catheter 510 to a syringe or catheter tubing via a mating connector. For example, the catheter connector 520 may be connected to catheter tubing to introduce a therapeutic, diagnostic, medication, or other fluid intravenously to a patient via the catheter tube 515 or to withdraw blood 620 or other fluid from the patient.

Figure 102:
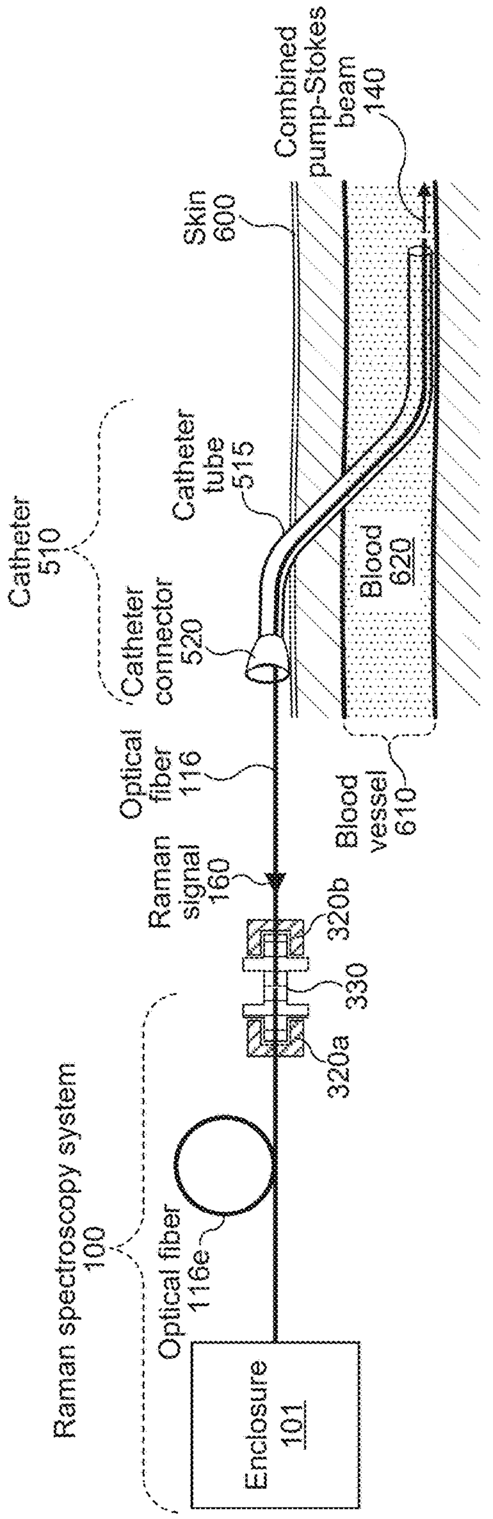
FIG. 102 illustrates an example catheter installed in a blood vessel with an optical fiber coupled to a Raman spectroscopy system.

FIG. 102 illustrates an example catheter 510 installed in a blood vessel 610 with an optical fiber 116 coupled to a Raman spectroscopy system 100. In addition to having the catheter 510 installed in the blood vessel 610, the optical fiber 116 also extends into the blood vessel. The optical fiber 116 is coupled to the Raman spectroscopy system 100 via the optical fiber 116*e*, and the Raman spectroscopy system produces a pump-Stokes beam 140 which is directed to the sample (blood 620) via the optical fiber 116. Additionally, a Raman signal 160 produced by the interaction of the pump-Stokes beam 140 with the blood 620 may be directed to the Raman spectroscopy system 100 via the optical fiber 116. The catheter needle with optical fiber 500 in FIG. 98 or 100 may be used to install the catheter 510 as illustrated in FIG. 102. The Raman spectroscopy system 100 may provide a feedback signal 102 to assist in directing the needle 410 to the blood vessel 610. After the needle tip 414 and an end portion of the catheter tube 515 are inserted into the blood vessel 610, the needle 410 may be withdrawn from within the catheter 510 and removed. This leaves the catheter 510 and the optical fiber 116 installed in the blood vessel 610 with the end portion of the catheter tube 515 and a portion of the optical fiber 116 located within the patient's body. The other portion of the optical fiber 116 extends outside the patient's body and is coupled to the Raman spectroscopy system 100. The optical fiber 116 may be used to make ongoing measurements of blood 620 in the blood vessel 610. For example, the Raman spectroscopy system 100 coupled to the optical fiber 116 may measure a Raman signal 160 to determine the concentration of oxygen, carbon dioxide, or bicarbonate in the blood 620, and the measurement may be used to provide operating parameters to a ventilator supplying air to the patient.

A technical advantage of a catheter needle with optical fiber 500 is the ability to install a catheter 510 into a desired location in a patient's body with relative ease and with minimal discomfort to the patient, as compared to conventional techniques. A conventional technique for installing a catheter into a patient's body may employ a catheter needle 530 (e.g., as illustrated in FIG. 56) which is directed to a desired location (e.g., a blood vessel or a part of the spine) by an operator. The operator may rely on medical imaging (e.g., ultrasound or fluoroscopy) to assist in guiding the needle, or the operator may use tactile feedback or visual inspection to guide the needle. However, these techniques may be difficult, expensive, or time-consuming and may cause discomfort to the patient. In FIG. 96, the catheter needle with optical fiber 500 may be coupled to a Raman spectroscopy system 100 that provides a feedback signal 102 to help an operator guide the needle 410 to the blood vessel 610 in FIG. 101. By providing a feedback signal 102 to the operator, the needle 410 may be guided to the blood vessel 610 and the catheter 510 may be installed relatively quickly and with minimal discomfort to the patient.

Figure 103:
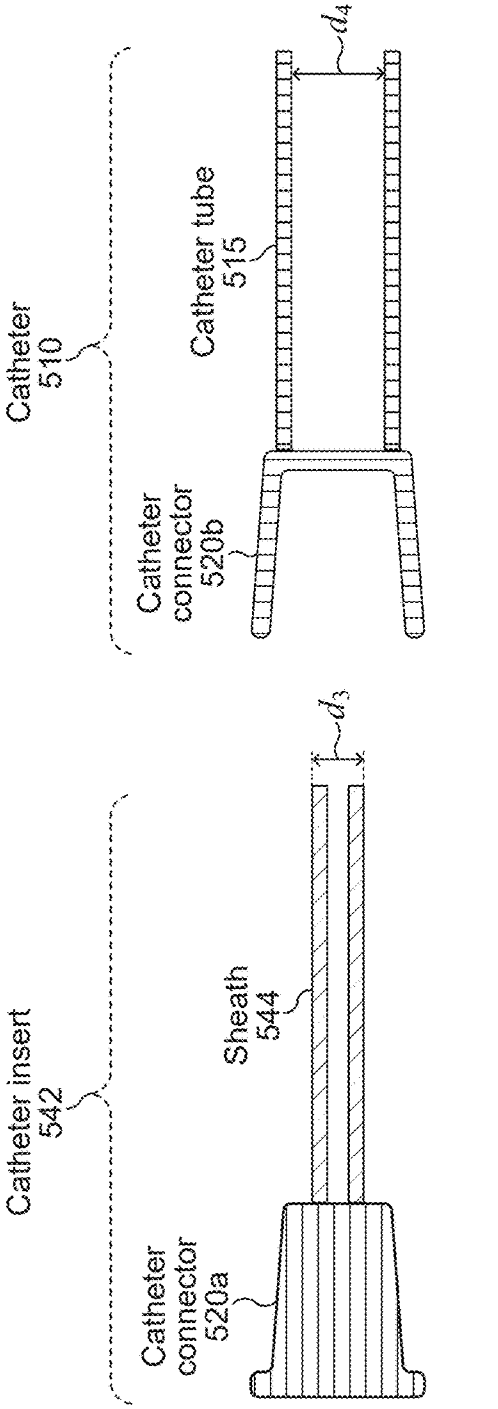
FIGS. 103-106 each illustrate an example catheter insert and a catheter.
Figure 104:
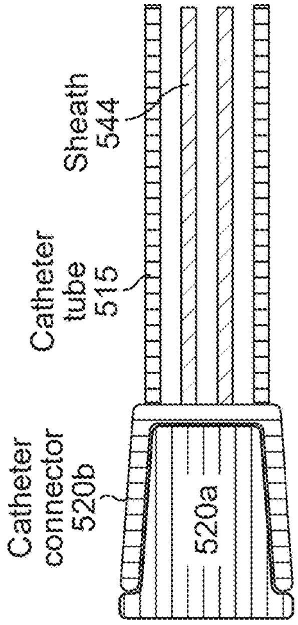
Figure 105:
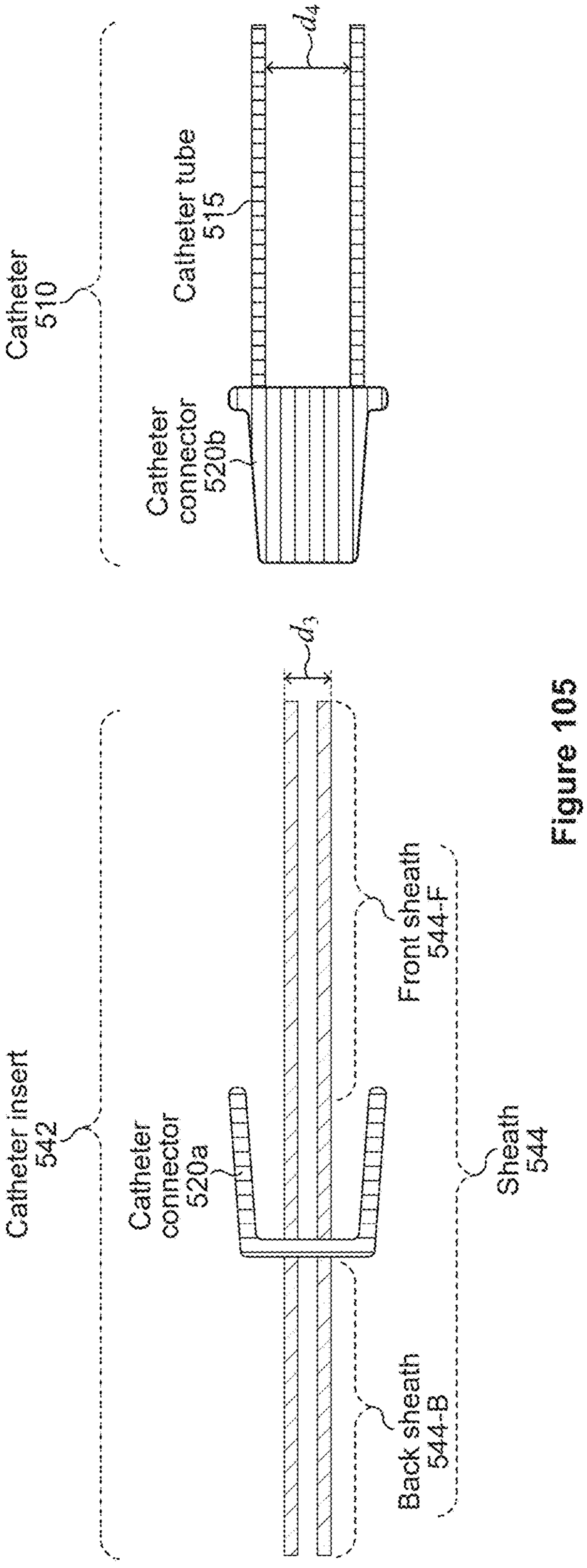
Figure 106:
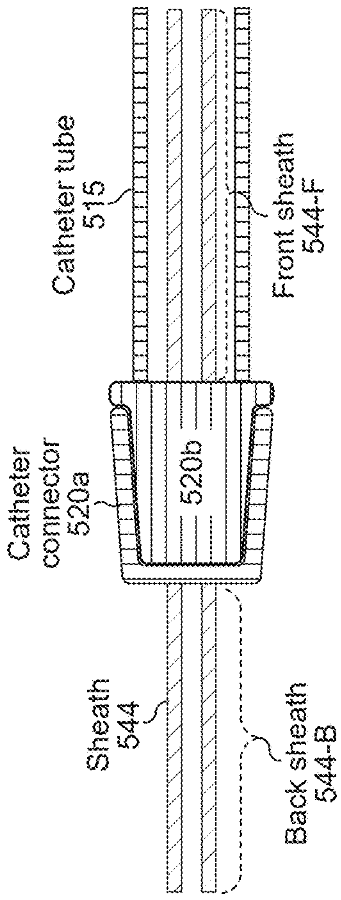

FIGS. 103-106 each illustrate an example catheter insert 542 and a catheter 510. A catheter insert 542 includes a catheter connector 520*a* and a sheath 544. The catheter-insert sheath 544 may be a flexible tube made from a plastic or rubber material, similar to that of a catheter tube 515. The sheath 544 may have a substantially cylindrical shape with an outer diameter $d_3$ that is less than or equal to the inner diameter $d_4$ of the catheter tube 515 of a catheter 510. A catheter insert 542 may be coupled to a catheter 510 by inserting at least a portion of the sheath 544 through the catheter connector 520*b* and into the catheter tube 515. The catheter connector 520*a* of the catheter insert 542 may then be connected to the mating catheter connector 520*b* of the catheter 510 to secure the catheter insert 542 to the catheter 510. The catheter connector 520*a* of a catheter insert 542 may be a male connector (e.g., as illustrated in FIG. 103) or a female connector (e.g., as illustrated in FIG. 105), and a catheter connector 520*a* may be connected to a catheter 510 by a catheter connector 520*b* of the opposite gender. FIG. 104 illustrates the catheter insert 542 and catheter 510 of FIG. 103 coupled together, and FIG. 106 illustrates the catheter insert 542 and catheter 510 of FIG. 105 coupled together.

The catheter insert 542 of FIG. 103 includes a single sheath 544 where one end of the sheath is attached to the catheter connector 520*a*. The catheter insert 542 of FIG. 103 is coupled to the catheter 510 by inserting the sheath 544 into the catheter tube 515 and then connecting the catheter connectors 520*a* and 520*b* together, as illustrated in FIG. 104. The catheter insert 542 of FIG. 105 includes a sheath 544 having a front sheath 544-F and a back sheath 544-B, where the catheter connector 520*a* is located between the front and back sheaths. The catheter insert 542 of FIG. 105 is coupled to the catheter 510 by inserting the front sheath 544-F into the catheter tube 515 and then connecting the catheter connectors 520*a* and 520*b* together, as illustrated in FIG. 106. Once the catheter insert 542 is coupled to the catheter 510, the back sheath 544-B remains external to the catheter tube 515.

The inner or outer surfaces of a sheath may be coated with an anticoagulant substance. For example, the end portion of the catheter tube 515 in FIG. 103 may be installed in a blood vessel, and the inner and outer surfaces of the catheter-insert sheath 544 may include an anticoagulant coating to prevent blood coagulation when the sheath is inserted into the catheter tube. As another example, the inner and outer surfaces of at least the front sheath 544-F of the catheter insert 542 in FIGS. 105-106 may be coated with an anticoagulant substance.

Figure 107:
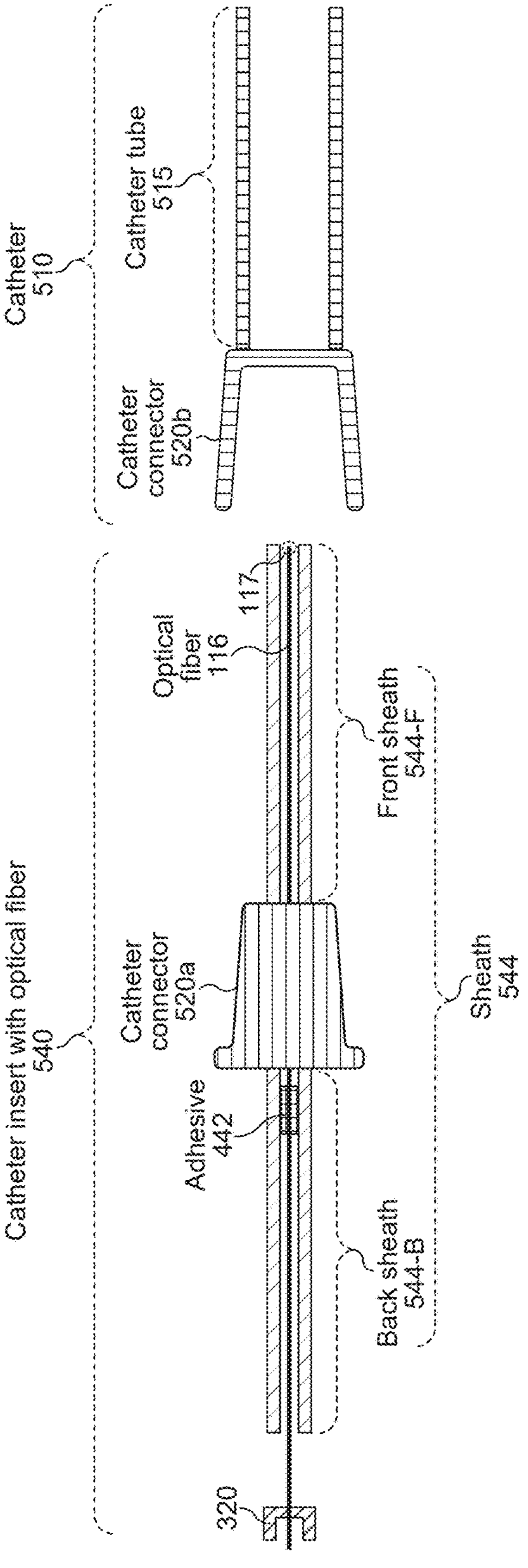
FIGS. 107-108 illustrate an example catheter insert with optical fiber.
Figure 108:
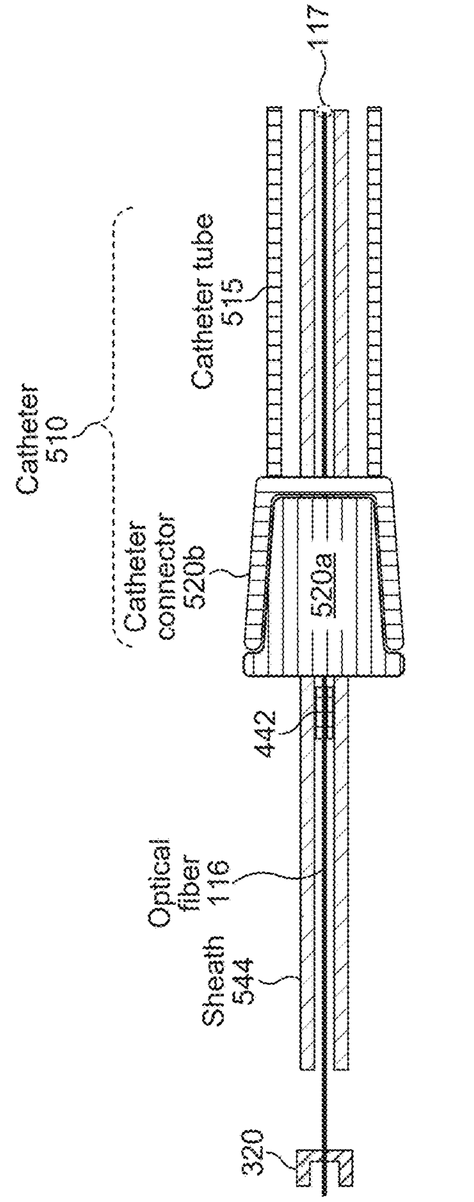

FIGS. 107-108 illustrate an example catheter insert with optical fiber 540. A catheter insert with optical fiber 540 includes a catheter insert 542 (which includes a catheter connector 520*a* and a sheath 544) and one or more optical fibers 116 and may be referred to as a catheter-fiber apparatus or a catheter-insert-with-optical-fiber apparatus. The catheter-insert portion of a catheter-fiber apparatus 540 may be similar to the catheter insert 542 illustrated in FIG. 103 or 105. For example, the catheter-insert portion of the catheter-fiber apparatus 540 in FIGS. 107-108 includes a sheath 544 having a front sheath 544-F and a back sheath 544-B and is similar to the catheter insert 542 in FIGS. 105-106. In other embodiments, the catheter-insert portion of a catheter-fiber apparatus 540 may include a single sheath 544 similar to the catheter insert 542 in FIGS. 103-104.

A catheter insert with optical fiber 540 may be coupled to a catheter 510 by inserting at least a portion of the sheath 544 through the catheter connector 520*b* and into the catheter tube 515 so that at least a portion of the sheath 544 is contained within the catheter tube 515. The catheter connector 520*a* of the catheter insert with optical fiber 540 may then be connected to the mating catheter connector 520*b* of the catheter 510 to secure the catheter-fiber apparatus 540 to the catheter 510. In FIG. 108, the catheter insert with optical fiber 540 and the catheter 510 of FIG. 107 are illustrated after being coupled together. In FIG. 108, the catheter connectors 520*a* and 520*b* are connected together, and the front sheath 544-F is contained within the catheter tube 515.

A catheter insert with optical fiber 540 includes one or more optical fibers 116, where at least a portion of each optical fiber is contained within a sheath 544. The catheter insert with optical fiber 540 in FIG. 107 includes one optical fiber 116 where a portion of the optical fiber is contained within the sheath 544, and another portion of the optical fiber extends out the end of the back sheath 544-B and is terminated by a fiber-optic connector 320. The fiber-optic connector 320 may be used to couple the optical fiber 116 to a Raman spectroscopy system 100. The Raman spectroscopy system 100 may produce a pump-Stokes beam 140 that is transmitted along the optical fiber 116 and emitted from the end face 117. The pump-Stokes beam 140 may be directed to a sample 150, and the optical fiber 116 may receive at least a portion of a Raman signal 160 produced by coherent Raman scattering of the pump and Stokes beams at the sample. The optical fiber 116 may transmit the received Raman signal 160 along the optical fiber in a direction opposite the pump-Stokes beam 140, and the Raman signal 160 may be transmitted to the Raman spectroscopy system 100 for measurement.

In other embodiments, a catheter insert with optical fiber 540 may include two or more optical fibers 116, where at least a portion of each optical fiber is contained with a catheter-insert sheath 544. For example, a catheter insert with optical fiber 540 may include two optical fibers: an output optical fiber and an input optical fiber. The two optical fibers may be coupled to a Raman spectroscopy system 100 which produces a pump-Stokes beam 140 that is transmitted along the output optical fiber and emitted from the output-fiber end face. The pump-Stokes beam 140 may be directed to a sample 150, and the input optical fiber may receive at least a portion of a Raman signal 160 produced by coherent Raman scattering of the pump and Stokes beams at the sample. The input optical fiber may transmit the received Raman signal 160 along the optical fiber in a direction away from the input-fiber end face, and the Raman signal 160 may be transmitted to the Raman spectroscopy system 100 for measurement.

A catheter insert with optical fiber 540 may include an optical fiber 116 that is attached to an interior surface of the sheath 544 by an adhesive 442. The adhesive 442 may be located in any suitable location along the length of a sheath 544. In FIGS. 107-108, the optical fiber 116 is attached to the interior of the sheath 544 by adhesive 442 located in the back sheath 544-B. Additionally or alternatively, the optical fiber 116 may be attached to the sheath 544 by an adhesive 442 located in the front sheath 544-F. An adhesive 442 may be configured to hold the optical fiber 116 in place so that the optical fiber does not move longitudinally within the sheath 544. For example, the adhesive 442 in FIG. 107 may fix the location of the optical fiber 116 relative to the sheath 544 so that the end face 117 remains in place at or near the end of the front sheath 544-F. In addition to holding an optical fiber

116 in place, an adhesive 442 may form a seal between the optical fiber and the interior surface of the sheath 544 to prevent a fluid from flowing into or through the sheath.

In some embodiments, a sheath 544 may include a coating or a jacket that encloses the optical fiber 116. A coating or a jacket may be used in addition to or instead of using an adhesive 442 to secure the optical fiber 116 and the sheath together. The coating or jacket may be attached to the optical fiber 116 and may hold the optical fiber in place relative to the sheath 544 and relative to the catheter connector 520*a*. For example, a sheath 544 may include a primary coating made of flexible plastic applied directly to the outer surface of the fiber cladding 192 and a secondary buffer applied over the primary coating. The outer diameter of the primary coating applied to the optical fiber 116 may be approximately 200-300 μm, and the outer diameter of the secondary buffer may be approximately 0.8-1.0 mm. In addition to or instead of the secondary buffer, a sheath 544 may include a jacket that surrounds the optical fiber 116 and may be in contact with the primary coating or the secondary buffer layer. The catheter-insert sheath 544 in FIGS. 111-112 may include a coating or a jacket that encloses a portion of the optical fiber 116, and the coating or jacket may be attached to or physically coupled to the optical fiber.

Figure 109:
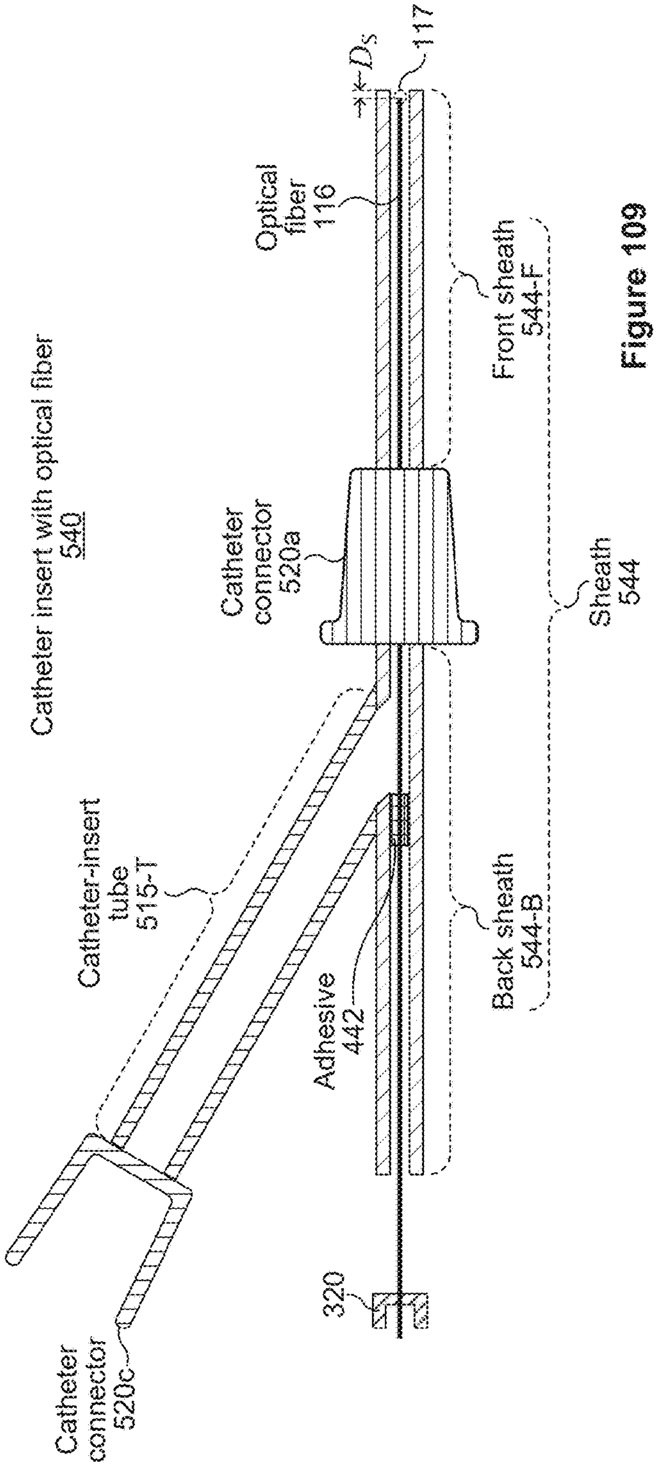
FIGS. 109-110 illustrate an example catheter insert with optical fiber that includes a catheter-insert tube.
Figure 110:
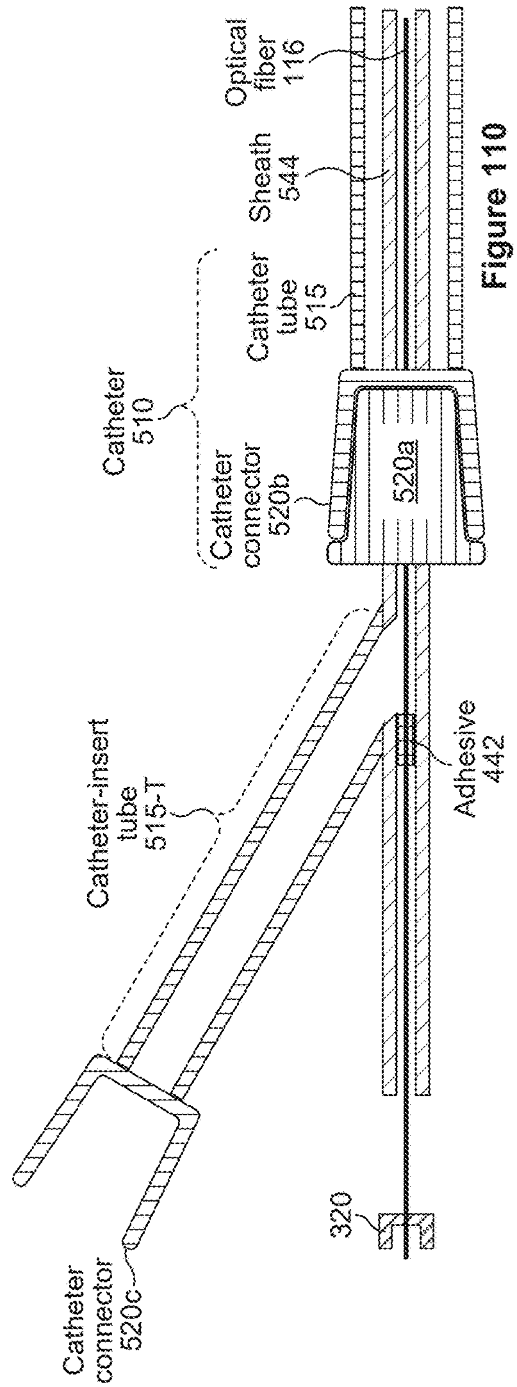

FIGS. 109-110 illustrate an example catheter insert with optical fiber 540 that includes a catheter-insert tube 515-T. The catheter insert with optical fiber 540 in FIGS. 109-110 is similar to that illustrated in FIGS. 107-108 with the addition of the catheter-insert tube 515-T connected to the back sheath 544-B. A catheter-insert tube 515-T may be a flexible tube made from plastic or rubber material and may be similar to a catheter tube 515. In FIG. 110, the catheter insert with optical fiber 540 of FIG. 109 is shown after being coupled to a catheter 510.

A catheter-insert tube 515-T may allow for a fluid to flow into or out of a catheter 510 when the catheter-fiber apparatus 540 is coupled to the catheter 110. For example, after a catheter 510 is installed in a blood vessel 610 (or some other location in a patient's body), the catheter insert with optical fiber 540 may be coupled to the catheter, as shown in FIG. 110. The catheter-insert tube 515-T may allow fluid to flow into the blood vessel 610 by flowing through the catheter-insert tube 515-T and then through the front sheath 544-F or the catheter tube 515. Additionally or alternatively, the catheter-insert tube 515-T may allow blood to be withdrawn from the blood vessel by flowing through the front sheath 544-F or the catheter tube 515 and then through the catheter-insert tube 515-T. A catheter connector 520*c* may be attached to the end of a catheter-insert tube 515-T (as illustrated in FIGS. 109-110) and may allow the catheter-insert-tube 515-T to be connected to a syringe or catheter tubing.

The catheter insert with optical fiber 540 in FIGS. 109-110 includes an adhesive 442 located within the back sheath 544-B. The adhesive 442 may attach the optical fiber 116 to the back sheath 544-B and may form a seal between the optical fiber 116 and the interior surface of the back sheath 544-B. The seal formed by the adhesive 442 may prevent a fluid from flowing into or through the back sheath 544-B. For example, a fluid may flow into or out of the catheter 510 in FIG. 110 via the catheter-insert tube 515-T, and the adhesive 442 may prevent the fluid from leaking out by flowing through the back sheath 544-B. In addition to or instead of using an adhesive 442 to seal the back sheath 544-B, the back sheath may include a coating or a jacket that encloses the optical fiber. The coating or jacket may be attached to or in contact with the exterior surface of the optical fiber 116. For example, the back sheath 544-B may include a primary coating and a secondary buffer applied over the primary coating. In addition to or instead of the secondary buffer, the back sheath 544-B may include a jacket that surrounds and is in contact with the primary coating or the secondary buffer layer. A back sheath 544-B that includes a coating or a jacket that encloses the optical fiber 116 may be attached to or physically coupled to the exterior surface of the optical fiber so that there are no gaps between the optical fiber and the back sheath, which may prevent a fluid from flowing into or through the back sheath.

The end face 117 of the optical fiber 116 of a catheter insert with optical fiber 540 may be located at or near the end of the sheath 544 within which the optical fiber is contained. For example, the end face 117 of the optical fiber 116 in FIGS. 107-108 may be located within 5 mm of the end of the front sheath 544-F opposite the catheter connector 520*a*. As another example, the distance $D_S$ between the optical-fiber end face 117 and the end of the front sheath 544-F in FIGS. 109-110 may be less than or equal to 5 mm. The end face 117 may be recessed within the front sheath 544-F by up to 5 mm, may be located approximately flush with the end of the front sheath 544-F, or may extend beyond the front sheath 544-F by up to 5 mm.

Figure 111:
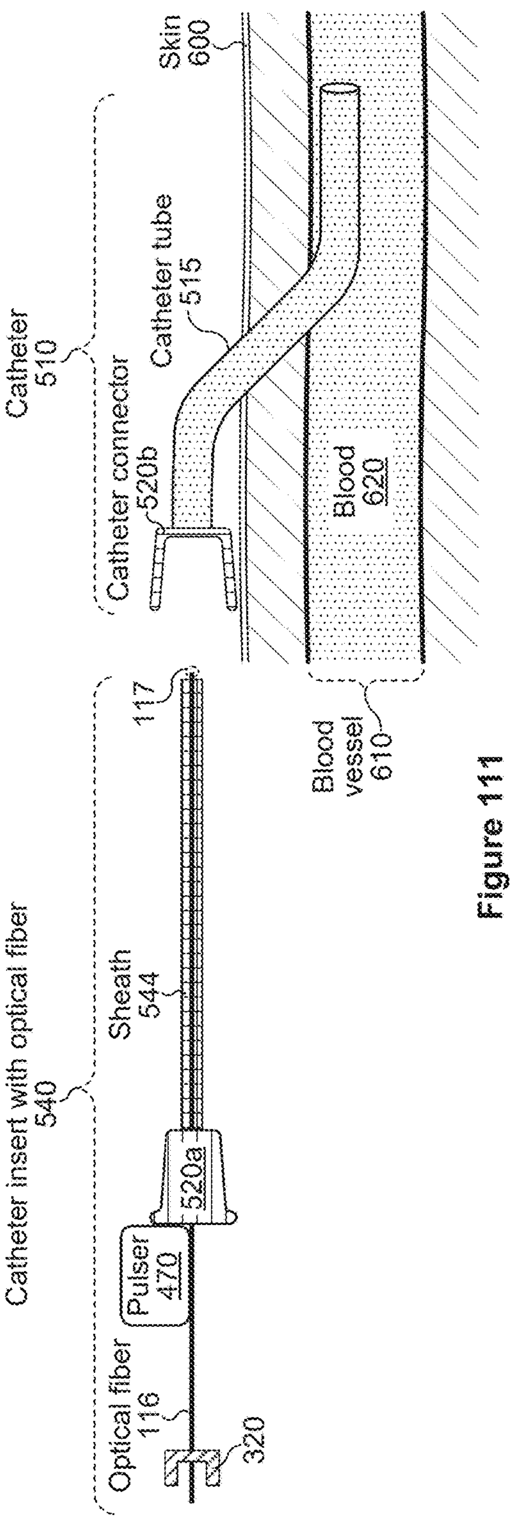
FIGS. 111-112 illustrate an example catheter insert with optical fiber that is being coupled to a catheter installed in a blood vessel.
Figure 112:
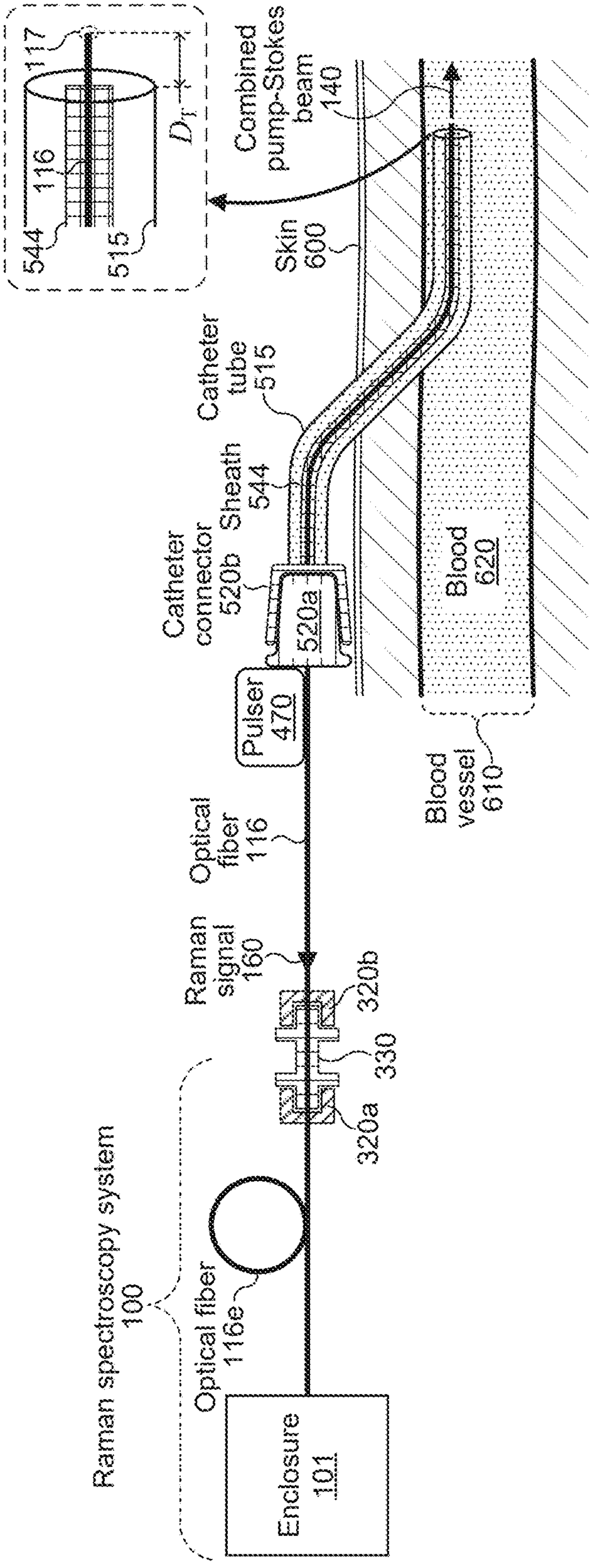

FIGS. 111-112 illustrate an example catheter insert with optical fiber 540 that is being coupled to a catheter 510 installed in a blood vessel 610. FIG. 111 illustrates the catheter 510 installed in the blood vessel 610 and the catheter insert with optical fiber 540 before being coupled to the catheter 510. The catheter 510 may be installed using a conventional catheter-installation technique or using a catheter needle with optical fiber 500 along with a feedback signal 102 that helps guide the needle apparatus 500 to the blood vessel 610, as described herein. Once the catheter 510 is installed and the end portion of the catheter tube 515 is located in the blood vessel 610, the catheter insert with optical fiber 540 may be coupled to the catheter 510.

FIG. 112 illustrates the catheter insert with optical fiber 540 after being coupled to the catheter 510. The catheter insert with optical fiber 540 is coupled to the catheter 510 by inserting the sheath 544 through the catheter connector 520*b* and into the catheter tube 515. The catheter connector 520*a* is then connected to the mating catheter connector 520*b* of the catheter 510 to secure the catheter-fiber apparatus 540 to the catheter 510. The sheath 544 in FIGS. 111-112 may include a coating or a jacket that encloses a portion of the optical fiber 116, and the coating or jacket may be attached to or physically coupled to the optical fiber.

The catheter insert with optical fiber 540 in FIGS. 111-112 includes a single sheath 544, similar to the sheath 544 of the catheter insert 542 in FIGS. 103-104. In other embodiments, the catheter 510 in FIGS. 111-112 may be coupled to a catheter insert with optical fiber 540 having a front sheath 544-F and a back sheath 544-B (e.g., similar to that in FIGS. 107-108). Alternatively, the catheter 510 in FIGS. 111-112 may be coupled to a catheter insert with optical fiber 540 having a front sheath 544-F, a back sheath 544-B, and a catheter-insert tube 515-T (e.g., similar to that in FIGS. 109-110). The catheter-insert tube 515-T may allow for introduction of a fluid into the blood vessel 610 or for blood 620 to be withdrawn from the blood vessel.

A catheter insert with optical fiber 540 may include a pulser 470 that is coupled to the catheter insert (e.g., the catheter connector 520*a* or the sheath 544) or to the optical fiber 116. The pulser 470 may impart a vibration to the catheter insert or the optical fiber to circulate fluid around the end face 117 of the optical fiber. In FIG. 112, the sample being measured is blood 620, and the pulser 470 may cause the blood to circulate in the region around the optical-fiber end face 117. For example, the pulser 470 may impart a vibration to the catheter connector 520*a*, which may couple the vibration to the catheter connector 520*b*, the sheath 544, or the catheter tube 515. The vibration of the sheath 544 or the catheter tube 515 may cause the blood 620 located near the optical-fiber end face 117 to circulate around the end face. The blood circulation around the end face 117 provided by the pulser 470 may allow multiple portions of the blood 620 to be measured by a Raman spectroscopy system 100 by preventing a small portion of blood from stagnating and remaining substantially still near the optical-fiber end face.

A catheter 510 may be installed into any suitable location in a patient's body (e.g., blood vessel, bladder, stomach, spine). Once a catheter 510 is installed and the end of the catheter tube 515 opposite the catheter connector 520*b* is located at or near a sample 150, a catheter insert with optical fiber 540 may be coupled to the catheter. After the catheter-fiber apparatus 540 is coupled to the catheter 510, the end face 117 of the optical fiber 116 may be positioned near the end of the catheter tube 515 and at or near the sample 150. The optical fiber 116 may be coupled to a Raman spectroscopy system 100 to perform Raman-signal measurements of the sample 150 located at or near the optical-fiber end face 117.

In FIGS. 111-112, the sample of interest is blood 620 located in a blood vessel 610. The catheter 510 is installed in the blood vessel 610, and the catheter tube 515 has blood located in and around at least the end of the catheter tube opposite the catheter connector 520*b*. After the catheter insert with optical fiber 540 is coupled to the catheter 510 (as illustrated in FIG. 112), the end face 117 of the optical fiber 116 is located at or near the end of the catheter tube 515. For example, the end face 117 of the optical fiber 116 in FIG. 112 may be located within 5 mm of the end of the catheter tube 515 so that the distance Dr is less than or equal to 5 mm (as shown in the dashed-line inset in FIG. 112). The end face 117 may be recessed within the catheter tube 515 by up to 5 mm, may be located approximately flush with the end of the catheter tube 515, or may extend beyond the catheter tube 515 by up to 5 mm.

In FIG. 112, the catheter insert with optical fiber 540 is coupled to a catheter 510, and the optical fiber 116 of the catheter-fiber apparatus 540 is coupled to a Raman spectroscopy system 100. The catheter 510 is installed in a blood vessel 610, and the end of the catheter tube 515 as well as the end face 117 of the optical fiber 116 are located within the blood 620 in the blood vessel 610. The Raman spectroscopy system 100 produces a pump-Stokes beam 140 that is transmitted along the optical fiber 116 and emitted from the end face 117. The sample measured by the Raman spectroscopy system 100 is blood 620 located in the blood vessel 610. The emitted pump-Stokes beam 140 may interact with the blood 620 located near the end face 117 to produce a Raman signal 160 by coherent Raman scattering of the pump and Stokes beams. A portion of the Raman signal 160 is coupled into the optical fiber 116 via the end face 117 and transmitted to the Raman spectroscopy system 100 for measurement. Based on the measurement of the Raman signal 160, the Raman spectroscopy system 100 may determine the concentration of oxygen, carbon dioxide, or bicarbonate in the blood 620. For example, the Raman spectroscopy system 100 may measure the Raman signal 160 to determine one or more signal characteristics 162 associated with the Raman signal, and the amount or the concentration of oxygen, carbon dioxide, or bicarbonate in the blood may be determined based on the signal characteristics. The concentration of oxygen may be expressed as pO2, the partial pressure of oxygen (e.g., in units of millimeters of mercury, mmHg), and the concentration of carbon dioxide may be expressed as pCO2, the partial pressure of carbon dioxide. The concentration of bicarbonate may be expressed in units of milliequivalents per liter (mEq/L) or millimoles per liter (mmol/L).

Figure 113:
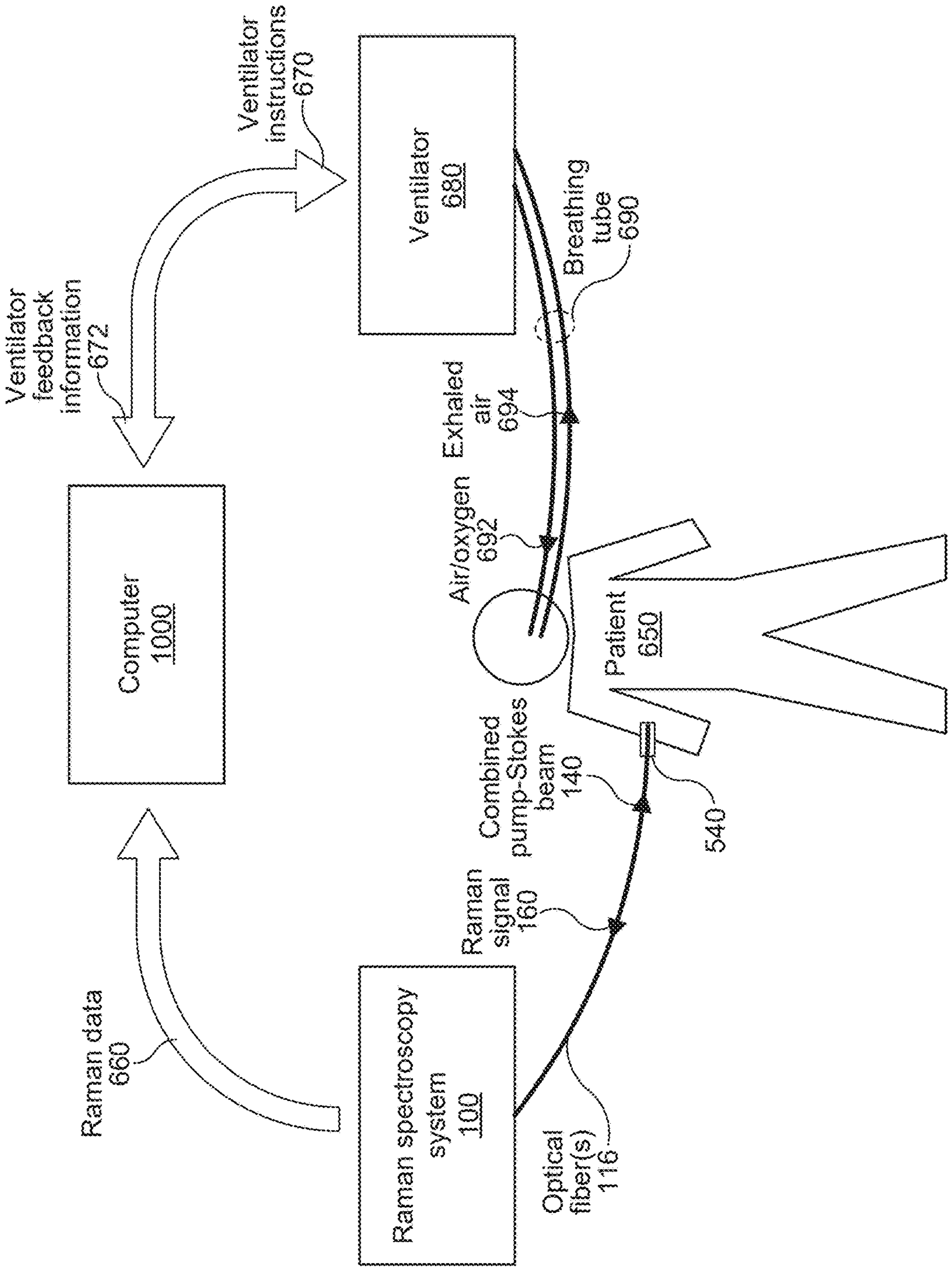
FIG. 113 illustrates an example Raman spectroscopy system and a ventilator that are both coupled to a patient.

FIG. 113 illustrates an example Raman spectroscopy system 100 and a ventilator 680 that are both coupled to a patient 650. The ventilator 680 provides breathing assistance to the patient 650 via a breathing tube 690. The breathing tube 690 delivers an air/oxygen mixture 692 from the ventilator 680 to the patient's lungs and removes the exhaled air 694.

The Raman spectroscopy system 100 is coupled to the patient 650 by one or more optical fibers 116. The one or more optical fibers 116 may be installed in a blood vessel 610 using a catheter insert with optical fiber 540 that is coupled to a catheter 510 (e.g., as illustrated in FIG. 112) or using an adjustable catheter insert with optical fiber 540-A (e.g., as illustrated in FIGS. 114-118). The Raman spectroscopy system 100 produces a pump-Stokes beam 140 that is transmitted via optical fiber 116 to the patient's blood vessel and produces a Raman signal 160 by coherent Raman scattering of the pump and Stokes beams while propagating in the blood 620. The Raman signal 160 is transmitted via optical fiber 116 to the Raman spectroscopy system 100 for measurement. Based on the Raman signal 160, the Raman spectroscopy system may determine Raman data 660 that is sent to the computer 1000. For example, the Raman spectroscopy system 100 may measure the Raman signal 160 to determine the concentration of oxygen, carbon dioxide, or bicarbonate in the blood 620, and the Raman data 660 sent to the computer 1000 may include the determined concentration of oxygen, carbon dioxide, or bicarbonate.

The computer 1000 in FIG. 113 (which is similar to the computer 1000 in FIG. 122) may be located within the Raman spectroscopy system 100, within the ventilator 680, or external to both the Raman spectroscopy system and ventilator. The computer 1000 receives (i) Raman data 660 from the Raman spectroscopy system 100 and (ii) ventilator feedback information 672 from the ventilator 680, and the computer 1000 provides ventilator instructions 670 to the ventilator. The Raman data 660 may include the concentrations of oxygen, carbon dioxide, or bicarbonate in the blood 620 as determined by the Raman spectroscopy system 100. The ventilator feedback information 672 may include patient-related parameters or ventilator operating parameters, such as for example, pressure, volume, and flow. Based at least in part on the Raman data 660 received from the Raman spectroscopy system 100, the computer 1000 determines instructions 670 to send to the ventilator 680. For example, the Raman data 660 may be used to determine blood acidity of the blood 620 (which may be referred to as the pH of the blood) or the oxygen concentration in the blood 620, and the ventilator instructions 670 may be used to adjust the operating parameters of the ventilator 680 to change the blood acidity to an optimal value or to ensure that the patient 650 is receiving an adequate supply of oxygen in the air/oxygen mixture 692 supplied by the ventilator. The ventilator instructions 670 may include one or more of the following operating parameters for the ventilator 680: a respiratory rate, a positive end-expiratory pressure (PEEP), a tidal volume, a fraction of inspired oxygen (FiO2), and an inspiratory-to-expiratory (I:E) ratio. Additionally, the Raman spectroscopy system 100 may remain coupled to the patient 650 to provide continual updates to the Raman data 660 supplied to the computer 1000, and the computer may update the ventilator instructions 670 accordingly to ensure that the operating parameters for the ventilator 680 remain optimized.

A technical advantage of a catheter insert with optical fiber 540 is the ability to perform Raman real-time measurements of a sample 150 in situ and continually over time. A Raman-signal measurement can be performed on a sample 150 using a catheter insert with optical fiber 540 without having to remove the sample from a patient's body. Additionally, using a catheter insert with optical fiber 540 allows Raman-signal measurements to be performed continually over a period of time, such as for example, over minutes, hours, or days. For example, a catheter 510 and catheter insert with optical fiber 540 may be able to remain installed in a patient's body for multiple days or weeks, and the optical fiber 116 of the catheter-fiber apparatus 540 may be used to make Raman-signal measurements continually over this time period. Additionally, the Raman-signal measurements may be performed in real time with each set of Raman data 660 available within seconds of a Raman signal 160 being measured and with updated Raman data 660 being sent to the computer 1000 every few seconds or minutes. For example, a catheter insert with optical fiber 540 installed in a blood vessel 610 (e.g., as illustrated in FIG. 112) may be used to provide real-time measurements of oxygen, carbon dioxide, and bicarbonate concentrations in the blood 620, and the time period between successive measurements may be approximately 10 seconds, 1 minute, 10 minutes, or 1 hour. This Raman data 660 may be used to provide real-time updates to ventilator instructions 670 sent to a ventilator 680 providing breathing assistance to the patient 650. A conventional approach to measuring oxygen, carbon dioxide, and bicarbonate concentrations requires withdrawing a sample of blood and sending the sample to be analyzed (e.g., using a blood gas analyzer). This process, which requires that a blood sample be withdrawn, may be time consuming and may be performed a few times per day or less. In contrast, a catheter insert with optical fiber 540 allows measurement of blood parameters without withdrawing blood, and the measurements may be performed continually and in real time.

Figure 114:
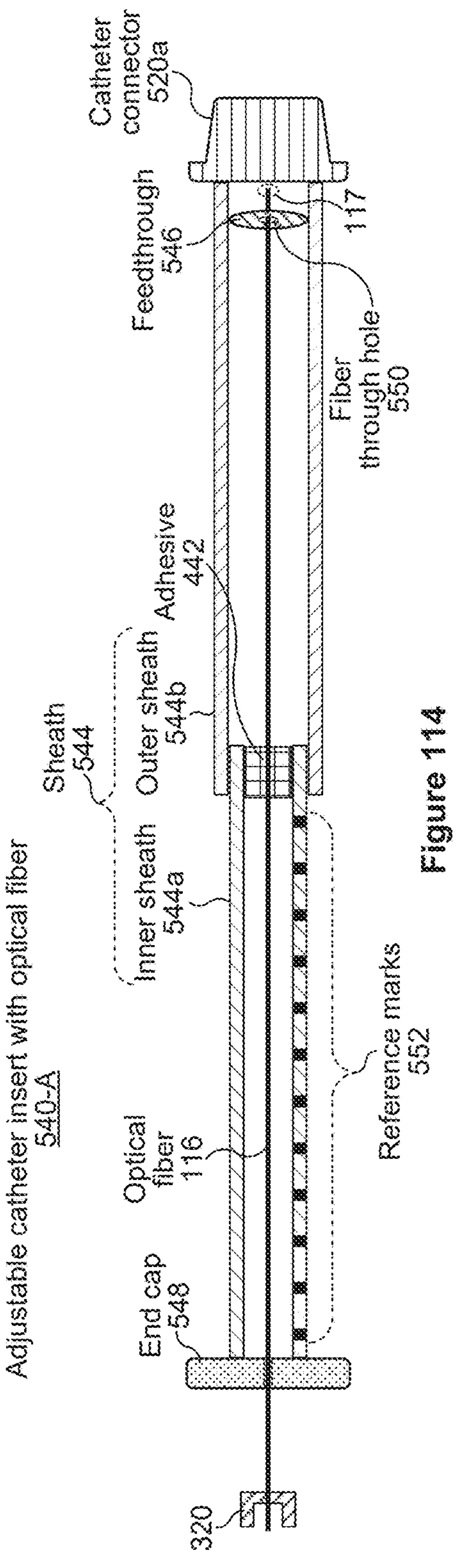
FIGS. 114-115 each illustrate an example adjustable catheter insert with optical fiber.
Figure 115:
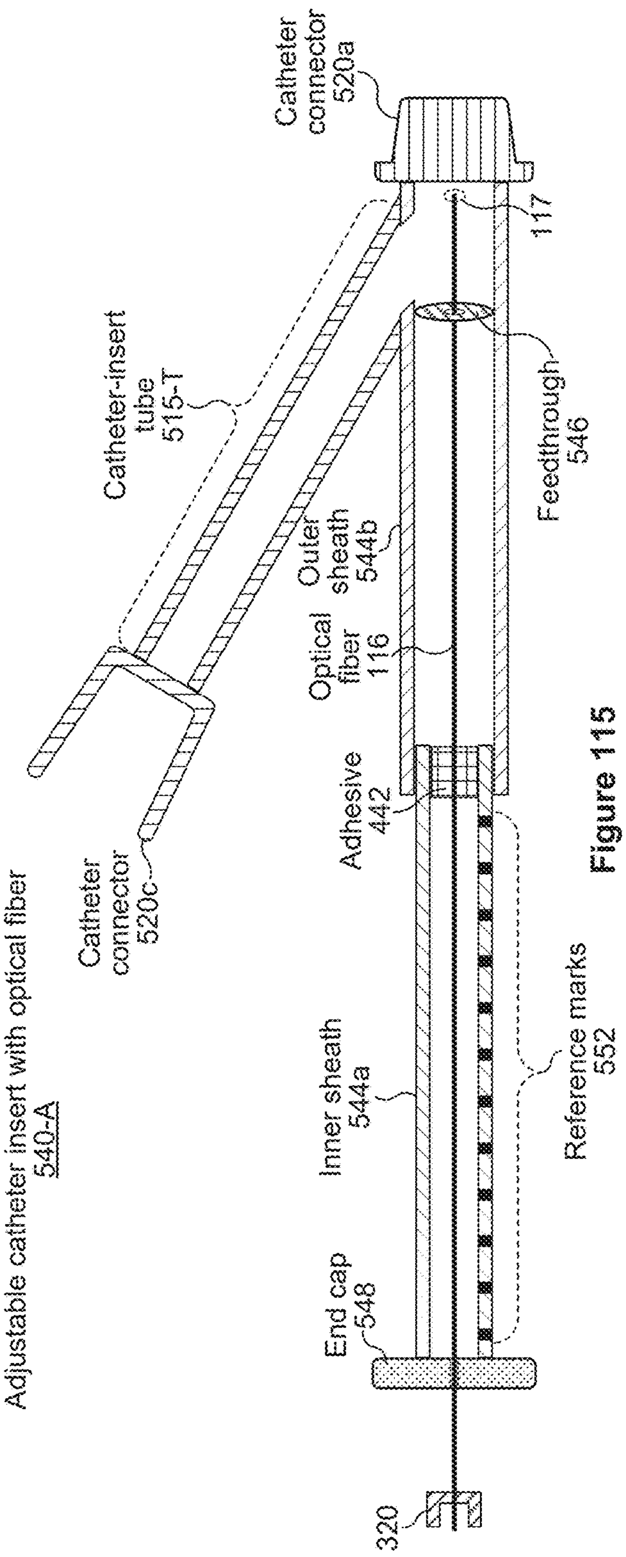

FIGS. 114-115 each illustrate an example adjustable catheter insert with optical fiber 540-A. An adjustable catheter insert with optical fiber 540-A includes a catheter insert 542 (which includes a catheter connector 520*a* and a sheath 544) and one or more optical fibers 116 and may be referred to as an adjustable catheter-fiber apparatus, an adjustable catheter-insert-with-optical-fiber apparatus, a catheter-fiber apparatus, or a catheter-insert-with-optical-fiber apparatus. An adjustable catheter insert with optical fiber 540-A may be used in a manner similar to a catheter insert with optical fiber 540. Additionally, the adjustable catheter insert with optical fiber 540-A provides the ability to move an optical fiber 116 to adjust the position of the optical-fiber end face 117.

The sheath 544 in FIGS. 114-115 includes an inner sheath 544*a* and an outer sheath 544*b*, where the inner sheath 544*a* is configured to slide back and forth within the outer sheath 544*b*. An operator may move the inner sheath 544*a* by holding or securing the outer sheath in place and pushing or pulling on the end cap 548 to move the inner sheath forward or backward. The optical fiber 116 is secured to the inner sheath 544*a* by an adhesive 442, and as the inner sheath 544*a* is moved forward or backward, the optical fiber 116 and the end face 117 are also moved in the same direction. The reference marks 552 located on the inner sheath 544*a* may include markings, numerals, or other indicators that provide a visual indication of the position of the optical-fiber end face 117. The inner and outer sheaths 544*a* and 544*b* may each be substantially rigid tubes made from a plastic or rubber material and configured to slidably engage with one another. Alternatively, the inner sheath 544*a* may include a coating or a jacket that encloses and secures the optical fiber 116, and the adjustable catheter-fiber apparatus 540-A may not include an adhesive that attaches the optical fiber to the inner sheath. In some embodiments, the sheath 544 in FIGS. 114-115 may be referred to as a back sheath that includes the inner and outer sheaths, and the adjustable catheter-fiber apparatus 540-A may include a front sheath (not included in FIGS. 114-115) similar to the front sheath 544-F in FIGS. 107-108.

Each adjustable catheter-fiber apparatus 540-A in FIGS. 114-115 includes a feedthrough 546 located near the catheter connector 520*a*. The feedthrough 546 may be attached to the interior surface of the outer sheath 544*b* and may prevent a fluid from flowing into or through the outer sheath 544*b*. The feedthrough 546 includes a fiber through hole 550 that allows the fiber to pass through the feedthrough and allows the fiber to move when the inner sheath 544*a* is moved.

The adjustable catheter-fiber apparatus 540-A in FIG. 115 includes a catheter-insert tube 515-T that is similar to the catheter-insert tube 515-T in FIGS. 109-110. When the adjustable catheter-fiber apparatus 540-A in FIG. 115 is coupled to a catheter 510, the catheter-insert tube 515-T may allow for a fluid to flow into or out of the catheter 510.

Figure 116:
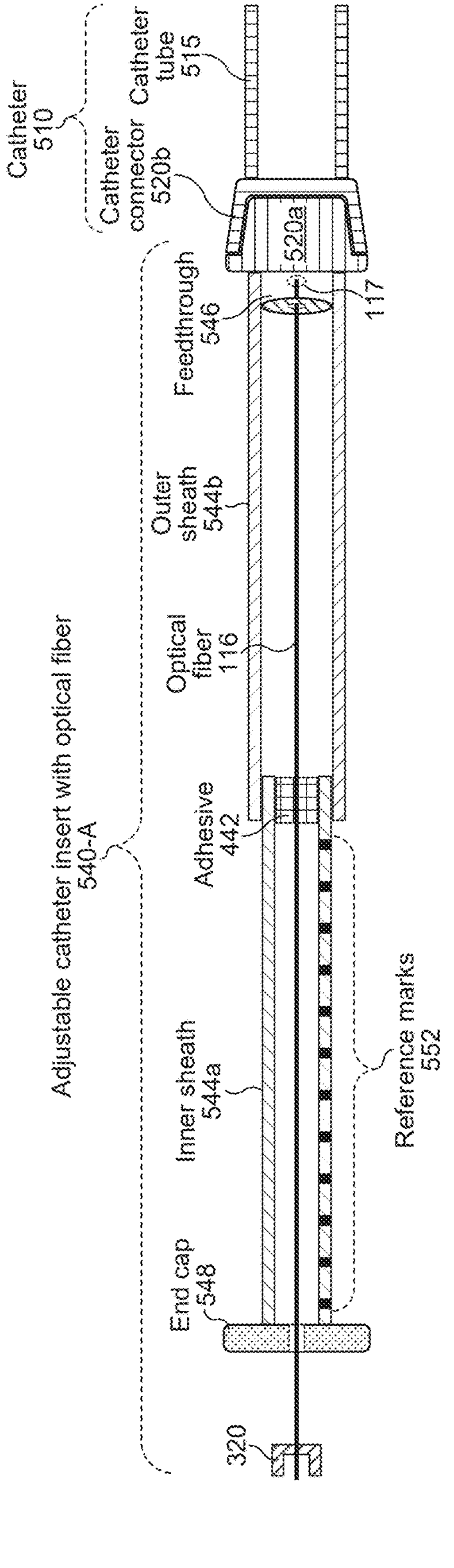
FIGS. 116-118 each illustrate an example adjustable catheter insert with optical fiber that is coupled to a catheter.
Figure 117:
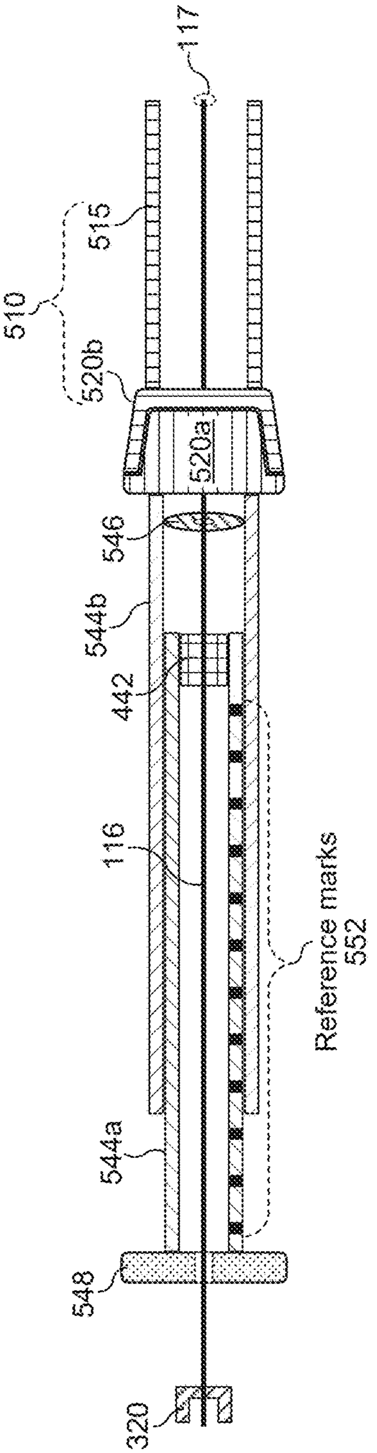
Figure 118:
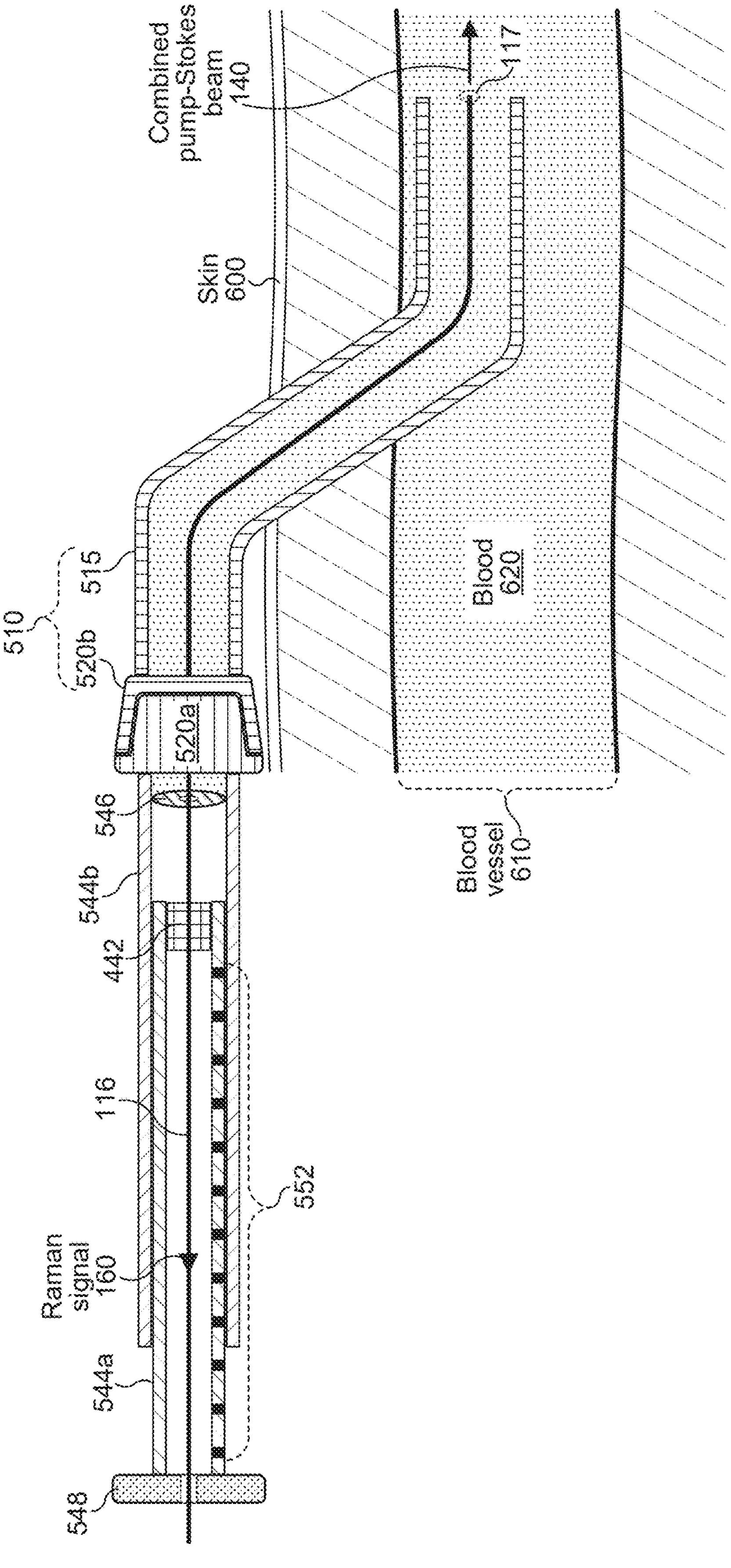

FIGS. 116-118 each illustrate an example adjustable catheter insert with optical fiber 540-A that is coupled to a catheter 510. FIG. 116 illustrates the adjustable catheter-fiber apparatus 540-A after being coupled to the catheter by connecting the catheter connectors 520*a* and 520*b* together. Once the adjustable catheter-fiber apparatus 540-A is secured to the catheter 510, the inner sheath 544*a* may be moved to move the optical fiber 116 and the end face 117. In FIG. 117, the inner sheath 544*a* has been pushed into the outer sheath 544*b* to move the end face 117 of the optical fiber 116 forward and into the catheter tube 515. The inner sheath 544*a* may be moved forward or backward to set the position of the optical-fiber end face 117 to a desired location, and the position of the optical-fiber end face 117 may be determined based on the reference marks 552. FIG. 118 illustrates the adjustable catheter-fiber apparatus 540-A coupled to a catheter 510 installed in a blood vessel 610. The optical fiber 116 may be coupled to a Raman spectroscopy system 100 to perform Raman-signal measurements of the blood 620 located at or near the optical-fiber end face 117. The inner sheath 544*a* may be moved forward or backward to set the position of the optical-fiber end face 117 to a desired location within the blood vessel 610. For example, the optical-fiber end face 117 may be moved to a location where the blood 620 is flowing within the blood vessel 610 to ensure that multiple portions of blood are measured (instead of measuring a small portion of blood that remains substantially still). Additionally, the optical-fiber end face 117 may be moved to a location to optimize the interaction of the pump-Stokes beam 140 with the blood 620 to produce an optimal Raman signal 160.

Figure 119:
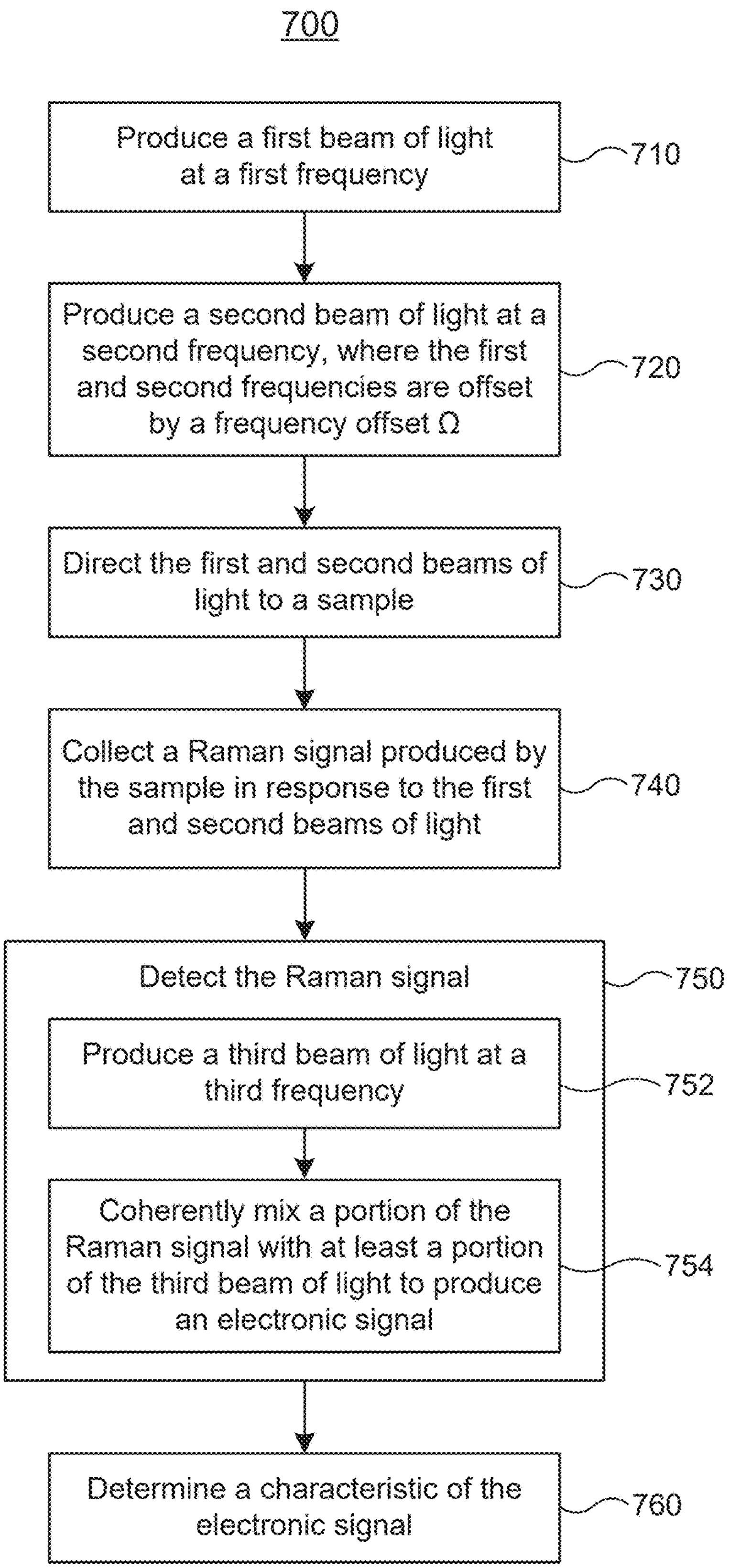
FIG. 119 illustrates an example method for measuring a Raman signal.

FIG. 119 illustrates an example method 700 for measuring a Raman signal 160. The method may be performed by a Raman spectroscopy system as described herein. For example, the method may be performed by the Raman spectroscopy system 100 illustrated in FIG. 1 or 2 and may be used to measure a Raman signal 160. The method may begin at step 710 by producing a first beam of light at a first frequency ($v_1$). At step 720, a second beam of light at a second frequency ($v_2$) is produced. The first beam of light may be referred to as a pump beam of light 120*pu*, and the second beam of light may be referred to as a Stokes beam of light 120S. The first and second frequencies may be offset by a frequency offset Ω, where $\Omega = v_1 - v_2$. For example, the first and second frequencies may each correspond to a wavelength between approximately 300 nm and approximately 5,000 nm, and the frequency offset Ω may be between approximately 5 THz and approximately 100 THz. The first and second beams of light may each be produced by a light source that includes one or more laser diodes, where each laser diode is a fixed-wavelength laser diode or a wavelength-tunable laser diode.

At step 730, the first and second beams of light are directed to a sample 150, and at step 740, a Raman signal 160 is collected, where the Raman signal is produced by the sample in response to the first and second beams of light. For example, the Raman signal may be produced by coherent Raman scattering of the first and second beams of light within the sample. The first and second beams of light may be directed to the sample by one or more optical elements that include a free-space optical element, an optical fiber, or an optical waveguide. Similarly, one or more optical elements (which may include a free-space optic, an optical fiber, or an optical waveguide) may collect the Raman signal and direct the Raman signal to an optical receiver. For example, the sample 150 may be located external to the Raman spectroscopy system 100, and one or more optical fibers 116 may (i) direct the first and second beams of light to the sample and (ii) direct the Raman signal back to the system.

At step 750, the Raman signal is detected. Detection of the Raman signal 160, which may be performed by an optical receiver 200, includes steps 752 and 754. At step 752, a third beam of light at a third frequency $v_3$ is produced. The third beam of light (which may be referred to as a probe beam of light 120*pr*) may be produced by a wavelength-tunable laser, where the third frequency is adjustable by changing a wavelength of light produced by the wavelength-tunable laser. At step 754, a portion of the Raman signal is coherently mixed with at least a portion of the third beam of light to produce an electronic signal (e.g., a photocurrent signal i). The Raman signal and the third beam of light may be coherently mixed at a detector of an optical receiver. The portion of the Raman signal that is coherently mixed with the third beam of light may include optical frequency components of the Raman signal that are within a particular frequency range of the third frequency, and the particular frequency range may depend on the electronic bandwidth of the detector. For example, the particular frequency range may extend from approximately $v_3 - \Delta f$ to approximately $v_3 + \Delta f$, where $v_3$ is the third frequency, and Δf is the electronic bandwidth of the detector.

At step 760, a characteristic of the electronic signal is determined, at which point the method may end. For example, a processor may receive a digital signal corresponding to the electronic signal, and the processor may determine the characteristic of the electronic signal based on the digital signal. The electronic signal may include a photocurrent signal i produced by a detector 220 or a corresponding voltage signal 234 produced by an electronic amplifier 232. The characteristic of the electronic signal may be associated with the Raman signal 160 and may include a peak amplitude, an average amplitude, an amplitude at a particular frequency, an amplitude at a particular time, an amplitude at a frequency center, an amplitude at a temporal center, a DC offset, an area, a frequency, a phase, or a polarization. Additionally, the characteristic of the electronic signal may be associated with a Raman shift at a frequency $v_1 - v_3$, where $v_1$ is the first frequency, and $v_3$ is the third frequency. Based on one or more determined signal characteristics 162, a processor may determine (i) whether a particular material is present in a sample or (ii) an amount or a concentration of the particular material in the sample.

Figure 120:
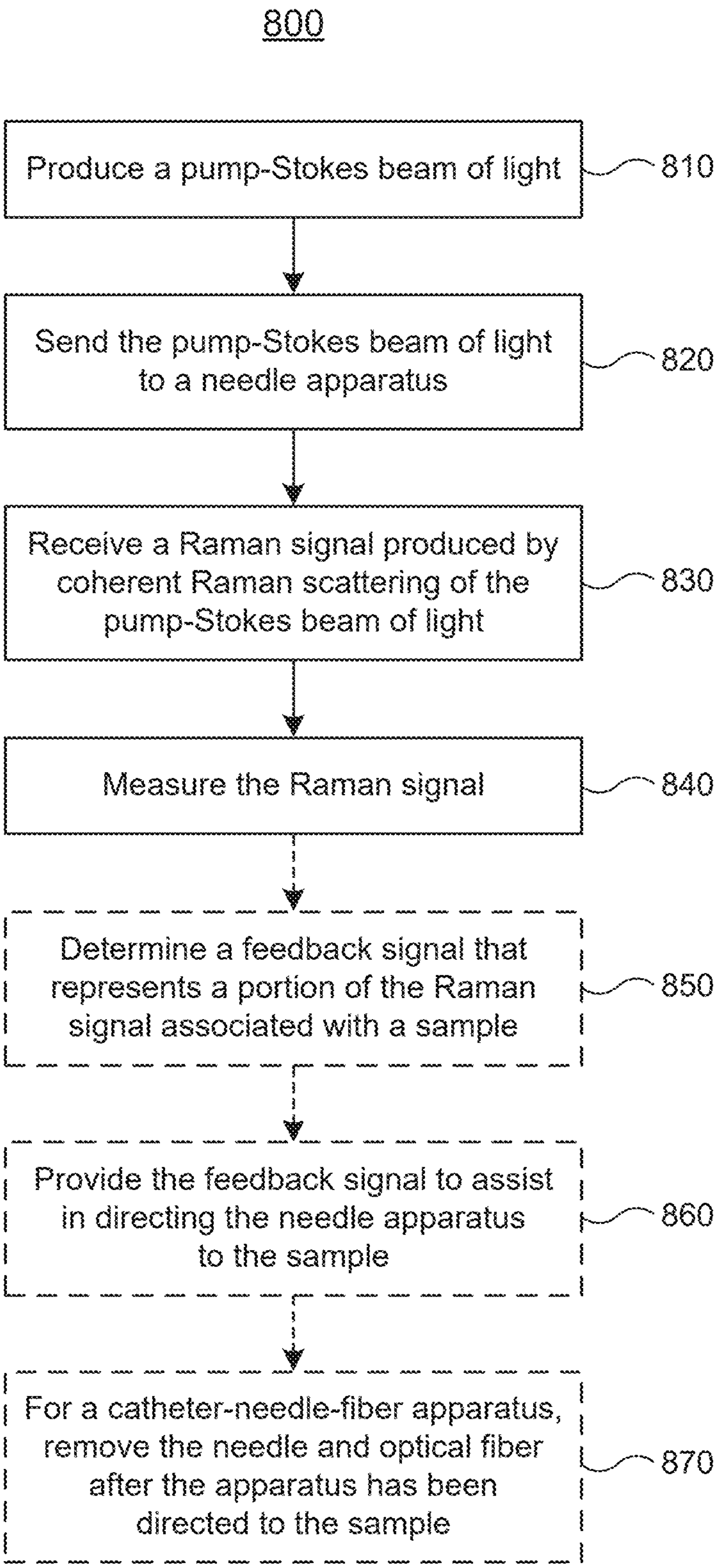
FIG. 120 illustrates an example method for measuring a Raman signal using a needle apparatus.

FIG. 120 illustrates an example method 800 for measuring a Raman signal 160 using a needle apparatus. The method may begin at step 810 in which a Raman spectroscopy system 100 produces a pump-Stokes beam of light 140. The pump-Stokes beam of light 140 may include a pump beam of light 120*pu* produced by a pump light source 110*pu* and a Stokes beam of light 120S produced by a Stokes light source 110S, where the pump and Stokes frequencies are offset by a frequency offset Ω. The pump and Stokes beams of light may be combined within the Raman system enclosure 101 to produce a combined pump-Stokes beam 140, and the pump-Stokes beam 140 may be directed outside the enclosure via one or more optical fibers 116.

At step 820, the pump-Stokes beam of light 140 is sent to a needle apparatus. The needle apparatus may be a needle with optical fiber 400 (which may be referred to as a needle-fiber apparatus), a needle with optical waveguide 400-W (which may be referred to as a needle-waveguide apparatus), or a catheter needle with optical fiber 500 (which may be referred to as a catheter-needle-fiber apparatus). A needle apparatus may include an optical fiber 116 or an optical waveguide 450 that receives a pump-Stokes beam 140 and directs the beam toward the needle tip 414 and (i) through the opening 418 of the needle 410 or (ii) to a sample 150 located in the needle lumen 430. For example, a needle apparatus may include a needle 410 and an optical fiber 116 and may be similar to the needle with optical fiber 400 in any of FIGS. 59-74 and 79-95. As another example, a needle apparatus may include a needle 410 and an optical waveguide 450 and may be similar to the needle with optical waveguide 400-W in any of FIGS. 75-78. As another example, a needle apparatus may include a needle 410, optical fiber 116, and catheter 510 and may be similar to the catheter needle with optical fiber 500 in any of FIGS. 96-100.

A needle apparatus may be coupled to a Raman spectroscopy system 100 by one or more optical fibers 116 (e.g., as illustrated in FIG. 79-81, 86, or 102), and a pump-Stokes beam 140 may be sent from the Raman spectroscopy system to the needle apparatus via one or more optical fibers. For example, as illustrated in FIG. 79, the needle apparatus may be a needle with optical fiber 400 that is coupled to a Raman spectroscopy system 100 by an optical fiber 116*e*. As another example, the needle apparatus may be the needle with optical waveguide 400-W in any of FIGS. 75-77 that is coupled to a Raman spectroscopy system 100 by the optical fiber 116*e*. As another example, the needle apparatus may be the catheter needle with optical fiber 500 in FIG. 96, and the optical fiber 116 may be coupled to a Raman spectroscopy system 100 by one or more additional optical fibers.

At step 830, the Raman spectroscopy system 100 receives a Raman signal 160 produced by coherent Raman scattering of the pump-Stokes beam of light 140. For example, the Raman signal 160 may be produced by coherent Raman scattering of the pump and Stokes beams of light at a sample 150, and an optical fiber 116 or an optical waveguide 450 of the needle apparatus may receive at least a portion of the Raman signal 160. The optical fiber or optical waveguide may convey the Raman signal 160 in a direction away from the needle tip 414, and the Raman signal may be sent to the Raman spectroscopy system 100 via an optical fiber 116 connected to the needle apparatus. An optical fiber 116 that couples a needle apparatus to a Raman spectroscopy system 100 may (i) transmit a pump-Stokes beam of light 140 from the Raman spectroscopy system to the needle apparatus or (ii) transmit a Raman signal 160 from the needle apparatus to the Raman spectroscopy system.

At step 840, the Raman spectroscopy system 100 measures the Raman signal 160. Measurement of the Raman signal 160 may include (i) detecting the Raman signal and (ii) determining a characteristic associated with the Raman signal. The Raman signal 160 may be detected by coherently mixing the Raman signal with a probe beam of light 120*pr* at a detector 220 to produce an electronic signal (e.g., a photocurrent signal i), and a characteristic associated with the Raman signal may be determined by determining a characteristic of the electronic signal. The method 800 may end after step 840, or the method may continue with the additional steps 850 and 860 illustrated by the dashed-line boxes in FIG. 120.

At step 850, a feedback signal 102 that represents a portion of the Raman signal 160 associated with a sample 150 is determined. For example, a needle apparatus may be inserted into the body of a subject (e.g., a human or animal patient), and the needle apparatus may be directed to a desired location referred to herein as a sample 150 (e.g., a particular organ or blood in a blood vessel). The feedback signal 102 may be determined from the measurement of the Raman signal 160 in step 840 and (i) may represent a portion of the Raman signal that is associated with the sample 150 or (ii) may indicate an angle or a direction in which the needle should be pointed to direct the needle apparatus to the sample. For example, the feedback signal may indicate a size or a relative amount of the Raman signal 160 that is produced by coherent Raman scattering of the pump and Stokes beams of light at the sample 150. If the needle 410 or needle tip 414 is located some distance from the sample 150 (e.g., as illustrated in FIG. 80), the feedback signal may be correspondingly small; and if the needle or needle tip is located relatively close to or in contact with the sample (e.g., as illustrated in FIG. 81), the feedback signal may be correspondingly large.

At step 860, the feedback signal 102 is provided to assist in directing the needle apparatus to the sample 150. For example, the feedback signal may be provided while the needle apparatus is being directed to the sample 150. A Raman spectroscopy system 100 (or a computing device coupled to the Raman spectroscopy system) may provide the feedback signal to an operator that is in the process of inserting the needle apparatus into the body of a subject and directing the needle to the sample 150. The Raman spectroscopy system 100 may measure multiple Raman signals 160 during insertion of the needle apparatus to provide real-time feedback to the operator. The feedback signal 102 may indicate an approximate distance to the sample 150 (e.g., based on the size or relative amount of the Raman signal 160 associated with the sample) or may indicate a direction or angle that the needle 410 should be steered to in order to reach the sample (e.g., as illustrated in FIG. 91). Once the needle apparatus has reached the sample 150 (e.g., the needle tip 414 or the optical-fiber end face 117 is located at the sample), the feedback signal may indicate that the needle apparatus has been successfully inserted into the desired location. For example, the feedback signal may include a value (e.g., a number from 0 to 10 or a percentage from 0 to 100%) or a colored light (e.g., red, yellow, green) corresponding to the amount of the Raman signal 160 that is produced by interaction of the pump-Stokes beam 140 with the sample 150. If little or no Raman signal 160 associated with the sample 150 is detected, then the feedback signal may include a red light, indicating that the needle apparatus is not located near the sample 150. The color of the light may change to yellow as the needle apparatus approaches the sample 150, and the color of the light may change to green when the needle apparatus reaches the sample.

The method 800 may end after step 860, or the method may continue with the additional step 870 illustrated by the dashed-line box in FIG. 120. Step 870 may be implemented when the needle apparatus is a catheter needle with optical fiber 500 (e.g., as illustrated in FIG. 96). At step 870, the needle 410 and optical fiber 116 of a catheter-needle-fiber apparatus 500 are removed after the apparatus has been directed to a sample 150, at which point the method may end. The feedback signal provided during insertion of the catheter-needle-fiber apparatus 500 may allow the apparatus to be directed to the desired location, and after the needle and optical fiber are removed, the catheter 510 remains installed. For example, the sample 150 may be blood 620 located in a blood vessel 610, and once the needle tip 414 has been inserted into the blood vessel (along with a portion of the catheter tube 515), the needle 410 and optical fiber 116 may be removed (e.g., as illustrated in FIG. 97). The needle 410 and optical fiber 116 may be removed by holding the installed catheter 510 in place and pulling on the needle hub 420 in a direction away from the catheter so that the needle 410 and optical fiber 116 are withdrawn from within the catheter tube 515. This leaves a portion of the catheter tube 515 inserted into the blood vessel 610, while the catheter connector 520 and another portion of the catheter tube 515 are located outside the patient's body (e.g., as illustrated in FIG. 101).

Figure 121:
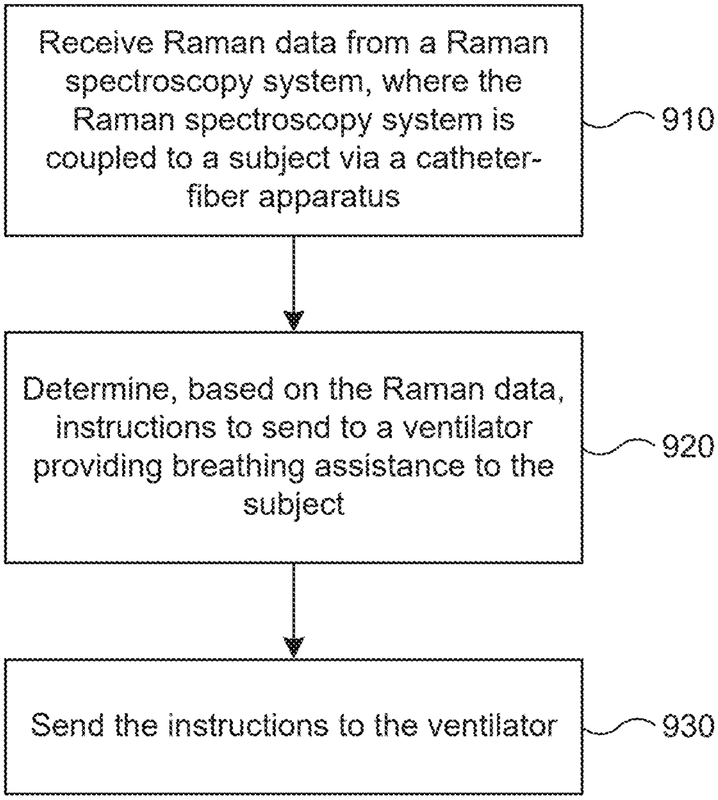
FIG. 121 illustrates an example method for using data from a Raman spectroscopy system to determine instructions to send to a ventilator.

FIG. 121 illustrates an example method 900 for using data from a Raman spectroscopy system 100 to determine instructions 670 to send to a ventilator 680. The method 900 may be performed by a computer 1000 similar to that illustrated in FIGS. 113 and 122. The computer 1000 may be located within a Raman spectroscopy system 100, within a ventilator 680, or external to both the Raman spectroscopy system and ventilator. The computer 1000 may send information to or receive information from the Raman spectroscopy system 100 or the ventilator 680 via a wired connection, a wireless connection, or a fiber-optic connection.

The method may begin at step 910 in which Raman data 660 is received from a Raman spectroscopy system 100, where the Raman spectroscopy system is coupled to a subject (e.g., patient 650 in FIG. 113) via a catheter-fiber apparatus. The catheter-fiber apparatus may be a catheter insert with optical fiber 540 that includes a catheter insert 542 and one or more optical fibers 116 (e.g., similar to that illustrated in any of FIGS. 107-112), or the catheter-fiber apparatus may be an adjustable catheter insert with optical fiber 540-A (e.g., similar to that illustrated in any of FIGS. 114-118). The catheter-fiber apparatus may be coupled to a catheter 510 that is installed in a blood vessel 610 of a subject. For example, as illustrated in FIGS. 111-112, the catheter-fiber apparatus may be a catheter insert with optical fiber 540 that is coupled to a catheter 510 installed in a blood vessel 610. As illustrated in FIG. 112, the optical fiber 116 may receive a pump-Stokes beam 140 produced by a Raman spectroscopy system 100 and direct the pump-Stokes beam to blood 620 in the blood vessel 610. Additionally, the optical fiber 116 may receive a Raman signal 160 produced by coherent Raman scattering of the pump-Stokes beam 140 while propagating in the blood 620, and the optical fiber may convey the Raman signal to the Raman spectroscopy system for measurement. Based on the Raman signal 160, the Raman spectroscopy system 100 may determine the Raman data 660 that is sent to the computer 1000. The Raman data 660 may include the concentration of oxygen, carbon dioxide, or bicarbonate in the blood 620.

At step 920, after receiving the Raman data 660, the computer 1000 determines instructions 670 to send to a ventilator 680, where the ventilator is providing breathing assistance to the subject (e.g., patient 650 in FIG. 113). The ventilator instructions 670 may be determined based at least in part on the Raman data 660 received from the Raman spectroscopy system 100. For example, the ventilator instructions 670 may be determined solely based on the Raman data 660, or the ventilator instructions may be determined based on the Raman data as well as information 672 received from the ventilator 680. The ventilator feedback information 672 may include patient-related parameters or ventilator operating parameters, such as for example, pressure, volume, and flow. The ventilator instructions 670 may include one or more of the following operating parameters for the ventilator 680: a respiratory rate, a positive end-expiratory pressure (PEEP), a tidal volume, a fraction of inspired oxygen (FiO2), and an inspiratory-to-expiratory (I:E) ratio.

At step 930, the ventilator instructions 670 are sent to the ventilator 680, at which point the method may end. The ventilator instructions 670 sent from the computer 1000 to the ventilator 680 may instruct the ventilator to adjust one or more of its operating parameters (e.g., respiratory rate, PEEP, tidal volume, FiO2, or I:E ratio). For example, the Raman data 660 may be used to determine blood acidity or oxygen concentration in the blood 620, and the ventilator instructions 670 may be adjusted to change the blood acidity to an optimal value or to ensure that the subject is receiving an adequate supply of oxygen in the air supplied by the ventilator. The method 900 may be performed substantially continually with Raman data 660 being received from the Raman spectroscopy system 100 periodically (e.g., approximately every minute, every 10 minutes, or every hour) and updated ventilator instructions 670 being sent to the ventilator 680 correspondingly. Additionally, the method 900 may be performed with little or no human intervention so that, based on the Raman data 660, the ventilator instructions 670 are automatically provided to the ventilator 680 to optimize the breathing and oxygen supply provided to the subject by the ventilator.

Figure 122:
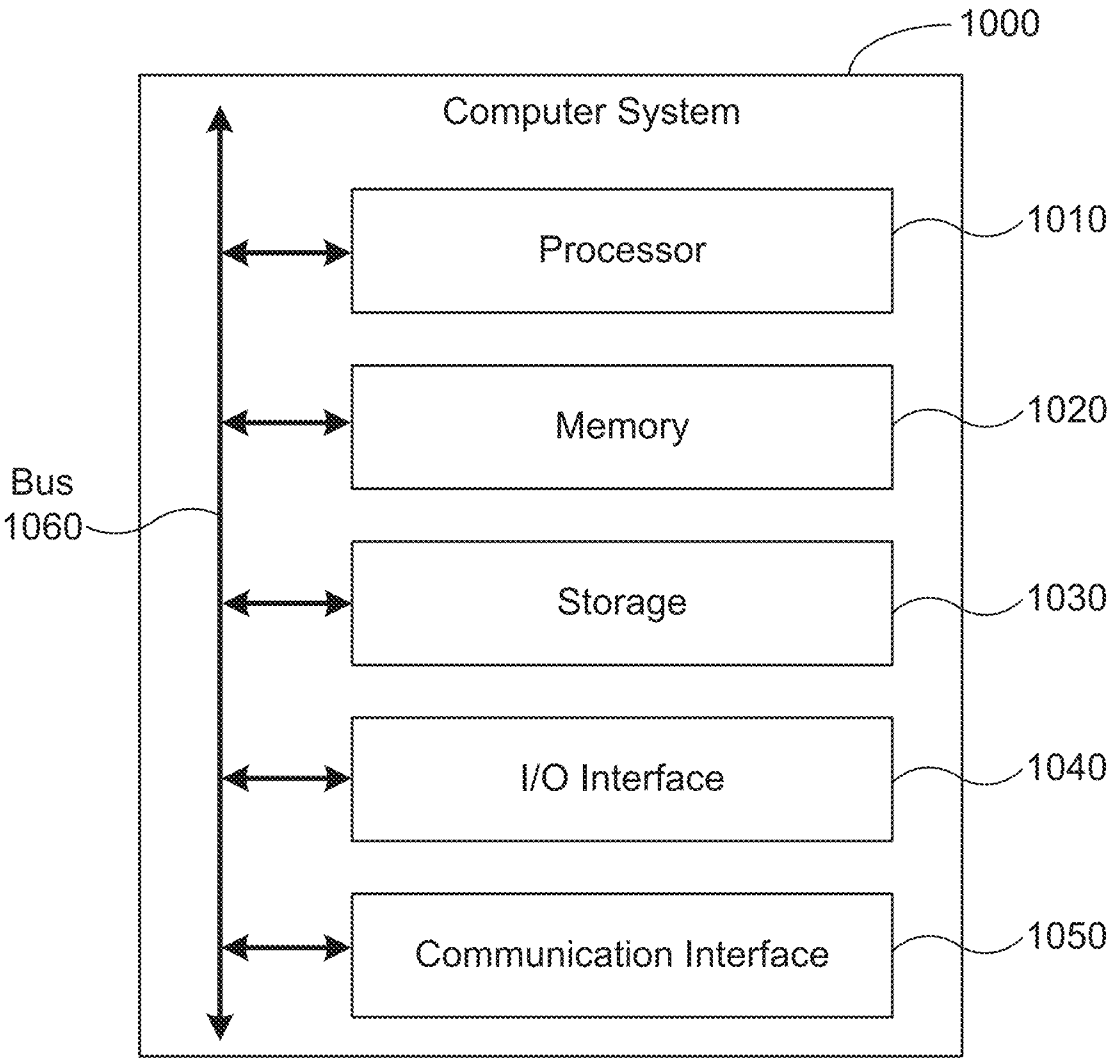
FIG. 122 illustrates an example computer system.

FIG. 122 illustrates an example computer system 1000. One or more computer systems 1000 may perform one or more steps of one or more methods described or illustrated herein. One or more computer systems 1000 may provide functionality described or illustrated herein. Software running on one or more computer systems 1000 may perform one or more steps of one or more methods described or illustrated herein or may provide functionality described or illustrated herein. A computer system 1000 may include or may be referred to as a processor, a controller, a computing device, a computing system, a computer, or a data-processing apparatus. Herein, reference to a computer system may encompass one or more computer systems, where appropriate. A processor of a Raman spectroscopy system 100 may include or may be referred to as a computer system, a controller, a computing device, a computing system, a computer, or a data-processing apparatus.

Computer system 1000 may take any suitable physical form. As an example, computer system 1000 may be an embedded computer system, a system-on-chip (SOC), an application-specific integrated circuit (ASIC), a field-programmable gate array (FPGA), a single-board computer system (SBC), a desktop computer system, a laptop or notebook computer system, a graphics processing unit (GPU), a mainframe, a mesh of computer systems, a server, a tablet computer system, or any suitable combination of two or more of these. As another example, all or part of computer system 1000 may be combined with, coupled to, or integrated into a variety of devices, including, but not limited to, a medical device, wearable device, camera, camcorder, personal digital assistant (PDA), mobile telephone, smartphone, electronic reading device (e.g., an e-reader), game console, smart watch, clock, calculator, television monitor, flat-panel display, computer monitor, eyewear, or head-mounted display. Where appropriate, computer system 1000 may include one or more computer systems 1000; be unitary or distributed; span multiple locations; span multiple machines; span multiple data centers; or reside in a cloud, which may include one or more cloud components in one or more networks. Where appropriate, one or more computer systems 1000 may perform without substantial spatial or temporal limitation one or more steps of one or more methods described or illustrated herein. As an example, one or more computer systems 1000 may perform in real time or in batch mode one or more steps of one or more methods described or illustrated herein. One or more computer systems 1000 may perform at different times or at different locations one or more steps of one or more methods described or illustrated herein, where appropriate.

As illustrated in the example of FIG. 122, computer system 1000 may include a processor 1010, memory 1020, storage 1030, an input/output (I/O) interface 1040, a communication interface 1050, or a bus 1060. Computer system 1000 may include any suitable number of any suitable components in any suitable arrangement.

Processor 1010 may include hardware for executing instructions, such as those making up a computer program. As an example, to execute instructions, processor 1010 may retrieve (or fetch) the instructions from an internal register, an internal cache, memory 1020, or storage 1030; decode and execute them; and then write one or more results to an internal register, an internal cache, memory 1020, or storage 1030. A processor 1010 may include one or more internal caches for data, instructions, or addresses. A processor 1010 may include one or more internal registers for data, instructions, or addresses. Processor 1010 may include any suitable number of any suitable internal registers, where appropriate. Where appropriate, processor 1010 may include one or more arithmetic logic units (ALUs); may be a multi-core processor; or may include one or more processors 1010.

Memory 1020 may include main memory for storing instructions for processor 1010 to execute or data for processor 1010 to operate on. As an example, computer system 1000 may load instructions from storage 1030 or another source (such as, for example, another computer system 1000) to memory 1020. Processor 1010 may then load the instructions from memory 1020 to an internal register or internal cache. To execute the instructions, processor 1010 may retrieve the instructions from the internal register or internal cache and decode them. During or after execution of the instructions, processor 1010 may write one or more results (which may be intermediate or final results) to the internal register or internal cache. Processor 1010 may then write one or more of those results to memory 1020. One or more memory buses (which may each include an address bus and a data bus) may couple processor 1010 to memory 1020. Bus 1060 may include one or more memory buses. Memory 1020 may include random access memory (RAM). This RAM may be volatile memory, where appropriate. Where appropriate, this RAM may be dynamic RAM (DRAM) or static RAM (SRAM). Memory 1020 may include one or more memories 1020, where appropriate.

Storage 1030 may include mass storage for data or instructions. As an example, storage 1030 may include a hard disk drive (HDD), a floppy disk drive, flash memory, an optical disc, a magneto-optical disc, magnetic tape, or a Universal Serial Bus (USB) drive or a combination of two or more of these. Storage 1030 may include removable or non-removable (or fixed) media, where appropriate. Storage 1030 may be internal or external to computer system 1000, where appropriate. Storage 1030 may be non-volatile, solid-state memory. Storage 1030 may include read-only memory (ROM). Where appropriate, this ROM may be mask ROM (MROM), programmable ROM (PROM), erasable PROM (EPROM), electrically erasable PROM (EEPROM), flash memory, or a combination of two or more of these. Storage 1030 may include one or more storage control units facilitating communication between processor 1010 and storage 1030, where appropriate. Where appropriate, storage 1030 may include one or more storages 1030.

I/O interface 1040 may include hardware, software, or both, providing one or more interfaces for communication between computer system 1000 and one or more I/O devices. Computer system 1000 may include one or more of these I/O devices, where appropriate. One or more of these I/O devices may enable communication between a person and computer system 1000. As an example, an I/O device may include a keyboard, keypad, microphone, monitor, mouse, printer, scanner, speaker, camera, stylus, tablet, touch screen, trackball, another suitable I/O device, or any suitable combination of two or more of these. An I/O device may include one or more sensors. Where appropriate, I/O interface 1040 may include one or more device or software drivers enabling processor 1010 to drive one or more of these I/O devices. I/O interface 1040 may include one or more I/O interfaces 1040, where appropriate.

Communication interface 1050 may include hardware, software, or both providing one or more interfaces for communication (such as, for example, packet-based communication) between computer system 1000 and one or more other computer systems 1000 or one or more networks. As an example, communication interface 1050 may include a network interface controller (NIC) or network adapter for communicating with an Ethernet or other wire-based network or a wireless NIC (WNIC); a wireless adapter for communicating with a wireless network, such as a WI-FI network; or an optical transmitter (e.g., a laser or a light-emitting diode) or an optical receiver (e.g., a photodetector) for communicating using fiber-optic communication or free-space optical communication. Computer system 1000 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1000 may communicate with a wireless PAN (WPAN) (such as, for example, a BLUETOOTH WPAN), a WI-FI network, a Worldwide Interoperability for Microwave Access (WiMAX) network, a cellular telephone network (such as, for example, a Global System for Mobile Communications (GSM) network), or other suitable wireless network or a combination of two or more of these. As another example, computer system 1000 may communicate using fiber-optic communication based on 100 Gigabit Ethernet (100 GbE), 10 Gigabit Ethernet (10 GbE), or Synchronous Optical Networking (SONET). Computer system 1000 may include any suitable communication interface 1050 for any of these networks, where appropriate. Communication interface 1050 may include one or more communication interfaces 1050, where appropriate.

Bus 1060 may include hardware, software, or both coupling components of computer system 1000 to each other. As an example, bus 1060 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local bus (VLB), or another suitable bus or a combination of two or more of these. Bus 1060 may include one or more buses 1060, where appropriate.

Various modules, circuits, systems, methods, or algorithm steps described in connection with the implementations disclosed herein may be implemented as electronic hardware, computer software, or any suitable combination of hardware and software. Computer software (which may be referred to as software, computer-executable code, computer code, a computer program, computer instructions, or instructions) may be used to perform various functions described or illustrated herein, and computer software may be configured to be executed by or to control the operation of computer system 1000. As an example, computer software may include instructions configured to be executed by processor 1010. Owing to the interchangeability of hardware and software, the various illustrative logical blocks, modules, circuits, or algorithm steps have been described generally in terms of functionality. Whether such functionality is implemented in hardware, software, or a combination of hardware and software may depend upon the particular application or design constraints imposed on the overall system.

A computing device may be used to implement various modules, circuits, systems, methods, or algorithm steps disclosed herein. As an example, all or part of a module, circuit, system, method, or algorithm disclosed herein may be implemented or performed by a general-purpose single- or multi-chip processor, a digital signal processor (DSP), an ASIC, a FPGA, a GPU, any other suitable programmable-logic device, discrete gate or transistor logic, discrete hardware components, or any suitable combination thereof. A general-purpose processor may be a microprocessor, or any conventional processor, controller, microcontroller, GPU, or state machine. A processor may also be implemented as a combination of computing devices, e.g., a combination of a DSP and a microprocessor, a plurality of microprocessors, one or more microprocessors in conjunction with a DSP core, or any other such configuration.

One or more implementations of the subject matter described herein may be implemented as one or more computer programs (e.g., one or more modules of computer-program instructions encoded or stored on a computer-readable non-transitory storage medium). As an example, the steps of a method or algorithm disclosed herein may be implemented in a processor-executable software module which may reside on a computer-readable non-transitory storage medium. A computer-readable non-transitory storage medium may include any suitable storage medium that may be used to store or transfer computer software and that may be accessed by a computer system. Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs (e.g., compact discs (CDs), CD-ROM, digital versatile discs (DVDs), Blu-ray discs, or laser discs), optical disc drives (ODDs), magneto-optical discs, magneto-optical drives, floppy diskettes, floppy disk drives (FDDs), magnetic tapes, flash memories, solid-state drives (SSDs), RAM, RAM-drives, ROM, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Certain features described herein in the context of separate implementations may also be combined and implemented in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

While operations may be depicted in the drawings as occurring in a particular order, this should not be understood as requiring that such operations be performed in the particular order shown or in sequential order, or that all operations be performed. Further, the drawings may schematically depict one more example processes or methods in the form of a flow diagram or a sequence diagram. However, other operations that are not depicted may be incorporated in the example processes or methods that are schematically illustrated. For example, one or more additional operations may be performed before, after, simultaneously with, or between any of the illustrated operations. Moreover, one or more operations depicted in a diagram may be repeated, where appropriate. Additionally, operations depicted in a diagram may be performed in any suitable order. Furthermore, although particular components, devices, or systems are described herein as carrying out particular operations, any suitable combination of any suitable components, devices, or systems may be used to carry out any suitable operation or combination of operations. In certain circumstances, multitasking or parallel processing operations may be performed. Moreover, the separation of various system components in the implementations described herein should not be understood as requiring such separation in all implementations, and it should be understood that the described program components and systems may be integrated together in a single software product or packaged into multiple software products.

Various embodiments have been described in connection with the accompanying drawings. However, it should be understood that the figures may not necessarily be drawn to scale. As an example, distances or angles depicted in the figures are illustrative and may not necessarily bear an exact relationship to actual dimensions or layout of the devices illustrated.

One or more of the figures described herein may include example data that is prophetic. For example, the graphs illustrated FIGS. 3-16 and 19 and the feedback signals 102 illustrated in FIGS. 79-81 and 91-92 may include or may be referred to as prophetic examples.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes or illustrates respective embodiments herein as including particular components, elements, functions, operations, or steps, any of these embodiments may include any combination or permutation of any of the components, elements, functions, operations, or steps described or illustrated anywhere herein that a person having ordinary skill in the art would comprehend.

The term "or" as used herein is to be interpreted as an inclusive or meaning any one or any combination, unless expressly indicated otherwise or indicated otherwise by context. Therefore, herein, the expression "A or B" means "A, B, or both A and B." As another example, herein, "A, B, or C" means at least one of the following: A; B; C; A and B; A and C; B and C; A, B, and C. An exception to this definition will occur if a combination of elements, devices, steps, or operations is in some way inherently mutually exclusive.

As used herein, words of approximation such as, without limitation, "approximately, "substantially," or "about" refer to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as having the required characteristics or capabilities of the unmodified feature. In general, but subject to the preceding discussion, a numerical value herein that is modified by a word of approximation such as "approximately" may vary from the stated value by ±0.5%, ±1%, ±2%, ±3%, ±4%, ±5%, ±10%, ±12%, or ±15%. The term "substantially constant" refers to a value that varies by less than a particular amount over any suitable time interval. For example, a value that is substantially constant may vary by less than or equal to 20%, 10%, 1%, 0.5%, or 0.1% over a time interval of approximately $10^4$ s, $10^3$ s, $10^2$ s, 10 s, 1 s, 100 ms, 10 ms, 1 ms, 100 μs, 10 μs, or 1 μs. The term "substantially constant" may be applied to any suitable value, such as for example, an optical power, an electrical current, a wavelength, an optical or electrical frequency, or an optical or electrical phase.

As used herein, the terms "first," "second," "third," etc. may be used as labels for nouns that they precede, and these terms may not necessarily imply a particular ordering (e.g., a particular spatial, temporal, or logical ordering). As an example, a system may be described as determining a "first result" and a "second result," and the terms "first" and "second" may not necessarily imply that the first result is determined before the second result.

As used herein, the terms "based on" and "based at least in part on" may be used to describe or present one or more factors that affect a determination, and these terms may not exclude additional factors that may affect a determination. A determination may be based solely on those factors which are presented or may be based at least in part on those factors. The phrase "determine A based on B" indicates that B is a factor that affects the determination of A. In some instances, other factors may also contribute to the determination of A. In other instances, A may be determined based solely on B.

Various example aspects included in this disclosure may be presented in a range format. It should be understood that a description in range format is merely for convenience and brevity and should not be construed as an inflexible limitation on the scope of a disclosed aspect. Accordingly, the description of a range should be considered to have specifically disclosed all suitable sub-ranges as well as individual numerical values within that range, unless expressly indicated otherwise or indicated otherwise by context. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual values within that range, for example, 1.1, 2, 2.3, 5, and 5.9.

Although the foregoing embodiments have been described in some detail for purposes of clarity of understanding, the invention is not limited to the details provided. There may be numerous alternative ways of implementing the invention. The disclosed embodiments are illustrative and not restrictive.

The invention claimed is:

1. An apparatus comprising:

a catheter insert comprising a catheter connector and a sheath having a substantially cylindrical shape, wherein the catheter insert is configured to be coupled to a catheter comprising a mating connector and a catheter tube, wherein at least a portion of the sheath is configured to be inserted into the catheter tube, and the catheter connector is configured to be connected to the mating connector; and an optical fiber comprising an end face, wherein at least a portion of the optical fiber is contained within the sheath, and wherein the optical fiber is configured to transmit a pump-Stokes beam of light along the optical fiber to the end face, wherein the pump-Stokes beam is emitted from the end face and directed to a sample.

2. The apparatus of claim 1, wherein the optical fiber is attached to an interior surface of the sheath by an adhesive.

3. The apparatus of claim 1, wherein the sheath comprises a coating or a jacket that is attached to or in contact with an exterior surface of the optical fiber.

4. The apparatus of claim 1, wherein the sheath comprises a front sheath and a back sheath, wherein:

the catheter connector is located between the front and back sheaths; and when coupling the catheter insert to the catheter, the front sheath is inserted into the catheter tube, and the back sheath remains external to the catheter tube.

5. The apparatus of claim 4, wherein the catheter insert further comprises a catheter-insert tube connected to the back sheath, wherein:

the catheter-insert tube is configured to allow for flow of a fluid when the catheter insert is coupled to the catheter, wherein the fluid is allowed to flow (i) through the catheter tube of the catheter and then through the catheter-insert tube or (ii) through the catheter-insert tube and then through the catheter tube; and the catheter insert further comprises an adhesive located within the back sheath, wherein the adhesive is configured to prevent the fluid from flowing through the back sheath.

6. The apparatus of claim 1, wherein:

when the catheter insert is coupled to the catheter, the end face of the optical fiber is located at or near an end of the catheter tube opposite the mating connector; and the end of the catheter tube is located at or near the sample.

7. The apparatus of claim 1, wherein a surface of the sheath is coated with an anticoagulant substance.

8. The apparatus of claim 1, further comprising a pulser coupled to the catheter insert or the optical fiber, wherein the pulser is configured to impart a vibration to the catheter insert or the optical fiber to circulate fluid around the end face of the optical fiber.

9. The apparatus of claim 1, wherein:

the pump-Stokes beam is configured to produce a Raman signal by coherent Raman scattering of the pump-Stokes beam at the sample; and the optical fiber is further configured to receive at least a portion of the Raman signal via the end face and transmit the received Raman signal along the optical fiber in a direction opposite the pump-Stokes beam.

10. The apparatus of claim 1, wherein:

the pump-Stokes beam is configured to produce a Raman signal by coherent Raman scattering of the pump-Stokes beam at the sample; and the optical fiber is an output optical fiber, and the apparatus further comprises an input optical fiber comprising an input-fiber end face, wherein at least a portion of the input optical fiber is contained within the sheath, and the input optical fiber is configured to receive at least a portion of the Raman signal via the input-fiber end face and transmit the received Raman signal along the input optical fiber in a direction away from the input-fiber end face.

11. The apparatus of claim 1, wherein:

the pump-Stokes beam of light comprises a pump beam of light at a pump frequency and a Stokes beam of light at a Stokes frequency, wherein the pump and Stokes frequencies are offset by a frequency offset Ω; and a Raman signal is produced by coherent Raman scattering of the pump and Stokes beams of light at the sample.

12. The apparatus of claim 1, wherein the optical fiber is configured to be coupled to a Raman spectroscopy system, wherein the Raman spectroscopy system is configured to:

produce the pump-Stokes beam of light that is sent to the sample via the optical fiber;

receive a Raman signal produced by coherent Raman scattering of the pump-Stokes beam of light at the sample; and measure the Raman signal.

13. The apparatus of claim 12, wherein the Raman spectroscopy system comprises:

a pump light source configured to produce a pump beam of light at a pump frequency;

a Stokes light source configured to produce a Stokes beam of light at a Stokes frequency, wherein the pump and Stokes frequencies are offset by a frequency offset Ω, and wherein the pump-Stokes beam of light comprises the pump beam of light and the Stokes beam of light;

an optical receiver configured to detect the Raman signal, the optical receiver comprising:

a probe light source configured to produce a probe beam of light at a probe frequency;

an optical detector configured to coherently mix a portion of the Raman signal with at least a portion of the probe beam of light to produce a corresponding photocurrent signal; and an electronic circuit configured to produce a digital output signal corresponding to the photocurrent signal; and a processor configured to determine a characteristic of the photocurrent signal based on the digital output signal.

14. The apparatus of claim 1, wherein the catheter insert is configured to be coupled to a catheter that is installed in a blood vessel of a subject, wherein the sample comprises blood in the blood vessel.

15. The apparatus of claim 14, wherein the optical fiber is configured to be coupled to a Raman spectroscopy system, wherein the Raman spectroscopy system is configured to:

produce the pump-Stokes beam of light that is directed to the blood via the optical fiber;

receive a Raman signal produced by coherent Raman scattering of the pump-Stokes beam of light while propagating in the blood;

measure the Raman signal; and determine, based on the measurement of the Raman signal, concentrations of oxygen, carbon dioxide, and bicarbonate in the blood.

16. The apparatus of claim 15, wherein the determined concentrations of oxygen, carbon dioxide, and bicarbonate are used to determine instructions to send to a ventilator providing breathing assistance to the subject, wherein the instructions comprise one or more of:

a respiratory rate, a positive end-expiratory pressure, a tidal volume, a fraction of inspired oxygen (FiO2), and an inspiratory-to-expiratory (I:E) ratio.

* * * * *